(12) United States Patent
Binggeli et al.

(10) Patent No.: US 7,855,194 B2
(45) Date of Patent: Dec. 21, 2010

(54) PYRIMIDINE, QUINAZOLINE, PTERIDINE AND TRIAZINE DERIVATIVES

(75) Inventors: Alfred Binggeli, Binningen (CH); Andreas Christ, Arlesheim (CH); Hans-Peter Maerki, Basel (CH); Rainer Eugen Martin, Basel (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 18 days.

(21) Appl. No.: 11/724,688

(22) Filed: Mar. 15, 2007

(65) Prior Publication Data
US 2007/0225271 A1    Sep. 27, 2007

(30) Foreign Application Priority Data
Mar. 27, 2006   (EP) .................. 06111751

(51) Int. Cl.
| | |
|---|---|
| A01N 43/00 | (2006.01) |
| A01N 43/66 | (2006.01) |
| A01N 43/90 | (2006.01) |
| A01N 43/54 | (2006.01) |
| A61K 31/00 | (2006.01) |
| A61K 33/53 | (2006.01) |
| A61K 33/519 | (2006.01) |
| A61K 33/517 | (2006.01) |
| A61K 33/515 | (2006.01) |
| C07D 403/00 | (2006.01) |
| C07D 471/00 | (2006.01) |
| C07D 487/00 | (2006.01) |
| C07D 491/00 | (2006.01) |
| C07D 401/00 | (2006.01) |
| C07D 405/00 | (2006.01) |
| C07D 409/00 | (2006.01) |
| C07D 411/00 | (2006.01) |
| C07D 413/00 | (2006.01) |
| C07D 417/00 | (2006.01) |
| C07D 419/00 | (2006.01) |
| C07D 495/00 | (2006.01) |

(52) U.S. Cl. .............. 514/210.21; 514/241; 514/262.1; 514/260.1; 514/266.22; 514/269; 544/209; 544/255; 544/256; 544/310; 544/284; 544/278

(58) Field of Classification Search ............ None
See application file for complete search history.

(56) References Cited

U.S. PATENT DOCUMENTS

| | | | |
|---|---|---|---|
| 3,931,181 | A | 1/1976 | Kompis et al. |
| 3,956,495 | A | 5/1976 | Lacefield |
| 4,255,429 | A | 3/1981 | Werner |
| 4,309,541 | A | 1/1982 | Werner |
| 4,499,092 | A | 2/1985 | Hallot et al. |
| 6,140,353 | A | 10/2000 | Ackermann et al. |
| 6,159,982 | A | 12/2000 | Bosmans et al. |

FOREIGN PATENT DOCUMENTS

| | | |
|---|---|---|
| DE | 2121 031 A1 | 11/1972 |
| DE | 243 59 34 | 2/1975 |
| EP | 0009 465 A1 | 4/1980 |
| EP | 488 861 | 6/1992 |
| EP | 0921 116 A1 | 6/1999 |
| EP | 1 571 146 A1 | 9/2005 |
| FR | 2514 765 A1 | 4/1983 |
| WO | WO 92/01687 A1 | 2/1992 |
| WO | WO 00/35 858 A1 | 6/2000 |
| WO | WO 01/32 633 A1 | 5/2001 |
| WO | WO 01/326 33 A1 | 5/2001 |
| WO | WO 01/74775 A1 | 10/2001 |
| WO | WO 01/83 476 A1 | 11/2001 |
| WO | WO 01/90 051 | 11/2001 |
| WO | WO 04/000 806 A1 | 12/2003 |
| WO | WO 2005/09 9711 A1 | 10/2005 |

OTHER PUBLICATIONS

Moragues, et. al. Farmaco, Edizione Scientifica (1980), 35(11), 951-64.*

G. C. Weir and J. L. Leahy, 1994, Pathogenesis of non-insulin dependent (Type II) diabetes mellitus, in Joslin's Diabetes Mellitus (Eds. C. R. Kahn and G. C. Weir), 13th Edition, 1994, Lea & Febiger, Malvern, PA, pp. 240-264.

H. E. Lebovitz, Oral antidiabetic agents, in Joslin's Diabetes Mellitus (Eds. C. R. Kahn and G. C. Weir), 13th Edition, 1994, Lea & Febiger, Malvern, PA, pp. 508-529.

(Continued)

*Primary Examiner*—James O Wilson
*Assistant Examiner*—Jeffrey H Murray
(74) *Attorney, Agent, or Firm*—George W. Johnston; Dennis P. Tramaloni; Samuel H. Megerditchian

(57) ABSTRACT

This invention is concerned with compounds of the formula

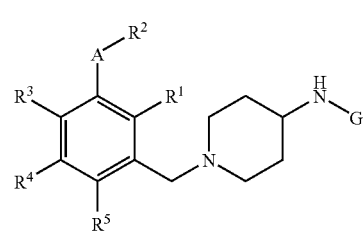

I wherein A, $R^1$ to $R^5$ and G are as defined in the description and claims, and pharmaceutically acceptable salts thereof. The invention further relates to pharmaceutical compositions containing such compounds, to a process for their preparation and to their use for the treatment and/or prevention of diseases which are associated with the modulation of SST receptors subtype 5.

11 Claims, No Drawings

OTHER PUBLICATIONS

C. J. Bailey, M. R. C. Path and R. C. Turner *N. Engl. J. Med* 1996, 334, 574-579.
G. L.Plosker and D. Faulds *Drugs* 1999, 57, 409-438.
Y. Zambre, et. al., *Biochem. Pharmacol.* 1999, 57, 1159-1164.
S. P. Fagan, et al, *Surgery* 1998, 124, 254-258.
M. Norman, et al., *Ann. Surg.* 2002, 235, 767-774.
T.A. Tirone, et al., *Pancreas* 2003, 26, e67-73.
M. Z. Strowski, et al., *Mol. Endocrinol.* 2003, 17, 93-106.
K. Cejvan, D. H. Coy and S. Efendic *Diabetes* 2003, 52, 1176-1181.
M. Z. Strowski, R. M. Parmar, A. D. Blake and J. M. Schaeffer *Endocrinology* 2000, 141, 111-117.
E. Näslund, et al., *Int. J. Obes.* 1999, 23, 304-311.
J.-P. Gutzwiller, et al., *Gut* 1999, 44, 81-88.
J.-P. Gutzwiller, et al., *Am. J. Physiol.* 1999, 276, R1541-1544.
M. D. Turton, et al., *Nature* 1996, 379, 69-72.
A. Flint, et al., *J. Clin. Invest.* 1998, 101, 515-520.
M. B. Toft-Nielsen, et al., *Diabetes Care* 1999, 22, 1137-1143.
P. K. Cheikani, et al., *Am. J. Physiol.* 2005, 288, R1695-R1706.
T. Miki, et al., *Diabetes* 2005, 54, 1056-1063.
L. Hansen, et al., *Am. J. Phys.* 2000, 278, E1010-1018.
D. G. Burrin, et al., *Domest. Anim. Endocrinol.* 2003, 24, 103-122.
K. V. Haderslev, et al., *Scand. J. Gastroenterol.* 2002, 37, 392-398.
P. B. Jeppesen *J. Nutr.* 2003, 133, 3721-3724.
T. Talme, et al., *Clin. Exp. Immunol.* 2001, 125, 71-79.
D. Ferone, et al., *Dig. Liver Dis.* 2004, 36, S68-77.
C. E. Ghamrawy, et al., *Peptides* 1999, 20, 305-311.
J. P. Wolfe, et al., *J. Am. Chem. Soc.* 1996, 118, 7215-7216.
J. P. Wolfe and S. L. Buchwald *Tetrahedron Lett.* 1997, 38, 6359-6362.
J. P. Wolfe, et al, *Acc. Chem. Res.* 1998, 31, 805-818.
B. H. Yang and S. L. Buchwald *J. Organomet. Chem.* 1999, 576, 125-146.
J. F. Hartwig *Angew. Chem. Int. Ed.* 1998, 37, 2046-2067.
Q. Shen, et al., *Angew. Chem. Int. Ed.* 2005, 44, 1371-1375.
Y.-Z. Kim, et al., *J. Med. Chem.* 1994, 37, 3828-3833.
A. R. Katritzky and T. I. Yousaf *Canad. J. Chem.* 1986, 64, 2087-2093.
H. H. Wasserman and J. L. Ives *J. Am. Chem. Soc.* 1976, 98, 7868-7869.
L. A. Paquette, *Principles of Modern Heterocyclic Chemistry*, 1968, W. A. Benjamin, Inc., New York (uracil synthesis pp. 313-315.
L. A. Paquette, *Principles of Modern Heterocyclic Chemistry*, 1968, W. A. Benjamin, Inc., New York ;pyrimidine synthesis pp. 313-316.
J. T. Bork, J. W. Lee and Y.-T. Chang *QSAR Comb. Sci.* 2004, 23, 245-260.
D. B. Harden, et al., *J. Org. Chem.* 1988, 53, 4137-4140.
V. Oakes, et al, *J. Chem. Soc., Abstracts* 1962, 4678-4685.
Z. Sui, et al., *Bioorg. Med. Chem. Lett.* 2003, 13, 761-765.
H.-J. Hess, et al., *J. Med. Chem.* 1968, 11, 130-136.
C. Flader, et al., *J. Med. Chem.* 2000, 43, 3157-3167.
M. J. Ashton, et al., *J. Med Chem.* 1994, 37, 1696-1703.
W. White, et al., *J. Med. Chem.* 2000, 43, 4084-4097.
I. Kompis and A. Wick *Helv. Chim. Acta* 1977, 60, 3025-3034.
S. P. Dudek, et al., Chidsey *J. Am. Chem. Soc.* 2001, 123, 8033-8038.
Moragues J., et al., Farmaco, Edizione Scientifica, Societa Chimica Italiana, Pavia, IT, vol. 35, No. 11, pp. 951-964 (1980), XP009032424.

\* cited by examiner

PYRIMIDINE, QUINAZOLINE, PTERIDINE AND TRIAZINE DERIVATIVES

PRIORITY TO RELATED APPLICATIONS

This application claims the benefit of European Application No. 06111751.1, filed Mar. 27, 2006, which is hereby incorporated by reference.

FIELD OF THE INVENTION

The present invention is concerned with novel pyrimidine, quinazoline, pteridine and triazine derivatives, their manufacture, pharmaceutical compositions containing them and their use as medicaments. The active compounds of the present invention are useful in the prevention and/or treatment of diabetes mellitus and other disorders.

In particular, the present invention is concerned with compounds of the general formula I

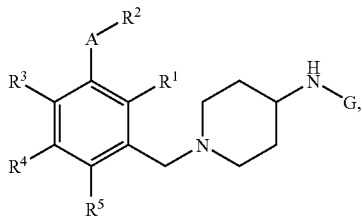

and pharmaceutically acceptable salts thereof.

All documents cited or relied upon below are expressly incorporated herein by reference.

BACKGROUND

The compounds of formula I possess pharmaceutical activity, in particular they are modulators of somatostatine receptor activity. More particularly, the compounds are antagonists of the somatostatine receptor subtype 5 (SSTR5).

Diabetes mellitus is a systemic disease characterized by metabolic disorders involving insulin, carbohydrates, fats and proteins, and disorders in the structure and function of blood vessels. The primary symptom of acute diabetes is hyperglycemia, often accompanied by glucosuria, the presence in urine of large amounts of glucose, and polyuria, the excretion of large volumes of urine. Additional symptoms arise in chronic diabetes, including degeneration of the walls of blood vessels. Although many different human organs are affected by these vascular changes, the eyes and kidneys appear to be the most susceptible. As such, long-standing diabetes mellitus, even when treated with insulin, is a leading cause of blindness.

There are three recognized types of diabetes mellitus. Type I diabetes or insulin dependent diabetes mellitus (IDDM) is typically of juvenile onset; ketosis develops early in life with much more severe symptoms and has a near-certain prospect of later vascular involvement. Control of Type I diabetes is difficult and requires exogenous insulin administration. Type II diabetes or non-insulin dependent diabetes mellitus (NIDDM) is ketosis-resistant, generally develops later in life, is milder and has a more gradual onset. Gestational diabetes is related to type II diabetes and associated with an increased risk of later development of that disease. Type III diabetes is malnutrition-related diabetes.

NIDDM is a condition that poses a major threat to the health of the citizens of the western world. NIDDM accounts for over 85% of diabetes incidence worldwide and about 160 million people are suffering from NIDDM. The incidence is expected to increase considerably within the next decades, especially in developing countries. NIDDM is associated with morbidity and premature mortality resulting from serious complications, e.g. cardiovascular disease (G. C. Weir and J. L. Leahy, 1994, Pathogenesis of non-insulin dependent (Type II) diabetes mellitus, in *Joslin's Diabetes Mellitus* (Eds. C. R. Kahn and G. C. Weir), 13th Edition, 1994, Lea & Febiger, Malvern, Pa., pp. 240-264). NIDDM is characterized by both fasting and post-prandial hyperglycemia resulting from abnormalities in insulin secretion and insulin action (G. C. Weir et al., vide supra).

The hyperglycemia in patients suffering from NIDDM can usually be initially treated by dieting, but eventually most NIDDM patients have to take oral antidiabetic agents and/or insulin injections to normalize their blood glucose levels. The introduction of orally effective hypoglycemic agents was an important development in the treatment of hyperglycemia by lowering blood glucose levels. Currently, the most widely used oral antidiabetic agents are the sulfonylureas, which act by increasing the secretion of insulin from the pancreas (H. E. Lebovitz, Oral antidiabetic agents, in *Joslin's Diabetes Mellitus* (Eds. C. R. Kahn and G. C. Weir), 13th Edition, 1994, Lea & Febiger, Malvern, Pa., pp. 508-529), the biguanides (e.g., metformin) which act on the liver and periphery by unknown mechanisms (C. J. Bailey, M. R. C. Path and R. C. Turner *N. Engl. J. Med.* 1996, 334, 574-579) and the thiazolidinediones (e.g., rosiglitazone/Avandia®) which enhance the effects of insulin at peripheral target sites (G. L. Plosker and D. Faulds *Drugs* 1999, 57, 409-438). These existing therapies which comprise a wide variety of biguanide, sulfonylurea and thiazolidinedione derivatives have been used clinically as hypoglycemic agents. However, all three classes of compound have side effects. The biguanides, for example metformin, are unspecific and in certain cases have been associated with lactic acidosis, and need to be given over a longer period of time, i.e. they are not suitable for acute administration (C. J. Bailey et al., vide supra). The sulfonylureas, though having good hypoglycemic activity, require great care during use because they frequently cause serious hypoglycemia and are most effective over a period of circa ten years. The thiazolidinediones may cause weight gain following chronic administration (G. L. Plosker and D. Faulds, vide supra) and troglitazone has been associated with the occurrence of serious hepatic dysfunction.

Thus, there is a significant and rising need for antidiabetic drugs that have novel mechanisms of action, thereby avoiding side effects produced by known therapies. The hormone somatostatin (SST) is primarily produced in the intestinal tract and in the pancreas. In addition it acts as a neurotransmitter. The hormone is involved through its receptors in the regulation of several other hormones and in immunoregulation. In particular, SST suppresses the secretion of insulin by pancreatic β cells and the secretion of glucagon-like peptide 1 (GLP-1) by L cells. GLP-1 in turn is one of the most potent stimulators of insulin production and secretion and is a trophic factor for β cells. β and L cells express SST receptor subtype 5 (SSTR5) and agonizing this receptor suppresses insulin and GLP-1 secretion in humans and in animal models (e.g., Y. Zambre, Z. Ling, M.-C. Chen, X. Hou, C.-W. Woon, M. Culler, J. E. Taylor, D. H. Coy, C. van Schravendijk, F. Schuit, D. G. Pipeleers and D. L. Eizirik *Biochem. Pharmacol.* 1999, 57, 1159-1164; S. P. Fagan, A. Azizzadeh, S. Moldovan, M. K. Ray, T. E. Adrian, X. Ding, D. H. Coy and F. C. Brunicardi *Surgery* 1998, 124, 254-258; M. Norman, S. Moldovan, V. Seghers, X.-P. Wang, F. J. DeMayo and F. C. Brunicardi *Ann. Surg.* 2002, 235, 767-774; T. A. Tirone, M. A. Norman, S. Moldovan, F. J. DeMayo, X.-P. Wang and F. C. Brunicardi *Pancreas* 2003, 26, e67-73; M. Z. Strowski, M. Köhler, H. Y. Chen, M. E. Trumbauer, Z. Li, D. Szalkowski, S. Gopal-Truter, J. K. Fisher, J. M. Schaeffer, A. D. Blake, B. B. Zhang and H. A. Wilkinson *Mol. Endocrinol.* 2003, 17, 93-106).

Consequently, antagonizing the effect of SST would lead to higher plasma insulin concentrations. In patients suffering from impaired glucose tolerance and NIDDM, a higher plasma insulin concentration would moderate the dangerous hyperglycemia and accordingly reduce the risk of tissue damage. If such SSTR5 antagonists are sufficiently selective over the other four SST receptors, little influence is expected on secretion of other hormones. Particularly, selectivity over SST receptor subtype 2 avoids influences on glucagon secretion (K. Cejvan, D. H. Coy and S. Efendic *Diabetes* 2003, 52, 1176-1181; M. Z. Strowski, R. M. Parmar, A. D. Blake and J. M. Schaeffer *Endocrinology* 2000, 141, 111-117). Advantageous over established therapies is the dual mechanism of action to increase insulin secretion: directly on pancreatic β cells and indirectly through GLP-1 release from L cells. Additionally, SSTR5 knockout mice demonstrated higher insulin sensitivity than littermates (M. Z. Strowski, M. Köhler et al., vide supra). Therefore, SSTR5 antagonists could have the potential to beneficially influence insulin resistance in patients with NIDDM. In summary, SSTR5 antagonists are expected to beneficially influence NIDDM, the underlying impaired fasting glucose and impaired glucose tolerance, as well as complications of long-standing, insufficiently controlled diabetes mellitus.

GLP-1 is known as an endogenous regulator of gastrointestinal motility and of food intake reducing appetite as shown in laboratory animals, healthy volunteers and patients with NIDDM (E. Näslund, B. Barkeling, N. King, M. Gutniak, J. E. Blundell, J. J. Holst, S. Rössner and P. M. Hellström *Int. J. Obes.* 1999, 23, 304-311; J.-P. Gutzwiller, B. Göke, J. Drewe, P. Hildebrand, S. Ketterer, D. Handschin, R. Winterhalder, D. Conen and C. Beglinger *Gut* 1999, 44, 81-88; J.-P. Gutzwiller, J. Drewe, B. Göke, H. Schmidt, B. Rohrer, J. Lareida and C. Beglinger *Am. J. Physiol.* 1999, 276, R1541-1544; M. D. Turton, D. O'Shea, I. Gunn, S. A. Beak, C. M. Edwards, K. Meeran, S. J. Choi, G. M. Taylor, M. M. Heath, P. D. Lambert, J. P. Wilding, D. M. Smith, M. A. Ghatei, J. Herbert and S. R. Bloom *Nature* 1996, 379, 69-72; A. Flint, A. Raben, A. Astrup and J. J. Holst *J. Clin. Invest.* 1998, 101, 515-520; M. B. Toft-Nielsen, S. Madsbad and J. J. Holst *Diabetes Care* 1999, 22, 1137-1143; P. K. Cheikani, A. C. Haver and R. D. Reidelberger *Am. J. Physiol.* 2005, 288, R1695-R1706; T. Miki, K. Minami, H. Shinozaki, K. Matsumura, A. Saraya, H. Ikeda, Y. Yamada, J. J. Holst and S. Seino *Diabetes* 2005, 54, 1056-1063); thus, elevated GLP-1 will also counteract obesity, a typical condition associated with and leading to NIDDM.

GLP-1 is co-secreted with GLP-2 that is, consequently, also regulated by SST through SSTR5 (L. Hansen, B. Hartmann, T. Bisgaard, H. Mineo, P. N. Jørgensen and J. J. Holst *Am. J. Phys.* 2000, 278, E1010-1018). GLP-2 is enterotrophic and beneficial in patients with malabsorption of certain origins, such as short bowel syndrome (D. G. Burrin, B. Stoll and X. Guan *Domest. Anim. Endocrinol.* 2003, 24, 103-122; K. V. Haderslev, P. B. Jeppesen, B. Hartmann, J. Thulesen, H. A. Sorensen, J. Graff, B. S. Hansen, F. Tofteng, S. S. Poulsen, J. L. Madsen, J. J. Holst, M. Staun and P. B. Mortensen *Scand. J. Gastroenterol.* 2002, 37, 392-398; P. B. Jeppesen *J. Nutr.* 2003, 133, 3721-3724).

Moreover, there is increasing evidence for a role of SST on immune cells and expression of SSTR5 on activated T lymphocytes (T. Talme, J. Ivanoff, M. Hägglund, R. J. J. van Neerven, A. Ivanoff and K. G. Sundqvist *Clin. Exp. Immunol.* 2001, 125, 71-79; D. Ferone, P. M. van Hagen, C. Semino, V. A. Dalm, A. Barreca, A. Colao, S. W. J. Lamberts, F. Minuto and L. J. Hofland *Dig. Liver Dis.* 2004, 36, S68-77; C. E. Ghamrawy, C. Rabourdin-Combe and S. Krantic *Peptides* 1999, 20, 305-311). Consequently, SSTR5 antagonists could also prove valuable in treating diseases characterized by a disturbed immune system, such as inflammatory bowel disease.

SUMMARY OF THE INVENTION

In an embodiment of the present invention, provided is a compound of formula I:

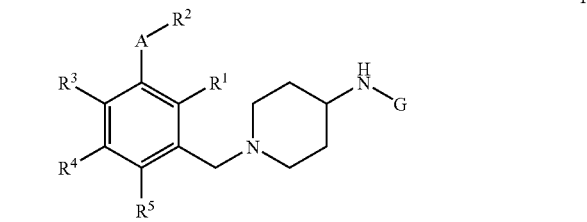

wherein

A is —O— or —NH—;

$R^1$ is selected from the group consisting of hydrogen, $C_{1-7}$-alkoxy and halogen;

$R^2$ is selected from the group consisting of $C_{2-7}$-alkyl, $C_{2-7}$-alkenyl, halogen-$C_{1-7}$-alkyl, $C_{1-7}$-alkoxy-$C_{1-7}$-alkyl, and benzyl, or, in case $R^3$ and $R^4$ form a ring, $R^2$ can also be methyl;

$R^3$ is selected from the group consisting of hydrogen, $C_{1-7}$-alkyl, hydroxy, $C_{1-7}$-alkoxy, $C_{2-7}$-alkenyloxy, hydroxy-$C_{1-7}$-alkoxy, $C_{1-7}$-alkoxy-$C_{1-7}$-alkoxy, —O—$C_{3-7}$-cycloalkyl, halogen, halogen-$C_{1-7}$-alkyl, —C(O)OR$^6$, wherein R$^6$ is $C_{1-7}$-alkyl, —NH—C(O)—R$^7$, wherein R$^7$ is $C_{1-7}$-alkyl, —S(O)—R$^8$, wherein R$^8$ is $C_{1-7}$-alkyl, —O—SO$_2$—R$^9$, wherein R$^9$ is $C_{1-7}$-alkyl, phenyl substituted by halogen, amino and pyrrolyl;

$R^4$ is selected from the group consisting of hydrogen, hydroxy, $C_{1-7}$-alkoxy, amino, nitro, hydroxy-$C_{1-7}$-alkoxy, $C_{1-7}$-alkoxy-$C_{1-7}$-alkoxy, and —O-benzyl;

or $R^3$ and $R^4$ are bonded to each other to form a ring together with the carbon atoms they are attached to and $R^3$ and $R^4$ together are —CH=CH—CH=CH— or —O—C(CH$_3$)$_2$—CH=CH—;

$R^5$ is selected from the group consisting of hydrogen, halogen, $C_{1-7}$-alkoxy and $C_{1-7}$-alkoxy-$C_{1-7}$-alkoxy;

G is

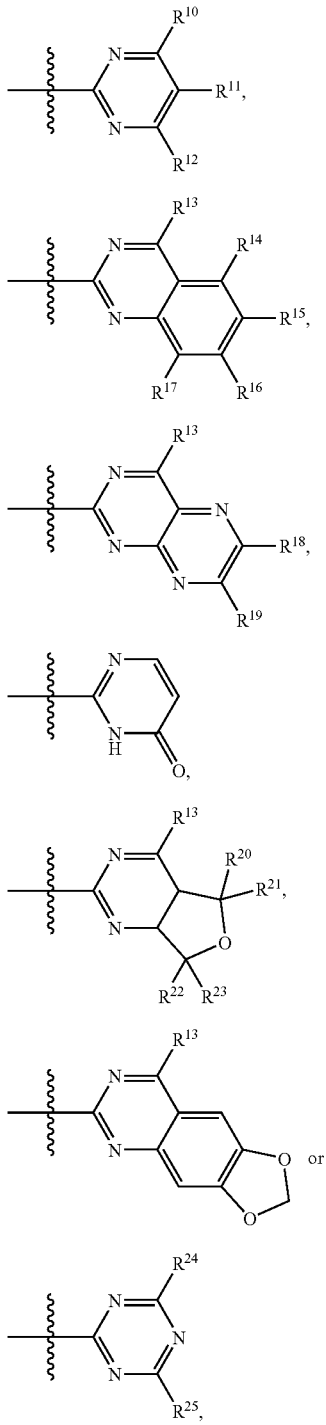

wherein $R^{10}$ is selected from the group consisting of hydrogen, $C_{1-7}$-alkyl, halogen, halogen-$C_{1-7}$-alkyl, unsubstituted phenyl, phenyl substituted by one to three groups selected from the group consisting of $C_{1-7}$-alkyl, $C_{1-7}$-alkoxy, halogen, halogen-$C_{1-7}$-alkyl and —COOH, —OR$^{26}$, wherein $R^{26}$ is selected from the group consisting of hydrogen, $C_{1-7}$-alkyl, unsubstituted phenyl and phenyl substituted by one to three groups selected from the group consisting of $C_{1-7}$-alkyl, $C_{1-7}$-alkoxy and halogen, —C(O)OR$^{27}$, wherein $R^{27}$ is $C_{1-7}$-alkyl, thiazolyl, thienyl, and azetidinyl, or, in case $R^{11}$ is cyano, $R^{10}$ can also be amino;

$R^{11}$ is selected from the group consisting of hydrogen, $C_{1-7}$-alkyl, halogen, halogen-$C_{1-7}$-alkyl, cyano, nitro, —COOH, —CONHR$^{28}$, wherein $R^{28}$ is selected from the group consisting of hydrogen, $C_{1-7}$-alkyl, unsubstituted phenyl and phenyl substituted by one to three groups selected from the group consisting of $C_{1-7}$-alkyl, $C_{1-7}$-alkoxy, halogen and halogen-$C_{1-7}$-alkyl, —OR$^{30}$, wherein $R^{30}$ is selected from the group consisting of hydroxy-$C_{1-7}$-alkyl, cyano-$C_{1-7}$-alkyl, $C_{1-7}$-alkylsulfonyl and —CH$_2$—CONH$_2$, unsubstituted phenyl, phenyl substituted by one to three groups selected from the group consisting of $C_{1-7}$-alkyl, $C_{1-7}$-alkoxy, halogen, halogen-$C_{1-7}$-alkyl, —COOH and —CONH$_2$, and pyridyl;

$R^{12}$ is selected from the group consisting of hydrogen, $C_{1-7}$-alkyl, $C_{1-7}$-alkoxy, halogen, halogen-$C_{1-7}$-alkyl, —COOR$^{28}$, wherein $R^{28}$ is hydrogen or $C_{1-7}$-alkyl, and hydroxy-$C_{1-7}$-alkylamino;

$R^{13}$ is selected from the group consisting of hydrogen, $C_{1-7}$-alkyl, $C_{1-7}$-alkoxy, amino, piperidinyl, morpholinyl, halogen, halogen-$C_{1-7}$-alkyl, unsubstituted phenyl, phenyl substituted by one to three groups selected from the group consisting of $C_{1-7}$-alkyl, $C_{1-7}$-alkoxy, halogen, halogen-$C_{1-7}$-alkyl and —COOH, —OR$^{29}$, wherein $R^{29}$ is selected from the group consisting of hydrogen, $C_{1-7}$-alkyl, unsubstituted phenyl and phenyl substituted by one to three groups selected from the group consisting of $C_{1-7}$-alkyl, $C_{1-7}$-alkoxy and halogen, thiazolyl, pyridyl and thienyl;

$R^{14}$, $R^{15}$, $R^{16}$ and $R^{17}$ independently from each other are selected from the group consisting of hydrogen, $C_{1-7}$-alkyl, halogen, hydroxy, and $C_{1-7}$-alkoxy;

$R^{18}$ and $R^{19}$ independently from each other are hydrogen or $C_{1-7}$-alkyl;

$R^{20}$, $R^{21}$, $R^{22}$ and $R^{23}$ independently from each other are hydrogen or $C_{1-7}$-alkyl;

$R^{24}$ and $R^{25}$ independently from each other are selected from the group consisting of hydrogen, $C_{1-7}$-alkyl, $C_{1-7}$-alkoxy, thiomorpholinyl and —NHR$^{31}$, wherein $R^{31}$ is selected from the group consisting of $C_{1-7}$-alkyl, hydroxy-$C_{1-7}$-alkyl, $C_{1-7}$-alkoxy-$C_{1-7}$-alkyl and —CH$_2$—COOR$^{32}$, wherein $R^{32}$ is hydrogen or $C_{1-7}$-alkyl;

and pharmaceutically acceptable salts thereof.

In another embodiment of the present invention, provided is a process for the manufacture of a compound according to formula I, which process comprises reacting a compound of the general formula

G-X    II wherein G is as defined above and X is a leaving group, with a compound of the formula

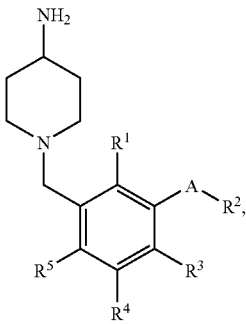

wherein A and $R^1$ to $R^5$ are as defined above,
to obtain a compound of the formula

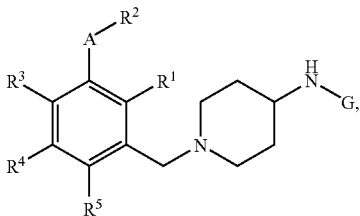

and, if desired, converting the compound of formula I into a pharmaceutically acceptable salt; or, alternatively,
reacting a compound of the general formula

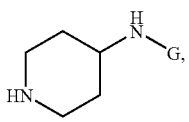

wherein G is as defined above,
with an aldehyde of the formula

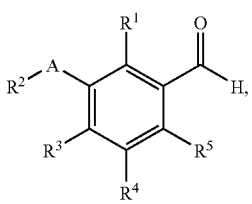

wherein A and $R^1$ to $R^5$ are as defined above, by employing a reducing agent to obtain a compound of the formula

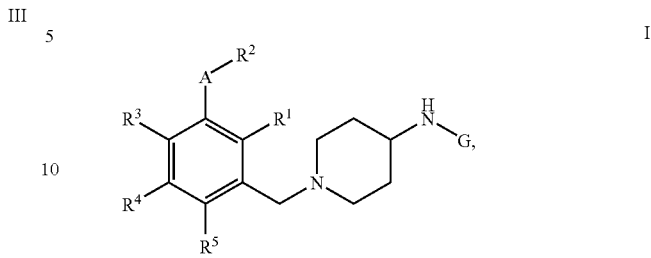

and, if desired, converting the compound of formula I into a pharmaceutically acceptable salt.

In a further embodiment of the present invention, provided is a pharmaceutical composition, comprising a therapeutically effective amount of a compound according to formula I as well as a pharmaceutically acceptable carrier and/or adjuvant.

In a yet another embodiment of the present invention, provided is a method for the treatment and/or prevention of diseases which are associated with the modulation of SST receptors subtype 5, comprising the step of administering a therapeutically effective amount of a compound according to formula I to a human being or animal in need thereof.

DETAILED DESCRIPTION

The present invention provides for selective, directly acting SSTR5 antagonists. Such antagonists are useful as therapeutically active substances, particularly in the treatment and/or prevention of diseases which are associated with the modulation of SST receptors subtype 5.

The compounds of formula I can be manufactured by the methods given below, by the methods given in the examples or by analogous methods. Appropriate reaction conditions for the individual reaction steps are known to a person skilled in the art. Starting materials are either commercially available or can be prepared by methods analogous to the methods given below, by methods described in references cited in the text or in the examples, or by methods known in the art.

In the present description the term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms.

The term "lower alkyl" or "$C_{1-7}$-alkyl", alone or in combination, signifies a straight-chain or branched-chain alkyl group with 1 to 7 carbon atoms, preferably a straight or branched-chain alkyl group with 1 to 4 carbon atoms. Examples of straight-chain and branched $C_1$-$C_7$ alkyl groups are methyl, ethyl, propyl, isopropyl, butyl, isobutyl, tert-butyl, the isomeric pentyls, the isomeric hexyls and the isomeric heptyls, preferably methyl, ethyl and isopropyl, and most preferred the groups specifically exemplified herein.

The term "lower alkenyl" or "$C_{2-7}$-alkenyl", alone or in combination, signifies a straight-chain or branched hydrocarbon residue comprising an olefinic bond and up to 7, preferably up to 6, particularly preferred up to 4 carbon atoms. Examples of alkenyl groups are ethenyl, 1-propenyl, 2-propenyl, isopropenyl, 1-butenyl, 2-butenyl, 3-butenyl and isobutenyl. A preferred example is 2-propenyl(allyl).

The term "alkoxy" refers to the group R'—O—, wherein R' is alkyl. The term "lower alkoxy" or "$C_{1-7}$-alkoxy" refers to the group R'—O—, wherein R' is lower alkyl and the term "lower alkyl" has the previously given significance. Examples of lower alkoxy groups are e.g., methoxy, ethoxy, n-propoxy, isopropoxy, n-butoxy, iso-butoxy, sec-butoxy and tert-butoxy, preferably methoxy and ethoxy and most preferred the groups specifically exemplified herein.

The term "lower hydroxyalkyl" or "hydroxy-$C_{1-7}$-alkyl" refers to lower alkyl groups as defined above wherein at least one of the hydrogen atoms of the lower alkyl group is replaced by a hydroxy group. Examples of lower hydroxyalkoxy groups are hydroxymethoxy and hydroxyethoxy, but also lower alkyl groups bearing more than one hydroxy group such as 2,3-dihydroxy-propan-1-yl.

The term "lower alkoxyalkyl" or "$C_{1-7}$-alkoxy-$C_{1-7}$-alkyl" refers to lower alkyl groups as defined above wherein at least one of the hydrogen atoms of the lower alkyl group is replaced by an alkoxy group as defined above. Among the preferred lower alkoxyalkyl groups are methoxymethyl, methoxyethyl and ethoxymethyl.

The term "lower alkoxyalkoxy" or "$C_{1-7}$-alkoxy-$C_{1-7}$-alkoxy" refers to lower alkoxy groups as defined above wherein at least one of the hydrogen atoms of the lower alkoxy group is replaced by an alkoxy group as defined above. Among the preferred lower alkoxyalkoxy groups are 2-methoxy-ethoxy and 3-methoxy-propoxy.

The term "halogen" refers to fluorine, chlorine, bromine and iodine, with fluorine, chlorine and bromine being preferred.

The term "lower halogenalkyl" or "halogen-$C_{1-7}$-alkyl" refers to lower alkyl groups as defined above wherein at least one of the hydrogen atoms of the lower alkyl group is replaced by a halogen atom, preferably fluoro or chloro, most preferably fluoro. Among the preferred halogenated lower alkyl groups are trifluoromethyl, difluoromethyl, fluoromethyl and chloromethyl, with trifluoromethyl being especially preferred.

The term "lower halogenalkoxy" or "halogen-$C_{1-7}$-alkoxy" refers to lower alkoxy groups as defined above wherein at least one of the hydrogen atoms of the lower alkoxy group is replaced by a halogen atom, preferably fluoro or chloro, most preferably fluoro. Among the preferred halogenated lower alkyl groups are trifluoromethoxy, difluoromethoxy, fluoromethoxy and chloromethoxy, with trifluoromethoxy being especially preferred.

The term "lower hydroxyalkoxy" or "hydroxy-$C_{1-7}$-alkoxy" refers to lower alkoxy groups as defined above wherein at least one of the hydrogen atoms of the lower alkoxy group is replaced by a hydroxy group. Examples of lower hydroxyalkoxy groups are hydroxymethoxy or hydroxyethoxy.

The term "lower alkylsulfonyl" or "$C_{1-7}$-alkylsulfonyl" refers to the group —S(O)$_2$—R', wherein R' is a lower alkyl group as defined herein before. Examples of lower alkylsulfonyl groups are methylsulfonyl or ethylsulfonyl.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxylic acid, maleic acid, malonic acid, salicylic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared from addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polymine resins and the like. The compound of formula I can also be present in the form of zwitterions. Particularly preferred pharmaceutically acceptable salts of compounds of formula I are the hydrochloride salts.

The compounds of formula I can also be solvated, e.g., hydrated. The solvation can be effected in the course of the manufacturing process or can take place e.g. as a consequence of hygroscopic properties of an initially anhydrous compound of formula I (hydration). The term "pharmaceutically acceptable salts" also includes physiologically acceptable solvates.

"Isomers" are compounds that have identical molecular formulae but that differ in the nature or the sequence of bonding of their atoms or in the arrangement of their atoms in space.

Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center".

In detail, the present invention relates to compounds of the general formula I

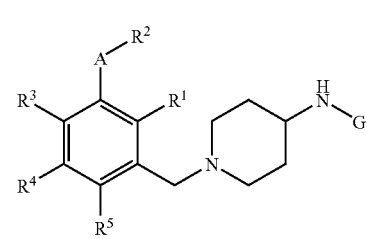

wherein

A is —O— or —NH—;

$R^1$ is selected from the group consisting of hydrogen, $C_{1-7}$-alkoxy and halogen;

$R^2$ is selected from the group consisting of $C_{2-7}$-alkyl, $C_{2-7}$-alkenyl,
   halogen-$C_{1-7}$-alkyl, $C_{1-7}$-alkoxy-$C_{1-7}$-alkyl, and benzyl,
   or, in case $R^3$ and $R^4$ form a ring, $R^2$ can also be methyl;

$R^3$ is selected from the group consisting of hydrogen, $C_{1-7}$-alkyl, hydroxy, $C_{1-7}$-alkoxy, $C_{2-7}$-alkenyloxy, hydroxy-$C_{1-7}$-alkoxy, $C_{1-7}$-alkoxy-$C_{1-7}$-alkoxy, —O—$C_{3-7}$-cycloalkyl, halogen, halogen-$C_{1-7}$-alkyl, —C(O)OR$^6$, wherein R$^6$ is $C_{1-7}$-alkyl, —NH—C(O)—R$^7$, wherein R$^7$ is $C_{1-7}$-alkyl, —S(O)—R$^8$, wherein R$^8$ is $C_{1-7}$-alkyl, —O—SO$_2$—R$^9$, wherein R$^9$ is $C_{1-7}$-alkyl, phenyl substituted by halogen, amino and pyrrolyl;

$R^4$ is selected from the group consisting of hydrogen, hydroxy, $C_{1-7}$-alkoxy, amino, nitro, hydroxy-$C_{1-7}$-alkoxy, $C_{1-7}$-alkoxy-$C_{1-7}$-alkoxy, and —O-benzyl;

or $R^3$ and $R^4$ are bonded to each other to form a ring together with the carbon atoms they are attached to and $R^3$ and $R^4$ together are —CH=CH—CH=CH— or —O—C(CH$_3$)$_2$—CH=CH—;

$R^5$ is selected from the group consisting of hydrogen, halogen, $C_{1-7}$-alkoxy and $C_{1-7}$-alkoxy-$C_{1-7}$-alkoxy;

G is selected from the groups

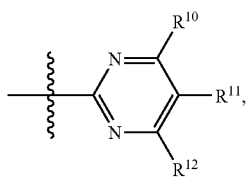
G1

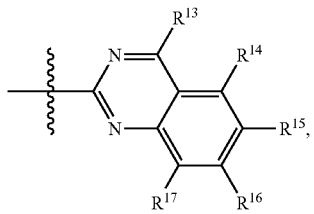
G2

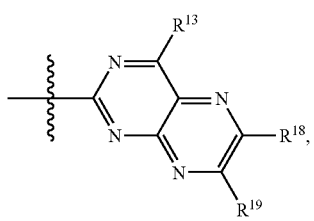
G3

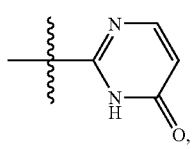
G4

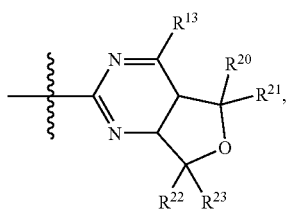
G5

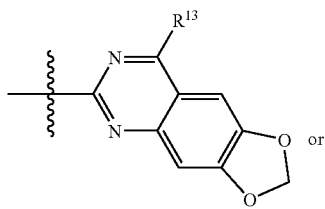
G6

-continued

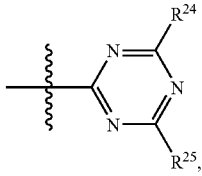
G7 wherein $R^{10}$ is selected from the group consisting of hydrogen, $C_{1-7}$-alkyl, halogen, halogen-$C_{1-7}$-alkyl, unsubstituted phenyl, phenyl substituted by one to three groups selected from the group consisting of $C_{1-7}$-alkyl, $C_{1-7}$-alkoxy, halogen, halogen-$C_{1-7}$-alkyl and —COOH, —OR$^{26}$, wherein R$^{26}$ is selected from the group consisting of hydrogen, $C_{1-7}$-alkyl, substituted phenyl and phenyl substituted by one to three groups selected from the group consisting of $C_{1-7}$-alkyl, $C_{1-7}$-alkoxy and halogen, —C(O)OR$^{27}$, wherein R$^{27}$ is $C_{1-7}$-alkyl, thiazolyl, thienyl, and azetidinyl, or, in case $R^{11}$ is cyano, $R^{10}$ can also be amino;

$R^{11}$ is selected from the group consisting of hydrogen, $C_{1-7}$-alkyl, halogen, halogen-$C_{1-7}$-alkyl, cyano, nitro, —COOH, —CONHR$^{28}$, wherein R$^{28}$ is selected from the group consisting of hydrogen, $C_{1-7}$-alkyl, unsubstituted phenyl and phenyl substituted by one to three groups selected from the group consisting of $C_{1-7}$-alkyl, $C_{1-7}$-alkoxy, halogen and halogen-$C_{1-7}$-alkoxy, —OR$^{30}$, wherein R$^{30}$ is selected from the group consisting of hydroxy-$C_{1-7}$-alkyl, cyano-$C_{1-7}$-alkyl, $C_{1-7}$-alkylsulfonyl and —CH$_2$—CONH$_2$, unsubstituted phenyl, phenyl substituted by one to three groups selected from the group consisting of $C_{1-7}$-alkyl, $C_{1-7}$-alkoxy, halogen, halogen-$C_{1-7}$-alkyl, —COOH and —CONH$_2$, and pyridyl;

$R^{12}$ is selected from the group consisting of hydrogen, $C_{1-7}$-alkyl, $C_{1-7}$-alkoxy, halogen, halogen-$C_{1-7}$-alkyl, —COOR$^{28}$, wherein R$^{28}$ is hydrogen or $C_{1-7}$-alkyl, and hydroxy-$C_{1-7}$-alkylamino;

$R^{13}$ is selected from the group consisting of hydrogen, $C_{1-7}$-alkyl, $C_{1-7}$-alkoxy, amino, piperidinyl, morpholinyl, halogen, halogen-$C_{1-7}$-alkyl, unsubstituted phenyl, phenyl substituted by one to three groups selected from the group consisting of $C_{1-7}$-alkyl, $C_{1-7}$-alkoxy, halogen, halogen-$C_{1-7}$-alkyl and —COOH, —OR$^{29}$, wherein R$^{29}$ is selected from the group consisting of hydrogen, $C_{1-7}$-alkyl, unsubstituted phenyl and phenyl substituted by one to three groups selected from the group consisting of $C_{1-7}$-alkyl, $C_{1-7}$-alkoxy and halogen, thiazolyl, pyridyl and thienyl;

$R^{14}$, $R^{15}$, $R^{16}$ and $R^{17}$ independently from each other are selected from the group consisting of hydrogen, $C_{1-7}$-alkyl, halogen, hydroxy, and $C_{1-7}$-alkoxy;

$R^{18}$ and $R^{19}$ independently from each other are hydrogen or $C_{1-7}$-alkyl;

$R^{20}$, $R^{21}$, $R^{22}$ and $R^{23}$ independently from each other are hydrogen or $C_{1-7}$-alkyl;

$R^{24}$ and $R^{25}$ independently from each other are selected from the group consisting of hydrogen, $C_{1-7}$-alkyl, $C_{1-7}$-alkoxy, thiomorpholinyl and —NHR$^{31}$, wherein R$^{31}$ is selected from the group consisting of $C_{1-7}$-alkyl, hydroxy-$C_{1-7}$- alkyl, $C_{1-7}$-alkoxy-$C_{1-7}$-alkyl and —$CH_2$—$COOR^{32}$, wherein $R^{32}$ is hydrogen or $C_{1-7}$-alkyl;
and pharmaceutically acceptable salts thereof.

Preferred compounds of formula I of the present invention are also those, wherein A is O.

Also preferred are compounds of formula I, wherein A is NH.

Furthermore, compounds of formula I according to the present invention are preferred, wherein $R^1$ is hydrogen or halogen.

Also preferred are compounds of formula I according to the invention, wherein $R^2$ is selected from the group consisting of $C_{2-7}$-alkyl, $C_{2-7}$-alkenyl, halogen-$C_{1-7}$-alkyl, $C_{1-7}$-alkoxy-$C_{1-7}$-alkyl and benzyl. Especially preferred are those compounds of formula I, wherein $R^2$ is selected from the group consisting of ethyl, propyl, isopropyl, allyl, 2-fluoroethyl, methoxymethyl, butyl, isobutyl and benzyl, with those compounds, wherein $R^2$ is ethyl or isopropyl, being most preferred.

Further preferred compounds of formula I according to the present invention are those, wherein $R^3$ is selected from the group consisting of hydrogen, $C_{1-7}$-alkyl, hydroxy, $C_{1-7}$-alkoxy, $C_{2-7}$-alkenyloxy, hydroxy-$C_{1-7}$-alkoxy, $C_{1-7}$-alkoxy-$C_{1-7}$-alkoxy, —O—$C_{3-7}$-cycloalkyl, halogen, halogen-$C_{1-7}$-alkyl, —C(O)$OR^6$, wherein $R^6$ is $C_{1-7}$-alkyl, —NH—C(O)—$R^7$, wherein $R^7$ is $C_{1-7}$-alkyl, —S(O)—$R^8$, wherein $R^8$ is $C_{1-7}$-alkyl, —O—$SO_2$—$R^9$, wherein $R^9$ is $C_{1-7}$-alkyl, amino and pyrrolyl. More preferred are those compounds of formula I, wherein $R^3$ is selected from the group consisting of hydrogen, hydroxy, $C_{1-7}$-alkoxy and halogen, with those compounds, wherein $R^3$ is halogen, being especially preferred. Most preferably, $R^3$ is chloro.

Also preferred are compounds of formula I according to the invention, wherein $R^3$ is phenyl substituted by halogen. Most preferably, $R^3$ is 4-fluorophenyl.

Furthermore, compounds of formula I of the present invention are preferred, wherein $R^4$ is selected from the group consisting of hydrogen, hydroxy, $C_{1-7}$-alkoxy, nitro, $C_{1-7}$-alkoxy-$C_{1-7}$-alkoxy, and —O-benzyl.

Another group of preferred compounds of formula I according to the present invention are those, wherein $R^3$ and $R^4$ are bonded to each other to form a ring together with the carbon atoms they are attached to and $R^3$ and $R^4$ together are —CH═CH—CH═CH— or —O—C(CH$_3$)$_2$—CH═CH—.

These are compounds of the formulae Ia or Ib, respectively:

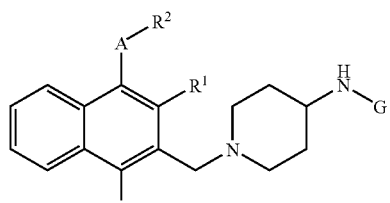

Ia

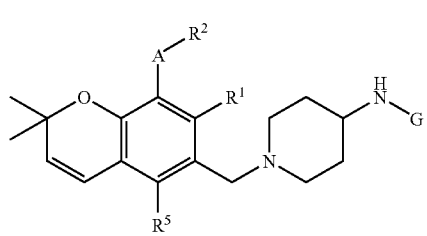

Ib

Furthermore, compounds of formula I according to the invention are preferred, wherein $R^5$ is hydrogen.

Especially preferred are compounds of formula I according to the present invention, wherein G is

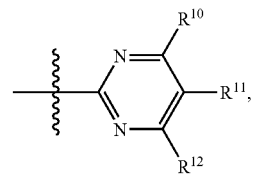

G1 and wherein $R^{10}$ is selected from the group consisting of hydrogen, $C_{1-7}$-alkyl, halogen, halogen-$C_{1-7}$-alkyl, unsubstituted phenyl, phenyl substituted by one to three groups selected from the group consisting of $C_{1-7}$-alkyl, $C_{1-7}$-alkoxy, halogen, halogen-$C_{1-7}$-alkyl and —COOH, —$OR^{26}$, wherein $R^{26}$ is selected from the group consisting of hydrogen, $C_{1-7}$-alkyl, unsubstituted phenyl and phenyl substituted by one to three groups selected from the group consisting of $C_{1-7}$-alkyl, $C_{1-7}$-alkoxy and halogen, —C(O)$OR^{27}$, wherein $R^{27}$ is $C_{1-7}$-alkyl, thiazolyl, thienyl, and azetidinyl, or, in case $R^{11}$ is cyano, $R^{10}$ can also be amino;

$R^{11}$ is selected from the group consisting of hydrogen, $C_{1-7}$-alkyl, halogen, halogen-$C_{1-7}$-alkyl, cyano, nitro, —COOH, —CONH$R^{28}$, wherein $R^{28}$ is selected from the group consisting of hydrogen, $C_{1-7}$-alkyl, unsubstituted phenyl and phenyl substituted by one to three groups selected from the group consisting of $C_{1-7}$-alkyl, $C_{1-7}$-alkoxy, halogen and halogen-$C_{1-7}$-alkoxy, —$OR^{30}$, wherein $R^{30}$ is selected from the group consisting of hydroxy-$C_{1-7}$-alkyl, cyano-$C_{1-7}$-alkyl, $C_{1-7}$-alkylsulfonyl and —CH$_2$—CONH$_2$, unsubstituted phenyl, phenyl substituted by one to three groups selected from the group consisting of $C_{1-7}$-alkyl, $C_{1-7}$-alkoxy, halogen, halogen-$C_{1-7}$-alkyl, —COOH and —CONH$_2$, and pyridyl;

$R^{12}$ is selected from the group consisting of hydrogen, $C_{1-7}$-alkyl, $C_{1-7}$-alkoxy, halogen, halogen-$C_{1-7}$-alkyl, —COO$R^{28}$, wherein $R^{28}$ is hydrogen or $C_{1-7}$-alkyl, and hydroxy-$C_{1-7}$-alkylamino.

Within this group, those compounds of formula I are preferred, wherein $R^{10}$ is hydrogen or $C_{1-7}$-alkyl;

$R^{11}$ is selected from the group consisting of hydrogen, $C_{1-7}$-alkyl, —COOH, —CONH$_2$, unsubstituted phenyl, phenyl substituted by one to three groups selected from the group consisting of $C_{1-7}$-alkyl, $C_{1-7}$-alkoxy, halogen, halogen-$C_{1-7}$-alkyl, —COOH and —CONH$_2$, and pyridyl; and $R^{12}$ is hydrogen or $C_{1-7}$-alkyl.

Another group of preferred compounds of formula I according to the invention are those, wherein G is

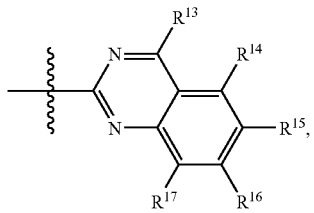

and wherein
R$^{13}$ is selected from the group consisting of hydrogen, C$_{1-7}$-alkyl, C$_{1-7}$-alkoxy, amino, piperidinyl, morpholinyl, halogen, halogen-C$_{1-7}$-alkyl, unsubstituted phenyl,
  phenyl substituted by one to three groups selected from the group consisting of C$_{1-7}$-alkyl, C$_{1-7}$-alkoxy, halogen, halogen-C$_{1-7}$-alkyl and —COOH,
—OR$^{29}$, wherein R$^{29}$ is selected from the group consisting of hydrogen, C$_{1-7}$-alkyl, unsubstituted phenyl and phenyl substituted by one to three groups selected from the group consisting of C$_{1-7}$-alkyl, C$_{1-7}$-alkoxy and halogen, thiazolyl, pyridyl and thienyl; and
R$^{14}$, R$^{15}$, R$^{16}$ and R$^{17}$ independently from each other are selected from the group consisting of hydrogen, C$_{1-7}$-alkyl, halogen, hydroxy, and C$_{1-7}$-alkoxy.

Within this group, those compounds are preferred, wherein R$^{15}$ and R$^{16}$ are C$_{1-7}$-alkoxy.

Also preferred are those compounds of formula I, wherein R$^{13}$ is piperidinyl or morpholinyl.

A further group of preferred compounds of formula I according to the invention are those, wherein G is

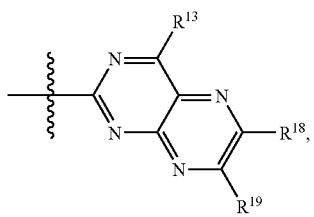

and wherein
R$^{13}$ is selected from the group consisting of hydrogen, C$_{1-7}$-alkyl, C$_{1-7}$-alkoxy, amino, piperidinyl, morpholinyl, halogen, halogen-C$_{1-7}$-alkyl,
  unsubstituted phenyl,
  phenyl substituted by one to three groups selected from the group consisting of C$_{1-7}$-alkyl, C$_{1-7}$-alkoxy, halogen, halogen-C$_{1-7}$-alkyl and —COOH,
—OR$^{29}$, wherein R$^{29}$ is selected from the group consisting of hydrogen, C$_{1-7}$-alkyl, unsubstituted phenyl and phenyl substituted by one to three groups selected from the group consisting of C$_{1-7}$-alkyl, C$_{1-7}$-alkoxy and halogen,
  thiazolyl, pyridyl and thienyl; and
R$^{18}$ and R$^{19}$ independently from each other are hydrogen or C$_{1-7}$-alkyl.

Also preferred are compounds of formula I according to the invention, wherein G is a group selected from

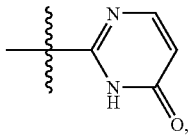

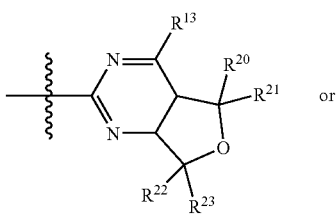

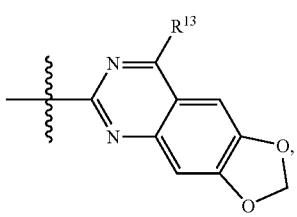

and wherein
R$^{13}$ is selected from the group consisting of hydrogen, C$_{1-7}$-alkyl, C$_{1-7}$-alkoxy, amino, piperidinyl, morpholinyl,
  halogen, halogen-C$_{1-7}$-alkyl,
  unsubstituted phenyl,
  phenyl substituted by one to three groups selected from the group consisting of C$_{1-7}$-alkyl, C$_{1-7}$-alkoxy, halogen, halogen-C$_{1-7}$-alkyl and —COOH,
—OR$^{29}$, wherein R$^{29}$ is selected from the group consisting of hydrogen, C$_{1-7}$-alkyl, unsubstituted phenyl and phenyl substituted by one to three groups selected from the group consisting of C$_{1-7}$-alkyl, C$_{1-7}$-alkoxy and halogen, thiazolyl, pyridyl and thienyl; and
R$^{20}$, R$^{21}$, R$^{22}$ and R$^{23}$ independently from each other are hydrogen or C$_{1-7}$-alkyl.

Another group of preferred compounds are those, wherein G is

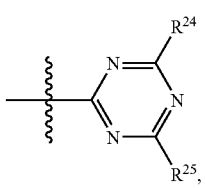

and wherein R$^{24}$ and R$^{25}$ independently from each other are selected from the group consisting of hydrogen, C$_{1-7}$-alkyl, C$_{1-7}$-alkoxy, thiomorpholinyl and —NHR$^{31}$, wherein R$^{31}$ is selected from the group consisting of C$_{1-7}$-alkyl, hydroxy-C$_{1-7}$-alkyl, C$_{1-7}$-alkoxy-C$_{1-7}$-alkyl and —CH$_2$—COOR$^{32}$, wherein R$^{32}$ is hydrogen or C$_{1-7}$-alkyl. More preferably, R$^{24}$ and R$^{25}$ independently from each other are selected from the group consisting of hydrogen, C$_{1-7}$-alkyl and C$_{1-7}$-alkoxy.

Furthermore, compounds of formula I are preferred having the formula

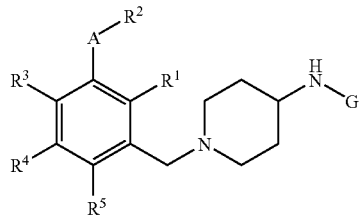
I-A wherein

A is —O— or —NH—;

$R^1$ is selected from the group consisting of hydrogen, $C_{1-7}$-alkoxy and halogen;

$R^2$ is selected from the group consisting of $C_{2-7}$-alkyl, $C_{2-7}$-alkenyl,
halogen-$C_{1-7}$-alkyl, $C_{1-7}$-alkoxy-$C_{1-7}$-alkyl, and benzyl,
or, in case $R^3$ and $R^4$ form a ring, $R^2$ can also be methyl;

$R^3$ is selected from the group consisting of hydrogen, $C_{1-7}$-alkyl, hydroxy, $C_{1-7}$-alkoxy, $C_{2-7}$-alkenyloxy, hydroxy-$C_{1-7}$-alkoxy, $C_{1-7}$-alkoxy-$C_{1-7}$-alkoxy, —O—$C_{3-7}$-cycloalkyl, halogen, halogen-$C_{1-7}$-alkyl, —C(O)OR$^6$, wherein R$^6$ is $C_{1-7}$-alkyl, —NH—C(O)—R$^7$, wherein R$^7$ is $C_{1-7}$-alkyl, —S(O)—R$^8$, wherein R$^8$ is $C_{1-7}$-alkyl, —O—SO$_2$—R$^9$, wherein R$^9$ is $C_{1-7}$-alkyl, amino and pyrrolyl;

$R^4$ is selected from the group consisting of hydrogen, hydroxy, $C_{1-7}$-alkoxy, amino, nitro, hydroxy-$C_{1-7}$-alkoxy, $C_{1-7}$-alkoxy-$C_{1-7}$-alkoxy, and —O-benzyl;

or $R^3$ and $R^4$ are bonded to each other to form a ring together with the carbon atoms they are attached to and $R^3$ and $R^4$ together are —CH=CH—CH=CH— or —O—C(CH$_3$)$_2$—CH=CH—;

$R^5$ is selected from the group consisting of hydrogen, halogen, $C_{1-7}$-alkoxy and $C_{1-7}$-alkoxy-$C_{1-7}$-alkyl;

G is selected from the groups

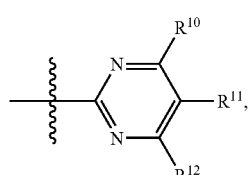
G1

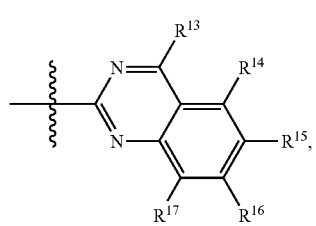
G2

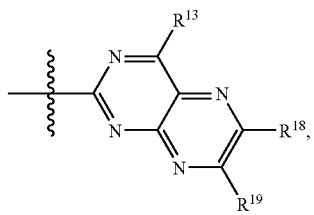
G3

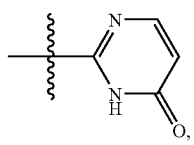
G4

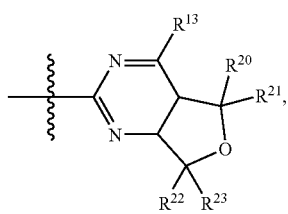
G5

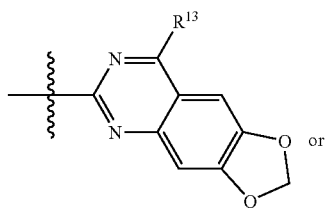
G6 or

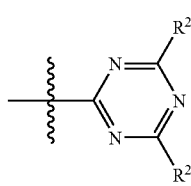
G7 wherein $R^{10}$ is selected from the group consisting of hydrogen, $C_{1-7}$-alkyl, halogen, halogen-$C_{1-7}$-alkyl, unsubstituted phenyl, phenyl substituted by one to three groups selected from the group consisting of $C_{1-7}$-alkyl, $C_{1-7}$-alkoxy, halogen, halogen-$C_{1-7}$-alkyl and —COOH,
—OR$^{26}$, wherein R$^{26}$ is selected from the group consisting of hydrogen, $C_{1-7}$-alkyl, unsubstituted phenyl and phenyl substituted by one to three groups selected from the group consisting of $C_{1-7}$-alkyl, $C_{1-7}$-alkoxy and halogen, —C(O)OR$^{27}$, wherein R$^{27}$ is $C_{1-7}$-alkyl, thiazolyl, thienyl, and azetidinyl, or, in case R$^{11}$ is cyano, R$^{10}$ can also be amino;

$R^{11}$ is selected from the group consisting of hydrogen, $C_{1-7}$-alkyl, halogen, halogen-$C_{1-7}$-alkyl, cyano, nitro, —COOH, —CONHR$^{28}$, wherein R$^{28}$ is selected from the group consisting of hydrogen, $C_{1-7}$-alkyl, unsubstituted phenyl and phenyl substituted by one to three groups selected from the group consisting of $C_{1-7}$-alkyl, $C_{1-7}$-alkoxy, halogen and halogen-$C_{1-7}$-alkyl, unsubstituted phenyl, phenyl substituted by one to three groups selected from the group consisting of $C_{1-7}$-alkyl, $C_{1-7}$-alkoxy, halogen, halogen-$C_{1-7}$-alkyl, —COOH and —CONH$_2$, and pyridyl;

$R^{12}$ is selected from the group consisting of hydrogen, $C_{1-7}$-alkyl, $C_{1-7}$-alkoxy, halogen, halogen-$C_{1-7}$-alkyl, —COOR$^{28}$, wherein R$^{28}$ is hydrogen or $C_{1-7}$-alkyl, and hydroxy-$C_{1-7}$-alkylamino;

$R^{13}$ is selected from the group consisting of hydrogen, $C_{1-7}$-alkyl, $C_{1-7}$-alkoxy, amino, piperidinyl, morpholinyl, halogen, halogen-$C_{1-7}$-alkyl, unsubstituted phenyl, phenyl substituted by one to three groups selected from the group consisting of $C_{1-7}$-alkyl, $C_{1-7}$-alkoxy, halogen, halogen-$C_{1-7}$-alkyl and —COOH, —OR$^{29}$, wherein R$^{29}$ is selected from the group consisting of hydrogen, $C_{1-7}$-alkyl, unsubstituted phenyl and phenyl substituted by one to three groups selected from the group consisting of $C_{1-7}$-alkyl, $C_{1-7}$-alkoxy and halogen, thiazolyl, pyridyl and thienyl;

$R^{14}$, $R^{15}$, $R^{16}$ and $R^{17}$ independently from each other are selected from the group consisting of hydrogen, $C_{1-7}$-alkyl, halogen, hydroxy, and $C_{1-7}$-alkoxy;

$R^{18}$ and $R^{19}$ independently from each other are hydrogen or $C_{1-7}$-alkyl;

$R^{20}$, $R^{21}$, $R^{22}$ and $R^{23}$ independently from each other are hydrogen or $C_{1-7}$-alkyl;

$R^{24}$ and $R^{25}$ independently from each other are selected from the group consisting of hydrogen, $C_{1-7}$-alkyl and $C_{1-7}$-alkoxy;

and pharmaceutically acceptable salts thereof.

Examples of preferred compounds of formula I are the following:

4-amino-2-[1-(3-ethoxy-4-methoxy-benzyl)-piperidin-4-ylamino]-pyrimidine-5-carbonitrile,
[1-(3-ethoxy-4-methoxy-benzyl)-piperidin-4-yl]-(5,5,7,7-tetramethyl-5,7-dihydro-furo[3,4-d]pyrimidin-2-yl)-amine,
6-(2,4-dichloro-phenoxy)-2-[1-(3-ethoxy-4-methoxy-benzyl)-piperidin-4-ylamino]-pyrimidine-4-carboxylic acid methyl ester,
[1-(3-ethoxy-4-methoxy-benzyl)-piperidin-4-yl]-(4-thiophen-2-yl-pyrimidin-2-yl)-amine,
[1-(3-ethoxy-4-methoxy-benzyl)-piperidin-4-yl]-[4-(2-fluoro-phenyl)-quinazolin-2-yl]-amine,
7-chloro-N$^2$-[1-(3-ethoxy-4-methoxy-benzyl)-piperidin-4-yl]-quinazoline-2,4-diamine,
(6,7-dimethoxy-4-piperidin-1-yl-quinazolin-2-yl)-[1-(3-ethoxy-4-methoxy-benzyl)-piperidin-4-yl]-amine,
N$^2$-[1-(3-ethoxy-4-methoxy-benzyl)-piperidin-4-yl]-6-methyl-quinazoline-2,4-diamine,
[5-(3,4-dimethoxy-phenyl)-pyrimidin-2-yl]-[1-(3-ethoxy-4-methoxy-benzyl)-piperidin-4-yl]-amine,
[1-(3-ethoxy-4-methoxy-benzyl)-piperidin-4-yl]-(5-propyl-pyrimidin-2-yl)-amine,
(5-bromo-pyrimidin-2-yl)-[1-(3-ethoxy-4-methoxy-benzyl)-piperidin-4-yl]-amine,
(4,6-dimethoxy-pyrimidin-2-yl)-[1-(3-ethoxy-4-methoxy-benzyl)-piperidin-4-yl]-amine,
N$^2$-[1-(3-ethoxy-4-methoxy-benzyl)-piperidin-4-yl]-quinazoline-2,4-diamine,
[1-(3-ethoxy-4-methoxy-benzyl)-piperidin-4-yl]-(4-thiazol-2-yl-quinazolin-2-yl)-amine,
[1-(3-ethoxy-4-methoxy-benzyl)-piperidin-4-yl]-(4-pyridin-2-yl-quinazolin-2-yl)-amine,
[1-(3-ethoxy-4-methoxy-benzyl)-piperidin-4-yl]-(5,6,7-trimethoxy-4-phenyl-quinazolin-2-yl)-amine,
(4,6-dimethoxy-[1,3,5]triazin-2-yl)-[1-(3-ethoxy-4-methoxy-benzyl)-piperidin-4-yl]-amine,
4-amino-2-[1-(4-chloro-3-ethoxy-benzyl)-piperidin-4-ylamino]-pyrimidine-5-carbonitrile,
[1-(4-chloro-3-ethoxy-benzyl)-piperidin-4-yl]-(4-thiophen-2-yl-pyrimidin-2-yl)-amine,
[1-(4-chloro-3-ethoxy-benzyl)-piperidin-4-yl]-(4,6-dimethyl-pyrimidin-2-yl)-amine,
2-[1-(4-chloro-3-ethoxy-benzyl)-piperidin-4-ylamino]-6-methyl-pyrimidine-4-carboxylic acid methyl ester,
[1-(4-chloro-3-ethoxy-benzyl)-piperidin-4-yl]-(5,5,7,7-tetramethyl-5,7-dihydro-furo[3,4-d]pyrimidin-2-yl)-amine,
6-chloro-N$^2$-[1-(4-chloro-3-ethoxy-benzyl)-piperidin-4-yl]-N$^4$-isopropyl-pyrimidine-2,4-diamine,
(4-azetidin-1-yl-6-chloro-pyrimidin-2-yl)-[1-(4-chloro-3-ethoxy-benzyl)-piperidin-4-yl]-amine,
N$^2$-[1-(4-chloro-3-ethoxy-benzyl)-piperidin-4-yl]-quinazoline-2,4-diamine,
2-[1-(4-chloro-3-ethoxy-benzyl)-piperidin-4-ylamino]-quinazolin-4-ol,
[1-(3-ethoxy-4-methoxy-benzyl)-piperidin-4-yl]-(5-ethyl-pyrimidin-2-yl)-amine,
[1-(1,4-dimethoxy-naphthalen-2-ylmethyl)-piperidin-4-yl]-(5-ethyl-pyrimidin-2-yl)-amine,
[1-(3-ethoxy-4-methyl-benzyl)-piperidin-4-yl]-(5-ethyl-pyrimidin-2-yl)-amine,
[1-(4-chloro-3-ethoxy-benzyl)-piperidin-4-yl]-(5-ethyl-pyrimidin-2-yl)-amine,
2-ethoxy-4-[4-(5-ethyl-pyrimidin-2-ylamino)-piperidin-1-ylmethyl]-phenol,
[1-(3-ethoxy-4-isopropoxy-benzyl)-piperidin-4-yl]-(5-ethyl-pyrimidin-2-yl)-amine,
{1-[3-ethoxy-4-(3-methyl-but-2-enyloxy)-benzyl]-piperidin-4-yl}-(5-ethyl-pyrimidin-2-yl)-amine,
methanesulfonic acid 2-ethoxy-4-[4-(5-ethyl-pyrimidin-2-ylamino)-piperidin-1-ylmethyl]-phenyl ester,
[1-(3,4-diisopropoxy-benzyl)-piperidin-4-yl]-(5-ethyl-pyrimidin-2-yl)-amine,
(5-ethyl-pyrimidin-2-yl)-[1-(4-methoxy-3-propoxy-benzyl)-piperidin-4-yl]-amine,
(5-ethyl-pyrimidin-2-yl)-{1-[3-(2-fluoro-ethoxy)-4-methoxy-benzyl]-piperidin-4-yl}-amine,
(5-ethyl-pyrimidin-2-yl)-[1-(3-isobutoxy-4-methoxy-benzyl)-piperidin-4-yl]-amine,
[1-(3,5-diisopropoxy-benzyl)-piperidin-4-yl]-(5-ethyl-pyrimidin-2-yl)-amine,
[1-(3-benzyloxy-5-ethoxy-benzyl)-piperidin-4-yl]-(5-ethyl-pyrimidin-2-yl)-amine,
[1-(3,5-diethoxy-4-fluoro-benzyl)-piperidin-4-yl]-(5-ethyl-pyrimidin-2-yl)-amine,
2,6-diethoxy-4-[4-(5-ethyl-pyrimidin-2-ylamino)-piperidin-1-ylmethyl]-benzoic acid ethyl ester,
[1-(3-ethoxy-4-iodo-5-methoxymethoxy-benzyl)-piperidin-4-yl]-(5-ethyl-pyrimidin-2-yl)-amine,
[1-(3,5-diethoxy-2-fluoro-benzyl)-piperidin-4-yl]-(5-ethyl-pyrimidin-2-yl)-amine,
(4,6-dimethyl-pyrimidin-2-yl)-[1-(3-ethoxy-4-methyl-benzyl)-piperidin-4-yl]-amine,
(4,6-dimethyl-pyrimidin-2-yl)-[1-(3-ethoxy-4-fluoro-benzyl)-piperidin-4-yl]-amine,
[1-(4-chloro-3-ethoxy-benzyl)-piperidin-4-yl]-(4,6-dimethyl-pyrimidin-2-yl)-amine,
4-[4-(4,6-dimethyl-pyrimidin-2-ylamino)-piperidin-1-ylmethyl]-2-ethoxy-phenol,
(4,6-dimethyl-pyrimidin-2-yl)-[1-(3-ethoxy-4-methoxy-benzyl)-piperidin-4-yl]-amine,
(4,6-dimethyl-pyrimidin-2-yl)-[1-(3-ethoxy-4-isopropoxy-benzyl)-piperidin-4-yl]-amine,
(4,6-dimethyl-pyrimidin-2-yl)-[1-(4-methoxy-3-propoxy-benzyl)-piperidin-4-yl]-amine,
(4,6-dimethyl-pyrimidin-2-yl)-{1-[3-(2-fluoro-ethoxy)-4-methoxy-benzyl]-piperidin-4-yl}-amine,

[1-(3-allyloxy-4-methoxy-benzyl)-piperidin-4-yl]-(4,6-dimethyl-pyrimidin-2-yl)-amine,
(4,6-dimethyl-pyrimidin-2-yl)-[1-(3-isobutoxy-4-methoxy-benzyl)-piperidin-4-yl]-amine,
(4,6-dimethyl-pyrimidin-2-yl)-[1-(8-ethoxy-2,2-dimethyl-2H-chromen-6-ylmethyl)-piperidin-4-yl]-amine,
[1-(3,5-diethoxy-benzyl)-piperidin-4-yl]-(4,6-dimethyl-pyrimidin-2-yl)-amine,
[1-(3,5-diisopropoxy-benzyl)-piperidin-4-yl]-(4,6-dimethyl-pyrimidin-2-yl)-amine,
[1-(3,5-diethoxy-4-fluoro-benzyl)-piperidin-4-yl]-(4,6-dimethyl-pyrimidin-2-yl)-amine,
[1-(4-chloro-3,5-diethoxy-benzyl)-piperidin-4-yl]-(4,6-dimethyl-pyrimidin-2-yl)-amine,
[1-(3,5-diethoxy-4-pyrrol-1-yl-benzyl)-piperidin-4-yl]-(4,6-dimethyl-pyrimidin-2-yl)-amine,
(4,6-dimethyl-pyrimidin-2-yl)-[1-(2-phenyl-1H-imidazol-4-ylmethyl)-piperidin-4-yl]-amine,
[1-(4-chloro-3-ethoxy-benzyl)-piperidin-4-yl]-pyrimidin-2-yl-amine,
[1-(3-ethoxy-4-methoxy-benzyl)-piperidin-4-yl]-pyrimidin-2-yl-amine,
{1-[3-ethoxy-4-(1-ethyl-propoxy)-benzyl]-piperidin-4-yl}-pyrimidin-2-yl-amine,
[1-(3,5-diethoxy-benzyl)-piperidin-4-yl]-pyrimidin-2-yl-amine,
[1-(3,5-diisopropoxy-benzyl)-piperidin-4-yl]-pyrimidin-2-yl-amine,
[1-(3,5-diethoxy-4-fluoro-benzyl)-piperidin-4-yl]-pyrimidin-2-yl-amine,
[1-(4-chloro-3,5-diethoxy-benzyl)-piperidin-4-yl]-pyrimidin-2-yl-amine,
[1-(4-bromo-3,5-diethoxy-benzyl)-piperidin-4-yl]-pyrimidin-2-yl-amine,
[1-(4-amino-3,5-diethoxy-benzyl)-piperidin-4-yl]-pyrimidin-2-yl-amine,
[1-(3,5-diethoxy-4-pyrrol-1-yl-benzyl)-piperidin-4-yl]-pyrimidin-2-yl-amine,
[1-(2-chloro-3,5-diethoxy-benzyl)-piperidin-4-yl]-pyrimidin-2-yl-amine,
2-[1-(3-ethoxy-4-methyl-benzyl)-piperidin-4-ylamino]-pyrimidine-4-carboxylic acid methyl ester,
2-[1-(4-chloro-3-ethoxy-benzyl)-piperidin-4-ylamino]-pyrimidine-4-carboxylic acid methyl ester,
2-[1-(3-isobutoxy-4-methoxy-benzyl)-piperidin-4-ylamino]-pyrimidine-4-carboxylic acid methyl ester,
2-[1-(3,5-diethoxy-benzyl)-piperidin-4-ylamino]-pyrimidine-4-carboxylic acid methyl ester,
2-[1-(3,5-diisopropoxy-benzyl)-piperidin-4-ylamino]-pyrimidine-4-carboxylic acid methyl ester,
2-[1-(3,5-diethoxy-4-fluoro-benzyl)-piperidin-4-ylamino]-pyrimidine-4-carboxylic acid methyl ester,
2-[1-(4-chloro-3,5-diethoxy-benzyl)-piperidin-4-ylamino]-pyrimidine-4-carboxylic acid methyl ester,
2-[1-(3,5-diethoxy-4-pyrrol-1-yl-benzyl)-piperidin-4-ylamino]-pyrimidine-4-carboxylic acid methyl ester,
[1-(4-amino-3,5-diethoxy-benzyl)-piperidin-4-yl]-(4-trifluoromethyl-pyrimidin-2-yl)-amine,
[1-(3,5-diethoxy-4-pyrrol-1-yl-benzyl)-piperidin-4-yl]-(4-trifluoromethyl-pyrimidin-2-yl)-amine,
2-[1-(4-chloro-3-ethoxy-benzyl)-piperidin-4-ylamino]-pyrimidin-4-ol,
2-[1-(3,5-diisopropoxy-benzyl)-piperidin-4-ylamino]-pyrimidin-4-ol,
2-[1-(4-amino-3,5-diethoxy-benzyl)-piperidin-4-ylamino]-pyrimidin-4-ol,
2-[1-(3,5-diethoxy-4-pyrrol-1-yl-benzyl)-piperidin-4-ylamino]-pyrimidin-4-ol,
2-[1-(3-ethoxy-4-methyl-benzyl)-piperidin-4-ylamino]-pyrimidine-5-carboxylic acid,
2-[1-(4-chloro-3-ethoxy-benzyl)-piperidin-4-ylamino]-pyrimidine-5-carboxylic acid,
2-[1-(3-isobutoxy-4-methoxy-benzyl)-piperidin-4-ylamino]-pyrimidine-5-carboxylic acid,
2-[1-(4-chloro-3,5-diethoxy-benzyl)-piperidin-4-ylamino]-pyrimidine-5-carboxylic acid,
(4,6-dimethoxy-pyrimidin-2-yl)-[1-(3-ethoxy-4-methyl-benzyl)-piperidin-4-yl]-amine,
(4,6-dimethoxy-pyrimidin-2-yl)-[1-(3-ethoxy-4-fluoro-benzyl)-piperidin-4-yl]-amine,
[1-(4-chloro-3-ethoxy-benzyl)-piperidin-4-yl]-(4,6-dimethoxy-pyrimidin-2-yl)-amine,
4-[4-(4,6-dimethoxy-pyrimidin-2-ylamino)-piperidin-1-ylmethyl]-2-ethoxy-phenol,
(4,6-dimethoxy-pyrimidin-2-yl)-[1-(3-ethoxy-4-isopropoxy-benzyl)-piperidin-4-yl]-amine,
methanesulfonic acid 4-[4-(4,6-dimethoxy-pyrimidin-2-ylamino)-piperidin-1-ylmethyl]-2-ethoxy-phenyl ester,
(4,6-dimethoxy-pyrimidin-2-yl)-{1-[3-(2-fluoro-ethoxy)-4-methoxy-benzyl]-piperidin-4-yl}-amine,
[1-(3-allyloxy-4-methoxy-benzyl)-piperidin-4-yl]-(4,6-dimethoxy-pyrimidin-2-yl)-amine,
[1-(3-butoxy-4-methoxy-benzyl)-piperidin-4-yl]-(4,6-dimethoxy-pyrimidin-2-yl)-amine,
(4,6-dimethoxy-pyrimidin-2-yl)-[1-(8-ethoxy-2,2-dimethyl-2H-chromen-6-ylmethyl)-piperidin-4-yl]-amine,
[1-(3,5-diethoxy-benzyl)-piperidin-4-yl]-(4,6-dimethoxy-pyrimidin-2-yl)-amine,
3-[4-(4,6-dimethoxy-pyrimidin-2-ylamino)-piperidin-1-ylmethyl]-5-isopropoxy-phenol,
[1-(3,5-diisopropoxy-benzyl)-piperidin-4-yl]-(4,6-dimethoxy-pyrimidin-2-yl)-amine,
[1-(3,5-diethoxy-4-fluoro-benzyl)-piperidin-4-yl]-(4,6-dimethoxy-pyrimidin-2-yl)-amine,
[1-(4-bromo-3,5-diethoxy-benzyl)-piperidin-4-yl]-(4,6-dimethoxy-pyrimidin-2-yl)-amine,
(4,6-dimethoxy-pyrimidin-2-yl)-[1-(3-ethoxy-4-iodo-5-methoxymethoxy-benzyl)-piperidin-4-yl]-amine,
[1-(3,5-diethoxy-4-pyrrol-1-yl-benzyl)-piperidin-4-yl]-(4,6-dimethoxy-pyrimidin-2-yl)-amine,
(4,6-dimethoxy-pyrimidin-2-yl)-[1-(3-ethoxy-4-methoxy-5-nitro-benzyl)-piperidin-4-yl]-amine,
(4,6-dimethoxy-pyrimidin-2-yl)-[1-(3-ethylamino-4-methoxy-benzyl)-piperidin-4-yl]-amine,
[1-(3-ethoxy-4-fluoro-benzyl)-piperidin-4-yl]-(5,5,7,7-tetramethyl-5,7-dihydro-furo[3,4-d]pyrimidin-2-yl)-amine,
[1-(4-chloro-3-ethoxy-benzyl)-piperidin-4-yl]-(5,5,7,7-tetramethyl-5,7-dihydro-furo[3,4-d]pyrimidin-2-yl)-amine,
2-ethoxy-4-[4-(5,5,7,7-tetramethyl-5,7-dihydro-furo[3,4-d]pyrimidin-2-ylamino)-piperidin-1-ylmethyl]-phenol,
{1-[3-(2-fluoro-ethoxy)-4-methoxy-benzyl]-piperidin-4-yl}-(5,5,7,7-tetramethyl-5,7-dihydro-furo[3,4-d]pyrimidin-2-yl)-amine,
[1-(3-allyloxy-4-methoxy-benzyl)-piperidin-4-yl]-(5,5,7,7-tetramethyl-5,7-dihydro-furo[3,4-d]pyrimidin-2-yl)-amine,
[1-(8-ethoxy-2,2-dimethyl-2H-chromen-6-ylmethyl)-piperidin-4-yl]-(5,5,7,7-tetramethyl-5,7-dihydro-furo[3,4-d]pyrimidin-2-yl)-amine,
[1-(3,5-diethoxy-benzyl)-piperidin-4-yl]-(5,5,7,7-tetramethyl-5,7-dihydro-furo[3,4-d]pyrimidin-2-yl)-amine,
3-isopropoxy-5-[4-(5,5,7,7-tetramethyl-5,7-dihydro-furo[3,4-d]pyrimidin-2-ylamino)-piperidin-1-ylmethyl]-phenol,

[1-(3,5-diethoxy-4-fluoro-benzyl)-piperidin-4-yl]-(5,5,7,7-tetramethyl-5,7-dihydro-furo[3,4-d]pyrimidin-2-yl)-amine,
[1-(3,5-diethoxy-4-pyrrol-1-yl-benzyl)-piperidin-4-yl]-(5,5,7,7-tetramethyl-5,7-dihydro-furo[3,4-d]pyrimidin-2-yl)-amine,
4-amino-2-[1-(3-ethoxy-4-methyl-benzyl)-piperidin-4-ylamino]-pyrimidine-5-carbonitrile,
4-amino-2-[1-(3-ethoxy-4-fluoro-benzyl)-piperidin-4-ylamino]-pyrimidine-5-carbonitrile,
4-amino-2-[1-(3-ethoxy-4-methoxy-benzyl)-piperidin-4-ylamino]-pyrimidine-5-carbonitrile,
4-amino-2-[1-(3-ethoxy-4-methoxy-benzyl)-piperidin-4-ylamino]-pyrimidine-5-carbonitrile,
4-amino-2-[1-(3-isobutoxy-4-methoxy-benzyl)-piperidin-4-ylamino]-pyrimidine-5-carbonitrile,
4-amino-2-[1-(3-ethoxy-4-isopropoxy-benzyl)-piperidin-4-ylamino]-pyrimidine-5-carbonitrile,
4-amino-2-{1-[3-ethoxy-4-(1-ethyl-propoxy)-benzyl]-piperidin-4-ylamino}-pyrimidine-5-carbonitrile,
4-amino-2-{1-[3-(2-fluoro-ethoxy)-4-methoxy-benzyl]-piperidin-4-ylamino}-pyrimidine-5-carbonitrile,
2-[1-(3-allyloxy-4-methoxy-benzyl)-piperidin-4-ylamino]-4-amino-pyrimidine-5-carbonitrile,
4-amino-2-[1-(3-butoxy-4-methoxy-benzyl)-piperidin-4-ylamino]-pyrimidine-5-carbonitrile,
4-amino-2-[1-(8-ethoxy-2,2-dimethyl-2H-chromen-6-ylmethyl)-piperidin-4-ylamino]-pyrimidine-5-carbonitrile,
4-amino-2-[1-(3,5-diethoxy-benzyl)-piperidin-4-ylamino]-pyrimidine-5-carbonitrile,
4-amino-2-[1-(3-hydroxy-5-isopropoxy-benzyl)-piperidin-4-ylamino]-pyrimidine-5-carbonitrile,
4-amino-2-[1-(3,5-diisopropoxy-benzyl)-piperidin-4-ylamino]-pyrimidine-5-carbonitrile,
4-amino-2-[1-(3,5-diethoxy-4-fluoro-benzyl)-piperidin-4-ylamino]-pyrimidine-5-carbonitrile,
4-amino-2-[1-(4-chloro-3,5-diethoxy-benzyl)-piperidin-4-ylamino]-pyrimidine-5-carbonitrile,
4-amino-2-[1-(4-bromo-3,5-diethoxy-benzyl)-piperidin-4-ylamino]-pyrimidine-5-carbonitrile,
4-amino-2-[1-(3-ethoxy-4-iodo-5-methoxymethoxy-benzyl)-piperidin-4-ylamino]-pyrimidine-5-carbonitrile,
4-amino-2-[1-(3,5-diethoxy-4-pyrrol-1-yl-benzyl)-piperidin-4-ylamino]-pyrimidine-5-carbonitrile,
4-amino-2-[1-(2-chloro-3,5-diethoxy-benzyl)-piperidin-4-ylamino]-pyrimidine-5-carbonitrile,
[1-(3-ethoxy-4-methyl-benzyl)-piperidin-4-yl]-(5-phenyl-pyrimidin-2-yl)-amine,
[1-(3-ethoxy-4-fluoro-benzyl)-piperidin-4-yl]-(5-phenyl-pyrimidin-2-yl)-amine,
[1-(4-chloro-3-ethoxy-benzyl)-piperidin-4-yl]-(5-phenyl-pyrimidin-2-yl)-amine,
2-ethoxy-4-[4-(5-phenyl-pyrimidin-2-ylamino)-piperidin-1-ylmethyl]-phenol,
[1-(3-ethoxy-4-methoxy-benzyl)-piperidin-4-yl]-(5-phenyl-pyrimidin-2-yl)-amine,
[1-(3-ethoxy-4-isopropoxy-benzyl)-piperidin-4-yl]-(5-phenyl-pyrimidin-2-yl)-amine,
{1-[3-ethoxy-4-(1-ethyl-propoxy)-benzyl]-piperidin-4-yl}-(5-phenyl-pyrimidin-2-yl)-amine,
{1-[3-(2-fluoro-ethoxy)-4-methoxy-benzyl]-piperidin-4-yl}-(5-phenyl-pyrimidin-2-yl)-amine,
[1-(3-allyloxy-4-methoxy-benzyl)-piperidin-4-yl]-(5-phenyl-pyrimidin-2-yl)-amine,
[1-(8-ethoxy-2,2-dimethyl-2H-chromen-6-ylmethyl)-piperidin-4-yl]-(5-phenyl-pyrimidin-2-yl)-amine,
[1-(3,5-diethoxy-benzyl)-piperidin-4-yl]-(5-phenyl-pyrimidin-2-yl)-amine,
3-isopropoxy-5-[4-(5-phenyl-pyrimidin-2-ylamino)-piperidin-1-ylmethyl]-phenol,
[1-(3,5-diisopropoxy-benzyl)-piperidin-4-yl]-(5-phenyl-pyrimidin-2-yl)-amine,
[1-(3,5-diethoxy-4-fluoro-benzyl)-piperidin-4-yl]-(5-phenyl-pyrimidin-2-yl)-amine,
[1-(4-chloro-3,5-diethoxy-benzyl)-piperidin-4-yl]-(5-phenyl-pyrimidin-2-yl)-amine,
[1-(4-bromo-3,5-diethoxy-benzyl)-piperidin-4-yl]-(5-phenyl-pyrimidin-2-yl)-amine,
[1-(4-amino-3,5-diethoxy-benzyl)-piperidin-4-yl]-(5-phenyl-pyrimidin-2-yl)-amine,
[1-(3,5-diethoxy-4-pyrrol-1-yl-benzyl)-piperidin-4-yl]-(5-phenyl-pyrimidin-2-yl)-amine,
[1-(2-phenyl-1H-imidazol-4-ylmethyl)-piperidin-4-yl]-(5-phenyl-pyrimidin-2-yl)-amine,
[1-(3-ethoxy-4-methyl-benzyl)-piperidin-4-yl]-[5-(4-methoxy-phenyl)-pyrimidin-2-yl]-amine,
[1-(3-ethoxy-4-fluoro-benzyl)-piperidin-4-yl]-[5-(4-methoxy-phenyl)-pyrimidin-2-yl]-amine,
[1-(4-chloro-3-ethoxy-benzyl)-piperidin-4-yl]-[5-(4-methoxy-phenyl)-pyrimidin-2-yl]-amine,
2-ethoxy-4-{4-[5-(4-methoxy-phenyl)-pyrimidin-2-ylamino]-piperidin-1-ylmethyl}-phenol,
[1-(3-ethoxy-4-methoxy-benzyl)-piperidin-4-yl]-[5-(4-methoxy-phenyl)-pyrimidin-2-yl]-amine,
[1-(3,5-diethoxy-benzyl)-piperidin-4-yl]-[5-(4-methoxy-phenyl)-pyrimidin-2-yl]-amine,
[1-(3,5-diisopropoxy-benzyl)-piperidin-4-yl]-[5-(4-methoxy-phenyl)-pyrimidin-2-yl]-amine,
[1-(3,5-diethoxy-4-fluoro-benzyl)-piperidin-4-yl]-[5-(4-methoxy-phenyl)-pyrimidin-2-yl]-amine,
[1-(4-chloro-3,5-diethoxy-benzyl)-piperidin-4-yl]-[5-(4-methoxy-phenyl)-pyrimidin-2-yl]-amine,
[1-(3-ethoxy-4-methyl-benzyl)-piperidin-4-yl]-(5-pyridin-3-yl-pyrimidin-2-yl)-amine,
[1-(3-ethoxy-4-fluoro-benzyl)-piperidin-4-yl]-(5-pyridin-3-yl-pyrimidin-2-yl)-amine,
[1-(4-chloro-3-ethoxy-benzyl)-piperidin-4-yl]-(5-pyridin-3-yl-pyrimidin-2-yl)-amine,
2-ethoxy-4-[4-(5-pyridin-3-yl-pyrimidin-2-ylamino)-piperidin-1-ylmethyl]-phenol,
[1-(3-ethoxy-4-methoxy-benzyl)-piperidin-4-yl]-(5-pyridin-3-yl-pyrimidin-2-yl)-amine,
[1-(3,5-diethoxy-benzyl)-piperidin-4-yl]-(5-pyridin-3-yl-pyrimidin-2-yl)-amine,
[1-(3,5-diisopropoxy-benzyl)-piperidin-4-yl]-(5-pyridin-3-yl-pyrimidin-2-yl)-amine,
[1-(3,5-diethoxy-4-fluoro-benzyl)-piperidin-4-yl]-(5-pyridin-3-yl-pyrimidin-2-yl)-amine,
[1-(4-chloro-3,5-diethoxy-benzyl)-piperidin-4-yl]-(5-pyridin-3-yl-pyrimidin-2-yl)-amine,
[1-(4-amino-3,5-diethoxy-benzyl)-piperidin-4-yl]-(5-pyridin-3-yl-pyrimidin-2-yl)-amine,
[1-(3,5-diethoxy-4-pyrrol-1-yl-benzyl)-piperidin-4-yl]-(5-pyridin-3-yl-pyrimidin-2-yl)-amine,
4-{2-[1-(3-ethoxy-4-methyl-benzyl)-piperidin-4-ylamino]-pyrimidin-5-yl}-benzamide,
4-{2-[1-(3-ethoxy-4-fluoro-benzyl)-piperidin-4-ylamino]-pyrimidin-5-yl}-benzamide,
4-{2-[1-(4-chloro-3-ethoxy-benzyl)-piperidin-4-ylamino]-pyrimidin-5-yl}-benzamide,
4-{2-[1-(3-ethoxy-4-hydroxy-benzyl)-piperidin-4-ylamino]-pyrimidin-5-yl}-benzamide, 4-{2-[1-(3-ethoxy-4-methoxy-benzyl)-piperidin-4-ylamino]-pyrimidin-5-yl}-benzamide,
2-[1-(3-ethoxy-4-methyl-benzyl)-piperidin-4-ylamino]-4-trifluoromethyl-pyrimidine-5-carboxylic acid (4-chloro-phenyl)-amide,
2-[1-(3-ethoxy-4-fluoro-benzyl)-piperidin-4-ylamino]-4-trifluoromethyl-pyrimidine-5-carboxylic acid (4-chloro-phenyl)-amide,
2-[1-(4-chloro-3-ethoxy-benzyl)-piperidin-4-ylamino]-4-trifluoromethyl-pyrimidine-5-carboxylic acid (4-chloro-phenyl)-amide,
2-[1-(3-ethoxy-4-hydroxy-benzyl)-piperidin-4-ylamino]-4-trifluoromethyl-pyrimidine-5-carboxylic acid (4-chloro-phenyl)-amide,
2-[1-(3-ethoxy-4-methoxy-benzyl)-piperidin-4-ylamino]-4-trifluoromethyl-pyrimidine-5-carboxylic acid (4-chloro-phenyl)-amide,
2-{1-[3-(2-fluoro-ethoxy)-4-methoxy-benzyl]-piperidin-4-ylamino}-4-trifluoromethyl-pyrimidine-5-carboxylic acid (4-chloro-phenyl)-amide,
2-[1-(3,5-diethoxy-benzyl)-piperidin-4-ylamino]-4-trifluoromethyl-pyrimidine-5-carboxylic acid (4-chloro-phenyl)-amide,
2-[1-(3,5-diisopropoxy-benzyl)-piperidin-4-ylamino]-4-trifluoromethyl-pyrimidine-5-carboxylic acid (4-chloro-phenyl)-amide,
2-[1-(3,5-diethoxy-4-fluoro-benzyl)-piperidin-4-ylamino]-4-trifluoromethyl-pyrimidine-5-carboxylic acid (4-chloro-phenyl)-amide,
2-[1-(4-chloro-3,5-diethoxy-benzyl)-piperidin-4-ylamino]-4-trifluoromethyl-pyrimidine-5-carboxylic acid (4-chloro-phenyl)-amide,
2-[1-(4-amino-3,5-diethoxy-benzyl)-piperidin-4-ylamino]-4-trifluoromethyl-pyrimidine-5-carboxylic acid (4-chloro-phenyl)-amide,
2-[1-(3,5-diethoxy-4-pyrrol-1-yl-benzyl)-piperidin-4-ylamino]-4-trifluoromethyl-pyrimidine-5-carboxylic acid (4-chloro-phenyl)-amide,
2-[1-(3-ethoxy-4-methyl-benzyl)-piperidin-4-ylamino]-4-trifluoromethyl-pyrimidine-5-carboxylic acid (4-trifluoromethoxy-phenyl)-amide,
2-[1-(3-ethoxy-4-hydroxy-benzyl)-piperidin-4-ylamino]-4-trifluoromethyl-pyrimidine-5-carboxylic acid (4-trifluoromethoxy-phenyl)-amide,
2-[1-(3-ethoxy-4-methoxy-benzyl)-piperidin-4-ylamino]-4-trifluoromethyl-pyrimidine-5-carboxylic acid (4-trifluoromethoxy-phenyl)-amide,
2-{1-[3-(2-fluoro-ethoxy)-4-methoxy-benzyl]-piperidin-4-ylamino}-4-trifluoromethyl-pyrimidine-5-carboxylic acid (4-trifluoromethoxy-phenyl)-amide,
2-[1-(3,5-diisopropoxy-benzyl)-piperidin-4-ylamino]-4-trifluoromethyl-pyrimidine-5-carboxylic acid (4-trifluoromethoxy-phenyl)-amide,
2-[1-(4-chloro-3,5-diethoxy-benzyl)-piperidin-4-ylamino]-4-trifluoromethyl-pyrimidine-5-carboxylic acid (4-trifluoromethoxy-phenyl)-amide,
2-[1-(4-amino-3,5-diethoxy-benzyl)-piperidin-4-ylamino]-4-trifluoromethyl-pyrimidine-5-carboxylic acid (4-trifluoromethoxy-phenyl)-amide,
2-[1-(3,5-diethoxy-4-pyrrol-1-yl-benzyl)-piperidin-4-ylamino]-4-trifluoromethyl-pyrimidine-5-carboxylic acid (4-trifluoromethoxy-phenyl)-amide,
[1-(3-ethoxy-4-fluoro-benzyl)-piperidin-4-yl]-(4,6,7-trimethoxy-quinazolin-2-yl)-amine,
[1-(4-chloro-3-ethoxy-benzyl)-piperidin-4-yl]-(4,6,7-trimethoxy-quinazolin-2-yl)-amine,
[1-(3,5-diethoxy-4-fluoro-benzyl)-piperidin-4-yl]-(4,6,7-trimethoxy-quinazolin-2-yl)-amine,
$N^6$-[1-(3,5-diethoxy-4-fluoro-benzyl)-piperidin-4-yl]-[1,3]dioxolo[4,5-g]quinazoline-6,8-diamine,
[1-(3-ethoxy-4-methyl-benzyl)-piperidin-4-yl]-[4-(2-fluoro-phenyl)-quinazolin-2-yl]-amine,
[1-(4-chloro-3-ethoxy-benzyl)-piperidin-4-yl]-[4-(2-fluoro-phenyl)-quinazolin-2-yl]-amine,
2-ethoxy-4-{4-[4-(2-fluoro-phenyl)-quinazolin-2-ylamino]-piperidin-1-ylmethyl}-phenol,
{1-[3-(2-fluoro-ethoxy)-4-methoxy-benzyl]-piperidin-4-yl}-[4-(2-fluoro-phenyl)-quinazolin-2-yl]-amine,
[4-(2-fluoro-phenyl)-quinazolin-2-yl]-[1-(3-isobutoxy-4-methoxy-benzyl)-piperidin-4-yl]-amine,
[1-(4-amino-3,5-diethoxy-benzyl)-piperidin-4-yl]-[4-(2-fluoro-phenyl)-quinazolin-2-yl]-amine,
N-(2,6-diethoxy-4-{4-[4-(2-fluoro-phenyl)-quinazolin-2-ylamino]-piperidin-1-ylmethyl}-phenyl)-acetamide,
[1-(4-chloro-3-ethoxy-benzyl)-piperidin-4-yl]-[6-chloro-4-(2-fluoro-phenyl)-quinazolin-2-yl]-amine,
[6-chloro-4-(2-fluoro-phenyl)-quinazolin-2-yl]-[1-(3-ethoxy-4-methoxy-benzyl)-piperidin-4-yl]-amine,
[6-chloro-4-(2-fluoro-phenyl)-quinazolin-2-yl]-[1-(3,5-diethoxy-4-iodo-benzyl)-piperidin-4-yl]-amine,
[1-(4-amino-3,5-diethoxy-benzyl)-piperidin-4-yl]-[6-chloro-4-(2-fluoro-phenyl)-quinazolin-2-yl]-amine,
[6-chloro-4-(2-fluoro-phenyl)-quinazolin-2-yl]-[1-(3,5-diethoxy-4-pyrrol-1-yl-benzyl)-piperidin-4-yl]-amine,
(6,7-dimethoxy-4-piperidin-1-yl-quinazolin-2-yl)-[1-(3-ethoxy-4-methyl-benzyl)-piperidin-4-yl]-amine,
(6,7-dimethoxy-4-piperidin-1-yl-quinazolin-2-yl)-[1-(3-ethoxy-4-fluoro-benzyl)-piperidin-4-yl]-amine,
[1-(4-chloro-3-ethoxy-benzyl)-piperidin-4-yl]-(6,7-dimethoxy-4-piperidin-1-yl-quinazolin-2-yl)-amine,
(6,7-dimethoxy-4-piperidin-1-yl-quinazolin-2-yl)-[1-(3-ethoxy-4-methoxy-benzyl)-piperidin-4-yl]-amine,
[1-(3,4-diethoxy-benzyl)-piperidin-4-yl]-(6,7-dimethoxy-4-piperidin-1-yl-quinazolin-2-yl)-amine,
(6,7-dimethoxy-4-piperidin-1-yl-quinazolin-2-yl)-[1-(3-ethoxy-4-isopropoxy-benzyl)-piperidin-4-yl]-amine,
2-{4-[4-(6,7-dimethoxy-4-piperidin-1-yl-quinazolin-2-ylamino)-piperidin-1-ylmethyl]-2-ethoxy-phenoxy}-ethanol,
(6,7-dimethoxy-4-piperidin-1-yl-quinazolin-2-yl)-[1-(4-methoxy-3-propoxy-benzyl)-piperidin-4-yl]-amine,
(6,7-dimethoxy-4-piperidin-1-yl-quinazolin-2-yl)-{1-[3-(2-fluoro-ethoxy)-4-methoxy-benzyl]-piperidin-4-yl}-amine,
[1-(3-allyloxy-4-methoxy-benzyl)-piperidin-4-yl]-(6,7-dimethoxy-4-piperidin-1-yl-quinazolin-2-yl)-amine,
[1-(3-butoxy-4-methoxy-benzyl)-piperidin-4-yl]-(6,7-dimethoxy-4-piperidin-1-yl-quinazolin-2-yl)-amine,
(6,7-dimethoxy-4-piperidin-1-yl-quinazolin-2-yl)-[1-(3-isobutoxy-4-methoxy-benzyl)-piperidin-4-yl]-amine,
[1-(3-benzyloxy-4-methoxy-benzyl)-piperidin-4-yl]-(6,7-dimethoxy-4-piperidin-1-yl-quinazolin-2-yl)-amine,
2-{4-[4-(6,7-dimethoxy-4-piperidin-1-yl-quinazolin-2-ylamino)-piperidin-1-ylmethyl]-2-ethoxy-5-fluoro-phenoxy}-ethanol,
(6,7-dimethoxy-4-piperidin-1-yl-quinazolin-2-yl)-[1-(8-ethoxy-2,2-dimethyl-2H-chromen-6-ylmethyl)-piperidin-4-yl]-amine,
[1-(3,5-diethoxy-benzyl)-piperidin-4-yl]-(6,7-dimethoxy-4-piperidin-1-yl-quinazolin-2-yl)-amine,
[1-(3,5-diisopropoxy-benzyl)-piperidin-4-yl]-(6,7-dimethoxy-4-piperidin-1-yl-quinazolin-2-yl)-amine,

[1-(3,5-diethoxy-4-fluoro-benzyl)-piperidin-4-yl]-(6,7-dimethoxy-4-piperidin-1-yl-quinazolin-2-yl)-amine,
[1-(4-chloro-3,5-diethoxy-benzyl)-piperidin-4-yl]-(6,7-dimethoxy-4-piperidin-1-yl-quinazolin-2-yl)-amine,
[1-(4-bromo-3,5-diethoxy-benzyl)-piperidin-4-yl]-(6,7-dimethoxy-4-piperidin-1-yl-quinazolin-2-yl)-amine,
[1-(3,5-diethoxy-4-pyrrol-1-yl-benzyl)-piperidin-4-yl]-(6,7-dimethoxy-4-piperidin-1-yl-quinazolin-2-yl)-amine,
(6-chloro-4-morpholin-4-yl-quinazolin-2-yl)-[1-(3-ethoxy-4-methyl-benzyl)-piperidin-4-yl]-amine,
(6-chloro-4-morpholin-4-yl-quinazolin-2-yl)-[1-(3-ethoxy-4-fluoro-benzyl)-piperidin-4-yl]-amine,
(6-chloro-4-morpholin-4-yl-quinazolin-2-yl)-[1-(3,5-diethoxy-4-fluoro-benzyl)-piperidin-4-yl]-amine,
[1-(4-amino-3,5-diethoxy-benzyl)-piperidin-4-yl]-(6-chloro-4-morpholin-4-yl-quinazolin-2-yl)-amine,
(6-chloro-4-morpholin-4-yl-quinazolin-2-yl)-[1-(3,5-diethoxy-4-pyrrol-1-yl-benzyl)-piperidin-4-yl]-amine,
(6,7-dimethoxy-4-morpholin-4-yl-quinazolin-2-yl)-[1-(3-ethoxy-4-methyl-benzyl)-piperidin-4-yl]-amine,
(6,7-dimethoxy-4-morpholin-4-yl-quinazolin-2-yl)-[1-(3-ethoxy-4-fluoro-benzyl)-piperidin-4-yl]-amine,
[1-(4-chloro-3-ethoxy-benzyl)-piperidin-4-yl]-(6,7-dimethoxy-4-morpholin-4-yl-quinazolin-2-yl)-amine,
4-[4-(6,7-dimethoxy-4-morpholin-4-yl-quinazolin-2-ylamino)-piperidin-1-ylmethyl]-2-ethoxy-phenol,
(6,7-dimethoxy-4-morpholin-4-yl-quinazolin-2-yl)-[1-(3-ethoxy-4-methoxy-benzyl)-piperidin-4-yl]-amine,
(6,7-dimethoxy-4-morpholin-4-yl-quinazolin-2-yl)-[1-(3-ethoxy-4-isopropoxy-benzyl)-piperidin-4-yl]-amine,
(6,7-dimethoxy-4-morpholin-4-yl-quinazolin-2-yl)-[1-(4-methoxy-3-propoxy-benzyl)-piperidin-4-yl]-amine,
(6,7-dimethoxy-4-morpholin-4-yl-quinazolin-2-yl)-{1-[3-(2-fluoro-ethoxy)-4-methoxy-benzyl]-piperidin-4-yl}-amine,
[1-(3-allyloxy-4-methoxy-benzyl)-piperidin-4-yl]-(6,7-dimethoxy-4-morpholin-4-yl-quinazolin-2-yl)-amine,
[1-(3-butoxy-4-methoxy-benzyl)-piperidin-4-yl]-(6,7-dimethoxy-4-morpholin-4-yl-quinazolin-2-yl)-amine,
(6,7-dimethoxy-4-morpholin-4-yl-quinazolin-2-yl)-[1-(3-isobutoxy-4-methoxy-benzyl)-piperidin-4-yl]-amine,
(6,7-dimethoxy-4-morpholin-4-yl-quinazolin-2-yl)-[1-(8-ethoxy-2,2-dimethyl-2H-chromen-6-ylmethyl)-piperidin-4-yl]-amine,
[1-(3,5-diethoxy-benzyl)-piperidin-4-yl]-(6,7-dimethoxy-4-morpholin-4-yl-quinazolin-2-yl)-amine,
3-[4-(6,7-dimethoxy-4-morpholin-4-yl-quinazolin-2-ylamino)-piperidin-1-ylmethyl]-5-isopropoxy-phenol,
[1-(3,5-diisopropoxy-benzyl)-piperidin-4-yl]-(6,7-dimethoxy-4-morpholin-4-yl-quinazolin-2-yl)-amine,
[1-(3,5-diethoxy-4-fluoro-benzyl)-piperidin-4-yl]-(6,7-dimethoxy-4-morpholin-4-yl-quinazolin-2-yl)-amine,
[1-(4-chloro-3,5-diethoxy-benzyl)-piperidin-4-yl]-(6,7-dimethoxy-4-morpholin-4-yl-quinazolin-2-yl)-amine,
[1-(4-bromo-3,5-diethoxy-benzyl)-piperidin-4-yl]-(6,7-dimethoxy-4-morpholin-4-yl-quinazolin-2-yl)-amine,
[1-(4-amino-3,5-diethoxy-benzyl)-piperidin-4-yl]-(6,7-dimethoxy-4-morpholin-4-yl-quinazolin-2-yl)-amine,
[1-(3,5-diethoxy-4-pyrrol-1-yl-benzyl)-piperidin-4-yl]-(6,7-dimethoxy-4-morpholin-4-yl-quinazolin-2-yl)-amine,
(6,7-dimethoxy-4-morpholin-4-yl-quinazolin-2-yl)-[1-(2-phenyl-1H-imidazol-4-ylmethyl)-piperidin-4-yl]-amine,
[1-(3-ethoxy-4-methoxy-benzyl)-piperidin-4-yl]-(4-phenyl-pteridin-2-yl)-amine,
[1-(3,5-diethoxy-benzyl)-piperidin-4-yl]-(4-phenyl-pteridin-2-yl)-amine,
[1-(3,5-diisopropoxy-benzyl)-piperidin-4-yl]-(4-phenyl-pteridin-2-yl)-amine,
(4,6-dimethoxy-[1,3,5]triazin-2-yl)-[1-(3-ethoxy-4-methyl-benzyl)-piperidin-4-yl]-amine,
(4,6-dimethoxy-[1,3,5]triazin-2-yl)-[1-(3-ethoxy-4-fluoro-benzyl)-piperidin-4-yl]-amine,
[1-(4-chloro-3-ethoxy-benzyl)-piperidin-4-yl]-(4,6-dimethoxy-[1,3,5]triazin-2-yl)-amine,
[1-(3,4-diethoxy-benzyl)-piperidin-4-yl]-(4,6-dimethoxy-[1,3,5]triazin-2-yl)-amine,
(4,6-dimethoxy-[1,3,5]triazin-2-yl)-[1-(4-methoxy-3-propoxy-benzyl)-piperidin-4-yl]-amine,
(4,6-dimethoxy-[1,3,5]triazin-2-yl)-{1-[3-(2-fluoro-ethoxy)-4-methoxy-benzyl]-piperidin-4-yl}-amine,
[1-(3-allyloxy-4-methoxy-benzyl)-piperidin-4-yl]-(4,6-dimethoxy-[1,3,5]triazin-2-yl)-amine,
[1-(3-butoxy-4-methoxy-benzyl)-piperidin-4-yl]-(4,6-dimethoxy-[1,3,5]triazin-2-yl)-amine,
(4,6-dimethoxy-[1,3,5]triazin-2-yl)-[1-(3-isobutoxy-4-methoxy-benzyl)-piperidin-4-yl]-amine,
[1-(3-benzyloxy-4-methoxy-benzyl)-piperidin-4-yl]-(4,6-dimethoxy-[1,3,5]triazin-2-yl)-amine,
(4,6-dimethoxy-[1,3,5]triazin-2-yl)-{1-[5-ethoxy-2-(2-methoxy-ethoxy)-benzyl]-piperidin-4-yl}-amine,
[1-(3,5-diethoxy-benzyl)-piperidin-4-yl]-(4,6-dimethoxy-[1,3,5]triazin-2-yl)-amine,
[1-(3,5-diethoxy-4-fluoro-benzyl)-piperidin-4-yl]-(4,6-dimethoxy-[1,3,5]triazin-2-yl)-amine,
[1-(4-bromo-3,5-diethoxy-benzyl)-piperidin-4-yl]-(4,6-dimethoxy-[1,3,5]triazin-2-yl)-amine,
[1-(3,5-diethoxy-4-pyrrol-1-yl-benzyl)-piperidin-4-yl]-(4,6-dimethoxy-[1,3,5]triazin-2-yl)-amine,
[1-(2,6-diethoxy-4'-fluoro-biphenyl-4-ylmethyl)-piperidin-4-yl]-(6,7-dimethoxy-4-piperidin-1-yl-quinazolin-2-yl)-amine,
4-[4-(6,7-dimethoxy-4-piperidin-1-yl-quinazolin-2-ylamino)-piperidin-1-ylmethyl]-2-ethoxy-phenol,
[1-(2,6-diethoxy-4'-fluoro-biphenyl-4-ylmethyl)-piperidin-4-yl]-(4,6-dimethoxy-[1,3,5]triazin-2-yl)-amine,
2-{4-[1-(3,5-diethoxy-4-fluoro-benzyl)-piperidin-4-ylamino]-6-methoxy-[1,3,5]triazine-2-ylamino}-ethanol,
2-{4-[1-(4-chloro-3,5-diethoxy-benzyl)-piperidin-4-ylamino]-6-methoxy-[1,3,5]triazin-2-ylamino}-ethanol,
2-{4-[1-(2,6-diethoxy-4'-fluoro-biphenyl-4-ylmethyl)-piperidin-4-ylamino]-6-methoxy-[1,3,5]triazin-2-ylamino}-ethanol,
N-[1-(3,5-diethoxy-4-fluoro-benzyl)-piperidin-4-yl]-6-methoxy-N'-(2-methoxy-ethyl)-[1,3,5]triazine-2,4-diamine,
N-[1-(4-chloro-3,5-diethoxy-benzyl)-piperidin-4-yl]-6-methoxy-N'-(2-methoxy-ethyl)-[1,3,5]triazine-2,4-diamine,
N-[1-(2,6-diethoxy-4'-fluoro-biphenyl-4-ylmethyl)-piperidin-4-yl]-6-methoxy-N'-(2-methoxy-ethyl)-[1,3,5]triazine-2,4-diamine,
N-[1-(3,5-diethoxy-4-fluoro-benzyl)-piperidin-4-yl]-6-methoxy-N'-methyl-[1,3,5]triazine-2,4-diamine,
N-[1-(4-chloro-3,5-diethoxy-benzyl)-piperidin-4-yl]-6-methoxy-N'-methyl-[1,3,5]triazine-2,4-diamine,
N-[1-(2,6-diethoxy-4'-fluoro-biphenyl-4-ylmethyl)-piperidin-4-yl]-6-methoxy-N'-methyl-[1,3,5]triazine-2,4-diamine,
{4-[1-(3,5-diethoxy-4-fluoro-benzyl)-piperidin-4-ylamino]-6-methoxy-[1,3,5]triazin-2-ylamino}-acetic acid tert-butyl ester, {4-[1-(4-chloro-3,5-diethoxy-benzyl)-piperidin-4-ylamino]-6-methoxy-[1,3,5]triazin-2-ylamino}-acetic acid tert-butyl ester,
{4-[1-(2,6-diethoxy-4'-fluoro-biphenyl-4-ylmethyl)-piperidin-4-ylamino]-6-methoxy-[1,3,5]triazin-2-ylamino}-acetic acid tert-butyl ester,
[1-(3,5-diethoxy-4-fluoro-benzyl)-piperidin-4-yl]-(4-methoxy-6-thiomorpholin-4-yl-[1,3,5]triazin-2-yl)-amine,
[1-(4-chloro-3,5-diethoxy-benzyl)-piperidin-4-yl]-(4-methoxy-6-thiomorpholin-4-yl-[1,3,5]triazin-2-yl)-amine,
[1-(2,6-diethoxy-4'-fluoro-biphenyl-4-ylmethyl)-piperidin-4-yl]-(4-methoxy-6-thiomorpholin-4-yl-[1,3,5]triazin-2-yl)-amine,
methanesulfonic acid 2-[1-(3,5-diethoxy-4-fluoro-benzyl)-piperidin-4-ylamino]-pyrimidin-5-yl ester,
methanesulfonic acid 2-[1-(4-chloro-3,5-diethoxy-benzyl)-piperidin-4-ylamino]-pyrimidin-5-yl ester,
methanesulfonic acid 2-[1-(2,6-diethoxy-4'-fluoro-biphenyl-4-ylmethyl)-piperidin-4-ylamino]-pyrimidin-5-yl ester,
{2-[1-(3,5-diethoxy-4-fluoro-benzyl)-piperidin-4-ylamino]-pyrimidin-5-yloxy}-acetonitrile,
{2-[1-(4-chloro-3,5-diethoxy-benzyl)-piperidin-4-ylamino]-pyrimidin-5-yloxy}-acetonitrile,
{2-[1-(2,6-diethoxy-4'-fluoro-biphenyl-4-ylmethyl)-piperidin-4-ylamino]-pyrimidin-5-yloxy}-acetonitrile,
3-{2-[1-(4-chloro-3,5-diethoxy-benzyl)-piperidin-4-ylamino]-pyrimidin-5-yloxy}-propane-1,2-diol,
3-{2-[1-(2,6-diethoxy-4'-fluoro-biphenyl-4-ylmethyl)-piperidin-4-ylamino]-pyrimidin-5-yloxy}-propane-1,2-diol,
3-{2-[1-(4-chloro-3,5-diethoxy-benzyl)-piperidin-4-ylamino]-pyrimidin-5-yloxy}-propan-1-ol,
3-{2-[1-(2,6-diethoxy-4'-fluoro-biphenyl-4-ylmethyl)-piperidin-4-ylamino]-pyrimidin-5-yloxy}-propan-1-ol,
2-{2-[1-(4-chloro-3,5-diethoxy-benzyl)-piperidin-4-ylamino]-pyrimidin-5-yloxy}-acetamide,
2-{2-[1-(2,6-diethoxy-4'-fluoro-biphenyl-4-ylmethyl)-piperidin-4-ylamino]-pyrimidin-5-yloxy}-acetamide,
{4-[1-(3,5-diethoxy-4-fluoro-benzyl)-piperidin-4-ylamino]-6-methoxy-[1,3,5]triazin-2-ylamino}-acetic acid,
{4-[1-(4-chloro-3,5-diethoxy-benzyl)-piperidin-4-ylamino]-6-methoxy-[1,3,5]triazin-2-ylamino}-acetic acid,
{4-[1-(2,6-diethoxy-4'-fluoro-biphenyl-4-ylmethyl)-piperidin-4-ylamino]-6-methoxy-[1,3,5]triazin-2-ylamino}-acetic acid, and pharmaceutically acceptable salts thereof.

Especially preferred are the following compounds of formula I of the present invention:
[1-(4-chloro-3-ethoxy-benzyl)-piperidin-4-yl]-(5-ethyl-pyrimidin-2-yl)-amine,
[1-(4-chloro-3,5-diethoxy-benzyl)-piperidin-4-yl]-(4,6-dimethyl-pyrimidin-2-yl)-amine,
[1-(3,5-diisopropoxy-benzyl)-piperidin-4-yl]-pyrimidin-2-yl-amine,
[1-(4-chloro-3,5-diethoxy-benzyl)-piperidin-4-yl]-pyrimidin-2-yl-amine,
2-[1-(4-chloro-3-ethoxy-benzyl)-piperidin-4-ylamino]-pyrimidine-5-carboxylic acid,
2-[1-(4-chloro-3,5-diethoxy-benzyl)-piperidin-4-ylamino]-pyrimidine-5-carboxylic acid,
[1-(4-chloro-3-ethoxy-benzyl)-piperidin-4-yl]-(5-phenyl-pyrimidin-2-yl)-amine,
[1-(4-chloro-3,5-diethoxy-benzyl)-piperidin-4-yl]-(5-phenyl-pyrimidin-2-yl)-amine,
[1-(4-chloro-3-ethoxy-benzyl)-piperidin-4-yl]-[5-(4-methoxy-phenyl)-pyrimidin-2-yl]-amine,
[1-(3,5-diisopropoxy-benzyl)-piperidin-4-yl]-[5-(4-methoxy-phenyl)-pyrimidin-2-yl]-amine,
[1-(4-chloro-3,5-diethoxy-benzyl)-piperidin-4-yl]-[5-(4-methoxy-phenyl)-pyrimidin-2-yl]-amine,
[1-(4-chloro-3-ethoxy-benzyl)-piperidin-4-yl]-(5-pyridin-3-yl-pyrimidin-2-yl)-amine,
[1-(3,5-diethoxy-4-fluoro-benzyl)-piperidin-4-yl]-(5-pyridin-3-yl-pyrimidin-2-yl)-amine,
[1-(4-chloro-3,5-diethoxy-benzyl)-piperidin-4-yl]-(5-pyridin-3-yl-pyrimidin-2-yl)-amine,
[1-(3,5-diethoxy-4-pyrrol-1-yl-benzyl)-piperidin-4-yl]-(5-pyridin-3-yl-pyrimidin-2-yl)-amine,
4-{2-[1-(4-chloro-3-ethoxy-benzyl)-piperidin-4-ylamino]-pyrimidin-5-yl}-benzamide,
[1-(4-chloro-3,5-diethoxy-benzyl)-piperidin-4-yl]-(6,7-dimethoxy-4-piperidin-1-yl-quinazolin-2-yl)-amine,
[1-(3,5-diisopropoxy-benzyl)-piperidin-4-yl]-(6,7-dimethoxy-4-morpholin-4-yl-quinazolin-2-yl)-amine, and pharmaceutically acceptable salts thereof.

Furthermore, the pharmaceutically acceptable salts of the compounds of formula I individually constitute preferred embodiments of the present invention.

Compounds of formula I can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbens or eluant). The invention embraces all of these forms.

It will be appreciated, that the compounds of general formula I in this invention may be derivatized at functional groups to provide derivatives which are capable of conversion back to the parent compound in vivo. Physiologically acceptable and metabolically labile derivatives, which are capable of producing the parent compounds of general formula I in vivo are also within the scope of this invention.

A further aspect of the present invention is the process for the manufacture of compounds of formula I as defined above, which process comprises reacting a compound of the general formula

G-X        II wherein G is as defined herein before and X is a leaving group,
with a compound of the formula

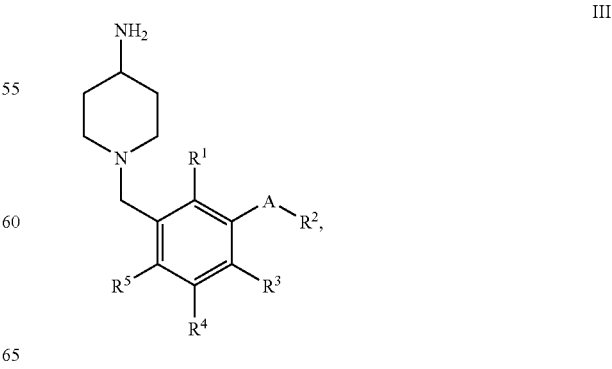

III wherein A and $R^1$ to $R^5$ are as defined herein before, to obtain a compound of the formula

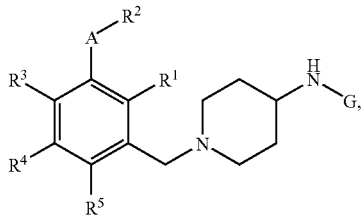

and, if desired, converting the compound of formula I into a pharmaceutically acceptable salt; or, alternatively,
reacting a compound of the general formula

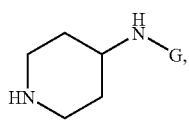

wherein G is as defined herein before,
with an aldehyde of the formula

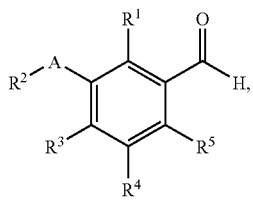

wherein A and $R^1$ to $R^5$ are as defined herein before,
by employing a reducing agent to obtain a compound of the formula

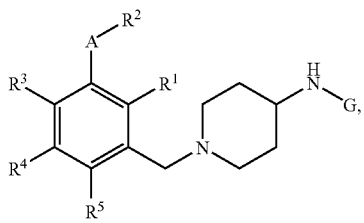

and, if desired, converting the compound of formula I into a pharmaceutically acceptable salt.

The invention further relates to compounds of formula I as defined above, when manufactured according to a process as defined above.

Suitable reducing agents are preferably selected from the group consisting of pyridine-$BH_3$ complex, $NaBH(OAc)_3$ and $NaCNBH_3$. The reaction can be carried out under acidic conditions by using an acid such as acetic acid or formic acid or an Lewis acid (e.g., $Ti(iPrO)_4$, $ZnCl_2$) or under basic conditions (no additive) in a suitable solvent such as dichloromethane, dichloroethane or ethanol (or mixtures thereof) at ambient or elevated temperatures using conventional heating or heating by microwave irradiation.

As described above, the compounds of formula I of the present invention can be used as medicaments for the treatment and/or prevention of diseases which are associated with the modulation of SST receptors subtype 5.

"Diseases which are associated with the modulation of SST receptors subtype 5" are such diseases as diabetes mellitus, particularly type II diabetes mellitus, impaired fasting glucose, impaired glucose tolerance, micro- and macrovascular diabetic complications, posttransplantation diabetes mellitus in patients having type I diabetes mellitus, gestational diabetes, obesity, inflammatory bowel diseases such as Crohn's disease or ulcerative colitis, malabsorption, autoimmune diseases such as rheumatoid arthritis, osteoarthritis, psoriasis and other skin disorder, and immunodeficiences. Microvascular diabetic complications include diabetic nephropathy and diabetic retinopathy, whereas macrovascular diabetes-associated complications lead to an increased risk for myocardial infarction, stroke and limb amputations.

The use as medicament for the treatment and/or prevention of diabetes mellitus, particularly type II diabetes mellitus, impaired fasting glucose or impaired glucose tolerance is preferred.

The invention therefore also relates to pharmaceutical compositions comprising a compound as defined above and a pharmaceutically acceptable carrier and/or adjuvant.

Further, the invention relates to compounds as defined above for use as therapeutically active substances, particularly as therapeutic active substances for the treatment and/or prevention of diseases which are associated with the modulation of SST receptors subtype 5.

In another embodiment, the invention relates to a method for the treatment and/or prevention of diseases which are which are associated with the modulation of SST receptors subtype 5, which method comprises administering a compound of formula I to a human or animal. The method for the treatment and/or prevention of diabetes mellitus, particularly type II diabetes mellitus, impaired fasting glucose or impaired glucose tolerance, is most preferred.

The invention further relates to the use of compounds as defined above for the treatment and/or prevention of diseases which are associated with the modulation of SST receptors subtype 5.

In addition, the invention relates to the use of compounds as defined above for the preparation of medicaments for the treatment and/or prevention of diseases which are associated with the modulation of SST receptors subtype 5. Preferred examples of such diseases are diabetes mellitus, particularly type II diabetes mellitus, impaired fasting glucose or impaired glucose tolerance.

The compounds of formula I can be manufactured by the methods given below, by the methods given in the examples or by analogous methods. Appropriate reaction conditions for the individual reaction steps are standard reactions and are known to a person skilled in the art. Starting materials are either commercially available or can be prepared by methods analogous to the methods given below, by methods described in references cited in the text or in the examples, or by methods known in the art.

The synthesis of compounds of the general formula I, particularly compounds according to formula Ic can be accomplished according to Scheme 1.

Scheme 1

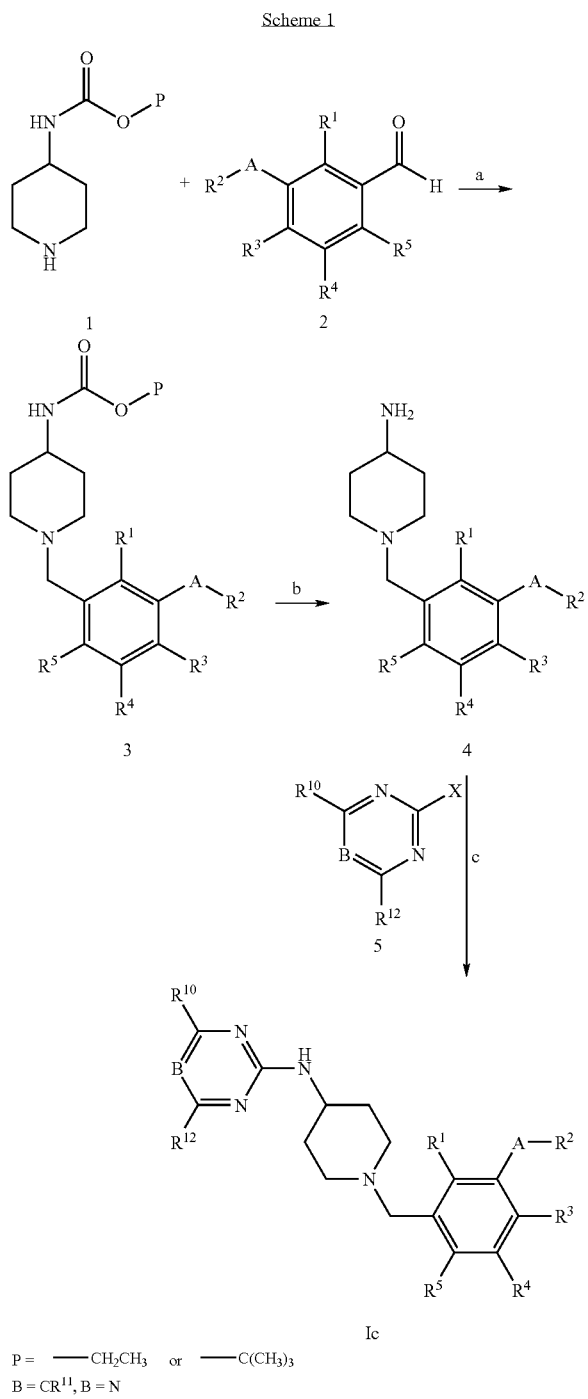

Reductive N-alkylation of suitably protected piperidines (for protecting groups see *Protective Groups in Organic Synthesis*, T. W. Greene and P. G. M. Wuts, 3$^{rd}$ Edition, 1999, Wiley-Interscience) of formula 1 with aldehydes 2 in the presence of a reducing agent such as pyridine-BH$_3$ complex, NaBH(OAc)$_3$ or NaCNBH$_3$ under acidic conditions (e.g., acetic acid, formic acid), by using a Lewis acid (e.g., Ti(iPr O)$_4$, ZnCl$_2$) or under buffered conditions, e.g., in the presence of acetic acid and a tertiary amine like N-ethyl diisopropylamine or triethylamine in a suitable solvent such as dichloromethane, dichloroethane, ethanol or isopropanol (or mixtures thereof) at ambient or elevated temperatures using conventional heating or heating by microwave irradiation provide piperidines of general formula 3 (Scheme 1, step a). The piperidines of formula 1 may thereby used either as a salt, e.g., hydrochloride or hydrobromide salt, or as the corresponding free amine. The alkyloxycarbonyl protecting group present in compounds 3 can be removed, using e.g., 48% aqueous hydrogen bromide or 37% aqueous hydrochloric acid as reagent preferably at elevated temperatures to remove an ethyl carbamate or using trifluoroacetic acid or hydrochloric acid in a solvent like dichloromethane, dioxane or THF preferable at room temperature to remove a tert-butyloxycarbonyl (BOC)-protective group (see *Protective Groups in Organic Synthesis*, T. W. Greene and P. G. M. Wuts, 3$^{rd}$ Edition, 1999, Wiley-Interscience), yielding 4-amino-piperidines of formula 4 (Scheme 1, step b).

Target compounds of formula I can be synthesized by nucleophilic replacement reaction of 4-amino-piperidines of formula 4 and a variety of pyrimidines, quinazolines, pteridines or triazines of general structure 5 at room or elevated temperatures (Scheme 1, step c), whereby X is a suitable leaving group such as fluorine, chlorine, bromine or methyl sulfone. Thereby heating can be achieved conventionally or by microwave irradiation using a suitable microwave irradiation apparatus. Furthermore the reaction can be conducted in the presence of or without solvent (typically an aprotic polar solvent such as DMF (N,N-dimethylformamide), DMAc (dimethylacetamide), NMP (N-methylpyrrolidon), ethylene glycol, acetonitrile or THF) and in the presence of or without a tertiary amine base such as triethylamine, N-ethyl diisopropylamine or pyridine and in the presence with or without copper(I) bromide or copper(I) iodide. In order to enhance the rate of conversion heating might be applied, whereby conventional heating or microwave assisted heating might be employed. The starting materials and some of the intermediates of general structure 5 (e.g., 2-chloro-pyrimidines, 2-chloro-quinazolines, 2-chloro-pteridines or 2-chloro-triazines) are known compounds and are commercially available or can be prepared by numerous methods using conventional reaction procedures generally known in the art. The 4-amino-piperidines of formula 4 may thereby used either as a salt, e.g., hydrochloride or hydrobromide salt, or as the corresponding free amine. Alternatively the nucleophilic displacement reaction can be conducted under basic conditions by using K$_2$CO$_3$, KOH, NaOCH$_3$, KOtert-Bu or in particular by using NaH. If the coupling reaction is conducted with 2,4-dihalo-pyrimidines or 2,4-dihalo-quinazolines, preferentially with 2,4-dichloro-pyrimidines, regioisomeric coupling products might be obtained, which can be separated by conventional chromatographic methods. In cases where nucleophilic substitution leads to regioisomeric products the regiochemistry of target structures I was unambiguously established by means of nuclear magnetic resonance spectroscopy employing 1D-NOE difference, 2D-NOESY and/or $^{13}$C/$^1$HMBC experiments. In some cases $^1$H NMR spectra revealed the presence of tautomeric structures at room temperature (rt).

Alternatively target structures I can be achieved using Pd(0)-catalyzed amination reactions of 2-halo pyrimidines of formula 5 with 4-amino-piperidines 4 (e.g., Buchwald-Hartwig coupling; see (a) J. P. Wolfe, S. Wagaw and S. L.

Buchwald *J. Am. Chem. Soc.* 1996, 118, 7215-7216; (b) J. P. Wolfe and S. L. Buchwald *Tetrahedron Lett.* 1997, 38, 6359-6362; (c) J. P. Wolfe, S. Wagaw, J.-F. Marcoux and S. L. Buchwald *Acc. Chem. Res.* 1998, 31, 805-818; (d) B. H. Yang and S. L. Buchwald *J. Organomet. Chem.* 1999, 576, 125-146; (e) J. F. Hartwig *Angew. Chem. Int. Ed.* 1998, 37, 2046-2067). Thereby halo-substituted heterocylces 5 are reacted with amines 4 under an inert atmosphere such as argon or nitrogen in the presence of a palladium catalys such as tris (dibenzylideneacetone)dipalladium(0) ($Pd_2(dba)_3$) or palladium(II) acetate ($Pd(COOCH_3)_2$), a phosphine ligand like triphenylphosphine, rac-2,2'-bis(diphenylphosphino)-1,1'-binaphthalene (rac-BINAP) or (R)-(−)-1-[(S)-2-(dicyclohexylphosphino)ferrocenyl]ethyldi-tert-butylphosphine (Josiphos; see Q. Shen, S. Shekhar, J. P. Stambuli and J. F. Hartwig, *Angew. Chem. Int. Ed.* 2005, 44, 1371-1375) and a base such as $Cs_2CO_3$ or KOtert-Bu in a solvent like toluene, ethanol or water or mixtures thereof (Scheme 1, step c). Said C—N formation reaction may be conducted at room temperature or elevated temperatures, whereby heating might be achieved conventionally or by microwave irradiation (see also Palladium(0) Complexes in Organic Chemistry, in *Organometallics in Synthesis* (Ed. M. Schlosser), Chapter 4, $2^{nd}$ Edition, 2002, JohnWiley & Sons, Ltd, Chichester, UK).

Target structures of formula I can also be accomplished employing an inverted reaction sequence, namely by first coupling halo-substituted heterocycles 5 with alkyloxycarbonyl protected amine 6 (Scheme 2, step a) yielding intermediate 7. Intermediates 7 can be further processed as such, or optionally, any of the substituents $R^{10}$, $R^{11}$ or $R^{12}$ can be exchanged, modified, extended or removed by methods well known in the art and described in more detail in the examples. The protection group(s) of piperidines 7 are then removed yielding the secondary amines 8 (Scheme 2, step b), which undergo reductive N-alkylation to target structures I (Scheme 2, step c). In contrast to the strategy outlined in Scheme 1 where the point of diversification is the heteroaryl moiety this synthetic route is of particular interest if the variation of the benzyl moiety is aimed for in a rapid and parallel fashion.

Scheme 2

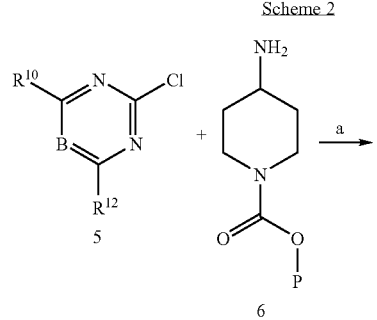

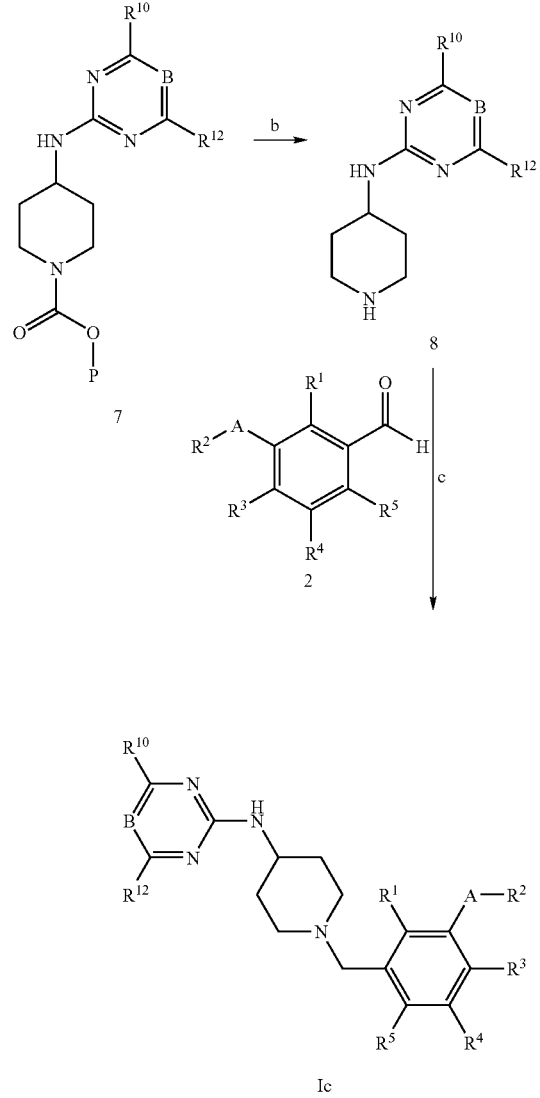

Target compounds of formula I might also be synthesized by direct alkylation of piperidines 8 with suitable halides, mesylates, tosylates or alcohols containing any other suitable leaving group of structure 9 in a solvents such as N,N-dimethylformamide, dichloromethane, dichloroethane or acetone at ambient or elevated temperatures using conventional heating or heating by microwave irradiation with the addition of a suitable tertiary amine base (e.g., triethylamine, N-ethyl diisopropylamine) or an inorganic base (e.g., $Cs_2CO_3$, $K_2CO_3$; Scheme 3, step a) or by analogous alkylation reactions. Alternatively target structures of formula I might be accessible by Mitsunobu reaction applying alcohols 10 activated by a mixture of triphenylphosphine and diethyl- or di-tert-butyl-azadicarboxylate (Scheme 3, step b).

Scheme 3

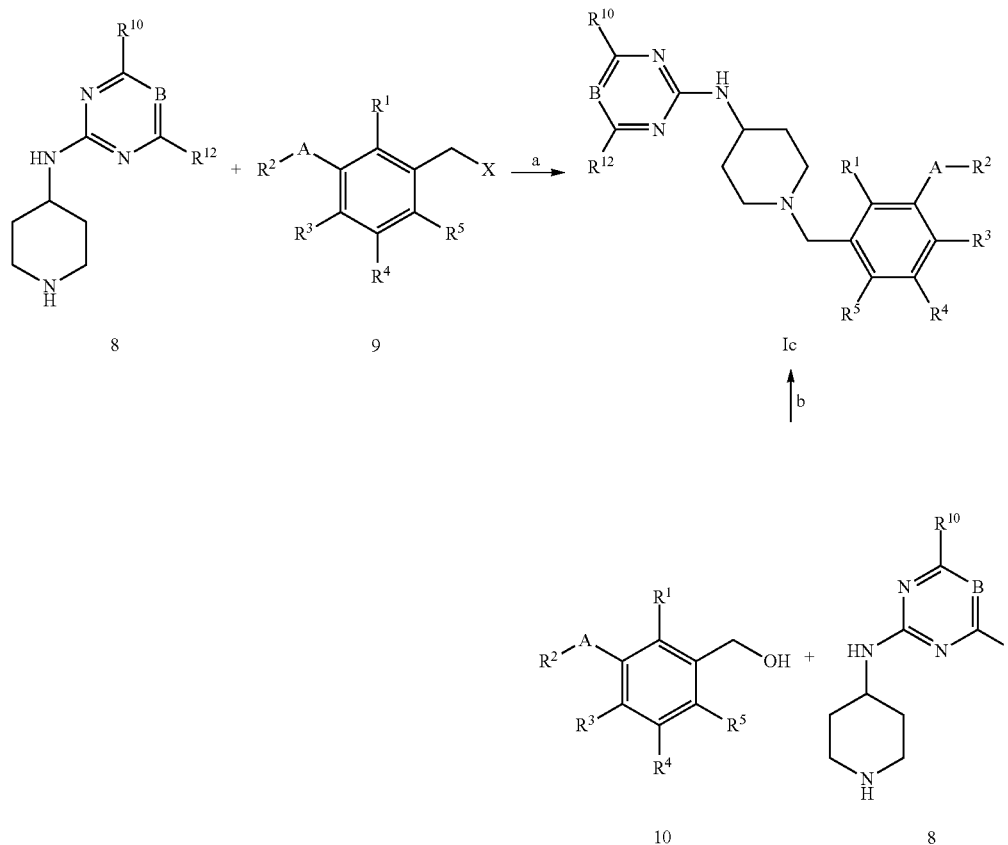

Synthesis of Pyrimidine and Quinazoline Intermediates

The starting materials of general formula IIa are either commercially available, known in the literature or can be obtained on application of classical methods of pyrimidine synthesis and subsequent functional group conversion such as by condensation of β-keto carboxylic acids 11 (malonic esters) with urea (12) as illustrated in step a of Scheme 4 (e.g., see Y.-Z. Kim, J.-C. Lim, J.-H. Yeo, C.-S. Bang, W.-S. Kim, S.-S. Kim, Y.-M. Woo, D.-H. Yang, H. Oh and K. Nahm *J. Med. Chem.* 1994, 37, 3828-3833). Halogenation of the pyrimidine intermediates 13 to provide compounds of general formula IIa can be accomplished in refluxing POCl₃ or PCl₃/PCl₅ (Scheme 4, step b; see also H. Krauch and W. Kunz, *Reaktionen der organischen Chemie,* 6., neubearbeitete Auflage, 1997, Hüthig GmbH, Heidelberg, Deutschland). The corresponding bromo derivatives of IIa are accessible when POBr₃ is used instead of POCl₃ as the halogenation agent. Furthermore, the halogenation step can be conducted in the presence or absence of catalytic amounts of N,N-dimethylaniline. All of these reactions are standard operations and can be carried out under conditions which are usual for such reactions and which are familiar to a person skilled in the art.

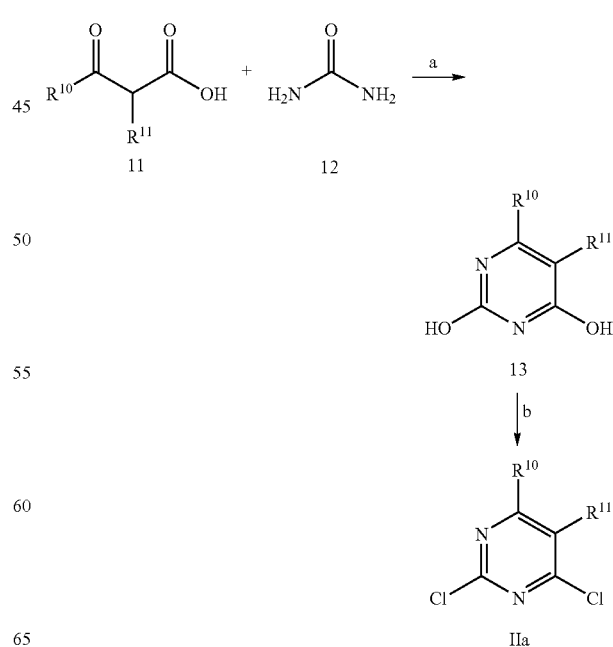

Scheme 4

Alternatively, the preparation of target structures Ia can be achieved by condensation of β-keto carboxylic acids 11 (malonic esters) with guanidine (14) yielding 2-amino pyrimidines 15 (Traube synthesis; see A. R. Katritzky and T. I. Yousaf *Canad. J. Chem.* 1986, 64, 2087-2093; Scheme 5, step a). The 4-hydroxy group in pyrimidines 15 can be converted to chloride employing standard halogenation conditions such as refluxing $POCl_3$ or $PCl_3/PCl_5$ (Scheme 5, step b). The 2-amino group in pyrimidines 16 can then be transformed to chloride employing standard Sandmeyer reaction conditions such as diazotization with sodium nitrite in the presence of hydrochloric acid at lower temperatures preferentially between −10° C. and 10° C. yielding 2,4-dichloro-pyrimidines (Scheme 5, step c). Alternatively, the Sandmeyer reaction can be conducted directly on pyrimidine 15 providing access to 2-chloro-4-hydroxy pyrimidines.

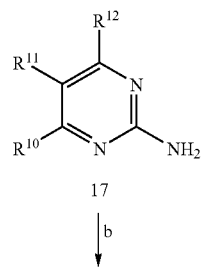

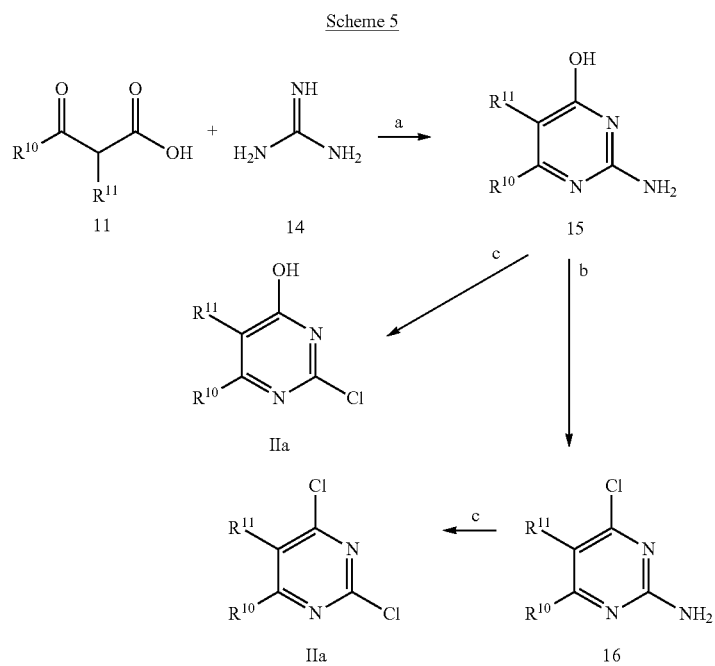

Scheme 5

Alternatively, 2-amino pyrimidines 17 can be obtained by ring closure reaction of enamino ketones 18 (H. H. Wasserman and J. L. Ives *J. Am. Chem. Soc.* 1976, 98, 7868-7869) with guanidine (15) in the presence of a base such as sodium methylate in a solvent like ethanol at room or elevated temperatures (Scheme 6, step a). Conversion of the 4-hydroxy group in pyrimidines 17 to chloride can be achieved using standard halogenation conditions such as refluxing $POCl_3$ or $PCl_3/PCl_5$ (Scheme 6, step b).

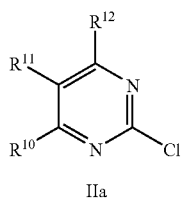

Scheme 6

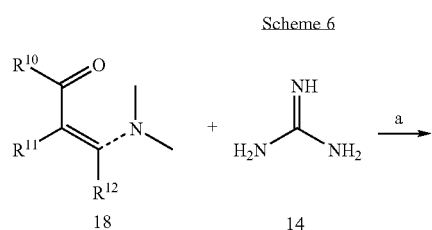

In case of $R^4$ is 2-thienyl regioselective lithiation at the a position to the nitrogen with (2-thienyl)lithium of pyrimidines 19 in diethyl ether at −30° C. followed by oxidation with 2,3-dichloro-5,6-dicyanobenzoquinone (DDQ) leads to the desired product IIa (Scheme 7, step a; D. B. Harden, M. J. Mokrosz and L. Strekowski *J. Org. Chem.* 1988, 53, 4137-4140). The method is also amenable to $R^4$=methyl, n-butyl, phenyl, 3-thienyl and therelike.

Scheme 7

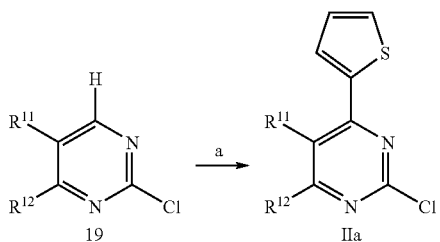

Scheme 8

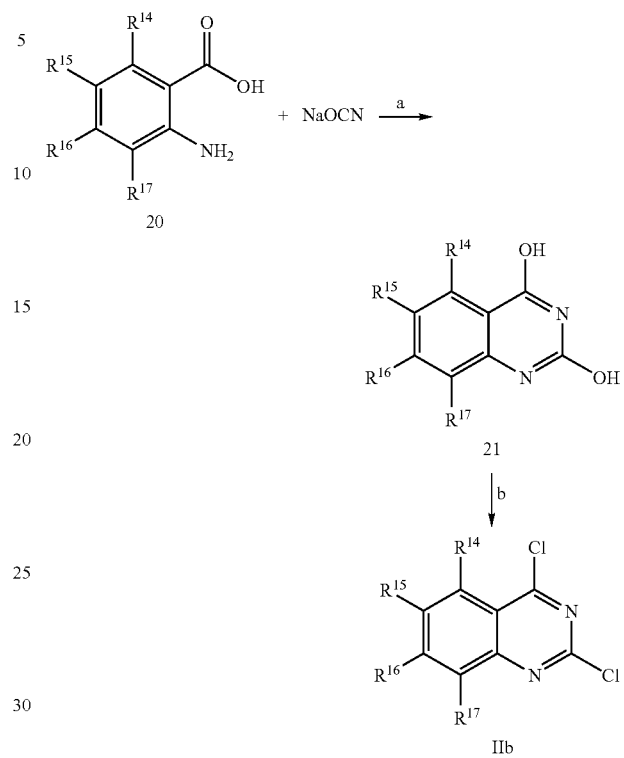

There are myriads of references known in the art teaching methods useful for the preparation of pyrimidines. The reader is referred to (a) D. J. Brown, The Pyrimidines, in *The Chemistry of Heterocyclic Compounds* (Ed. A. Weissberger), Volume 16, 1962, Interscience Publishers, New York; (b) D. J. Brown, The Pyrimidines, in *The Chemistry of Heterocyclic Compounds* (Eds. A. Weissberger and E. C. Taylor), Volume 16, Supplement I, 1970, Interscience Publishers, New York; (c) D. J. Brown, R. F. Evans, W. B. Cowden and M. D. Fenn, The Pyrimidines, in *The Chemistry of Heterocyclic Compounds* (Eds. A. Weissberger and E. C. Taylor), Volume 16, Supplement II, 1985, Interscience Publishers, New York; (d) D. J. Brown, The Pyrimidines, in *The Chemistry of Heterocyclic Compounds* (Eds. A. Weissberger and E. C. Taylor), Volume 52, Supplement I, 1994, Interscience Publishers, New York; (e) L. A. Paquette, *Principles of Modern Heterocyclic Chemistry*, 1968, W. A. Benjamin, Inc., New York (uracil synthesis pp. 313-315; pyrimidine synthesis pp. 313-316); (f) *Comprehensive Organic Synthesis* (Eds. B. M. Trost and I. Fleming), 1992, Pergamon Press, Oxford, UK.

Further syntheses of pyrimidines of formula IIa are described in the examples.

The starting materials of general formula IIb are either commercially available, known in the literature or can be obtained on application of classical methods of quinazoline synthesis. A classical route for the synthesis of quinazolines IIb is outlined in Scheme 8. Condensation of anthranilic acids 20 and sodium cyanate in water and glacial acetic acid furnishes quinazoline-2,4-diols 21 (step a), which upon subsequent functional group conversion, e.g., treatment at elevated temperatures with phosphorus oxychloride in chloroform or neat and in the presence or absence of N,N-dimethylaniline as a catalyst, provide 2,4-dichloro-quinazolines IIb (step b). The two halogenes in IIb exhibit different chemical reactivity, with the chloride at the C2 position being inherently less reactive. This allows the sequential replacement of first the C4 and second the C2 chloride atom, e.g., by nucleophilic substitution reactions with amines or aliphatic or aromatic alcohols or by Pd(0)-catalyzed Suzuki, Buchwald-Hartwig or Stille-type coupling reactions, providing access to a large number of differently substituted intermediates of general structure IIb. Likewise this synthetic strategy can be applied to 2,4-dichloro-pyrimidines, where a similar difference in reactivity of the two halogen atoms is also observed. The regiochemistry of target structures IIb can unambiguously be established by means of nuclear magnetic resonance spectroscopy employing 1D-NOE difference, 2D-NOESY and/or $^{13}C/^{1}$HMBC experiments.

Most of the synthetic routes outlined in Scheme 4 to Scheme 8 are amenable to both solution and solid-phase synthesis (see J. T. Bork, J. W. Lee and Y.-T. Chang *QSAR Comb. Sci.* 2004, 23, 245-260).

Further syntheses of quinazolines of formula IIb are described in the examples.

Synthesis of Aldehyde Intermediates

The requisite aldehyde partners are either commercially available or can be derived by alkylation with alkyl halides, alkyl mesylates, alkyl tosylates or alcohols containing any other suitable leaving group in a polar solvent such as DMF or acetone and a suitable base (e.g., $Cs_2CO_3$, $K_2CO_3$) at room temperature or elevated temperatures, by Mitsunobu reaction with alcohols activated by a mixture of triphenylphosphine and diethylazadicarboxylate, or by analogous alkylation of the phenolic carboxylic esters or acids of formula 22 (Scheme 9, step a). Reduction of the esters of formula 23 by a suitable reducing agent (e.g., diisobutylaluminium hydride at low temperature, with $LiAlH_4$ at elevated or ambient temperature) in a solvent such as THF provides the corresponding benzylalcohols of formula 24 (Scheme 9, step b). These can then be oxidized to the aldehydes of formula 25, preferably with activated $MnO_2$ as oxidant in dichloromethane (Scheme 9, step c).

Alternatively the introduction of the side-chain can be accomplished by direct alkylation (sequential for unsymmetrical compounds) of the phenolic benzaldehydes of formula 26 providing the desired compounds of formula 25 directly (Scheme 9, step d).

A further well-established route towards the synthesis of benzylaldehydes of formula 28 consists in the reduction of the corresponding benzonitriles of formula 27 by a suitable reducing agent such as diisobutylaluminium hydride at low temperature in a non-protic polar solvent (e.g., THF; Scheme 9, step e).

Additional syntheses of aldehydes of formula III are described in the examples.

buffer (50 mM Tris-HCl at pH 7.4, 5 mM $MgCl_2$ and 0.20% BSA) and subjected to dounce homogenization.

For binding studies, 0.1 mL membrane suspension, corresponding to app. $6\times10^{-15}$ mol receptor, was incubated for 1 h at room temperature with 0.05 nM $^{125}$I-labeled tracer (11-Tyr

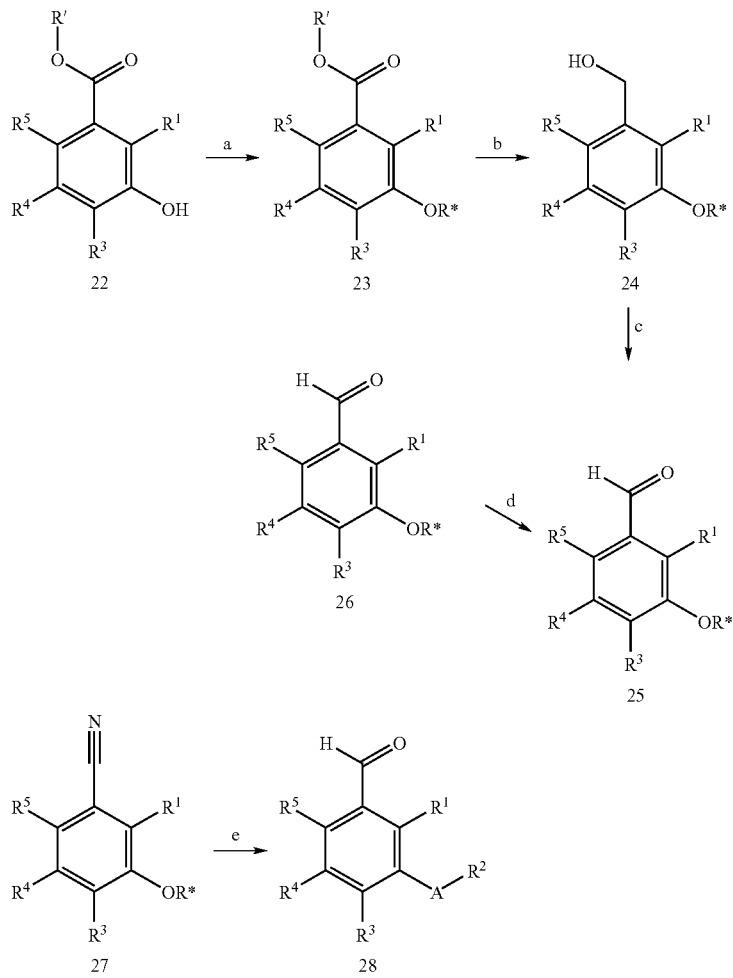

Scheme 9 somatostatin-14, Perkin-Elmer) and either test compounds in varying concentrations or, for the determination of non-specific binding, 0.001 mM non-labeled somatostatin-14. The incubation was stopped by filtration through GF/B glassfiber filters and washing with ice-cold wash buffer (50 mM Tris-HCl at pH 7.4). The bound radioactivity was measured after application of a scintillation cocktail (Microscint 40) and expressed as disintegrations per minute (dpm).

The receptor concentration was determined in a prior saturation experiment where a fixed, arbitrary amount of membranes was incubated with a concentration range of radio-labeled tracer. This allows estimating the total number of specific binding sites per amount of protein (i.e., $B_{max}$), typically between 1 and 5 pmol/mg.

The concentration of the test compound required to result in half maximal inhibition of binding of the radio-labeled tracer ($IC_{50}$) was estimated from a concentration-versus-dpm As described hereinbefore, it has been found that the compounds of formula I possess pharmaceutical activity, in particular they are modulators of somatostatin receptor activity. More particularly, the compounds of the present invention have been found to be antagonists of the somatostatin receptor subtype 5 (SSTR5).

The following tests were carried out in order to determine the activity of the compounds of formula I.

A CHO cell line stably transfected with a plasmid encoding the human subtype 5 somatostatin receptor (GenBank accession number D16827) was obtained from Euroscreen. Cells were cultured and used for binding and functional assays.

Membranes of these cells were prepared by sonication in the presence of protease inhibitors and subsequent fractionating centrifugation. The protein concentration in the membrane preparation was determined using a commercial kit (BCA kit, Pierce, USA). Membranes were stored at −80° C. until use. After thawing, membranes were diluted in assay graph. The binding affinity ($K_i$) was calculated from the $IC_{50}$ by applying the Cheng-Prussoff equation for single binding sites.

For functional experiments, 50,000 cells were incubated in Krebs Ringer HEPES buffer (115 mM NaCl, 4.7 mM KCl, 2.56 mM $CaCl_2$, 1.2 mM $KH_2PO_4$, 1.2 mM $MgSO_4$, 20 mM $NaHCO_3$ and 16 mM HEPES, adjusted to pH 7.4) supplemented with 1 mM IBMX and 0.1% BSA, then stimulated with 0.004 mM forskolin. Simultaneously with forskolin, test compounds in varying concentrations were applied. Cells were then incubated for 20 minutes at 37° C. and 5% $CO_2$. Subsequently, cells were lysed and cAMP concentration measured using a fluorescence-based commercial kit according to the manufacturer (HitHunter cAMP, DiscoverX).

The concentration of the test compound to induce a half maximal effect (i.e., $EC_{50}$) as well as the efficacy as compared to 0.15 nM somatostatin-14 were determined from concentration-versus-fluorescence (arbitrary units) graphs. For the determination of potential antagonism, 0.15 nM somatostatin-14 was applied together with the test compounds and the concentration of the test compounds to half maximally reverse the effect of somatostatin-14 (i.e., $IC_{50}$) were deduced from concentration-versus-fluorescence graphs.

The compounds of the present invention exhibit $K_i$ values of 0.1 nM to 10 □M, preferably $K_i$ values of 1 nM to 500 nM and more preferably 0.1 nM to 100 nM for human subtype 5 somatostatin receptor. The following table shows measured values for selected compounds of the present invention.

| | SSTR5 $K_i$ (nmol/l) |
|---|---|
| Example 8 | 490 |
| Example 137 | 6.4 |
| Example 161 | 31 |

The compounds of formula I and their pharmaceutically acceptable salts and esters can be used as medicaments, e.g., in the form of pharmaceutical preparations for enteral, parenteral or topical administration. They can be administered, for example, perorally, e.g., in the form of tablets, coated tablets, dragées, hard and soft gelatine capsules, solutions, emulsions or suspensions, rectally, e.g., in the form of suppositories, parenterally, e.g., in the form of injection solutions or infusion solutions, or topically, e.g., in the form of ointments, creams or oils.

The production of the pharmaceutical preparations can be effected in a manner which will be familiar to any person skilled in the art by bringing the described compounds of formula I and their pharmaceutically acceptable, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers are, however, required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavor-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 mg to about 1000 mg, especially about 1 mg to about 100 mg, comes into consideration. Depending on the dosage it is convenient to administer the daily dosage in several dosage units.

The pharmaceutical preparations conveniently contain about 0.1-500 mg, preferably 0.5-100 mg, of a compound of formula I.

The present invention will be further explained by reference to the following illustrative examples. They are, however, not intended to limit its scope in any manner.

EXAMPLES

Abbreviations

Ar=argon, BOC=tert-butyloxycarbonyl, DMAc=dimethylacetamide, DMF=N,N-dimethylformamide, DMSO=dimethyl sulfoxide, EI=electron impact (ionization), ESI=electron spray ionisation, HPLC=high performance liquid chromatography, Hyflo Super Cel®=filtration aid (Fluka), ISN=ion spray negative (mode), ISP=ion spray positive (mode), NMP=N-methylpyrrolidone, NMR=nuclear magnetic resonance, MPLC=medium pressure liquid chromatography, MS=mass spectrum, P=protecting group, R=any group, rt=room temperature, THF=tetrahydrofuran, THP=tetrahydropyranyl, X=halogen, Y=any group including heteroatoms and halides.

Example 1

4-Amino-2-[1-(3-ethoxy-4-methoxy-benzyl)-piperidin-4-ylamino]-pyrimidine-5-carbonitrile Step 1

[1-(3-Ethoxy-4-methoxy-benzyl)-piperidin-4-yl]-carbamic acid tert-butyl ester

A mixture of piperidin-4-yl-carbamic acid tert-butyl ester (10.0 g, 50.0 mmol, 1.0 equiv; commercially available), 3-ethoxy-4-methoxy-benzaldehyde (10.8 g, 60.0 mmol, 1.2 equiv; commercially available) and acetic acid (11.4 mL, 200.0 mmol, 4.0 equiv) in ethanol (40 mL) was heated by microwave irradiation to 100° C. for 5 min. Sodium cyano borohydride (6.27 g, 100.0 mmol, 2.0 equiv), dissolved in ethanol (20 mL), was added and the reaction mixture heated by microwave irradiation to 100° C. for an additional time period of 5 min. The solvent was removed under reduced pressure and the crude reaction product extracted from a solution of 1 M NaOH (200 mL) with ethyl acetate (3×100 mL). The combined organic phases were dried over MgSO$_4$, concentrated by evaporation under reduced pressure and the crude material purified with column chromatography on silica eluting with ethyl acetate to yield 9.71 g (53%) of the title compound as a white solid. MS (ISP): 365.3 [M+H]$^+$.

Step 2

1-(3-Ethoxy-4-methoxy-benzyl)-piperidin-4-ylamine (Intermediate A1)

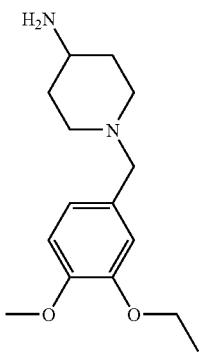

A solution of [1-(3-ethoxy-4-methoxy-benzyl)-piperidin-4-yl]-carbamic acid tert-butyl ester (9.71 g, 26.64 mmol) in ethanol (50 mL) and 4 M HCl in dioxane (75 mL) was stirred at rt for 2 h. The hydrochloric acid was removed under reduced pressure and the crude reaction product extracted from a solution of 1 M NaOH (200 mL) with ethyl acetate (3×100 mL). The combined organic phases were dried over MgSO$_4$ and concentrated by evaporation under reduced pressure yielding 4.69 g (89%) of the title compound as a white solid. The crude material was directly used in the following reaction step without further purification. MS (ISP): 265.0 [M+H]$^+$.

Step 3 (Method A)

To a solution of 1-(3-ethoxy-4-methoxy-benzyl)-piperidin-4-ylamine (39.7 mg, 0.15 mmol, 1.5 equiv; intermediate A1) in dry DMF (1.5 mL) under Ar was added sodium hydride (6.6 mg, 0.15 mmol, 1.5 equiv; 55% free-flowing powder moistened with oil) and the reaction mixture stirred at rt. After 2 h 4-amino-2-chloro-pyrimidine-5-carbonitrile (15.5 mg, 0.10 mmol, 1.0 equiv; commercially available) was added and the mixture heated by microwave irradiation to 140° C. for 1 h. Removal of the solvent under reduced pressure and purification by preparative HPLC on reversed phase eluting with a gradient of acetonitrile/water provided 19.7 mg (34%) of the title compound. MS (ISP): 383.4 [M+H]$^+$.

Example 2

[1-(3-Ethoxy-4-methoxy-benzyl)-piperidin-4-yl]-(5,5,7,7-tetramethyl-5,7-dihydro-furo[3,4-d]pyrimidin-2-yl)-amine Step 1: 4-Dimethylaminomethylene-2,2,5,5-tetramethyl-dihydro-furan-3-one A mixture of 2,2,5,5-tetramethyl-dihydro-furan-3-one (2.84 g, 20.0 mmol, 1.0 equiv; commercially available) and tert-butoxy-bis(dimethylamino)methane (3.65 g, 20.9 mmol, 1.05 equiv; commercially available) was heated to 60° C. for 24 h (in analogy to a procedure described in H. H. Wasserman and J. L. Ives J. Am. Chem. Soc. 1976, 98, 7868-7869). The residue was purified by flash column chromatography on silica eluting with diethyl ether to yield 3.3 g (84% yield) of the title compound. MS (EI): 197 [M]$^+$.

Step 2: 5,5,7,7-Tetramethyl-5,7-dihydro-furo[3,4-d]pyrimidin-2-ylamine

To a solution of 4-dimethylaminomethylene-2,2,5,5-tetramethyl-dihydro-furan-3-one (1.97 g, 10.0 mmol, 1.0 equiv) and guanidine acetate (1.19 g, 10.0 mmol, 1.0 equiv) in ethanol (40 mL) was added sodium methylate (0.54 g, 10.0 mmol, 1.0 equiv) and the reaction mixture heated to 100° C. for 3 h. The solvent was removed under reduced pressure and the reaction product purified by crystallization from a mixture of hot heptane/ethyl acetate to yield 1.3 g (67% yield) of the title compound. MS (EI): 193 [M]$^+$.

Step 3: 2-Chloro-5,5,7,7-tetramethyl-5,7-dihydro-furo[3,4-d]pyrimidine (Intermediate B1)

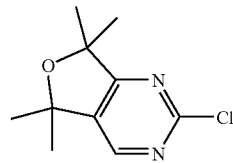

To a solution of 5,5,7,7-tetramethyl-5,7-dihydro-furo[3,4-d]pyrimidin-2-ylamine (38.6 g, 200.0 mmol, 1.0 equiv) in dichloromethane (80 mL) and 37% HCl (70 mL) at 0° C. was added zinc(II) chloride (46.3 g, 340.0 mmol, 1.7 equiv) in portions within 30 min. After the addition was completed, sodium nitrite (23.5 g, 340.0 mmol, 1.7 equiv) was added slowly within 3 h keeping the reaction temperature below 5° C. After stirring for an additional time period of 1 h, the reaction mixture was poured on ice and then extracted with dichloromethane (3×200 mL), the combined organic phases washed with a sat. solution of sodium carbonate (2×100 mL), dried over MgSO$_4$ and concentrated by evaporation under reduced pressure. The reaction product was dissolved in diethyl ether (200 mL), filtered and the organic solvent removed by evaporation under reduced pressure yielding 33.2 g (78%) of the title compound. MS (EI): 213 [M]$^+$.

Step 4 (Method B)

To a solution of 1-(3-ethoxy-4-methoxy-benzyl)-piperidin-4-ylamine (39.7 mg, 0.15 mmol, 1.5 equiv; intermediate A1) in dry DMF (1.5 mL) was added sodium hydride (6.6 mg, 0.15 mmol, 1.5 equiv; 55% free-flowing powder moistened with oil) and the reaction mixture stirred at rt under Ar. After 2 h 2-chloro-5,5,7,7-tetramethyl-5,7-dihydro-furo[3,4-d]pyrimidine (15.5 mg, 0.10 mmol, 1.0 equiv) was added and the mixture heated to 120° C. for 48 h. Removal of the solvent under reduced pressure and purification by preparative HPLC on reversed phase eluting with a gradient of acetonitrile/water provided 8.5 mg (12%) of the title compound. MS (ISP): 441.5 [M+H]$^+$.

Example 3

6-(2,4-Dichloro-phenoxy)-2-[1-(3-ethoxy-4-methoxy-benzyl)-piperidin-4-ylamino]-pyrimidine-4-carboxylic acid methyl ester Step 1: 2-Chloro-6-(2,4-dichloro-phenoxy)-pyrimidine-4-carboxylic acid methyl ester The title compound was prepared in analogy to examples described in WO 01/85700 A2 (Janssen Pharmaceutica) from 2,6-dichloro-pyrimidine-4-carboxylic acid methyl ester (commercially available) and 2,4-dichloro-phenol in 90% yield. MS (ISP): 335.0 [M+H]$^+$.

Step 2 (Method C)

A solution of 2-chloro-6-(2,4-dichloro-phenoxy)-pyrimidine-4-carboxylic acid methyl ester (50.0 mg, 0.15 mmol, 1.0 equiv) and 1-(3-ethoxy-4-methoxy-benzyl)-piperidin-4-ylamine (47.6 mg, 0.18 mmol, 1.2 equiv; intermediate A1) in DMAc (2 mL) was heated by microwave irradiation to 180° C. for 15 min. Removal of the solvent under reduced pressure and purification by preparative HPLC on reversed phase eluting with a gradient of acetonitrile/water provided 15.0 mg (15%) of the title compound. MS (ISP): 561.2 [M+H]$^+$.

Example 4

[1-(3-Ethoxy-4-methoxy-benzyl)-piperidin-4-yl]-(4-thiophen-2-yl-pyrimidin-2-yl)-amine Step 1: 2-Chloro-4-thiophen-2-yl-pyrimidine [CAS RN 83726-75-4]

The title compound was prepared according to D. B. Harden, M. J. Mokrosz and L. Strekowski *J. Org. Chem.* 1988, 53, 4137-4140.

Step 2 (Method D)

A solution of 2-chloro-4-thiophen-2-yl-pyrimidine (29.5 mg, 0.15 mmol, 1.0 equiv) and 1-(3-ethoxy-4-methoxy-benzyl)-piperidin-4-ylamine (47.6 mg, 0.18 mmol, 1.2 equiv; intermediate A1) in DMAc (2 mL) was heated by microwave irradiation to 220° C. for 30 min. Removal of the solvent under reduced pressure and purification by preparative HPLC on reversed phase eluting with a gradient of acetonitrile/water provided 11.5 mg (15%) of the title compound. MS (ISP): 425.3 [M+H]$^+$.

Example 5

[1-(3-Ethoxy-4-methoxy-benzyl)-piperidin-4-yl]-[4-(2-fluoro-phenyl)-quinazolin-2-yl]-amine Step 1: 2-Chloro-4-(2-fluoro-phenyl)-quinazoline [CAS RN 851012-56-1]

The title compound was prepared according to US 05/0096 327 A1 (Warner-Lambert Company).

Step 2 (Method E)

A solution of 2-chloro-4-(2-fluoro-phenyl)-quinazoline (38.8 mg, 0.15 mmol, 1.0 equiv) and 1-(3-ethoxy-4-methoxy-benzyl)-piperidin-4-ylamine (47.6 mg, 0.18 mmol, 1.2 equiv; intermediate A1) in NMP (2 mL) was heated by microwave irradiation to 200° C. for 30 min. Removal of the solvent under reduced pressure and purification by preparative HPLC on reversed phase eluting with a gradient of acetonitrile/water provided 14.9 mg (20%) of the title compound. MS (ISP): 487.5 [M+H]$^+$.

Example 6

7-Chloro-N$^2$-[1-(3-ethoxy-4-methoxy-benzyl)-piperidin-4-yl]-quinazoline-2,4-diamine Method F:
A solution of 2,7-dichloro-quinazolin-4-ylamine (32.1 mg, 0.15 mmol, 1.0 equiv; commercially available) and 1-(3-ethoxy-4-methoxy-benzyl)-piperidin-4-ylamine (47.6 mg, 0.18 mmol, 1.2 equiv; intermediate A1) in DMAc (2 mL) was heated by microwave irradiation to 200° C. for 15 min. Removal of the solvent under reduced pressure and purification by preparative HPLC on reversed phase eluting with a gradient of acetonitrile/water provided 22.0 mg (28%) of the title compound. MS (ISP): 442.4 [M+H]$^+$.

Example 7

(6,7-Dimethoxy-4-piperidin-1-yl-quinazolin-2-yl)-[1-(3-ethoxy-4-methoxy-benzyl)-piperidin-4-yl]-amine Method G:
A solution of 2-chloro-6,7-dimethoxy-4-piperidin-1-yl-quinazoline (30.8 mg, 0.10 mmol 1.0 equiv; commercially available) and 1-(3-ethoxy-4-methoxy-benzyl)-piperidin-4-ylamine (39.7 mg, 0.15 mmol, 1.5 equiv; intermediate A1) in ethylene glycol (2 mL) was heated by microwave irradiation to 220° C. for 20 min. Removal of the solvent under reduced pressure and purification by preparative HPLC on reversed phase eluting with a gradient of acetonitrile/water provided 8.7 mg (16%) of the title compound. MS (ISP): 391.4 [M+H]$^+$.

Example 8

N$^2$-[1-(3-Ethoxy-4-methoxy-benzyl)-piperidin-4-yl]-6-methyl-quinazoline-2,4-diamine Step 1

2-Chloro-6-methyl-quinazolin-4-ylamine [CAS RN 90537-56-7]

The title compound was prepared as described in V. Oakes, H. N. Rydon and K. Undheim *J. Chem. Soc., Abstracts* 1962, 4678-4685.

Step 2 (Method H)

A solution of 2-chloro-6-methyl-quinazolin-4-ylamine (29.1 mg, 0.15 mmol, 1.0 equiv) and 1-(3-ethoxy-4-methoxy-benzyl)-piperidin-4-ylamine (47.6 mg, 0.18 mmol, 1.2 equiv; intermediate A1) in NMP (2 mL) was heated by microwave irradiation to 220° C. for 30 min. Removal of the solvent under reduced pressure and purification by preparative HPLC on reversed phase eluting with a gradient of acetonitrile/water provided 29.7 mg (39%) of the title compound. MS (ISP): 422.5 [M+H]$^+$.

The pyrimidine and quinazoline intermediates B2 to B6 were prepared following literature precedents or as described below.

Synthesis of Pyrimidine and Quinazoline Intermediates B2 to B6 to be used in Table 1 and 2

Intermediate B2

2-Chloro-5-(3,4-dimethoxy-phenyl)-pyrimidine [CAS RN 76972-10-6]

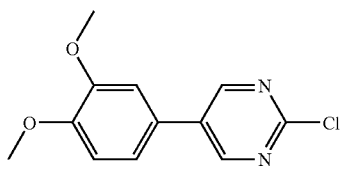

The title compound was prepared according to Z. Sui, J. Guan, M. J. Macielag, W. Jiang, Y. Qiu, P. Kraft, S. Bhattacharjee, T. M. John, E. Craig, D. Haynes-Johnson and J. Clancy *Bioorg. Med. Chem. Lett.* 2003, 13, 761-765.

Intermediate B3

2-Chloro-quinazolin-4-ylamine [CAS RN 59870-43-8]

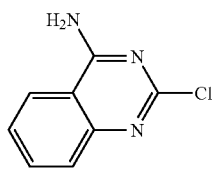

The title compound was prepared according to U.S. Pat. No. 3,956,495 (Eli Lilly and Company).

Intermediate B4

2-Chloro-4-thiazol-2-yl-quinazoline

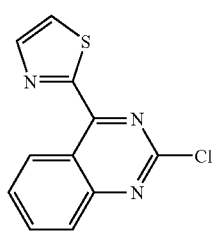

To a 0.5 M solution of 2-thiazolyl zinc bromide in THF (12.1 mL, 6.03 mmol, 1.2 equiv; commercially available from Aldrich) under Ar was added 2,4-dichloro-quinazoline (1.0 g, 5.02 mmol, 1.0 equiv) and tetrakis(triphenylphosphine) palladium(0) (232.2 mg, 0.20 mmol, 0.04 equiv) and the reaction mixture heated by microwave irradiation to 110° C. After 30 min additional 2-thiazolyl zinc bromide in THF (12.1 mL, 6.03 mmol, 1.2 equiv) was added and the reaction mixture heated to 110° C. for another 30 min. The crude reaction mixture was concentrated by evaporation under reduced pressure and the residue purified by silica column chromatography using a MPLC system (CombiFlash Companion, Isco Inc.) eluting with a gradient of heptane/ethyl acetate providing 0.36 g (29%) of the title compound. MS (ISP): 248.3 [M+H]+.

Intermediate B5

2-Chloro-4-pyridin-2-yl-quinazoline [CAS RN 858235-91-3]

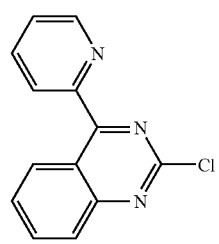

The title compound was prepared as described in WO 05/09 9711 A1 (Icagen Inc. and Astellas Pharma Inc.).

Intermediate B6

2-Chloro-5,6,7-trimethoxy-4-phenyl-quinazoline

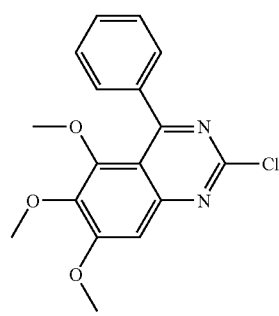

Step 1: 1-Benzoyl-3-(3,4,5-trimethoxy-phenyl)-urea

A mixture of benzamide (0.5 g, 4.13 mmol, 1.0 equiv) and 5-isocyanato-1,2,3-trimethoxy-benzene (1.30 g, 6.19 mmol, 1.5 equiv; commercially available) was heated by microwave irradiation to 140° C. for 30 min. Recrystallization from ethanol provided 1.04 g (76%) of the title compound. MS (ISP): 331.3 [M+H]+.

Step 2: 5,6,7-Trimethoxy-4-phenyl-quinazolin-2-ol

A mixture of 1-benzoyl-3-(3,4,5-trimethoxy-phenyl)-urea (0.9 g, 2.72 mmol, 1.0 equiv) and polyphosphoric acid (7.6 g, 2.79 g/mmol) was heated by microwave irradiation to 120° C. for 20 min. The residue was purified with column chromatography on silica eluting with ethyl acetate and by silica column chromatography using a MPLC system (CombiFlash Companion, Isco Inc.) eluting with a gradient of heptane/ethyl acetate providing 0.21 g (25%) of the title compound. MS (ISP): 313.4 [M+H]+.

Step 3

A solution of 5,6,7-trimethoxy-4-phenyl-quinazolin-2-ol (0.21 g, 0.67 mmol, 1.0 equiv) in phosphorus oxychloride (25.0 mL, 41.9 g, 273.1 mmol, 407.6 equiv) was heated to 110° C. for 1.5 h. The reaction mixture was poured on ice, the pH adjusted to 9 by addition of a 1 M solution of NaOH and the solution extracted with ethyl acetate (3×10 mL). The organic phase was dried over $Na_2SO_4$ and concentrated by evaporation under reduced pressure yielding 25.0 mg (11%) of the title compound which was used in the consecutive step without further purification. MS (ISP): 331.3 $[M+H]^+$.

Examples 9 to 17

According to the procedure described for the synthesis of example 1/step 3 (Method A), example 2/step 4 (Method B), example 3/step 2 (Method C), example 4/step 2 (Method D) and example 5/step 2 (Method E) further pyrimidine and quinazoline derivatives have been synthesized from 1-(3-ethoxy-4-methoxy-benzyl)-piperidin-4-ylamine (intermediate A1) and the respective pyrimidine and quinazoline intermediate as indicated in Table 1. The results are compiled in Table 1 and comprise example 9 to example 17.

TABLE 1

| No. | MW | Compound Name | Preparation | Starting Materials | ISP $[M + H]^+$ found |
|---|---|---|---|---|---|
| 9 | 478.59 | [5-(3,4-dimethoxy-phenyl)-pyrimidin-2-yl]-[1-(3-ethoxy-4-methoxy-benzyl)-piperidin-4-yl]-amine | Method A | 1-(3-ethoxy-4-methoxy-benzyl)-piperidin-4-ylamine (intermediate A1) and 2-chloro-5-(3,4-dimethoxy-phenyl)-pyrimidine (intermediate B2) | 479.5 |
| 10 | 384.52 | [1-(3-ethoxy-4-methoxy-benzyl)-piperidin-4-yl]-(5-propyl-pyrimidin-2-yl)-amine | Method B | 1-(3-ethoxy-4-methoxy-benzyl)-piperidin-4-ylamine (intermediate A1) and 2-chloro-5-propyl-pyrimidine (commercially available) | 385.3 |
| 11 | 421.34 | (5-bromo-pyrimidin-2-yl)-[1-(3-ethoxy-4-methoxy-benzyl)-piperidin-4-yl]-amine | Method B | 1-(3-ethoxy-4-methoxy-benzyl)-piperidin-4-ylamine (intermediate A1) and 5-bromo-2-chloro-pyrimidine (commercially available) | 421.1 |
| 12 | 402.49 | (4,6-dimethoxy-pyrimidin-2-yl)-[1-(3-ethoxy-4-methoxy-benzyl)-piperidin-4-yl]-amine | Method A | 1-(3-ethoxy-4-methoxy-benzyl)-piperidin-4-ylamine (intermediate A1) and 2-chloro-4,6-dimethoxy-pyrimidine (commercially available) | 403.4 |
| 13 | 407.52 | $N^2$-[1-(3-ethoxy-4-methoxy-benzyl)-piperidin-4-yl]-quinazoline-2,4-diamine | Method D | 1-(3-ethoxy-4-methoxy-benzyl)-piperidin-4-ylamine (intermediate A1) and 2-chloro-quinazolin-4-ylamine (intermediate B3) | 408.4 |
| 14 | 475.61 | [1-(3-ethoxy-4-methoxy-benzyl)-piperidin-4-yl]-(4-thiazol-2-yl-quinazolin-2-yl)-amine | Method E | 1-(3-ethoxy-4-methoxy-benzyl)-piperidin-4-ylamine (intermediate A1) and 2-chloro-4-thiazol-2-yl-quinazoline (intermediate B4) | 476.7 |
| 15 | 469.59 | [1-(3-ethoxy-4-methoxy-benzyl)-piperidin-4-yl]-(4-pyridin-2-yl-quinazolin-2-yl)-amine | Method B | 1-(3-ethoxy-4-methoxy-benzyl)-piperidin-4-ylamine (intermediate A1) and 2-chloro-4-pyridin-2-yl-quinazoline (intermediate B5) | 470.5 |
| 16 | 558.68 | [1-(3-ethoxy-4-methoxy-benzyl)-piperidin-4-yl]-(5,6,7-trimethoxy-4-phenyl-quinazolin-2-yl)-amine | Method E | 1-(3-ethoxy-4-methoxy-benzyl)-piperidin-4-ylamine (intermediate A1) and 2-chloro-5,6,7-trimethoxy-4-phenyl-quinazoline (intermediate B6) | 559.5 |
| 17 | 403.49 | (4,6-dimethoxy-[1,3,5]triazin-2-yl)-[1-(3-ethoxy-4-methoxy-benzyl)-piperidin-4-yl]-amine | Method C | 1-(3-ethoxy-4-methoxy-benzyl)-piperidin-4-ylamine (intermediate A1) and 2-chloro-4,6-dimethoxy-[1,3,5]triazine (commercially available) | 404.5 |

Example 18

4-Amino-2-[1-(4-chloro-3-ethoxy-benzyl)-piperidin-4-ylamino]-pyrimidine-5-carbonitrile Step 1: [1-(4-Chloro-3-ethoxy-benzyl)-piperidin-4-yl]-carbamic acid tert-butyl ester A mixture of piperidin-4-yl-carbamic acid tert-butyl ester (5.0 g, 25.0 mmol, 1.0 equiv; commercially available), 4-chloro-3-ethoxy-benzaldehyde (5.54 g, 30.0 mmol, 1.2 equiv; intermediate D3, vide infra) and acetic acid (5.7 mL, 100.0 mmol, 4.0 equiv) in ethanol (25 mL) was heated by microwave irradiation to 100° C. for 5 min. Sodium cyano borohydride (3.14 g, 50.0 mmol, 2.0 equiv), dissolved in ethanol (10 mL), was added and the reaction mixture heated by microwave irradiation to 100° C. for an additional time period of 10 min. The solvent was removed under reduced pressure and the crude reaction product extracted from a solution of 1 M NaOH (100 mL) with ethyl acetate (3×100 mL). The combined organic phases were dried over $MgSO_4$, concentrated by evaporation under reduced pressure and the crude material purified by silica column chromatography using a MPLC system (CombiFlash Companion, Isco Inc.) eluting with a gradient of heptane/ethyl acetate providing 3.91 g (42%) of the title compound. MS (ISP): 369.0 [M+H]+.

Step 2: 1-(4-Chloro-3-ethoxy-benzyl)-piperidin-4-ylamine (Intermediate A2)

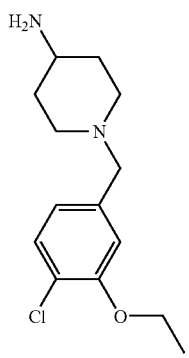

A solution of [1-(4-chloro-3-ethoxy-benzyl)-piperidin-4-yl]-carbamic acid tert-butyl ester (0.78 g, 2.12 mmol) in ethanol (10 mL) and 4 M HCl (15 mL) was stirred at rt for 2 h. The hydrochloric acid was removed under reduced pressure and the crude reaction product extracted from a solution of 1 M NaOH (50 mL) with ethyl acetate (3×50 mL). The combined organic phases were dried over $MgSO_4$ and concentrated by evaporation under reduced pressure yielding 0.32 g (57%) of a white solid. The crude material was directly used in the following reaction step without further purification. MS (ISP): 269.0 [M+H]+.

Step 3 (Method I)

To a solution of 1-(4-chloro-3-ethoxy-benzyl)-piperidin-4-ylamine (40.3 mg, 0.15 mmol, 1.2 equiv; intermediate A2) in dry DMF (1.5 mL) under Ar was added sodium hydride (6.6 mg, 0.15 mmol, 1.2 equiv; 55% free-flowing powder moistened with oil) and the reaction mixture stirred at rt. After 2 h 4-amino-2-chloro-pyrimidine-5-carbonitrile (19.3 mg, 0.125 mmol, 1.0 equiv; commercially available) was added and the mixture heated by microwave irradiation to 140° C. for 1 h. Removal of the solvent under reduced pressure and purification by preparative HPLC on reversed phase eluting with a gradient of acetonitrile/water provided 17.1 mg (35%) of the title compound. MS (ISP): 387.3 [M+H]+.

Example 19

[1-(4-Chloro-3-ethoxy-benzyl)-piperidin-4-yl]-(4-thiophen-2-yl-pyrimidin-2-yl)-amine Method J:

A solution of 2-chloro-4-thiophen-2-yl-pyrimidine (49.2 mg, 0.25 mmol, 1.0 equiv; example 4/step 1) and 1-(4-chloro-3-ethoxy-benzyl)-piperidin-4-ylamine (80.6 mg, 0.30 mmol, 1.2 equiv; intermediate A2) in DMAc (2 mL) was heated by microwave irradiation to 220° C. for 1 h. Removal of the solvent under reduced pressure and purification by preparative HPLC on reversed phase eluting with a gradient of acetonitrile/water provided 14.3 mg (13%) of the title compound. MS (ISP): 429.5 [M+H]+.

Synthesis of Pyrimidine and Quinazoline Intermediates B7 and B8 to be used in Table 2

Intermediate B7

(2,6-Dichloro-pyrimidin-4-yl)-isopropyl-amine [CAS RN 30297-43-9]

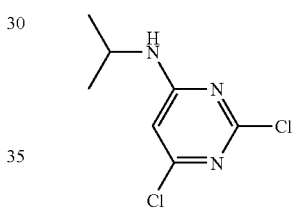

The title compound was prepared according to DE 2006 145 A1 (Sandoz A G).

Intermediate B8

4-Azetidin-1-yl-2,6-dichloro-pyrimidine [CAS RN 202467-33-2]

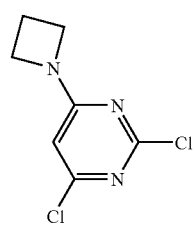

The title compound was prepared according to EP 0815 861 A1 (F. Hoffmann-La Roche A G).

Examples 20 to 26

According to the procedure described for the synthesis of example 2/step 4 (Method B), example 18/step 3 (Method I) and example 19 (Method J) further pyrimidine and quinazoline derivatives have been synthesized from 1-(4-chloro-3-ethoxy-benzyl)-piperidin-4-ylamine (intermediate A2) and the respective pyrimidine and quinazoline intermediate as indicated in Table 2. The results are compiled in Table 2 and comprise example 20 to example 26.

TABLE 2

| No. | MW | Compound Name | Preparation | Starting Materials | ISP [M + H]+ found |
|---|---|---|---|---|---|
| 20 | 374.92 | [1-(4-chloro-3-ethoxy-benzyl)-piperidin-4-yl]-(4,6-dimethyl-pyrimidin-2-yl)-amine | Method I | 1-(4-chloro-3-ethoxy-benzyl)-piperidin-4-ylamine (intermediate A2) and 2-chloro-4,6-dimethyl-pyrimidine (commercially available) | 375.3 |
| 21 | 418.93 | 2-[1-(4-chloro-3-ethoxy-benzyl)-piperidin-4-ylamino]-6-methyl-pyrimidine-4-carboxylic acid methyl ester | Method B | 1-(4-chloro-3-ethoxy-benzyl)-piperidin-4-ylamine (intermediate A2) and 2-chloro-6-methyl-pyrimidine-4-carboxylic acid methyl ester (commercially available) | 419.4 |
| 22 | 445.01 | [1-(4-chloro-3-ethoxy-benzyl)-piperidin-4-yl]-(5,5,7,7-tetramethyl-5,7-dihydro-furo[3,4-d]pyrimidin-2-yl)-amine | Method B | 1-(4-chloro-3-ethoxy-benzyl)-piperidin-4-ylamine (intermediate A2) and 2-chloro-5,5,7,7-tetramethyl-5,7-dihydro-furo[3,4-d]pyrimidine (intermediate B1) | 445.3 |
| 23 | 438.40 | 6-chloro-$N^2$-[1-(4-chloro-3-ethoxy-benzyl)-piperidin-4-yl]-$N^4$-isopropyl-pyrimidine-2,4-diamine | Method B | 1-(4-chloro-3ethoxy-benzyl)-piperidin-4-ylamine (intermediate A2) and (2,6-dichloro-pyrimidin-4-yl)-isopropyl-amine (intermediate B7) | 438.3 |
| 24 | 436.39 | (4-azetidin-1-yl-6-chloro-pyrimidin-2-yl)-[1-(4-chloro-3-ethoxy-benzyl)-piperidin-4-yl]-amine | Method B | 1-(4-chloro-3-ethoxy-benzyl)-piperidin-4-ylamine (intermediate A2) and 4-azetidin-1-yl-2,6-dichloro-pyrimidine (intermediate B8) | 436.3 |
| 25 | 411.94 | $N^2$-[1-(4-chloro-3-ethoxy-benzyl)-piperidin-4-yl]-quinazoline-2,4-diamine | Method B | 1-(4-chloro-3-ethoxy-benzyl)-piperidin-4-ylamine (intermediate A2) and 2-chloro-quinazolin-4-ylamine (intermediate B3) | 412.4 |
| 26 | 412.92 | 2-[1-(4-chloro-3-ethoxy-benzyl)-piperidin-4-ylamino]-quinazolin-4-ol | Method J | 1-(4-chloro-3-ethoxy-benzyl)-piperidin-4-ylamine (intermediate A2) and 2-chloro-quinazolin-4-ol (commercially available) | 413.3 |

Example 27

[1-(3-Ethoxy-4-methoxy-benzyl)-piperidin-4-yl]-(5-ethyl-pyrimidin-2-yl)-amine

Step 1: 4-(5-Ethyl-pyrimidin-2-ylamino)-piperidine-1-carboxylic acid ethyl ester A mixture of 2-chloro-5-ethylpyrimidine (5.0 g, 35.1 mmol, 1.0 equiv; commercially available), ethyl 4-amino-1-piperidine carboxylate (7.2 g, 42.1 mmol, 1.2 equiv) and triethylamine (5.3 g, 52.7 mmol, 1.5 equiv) in ethylene glycol (60 mL) was heated by microwave irradiation to 200° C. for 15 min. To the crude reaction mixture was added water (120 mL) and the solution extracted with dichloromethane (3×20 mL). The combined organic layers were washed with water (20 mL) and a sat. solution of sodium chloride (20 mL), dried over MgSO$_4$ and evaporated under reduced pressure to give an amber oil. The residue was purified by column chromatography on silica eluting with heptane/ethyl acetate (1:1) followed by recrystallization from heptane (200 mL) to afford 4.53 g (46%) of the title compound as a white solid. MS (ISP): 279.3 [M+H]+.

Step 2: (5-Ethyl-pyrimidin-2-yl)-piperidin-4-yl-amine (Intermediate C1)

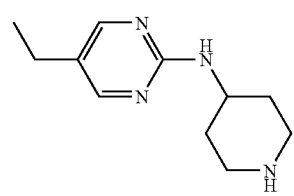

A solution of 4-(5-ethyl-pyrimidin-2-ylamino)-piperidine-1-carboxylic acid tert-butyl ester (4.53 g, 16.3 mmol) in 48%

HBr in water (45 mL) and acetic acid (45 mL) was heated to 100° C. After 4 h the solvents were removed under reduced pressure and the crude reaction product extracted from a solution of 1 M NaOH (200 mL) with ethyl acetate (3×100 mL). The combined organic phases were dried over MgSO$_4$ and concentrated by evaporation under reduced pressure to yield 3.1 g (92%) of the title compound which was directly used in the consecutive step. MS (ISP): 207.1 [M+H]$^+$.

Step 3

To a solution of (5-ethyl-pyrimidin-2-yl)-piperidin-4-yl-amine (30.9 mg, 0.15 mmol, 1.0 equiv; intermediate C1) and 3-ethoxy-4-methoxy-benzaldehyde (32.4 mg, 0.18 mmol, 1.2 equiv; commercially available) in ethanol (2 mL) was added acetic acid (27.0 mg, 0.45 mmol, 3.0 equiv) and the mixture stirred at 55° C. After 1 h sodium cyano borohydride (47.1 mg, 0.75 mmol, 5.0 equiv), dissolved in ethanol (0.5 mL), was added and the mixture stirred at 55° C. over night. Removal of the solvent under reduced pressure and purification by preparative HPLC on reversed phase eluting with a gradient of acetonitrile/water provided 21.0 mg (38%) of the title compound. MS (ESI): 371.5 [M+H]$^+$.

The pyrimidine, quinazoline, pteridine and triazine piperidine intermediates C2 to C25 were prepared following literature precedents or as described below.

Synthesis of Pyrimidine, Quinazoline, Pteridine and Triazine Piperidine Intermediates C2 to C25 to be used in Table 3

Intermediate C2

(4,6-Dimethyl-pyrimidin-2-yl)-piperidin-4-yl-amine dihydrochloride

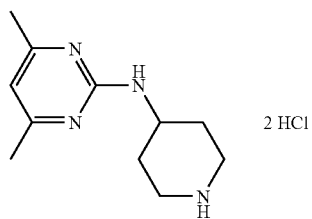

Step 1: 4-(4,6-Dimethyl-pyrimidin-2-ylamino)-piperidine-1-carboxylic acid tert-butyl ester A mixture of 2-chloro-4,6-dimethyl-pyrimidine (1.50 g, 10.52 mmol, 1.0 equiv; commercially available), 4-amino-piperidine-1-carboxylic acid tert-butyl ester (2.53 g, 12.62 mmol, 1.2 equiv; commercially available) and N-ethyl diisopropylamine (2.15 mL, 1.63 g, 12.62 mmol, 1.2 equiv) in acetonitrile (8 mL) and DMAc (2 mL) was heated by microwave irradiation to 160° C. for 1 h and then to 180° C. for 30 min. The reaction mixture was concentrated under reduced pressure and the crude material purified by silica column chromatography using a MPLC system (CombiFlash Companion, Isco Inc.) eluting with a gradient of heptane/ethyl acetate providing 1.47 g (46%) of the title compound. MS (ISP): 307.5 [M+H]$^+$.

Step 2

A solution of 4-(4,6-dimethyl-pyrimidin-2-ylamino)-piperidine-1-carboxylic acid tert-butyl ester (1.47 g, 4.80 mmol) in ethanol (20 mL) and 4 M HCl in dioxane (40 mL) was stirred at rt for 2 h. The solvent was removed under reduced pressure and the crude product used in the consecutive step without further purification assuming quantitative deprotection and formation of the dihydrochloride salt. MS (ISP): 207.3 [M+H]$^+$.

Intermediate C3

Piperidin-4-yl-pyrimidin-2-yl-amine dihydrobromide

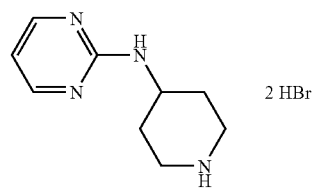

Step 1: 4-(Pyrimidin-2-ylamino)-piperidine-1-carboxylic acid ethyl ester

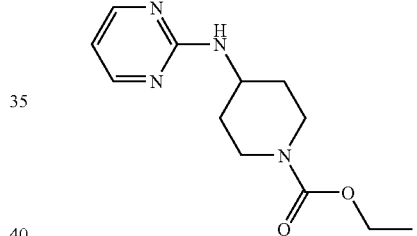

A mixture of 2-chloro-pyrimidine (2.00 g, 17.46 mmol, 1.0 equiv), 4-amino-piperidine-1-carboxylic acid ethyl ester (3.61 g, 20.95 mmol, 1.2 equiv) and copper(I) bromide (0.25 g, 1.75 mmol, 0.1 equiv) in anhydrous DMAc (5 mL) and triethylamine (5 mL) was heated by microwave irradiation to 200° C. for 20 min. The organic phase was concentrated under reduced pressure and the residue extracted with ethyl acetate (3×50 mL). The combined organic phases were dried over MgSO$_4$ and the product purified by silica column chromatography using a MPLC system (CombiFlash Companion, Isco Inc.) eluting with a gradient of dichloromethane (+1% triethylamine)/methanol providing 1.07 g (25%) of the title compound. MS (ISP): 251.4 [M+H]$^+$.

Step 2

A solution of 4-(pyrimidin-2-ylamino)-piperidine-1-carboxylic acid ethyl ester (1.07 g, 4.28 mmol) in 48% HBr in water (60 mL) was heated to reflux for 18 h. The solvent was removed under reduced pressure and the crude product used in the consecutive step without further purification assuming quantitative deprotection and formation of the dihydrobromide salt. MS (ISP): 179.3 [M+H]$^+$.

Intermediate C4

2-(Piperidin-4-ylamino)-pyrimidine-4-carboxylic acid methyl ester dihydrochloride

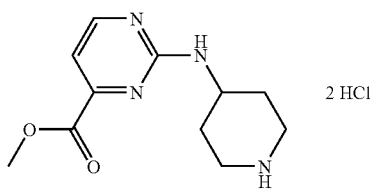

Step 1: 2-Chloro-pyrimidine-4-carboxylic acid methyl ester [CAS RN 149849-94-5]

To a solution of 2,6-dichloro-pyrimidine-4-carboxylic acid methyl ester (2.0 g, 9.66 mmol, 1.0 equiv; commercially available from Peakdale Molecular, UK) in ethanol (50 mL) was added palladium on activated charcoal 5% (0.10 g, 0.048 mmol, 0.5 equiv) and the reaction vessel filled with hydrogen (2.5 bar). After stirring at rt for 18 h, the reaction mixture was filtered over celite, concentrated under reduced pressure and the residue purified by silica column chromatography using a MPLC system (CombiFlash Companion, Isco Inc.) eluting with a gradient of heptane/ethyl acetate providing 0.19 g (11%) of the title compound. $^1$H NMR (300 MHz, CDCl$_3$): δ 3.97 (s, 3H), 7.89 (d, J=4.9 Hz, 1H), 8.81 (d, J=4.9 Hz, 1H). $^{13}$C NMR (75 MHz, CDCl$_3$): δ 52.67, 118.22, 156.45, 160.62, 161.18, 162.31. MS (ISP): 172.5 [M+H]$^+$.

Step 2: 2-(1-tert-Butoxycarbonyl-piperidin-4-ylamino)-pyrimidine-4-carboxylic acid methyl ester A mixture of 2-chloro-pyrimidine-4-carboxylic acid methyl ester (0.62 g, 3.59 mmol, 1.0 equiv), 4-amino-piperidine-1-carboxylic acid tert-butyl ester (0.86 g, 4.31 mmol, 1.2 equiv; commercially available) and N-ethyl diisopropylamine (0.73 mL, 0.56 g, 4.31 mmol, 1.2 equiv) in acetonitrile (60 mL) was heated by microwave irradiation to 110° C. After stirring for 40 min, the reaction mixture was concentrated under reduced pressure and the residue purified by silica column chromatography using a MPLC system (CombiFlash Companion, Isco Inc.) eluting with a gradient of heptane/ethyl acetate providing 0.48 g (34%) of the title compound. MS (ISP): 337.5 [M+H]$^+$.

Step 3

A solution of 2-(1-tert-butoxycarbonyl-piperidin-4-ylamino)-pyrimidine-4-carboxylic acid methyl ester (0.48 g, 1.43 mmol) in ethanol (10 mL) and 4 M HCl in dioxane (10 mL) was stirred at rt for 2 h. The solvent was removed under reduced pressure and the crude product used in the consecutive step without further purification assuming quantitative deprotection and formation of the dihydrochloride salt. MS (ISP): 237.4 [M+H]$^+$.

Intermediate C5

Piperidin-4-yl-(4-trifluoromethyl-pyrimidin-2-yl)-amine dihydrochloride

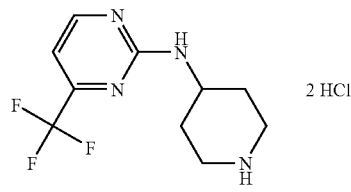

Step 1: 4-(4-Trifluoromethyl-pyrimidin-2-ylamino)-piperidine-1-carboxylic acid tert-butyl ester A mixture of 2-chloro-4-trifluoromethyl-pyrimidine (2.15 g, 11.78 mmol, 1.0 equiv; commercially available) and 4-amino-piperidine-1-carboxylic acid tert-butyl ester (3.07 g, 15.31 mmol, 1.3 equiv; commercially available) in anhydrous DMF (15 mL) and triethylamine (5 mL) was heated to 100° C. for 3 h. The organic phase was concentrated under reduced pressure and the residue extracted with dichloromethane (3×50 mL) from a sat. solution of sodium bicarbonate (100 mL). The combined organic phases were dried over MgSO$_4$ and the product purified with column chromatography on silica eluting with heptane/ethyl acetate (5:1+1% triethylamine) providing 3.47 g (85%) of the title compound. MS (ISP): 347.1 [M+H]$^+$.

Step 2

A solution of 4-(4-trifluoromethyl-pyrimidin-2-ylamino)-piperidine-1-carboxylic acid tert-butyl ester (3.47 g, 10.02 mmol) in ethanol (50 mL) and 4 M HCl in dioxane (75 mL) was stirred at rt for 2 h. The solvent was removed under reduced pressure and the crude product used in the consecutive step without further purification assuming quantitative deprotection and formation of the dihydrochloride salt. MS (ISP): 247.1 [M+H]$^+$.

Intermediate C6

2-(Piperidin-4-ylamino)-pyrimidin-4-ol dihydrochloride

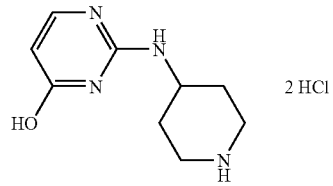

Step 1: 4-(4-Methoxy-pyrimidin-2-ylamino)-piperidine-1-carboxylic acid ethyl ester A mixture of 2-chloro-4-methoxy-pyrimidine (3.64 g, 25.21 mmol, 1.0 equiv; commercially available) and 4-amino-piperidine-1-carboxylic acid ethyl ester (4.34 g, 25.21 mmol, 1.0 equiv; commercially available) in anhydrous NMP (32 mL) was heated by microwave irradiation to 200° C. for 15 min. The organic phase was concentrated under reduced pressure and the residue extracted with ethyl acetate (3×50 mL) from a solution of 1 M NaOH (100 mL). The combined organic phases were dried over MgSO$_4$ and the product purified with column chromatography on silica eluting with heptane/ethyl acetate (1:1) providing 2.93 g (42%) of the title compound. MS (ISP): 281.3 [M+H]$^+$.

Step 2

A solution of 4-(4-methoxy-pyrimidin-2-ylamino)-piperidine-1-carboxylic acid ethyl ester (1.5 g, 5.35 mmol) in ethanol (50 mL) and conc. HCl (75 mL) was heated to reflux for 18 h. The solvent was removed under reduced pressure and the crude product used in the consecutive step without further purification assuming quantitative deprotection and formation of the dihydrochloride salt. MS (ISP): 194.9 [M+H]$^+$.

Intermediate C7

2-(Piperidin-4-ylamino)-pyrimidine-5-carboxylic acid dihydrochloride

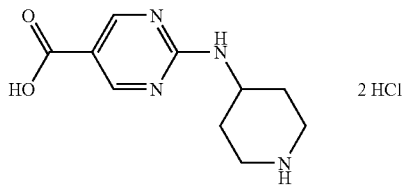

Step 1: 4-(5-Bromo-pyrimidin-2-ylamino)-piperidine-1-carboxylic acid tert-butyl ester A mixture of 5-bromo-2-chloro-pyrimidine (1.67 g, 8.63 mmol, 1.0 equiv; commercially available) and 4-amino-piperidine-1-carboxylic acid tert-butyl ester (2.08 g, 10.36 mmol, 1.2 equiv; commercially available) in acetonitrile (10 mL) was heated by microwave irradiation to 120° C. for 40 min. The organic phase was concentrated under reduced pressure and the residue purified by silica column chromatography using a MPLC system (CombiFlash Companion, Isco Inc.) eluting with a gradient of heptane/ethyl acetate providing 1.48 g (48%) of the title compound. MS (ISP): 357.3 [M+H]$^+$.

Step 2: 4-(5-Cyano-pyrimidin-2-ylamino)-piperidine-1-carboxylic acid tert-butyl ester A mixture of 4-(5-bromo-pyrimidin-2-ylamino)-piperidine-1-carboxylic acid tert-butyl ester (1.00 g, 2.80 mmol, 1.0 equiv), copper(I) cyanide (0.38 g, 4.20 mmol, 1.5 equiv), tris(dibenzylideneacetone)dipalladium(0) (0.58 g, 0.56 mmol, 0.2 equiv) and 1,1'-bis(diphenylphosphino)ferrocene (0.31 g, 0.56 mmol, 0.2 equiv) in DMAc (8 mL) was heated by microwave irradiation to 180° C. for 30 min. The organic phase was concentrated under reduced pressure and the residue purified by silica column chromatography using a MPLC system (CombiFlash Companion, Isco Inc.) eluting with a gradient of heptane/ethyl acetate providing 0.20 g (23%) of the title compound. MS (ISP): 304.4 [M+H]$^+$.

Step 3: 2-(1-tert-Butoxycarbonyl-piperidin-4-ylamino)-pyrimidine-5-carboxylic acid To a solution of 4-(5-cyano-pyrimidin-2-ylamino)-piperidine-1-carboxylic acid tert-butyl ester (0.2 g, 0.66 mmol, 1.0 equiv) in ethanol (3 mL) was added a solution of 1 M NaOH (3.3 mL, 3.29 mmol, 5.0 equiv) and the reaction mixture heated by microwave irradiation to 120° C. for 1 h. The organic phase was concentrated under reduced pressure and the residue purified by silica column chromatography using a MPLC system (CombiFlash Companion, Isco Inc.) eluting with a gradient of dichloromethane/methanol providing 0.18 g (87%) of the title compound. MS (ISP): 323.4 [M+H]$^+$.

Step 4

A solution of 2-(1-tert-butoxycarbonyl-piperidin-4-ylamino)-pyrimidine-5-carboxylic acid (0.18 g, 0.56 mmol) in ethanol (5 mL) and 4 M HCl in dioxane (10 mL) was stirred at rt for 2 h. The solvent was removed under reduced pressure and the crude product used in the consecutive step without further purification assuming quantitative deprotection and formation of the dihydrochloride salt. MS (ISP): 223.3 [M+H]$^+$.

Intermediate C8

(4,6-Dimethoxy-pyrimidin-2-yl)-piperidin-4-ylamine dihydrochloride

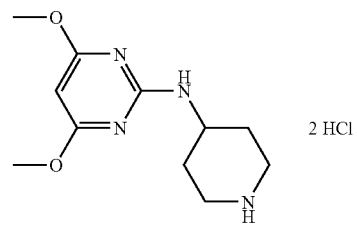

Step 1: 4-(4,6-Dimethoxy-pyrimidin-2-ylamino)-piperidine-1-carboxylic acid tert-butyl ester A mixture of 2-chloro-4,6-dimethoxy-pyrimidine (3.35 g, 19.19 mmol, 1.0 equiv; commercially available) and 4-amino-piperidine-1-carboxylic acid tert-butyl ester (5.0 g, 24.94 mmol, 1.3 equiv; commercially available) in anhydrous DMF (100 mL) was heated to 100° C. for 48 h. The organic phase was concentrated under reduced pressure and the residue extracted with ethyl acetate (3×50 mL) from a solution of 1 M NaOH (100 mL). The combined organic phases were dried over MgSO$_4$ and the product purified by silica column chromatography using a MPLC system (CombiFlash Companion, Isco Inc.) eluting with a gradient of heptane/ethyl acetate providing 1.97 g (30%) of the title compound. MS (ISP): 339.3 [M+H]$^+$.

Step 2

A solution of 4-(4,6-dimethoxy-pyrimidin-2-ylamino)-piperidine-1-carboxylic acid tert-butyl ester (1.97 g, 5.82 mmol) in ethanol (50 mL) and 4 M HCl in dioxane (75 mL) was stirred at rt for 2 h. The solvent was removed under reduced pressure and the crude product used in the consecutive step without further purification assuming quantitative deprotection and formation of the dihydrochloride salt. MS (ISP): 239.1 [M+H]+.

Intermediate C9

Piperidin-4-yl-(5,5,7,7-tetramethyl-5,7-dihydro-furo[3,4-d]pyrimidin-2-yl)-amine dihydrochloride

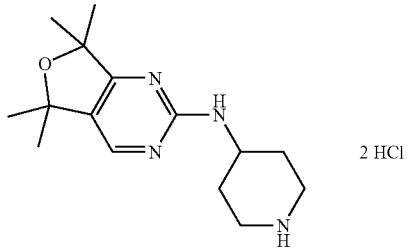

Step 1: 4-(5,5,7,7-Tetramethyl-5,7-dihydro-furo[3,4-d]pyrimidin-2-ylamino)-piperidine-1-carboxylic acid tert-butyl ester A mixture of 2-chloro-5,5,7,7-tetramethyl-5,7-dihydro-furo[3,4-d]pyrimidine (1.60 g, 7.52 mmol, 1.0 equiv; intermediate B1) and 4-amino-piperidine-1-carboxylic acid tert-butyl ester (1.81 g, 9.03 mmol, 1.2 equiv; commercially available) in anhydrous DMF (6 mL) was heated by microwave irradiation to 150° C. for 30 min. The organic phase was concentrated under reduced pressure and the residue purified with column chromatography on silica eluting with a gradient of heptane/ethyl acetate (10:1)→ethyl acetate providing 1.26 g (45%) of the title compound. MS (ISP): 377.4 [M+H]+.

Step 2

A solution of 4-(5,5,7,7-tetramethyl-5,7-dihydro-furo[3,4-d]pyrimidin-2-ylamino)-piperidine-1-carboxylic acid tert-butyl ester (1.23 g, 3.27 mmol) in 4 M HCl in dioxane (20 mL) was stirred at rt for 2 h. The solvent was removed under reduced pressure and the crude product used in the consecutive step without further purification assuming quantitative deprotection and formation of the dihydrochloride salt. MS (ISP): 277.3 [M+H]+.

Intermediate C10

4-Amino-2-(piperidin-4-ylamino)-pyrimidine-5-carbonitrile dihydrochloride

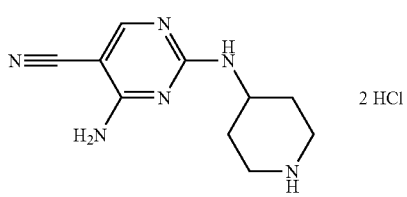

Step 1: 4-(4-Amino-5-cyano-pyrimidin-2-ylamino)-piperidine-1-carboxylic acid tert-butyl ester A mixture of 4-amino-2-chloro-pyrimidine-5-carbonitrile (2.0 g, 12.94 mmol, 1.0 equiv; commercially available) and 4-amino-piperidine-1-carboxylic acid tert-butyl ester (3.1 g, 15.53 mmol, 1.2 equiv; commercially available) in anhydrous DMF (20 mL) was heated to 60° C. for 4 h. The organic phase was concentrated under reduced pressure and the crude product purified by crystallization from ethyl acetate providing 3.02 g (74%) of the title compound. MS (ISN): 317.1 [M–H]−.

Step 2

To a suspension of 4-(4-amino-5-cyano-pyrimidin-2-ylamino)-piperidine-1-carboxylic acid tert-butyl ester (3.02 g, 9.49 mmol) in dioxane (10 mL) and THF (10 mL) was added 4 M HCl in dioxane (50 mL) and the reaction mixture stirred at rt for 18 h. The solvent was removed under reduced pressure and the crude product used in the consecutive step without further purification assuming quantitative deprotection and formation of the dihydrochloride salt. MS (ISP): 219.1 [M+H]+.

Intermediate C11

(5-Phenyl-pyrimidin-2-yl)-piperidin-4-yl-amine dihydrochloride

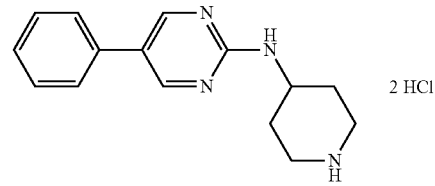

Step 1: 4-(5-Phenyl-pyrimidin-2-ylamino)-piperidine-1-carboxylic acid tert-butyl ester A mixture of 2-chloro-5-phenyl-pyrimidine (1.2 g, 6.29 mmol, 1.0 equiv; commercially available from Acme Bioscience Inc., USA), 4-amino-piperidine-1-carboxylic acid tert-butyl ester (2.52 g, 12.59 mmol, 2.0 equiv; commercially available) and triethylamine (1.75 mL, 1.27 g, 12.59 mmol, 2.0 equiv) in anhydrous acetonitrile (5 mL) was heated by microwave irradiation to 150° C. for 30 min. The organic phase was concentrated under reduced pressure and the crude material purified by silica column chromatography using a MPLC system (CombiFlash Companion, Isco Inc.) eluting with a gradient of heptane/ethyl acetate providing 1.06 g (48%) of the title compound. MS (ISP): 355.5 [M+H]+.

Step 2

To a solution of 4-(5-phenyl-pyrimidin-2-ylamino)-piperidine-1-carboxylic acid tert-butyl ester (1.06 g, 3.00 mmol) in ethanol (10 mL) was added 4 M HCl in dioxane (10 mL) and the reaction mixture stirred at rt for 2 h. The solvent was removed under reduced pressure and the crude product used in the consecutive step without further purification assuming quantitative deprotection and formation of the dihydrochloride salt. MS (ISP): 255.6 [M+H]+.

Intermediate C12

[5-(4-Methoxy-phenyl)-pyrimidin-2-yl]-piperidin-4-yl-amine dihydrochloride

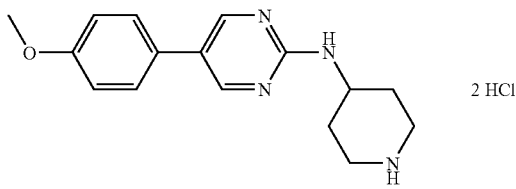

Step 1: 4-[5-(4-Methoxy-phenyl)-pyrimidin-2-ylamino]-piperidine-1-carboxylic acid tert-butyl ester To a solution of 4-amino-piperidine-1-carboxylic acid tert-butyl ester (4.0 g, 20.0 mmol, 1.3 equiv; commercially available) in dry DMF (100 mL) under Ar was added sodium hydride (1.01 g, 23.1 mmol, 1.5 equiv; 55% free-flowing powder moistened with oil) and the reaction mixture stirred at rt. After 2 h 2-chloro-5-(4-methoxy-phenyl)-pyrimidine (3.39 g, 15.4 mmol, 1.0 equiv; commercially available from Peakdale Molecular, UK) was added and the mixture stirred at rt for 48 h. The solvent was removed under reduced pressure and the crude reaction product extracted from a solution of 1 M NaOH (100 mL) with ethyl acetate (3×100 mL). The combined organic phases were dried over MgSO$_4$, concentrated by evaporation under reduced pressure and the crude material purified by silica column chromatography using a MPLC system (CombiFlash Companion, Isco Inc.) eluting with a gradient of heptane/ethyl acetate to provide 0.55 g (9%) of the title compound. MS (ISP): 385.4 [M+H]$^+$.

Step 2

To a solution of 4-[5-(4-methoxy-phenyl)-pyrimidin-2-ylamino]-piperidine-1-carboxylic acid tert-butyl ester (0.55 g, 1.43 mmol) in ethanol (10 mL) was added 4 M HCl in dioxane (10 mL) and the reaction mixture stirred at rt for 2 h. The solvent was removed under reduced pressure and the crude product used in the consecutive step without further purification assuming quantitative deprotection and formation of the dihydrochloride salt. MS (ISP): 285.5 [M+H]$^+$.

Intermediate C13

Piperidin-4-yl-(5-pyridin-3-yl-pyrimidin-2-yl)-amine dihydrochloride

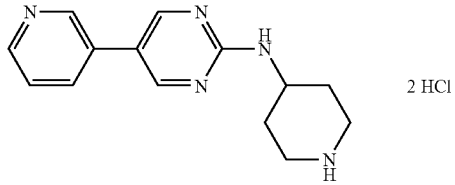

Step 1: 4-(5-Bromo-pyrimidin-2-ylamino)-piperidine-1-carboxylic acid tert-butyl ester To a solution of 5-bromo-2-chloro-pyrimidine (3.0 g, 15.51 mmol, 1.0 equiv; commercially available) and 4-amino-piperidine-1-carboxylic acid tert-butyl ester (3.42 g, 17.06 mmol, 1.1 equiv; commercially available) in DMAc (50 mL) was added anhydrous K$_2$CO$_3$ (5.36 g, 38.78 mmol, 2.5 equiv) and the reaction mixture stirred at rt for 18 h. The reaction mixture was heated for an additional time period of 2 h to 60° C. and then extracted with ethyl acetate (3×100 mL) and the combined organic phases washed with a sat. solution of sodium chloride (2×50 mL). The organic phase was dried over MgSO$_4$, concentrated by evaporation under reduced pressure and the residue purified by silica column chromatography using a MPLC system (CombiFlash Companion, Isco Inc.) eluting with a gradient of heptane/ethyl acetate providing 2.22 g (40%) of the title compound. MS (ISP): 357.0 [M+H]$^+$.

Step 2: 4-(5-Pyridin-3-yl-pyrimidin-2-ylamino)-piperidine-1-carboxylic acid tert-butyl ester To a degassed solution of 4-(5-bromo-pyrimidin-2-ylamino)-piperidine-1-carboxylic acid tert-butyl ester (0.87 g, 2.44 mmol, 1.0 equiv) in dimethoxyethane (10 mL) was added pyridyl-3-boronic acid (0.60 g, 4.87 mmol, 2.0 equiv; commercially available), tetrakis(triphenylphosphine) palladium(0) (84.6 mg, 0.07 mmol, 0.03 equiv) and an aqueous solution of 2 M sodium carbonate (5.6 mL) and the reaction mixture heated by microwave irradiation under Ar to 130° C. for 30 min. The crude reaction mixture was extracted with ethyl acetate (3×50 mL) and the combined organic phases washed with a sat. solution of sodium chloride (2×50 mL). The organic phase was dried over MgSO$_4$, concentrated by evaporation under reduced pressure and the residue purified by silica column chromatography using a MPLC system (CombiFlash Companion, Isco Inc.) eluting with a gradient of dichloromethane/methanol providing 0.68 g (76%) of the title compound. MS (ISP): 356.3 [M+H]$^+$.

Step 3

A solution of 4-(5-pyridin-3-yl-pyrimidin-2-ylamino)-piperidine-1-carboxylic acid tert-butyl ester (0.68 g, 1.91 mmol) in 4 M HCl in dioxane (40 mL) was stirred at rt for 2 h. The solvent was removed under reduced pressure and the crude product used in the consecutive step without further purification assuming quantitative deprotection and formation of the dihydrochloride salt. MS (ISP): 256.5 [M+H]$^+$.

Intermediate C14

4-[2-(Piperidin-4-ylamino)-pyrimidin-5-yl]-benzamide dihydrochloride

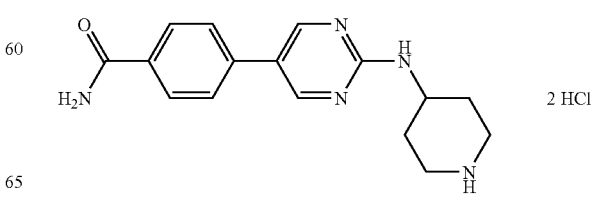

Step 1: 4-[5-(4-Carbamoyl-phenyl)-pyrimidin-2-ylamino]-piperidine-1-carboxylic acid tert-butyl ester To a degassed solution of 4-(5-bromo-pyrimidin-2-ylamino)-piperidine-1-carboxylic acid tert-butyl ester (1.0 g, 2.80 mmol, 1.0 equiv; intermediate C13/step 1) in dimethoxyethane (15 mL) was added 4-(4,4,5,5-tetramethyl-[1,3,2]dioxaborolan-2-yl)-benzamide (1.38 g, 5.60 mmol, 2.0 equiv; commercially available from CSIRO Molecular Science, Australia), tetrakis(triphenylphosphine)palladium (0) (97.0 mg, 0.08 mmol, 0.03 equiv) and an aqueous solution of 2 M sodium carbonate (5.6 mL) and the reaction mixture heated by microwave irradiation under Ar to 130° C. for 30 min. The crude reaction mixture was extracted with ethyl acetate (3×50 mL) and the combined organic phases washed with a sat. solution of sodium chloride (2×50 mL). The organic phase was dried over MgSO₄, concentrated by evaporation under reduced pressure and the crude material purified by silica column chromatography using a MPLC system (CombiFlash Companion, Isco Inc.) eluting with a gradient of dichloromethane/methanol providing 0.31 g (28%) of the title compound. MS (ISP): 398.4 [M+H]⁺.

Step 2

A solution of 4-[5-(4-carbamoyl-phenyl)-pyrimidin-2-ylamino]-piperidine-1-carboxylic acid tert-butyl ester (0.31 g, 0.78 mmol) in 4 M HCl in dioxane (40 mL) was stirred at rt for 2 h. The solvent was removed under reduced pressure and the crude product used in the consecutive step without further purification assuming quantitative deprotection and formation of the dihydrochloride salt. MS (ISP): 298.4 [M+H]⁺.

Intermediate C15

2-(Piperidin-4-ylamino)-4-trifluoromethyl-pyrimidine-5-carboxylic acid (4-chloro-phenyl)-amide dihydrochloride

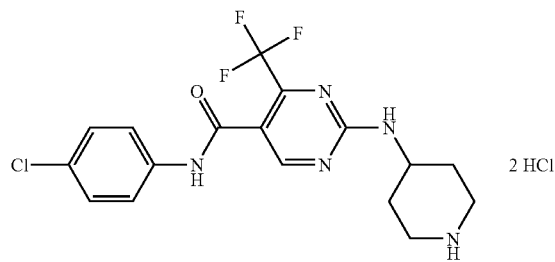

Step 1: 4-[5-(4-Chloro-phenylcarbamoyl)-4-trifluoromethyl-pyrimidin-2-ylamino]-piperidine-1-carboxylic acid tert-butyl ester A mixture of 2-chloro-4-trifluoromethyl-pyrimidine-5-carboxylic acid (4-chloro-phenyl)-amide (0.8 g, 2.38 mmol, 1.0 equiv; commercially available from Maybridge, UK), 4-amino-piperidine-1-carboxylic acid tert-butyl ester (0.72 g, 3.57 mmol, 1.5 equiv; commercially available) and triethylamine (0.49 mL, 0.36 g, 3.57 mmol, 1.5 equiv) in anhydrous DMAc (2 mL) and acetonitrile (9 mL) was heated by microwave irradiation to 120° C. for 20 min. The organic phase was concentrated under reduced pressure and the crude material purified by silica column chromatography using a MPLC system (CombiFlash Companion, Isco Inc.) eluting with a gradient of heptane/ethyl acetate providing 1.0 g (84%) of the title compound. MS (ISP): 500.3 [M+H]⁺.

Step 2

A solution of 4-[5-(4-chloro-phenylcarbamoyl)-4-trifluoromethyl-pyrimidin-2-ylamino]-piperidine-1-carboxylic acid tert-butyl ester (1.0 g, 2.00 mmol) in 4 M HCl in dioxane (20 mL) was stirred at rt for 2 h. The solvent was removed under reduced pressure and the crude product used in the consecutive step without further purification assuming quantitative deprotection and formation of the dihydrochloride salt. MS (ISP): 400.1 [M+H]⁺.

Intermediate C16

2-(Piperidin-4-ylamino)-4-trifluoromethyl-pyrimidine-5-carboxylic acid (4-trifluoromethoxy-phenyl)-amide dihydrochloride

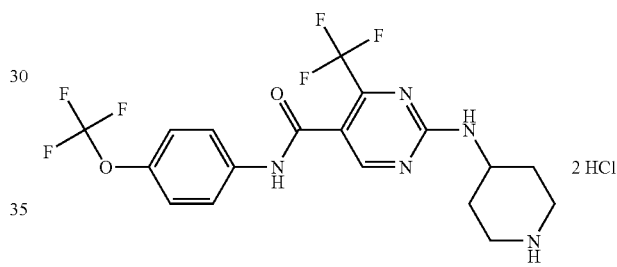

Step 1: 4-[5-(4-Trifluoromethoxy-phenylcarbamoyl)-4-trifluoromethyl-pyrimidin-2-ylamino]-piperidine-1-carboxylic acid tert-butyl ester A mixture of 2-chloro-4-trifluoromethyl-pyrimidine-5-carboxylic acid (4-trifluoromethoxy-phenyl)-amide (0.8 g, 2.07 mmol, 1.0 equiv; commercially available from Maybridge, UK), 4-amino-piperidine-1-carboxylic acid tert-butyl ester (0.62 g, 3.11 mmol, 1.5 equiv; commercially available) and triethylamine (0.43 mL, 0.32 g, 3.11 mmol, 1.5 equiv) in anhydrous DMAc (2 mL) and acetonitrile (9 mL) was heated by microwave irradiation to 120° C. for 20 min. The organic phase was concentrated under reduced pressure and the crude material purified by silica column chromatography using a MPLC system (CombiFlash Companion, Isco Inc.) eluting with a gradient of heptane/ethyl acetate providing 0.92 g (81%) of the title compound. MS (ISP): 550.2 [M+H]⁺.

Step 2

A solution of 4-[5-(4-trifluoromethoxy-phenylcarbamoyl)-4-trifluoromethyl-pyrimidin-2-ylamino]-piperidine-1-carboxylic acid tert-butyl ester (0.92 g, 1.67 mmol) in 4 M HCl in dioxane (20 mL) was stirred at rt for 2 h. The solvent was removed under reduced pressure and the crude product used in the consecutive step without further purification

Intermediate C17

Piperidin-4-yl-(4,6,7-trimethoxy-quinazolin-2-yl)-amine dihydrochloride

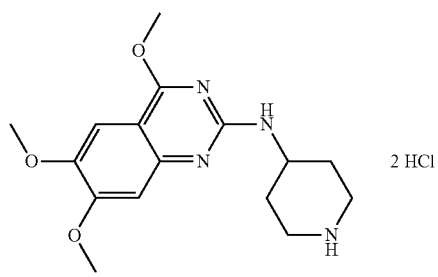

Step 1: 2-Chloro-4,6,7-trimethoxy-quinazoline [CAS RN 20197-85-7]

The title compound was prepared as described in H.-J. Hess, T. H. Cronin and A. Scriabine *J. Med. Chem.* 1968, 11, 130-136.

Step 2: 4-(4,6,7-Trimethoxy-quinazolin-2-ylamino)-piperidine-1-carboxylic acid tert-butyl ester A mixture of 2-chloro-4,6,7-trimethoxy-quinazoline (0.8 g, 3.14 mmol, 1.0 equiv) and 4-amino-piperidine-1-carboxylic acid tert-butyl ester (1.26 g, 6.28 mmol, 2.0 equiv; commercially available) in anhydrous NMP (8 mL) and triethylamine (2 mL) was heated by microwave irradiation to 170° C. for 1 h. The organic phase was concentrated under reduced pressure and the residue extracted with dichloromethane (3×50 mL) from a sat. solution of sodium bicarbonate (100 mL). The combined organic phases were dried over MgSO$_4$ and the product purified by column chromatography on silica eluting with a gradient of toluene/ethyl acetate (4:1→2:1) providing 0.2 g (15%) of the title compound. MS (ISP): 419.4 [M+H]$^+$.

Step 3

A solution of 4-(4,6,7-trimethoxy-quinazolin-2-ylamino)-piperidine-1-carboxylic acid tert-butyl ester (0.2 g, 0.48 mmol) in ethanol (5 mL) and 4 M HCl in dioxane (20 mL) was stirred at rt for 2 h. The solvent was removed under reduced pressure and the crude product used in the consecutive step without further purification assuming quantitative deprotection and formation of the dihydrochloride salt. MS (ESI): 319.4 [M+H]$^+$.

Intermediate C18

N$^6$-Piperidin-4-yl-[1,3]dioxolo[4,5-g]quinazoline-6,8-diamine dihydrochloride

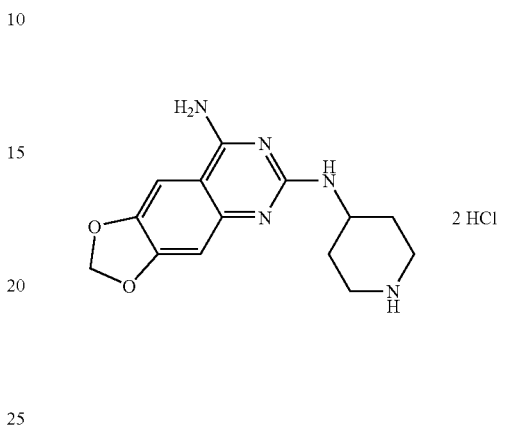

Step 1: 6-Chloro-[1,3]dioxolo[4,5-g]quinazolin-8-ylamine [CAS RN 75483-94-2]

The title compound was prepared according to EP 0009 465 A1 (Ciba-Geigy A G).

Step 2: 4-(8-Amino-[1,3]dioxolo[4,5-g]quinazolin-6-ylamino)-piperidine-1-carboxylic acid tert-butyl ester A mixture of 6-chloro-[1,3]dioxolo[4,5-g]quinazolin-8-ylamine (0.9 g, 4.02 mmol equiv) and 4-amino-piperidine-1-carboxylic acid tert-butyl ester (1.61 g, 8.05 mmol, 2.0 equiv; commercially available) in anhydrous NMP (8 mL) and triethylamine (2 mL) was heated by microwave irradiation to 170° C. for 1 h. The organic phase was concentrated under reduced pressure and the residue extracted with dichloromethane (3×50 mL) from a sat. solution of sodium bicarbonate (100 mL). The combined organic phases were dried over MgSO$_4$ and the product purified with column chromatography on silica eluting with a gradient of toluene/ethyl acetate (4:1→2:1) providing 0.6 g (39%) of the title compound. MS (ISP): 388.4 [M+H]$^+$.

Step 3

A solution of 4-(8-amino-[1,3]dioxolo[4,5-g]quinazolin-6-ylamino)-piperidine-1-carboxylic acid tert-butyl ester (0.6 g, 1.55 mmol) in ethanol (5 mL) and 4 M HCl in dioxane (20 mL) was stirred at rt for 2 h. The solvent was removed under reduced pressure and the crude product used in the consecutive step without further purification assuming quantitative deprotection and formation of the dihydrochloride salt. MS (ESI): 288.4 [M+H]$^+$.

Intermediate C19

[4-(2-Fluoro-phenyl)-quinazolin-2-yl]-piperidin-4-yl-amine dihydrochloride

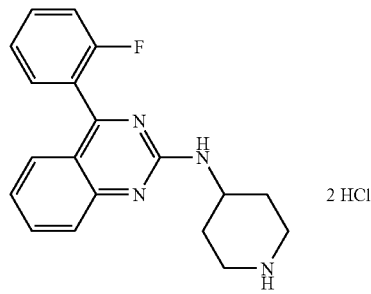

Step 1: 2-Chloro-4-(2-fluoro-phenyl)-quinazoline [CAS RN 851012-56-1]

The title compound was prepared according to US 05/0096 327 A1 (Warner-Lambert Company).

Step 2: 4-[4-(2-Fluoro-phenyl)-quinazolin-2-ylamino]-piperidine-1-carboxylic acid tert-butyl ester A mixture of 2-chloro-4-(2-fluoro-phenyl)-quinazoline (0.8 g, 3.09 mmol, 1.0 equiv) and 4-amino-piperidine-1-carboxylic acid tert-butyl ester (0.81 g, 4.02 mmol, 1.3 equiv; commercially available) in anhydrous NMP (8 mL) was heated by microwave irradiation to 180° C. for 40 min. The organic phase was concentrated under reduced pressure and the residue extracted with dichloromethane (3×50 mL) from a sat. solution of sodium bicarbonate (100 mL). The combined organic phases were dried over $MgSO_4$ and the product purified by column chromatography on silica eluting with heptane/ethyl acetate (10:1) providing 0.86 g (66%) of the title compound. MS (ISP): 423.3 $[M+H]^+$.

Step 3

A solution of 4-[4-(2-fluoro-phenyl)-quinazolin-2-ylamino]-piperidine-1-carboxylic acid tert-butyl ester (0.86 g, 2.04 mmol) in ethanol (5 mL) and 4 M HCl in dioxane (20 mL) was stirred at rt for 2 h. The solvent was removed under reduced pressure and the crude product used in the consecutive step without further purification assuming quantitative deprotection and formation of the dihydrochloride salt. MS (ISP): 322.9 $[M+H]^+$.

Intermediate C20

[6-Chloro-4-(2-fluoro-phenyl)-quinazolin-2-yl]-piperidin-4-yl-amine dihydrochloride

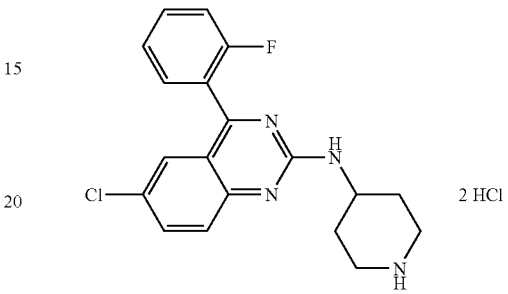

Step 1: 2,6-Dichloro-4-(2-fluoro-phenyl)-quinazoline [CAS RN 86892-34-4]

The title compound was prepared according to FR 2514 765 A1 (Sanofi).

Step 2: 4-[6-Chloro-4-(2-fluoro-phenyl)-quinazolin-2-ylamino]-piperidine-1-carboxylic acid tert-butyl ester A mixture of 2,6-dichloro-4-(2-fluoro-phenyl)-quinazoline (0.92 g, 3.14 mmol, 1.0 equiv) and 4-amino-piperidine-1-carboxylic acid tert-butyl ester (0.82 g, 4.08 mmol, 1.3 equiv; commercially available) in anhydrous NMP (8 mL) was heated by microwave irradiation to 180° C. for 40 min. The organic phase was concentrated under reduced pressure and the residue extracted with dichloromethane (3×50 mL) from a sat. solution of sodium bicarbonate (100 mL). The combined organic phases were dried over $MgSO_4$ and the product purified by column chromatography on silica eluting with a gradient of heptane/ethyl acetate (6:1 h 1:1) providing 0.66 g (66%) of the title compound. MS (ISP): 457.4 $[M+H]^+$.

Step 3

A solution of 4-[6-chloro-4-(2-fluoro-phenyl)-quinazolin-2-ylamino]-piperidine-1-carboxylic acid tert-butyl ester (0.66 g, 1.44 mmol) in ethanol (5 mL) and 4 M HCl in dioxane (20 mL) was stirred at rt for 2 h. The solvent was removed under reduced pressure and the crude product used in the consecutive step without further purification assuming quantitative deprotection and formation of the dihydrochloride salt. MS (ISP): 356.9 $[M+H]^+$.

Intermediate C21

(6,7-Dimethoxy-4-piperidin-1-yl-quinazolin-2-yl)-piperidin-4-yl-amine dihydrochloride

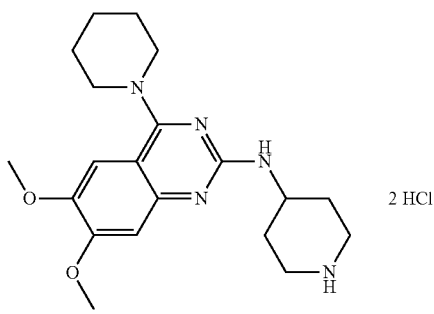

Step 1: 4-(6,7-Dimethoxy-4-piperidin-1-yl-quinazolin-2-ylamino)-piperidine-1-carboxylic acid tert-butyl ester A mixture of 2-chloro-6,7-dimethoxy-4-piperidin-1-yl-quinazoline (3.08 g, 10.00 mmol, 1.0 equiv; commercially available from Specs Research Laboratory, The Netherlands), 4-amino-piperidine-1-carboxylic acid tert-butyl ester (2.00 g, 10.00 mmol, 1.0 equiv; commercially available), rac-2,2'-bis(diphenylphosphino)-1,1'-binaphthalene (0.25 g, 0.40 mmol, 0.04 equiv), tris(dibenzylideneacetone)dipalladium(0) (0.21 g, 0.20 mmol, 0.02 equiv) and KOtert-Bu (1.35 g, 12.01 mmol, 1.2 equiv) in toluene (10 mL) was heated under Ar by microwave irradiation to 120° C. for 2 h. The crude reaction mixture was filtered through Hyflo Super Cel, a sat. solution of sodium chloride (100 mL) was added and the mixture extracted with ethyl acetate (3×50 mL). The combined organic phases were concentrated by evaporation under reduced pressure and the residue purified on a Isolute flash NH2 chromatography column using a MPLC system (CombiFlash Companion, Isco Inc.) eluting with a gradient of heptane/ethyl acetate providing 1.90 g (40%) of the title compound. MS (ISP): 472.4 [M+H]$^+$.

Step 2

A solution of 4-(6,7-dimethoxy-4-piperidin-1-yl-quinazolin-2-ylamino)-piperidine-1-carboxylic acid tert-butyl ester (1.90 g, 4.03 mmol) in ethanol (10 mL) and 4 M HCl in dioxane (40 mL) was stirred at rt for 2 h. The solvent was removed under reduced pressure and the crude product used in the consecutive step without further purification assuming quantitative deprotection and formation of the dihydrochloride salt. MS (ISP): 372.1 [M+H]$^+$.

Intermediate C22

(6-Chloro-4-morpholin-4-yl-quinazolin-2-yl)-piperidin-4-yl-amine dihydrochloride

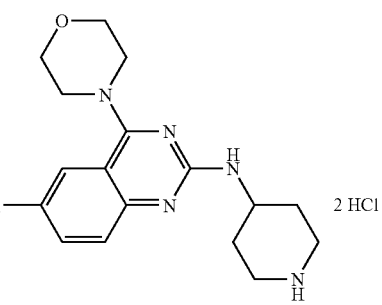

Step 1: 2,6-Dichloro-4-morpholin-4-yl-quinazoline [CAS RN 39216-94-9]

The title compound was prepared according to DE 2121 031 A1 (Dr. Karl Thomae GmbH).

Step 2: 4-(6-Chloro-4-morpholin-4-yl-quinazolin-2-ylamino)-piperidine-1-carboxylic acid tert-butyl ester A mixture of 2,6-dichloro-4-morpholin-4-yl-quinazoline (0.9 g, 3.17 mmol, 1.0 equiv) and 4-amino-piperidine-1-carboxylic acid tert-butyl ester (1.27 g, 6.33 mmol, 2.0 equiv; commercially available) in anhydrous NMP (8 mL) and triethylamine (2 mL) was heated by microwave irradiation to 170° C. for 1 h. The organic phase was concentrated under reduced pressure and the residue extracted with dichloromethane (3×50 mL) from a sat. solution of sodium bicarbonate (100 mL). The combined organic phases were dried over MgSO$_4$ and the product purified by column chromatography on silica eluting with a gradient of toluene/ethyl acetate (4:1→2:1) providing 0.6 g (42%) of the title compound. MS (ISP): 448.3 [M+H]$^+$.

Step 3

A solution of 4-(6-chloro-4-morpholin-4-yl-quinazolin-2-ylamino)-piperidine-1-carboxylic acid tert-butyl ester (0.6 g, 1.34 mmol) in ethanol (5 mL) and 4 M HCl in dioxane (20 mL) was stirred at rt for 2 h. The solvent was removed under reduced pressure and the crude product used in the consecutive step without further purification assuming quantitative deprotection and formation of the dihydrochloride salt. MS (ISP): 348.4 [M+H]$^+$.

Intermediate C23

(6,7-Dimethoxy-4-morpholin-4-yl-quinazolin-2-yl)-piperidin-4-yl-amine dihydrochloride

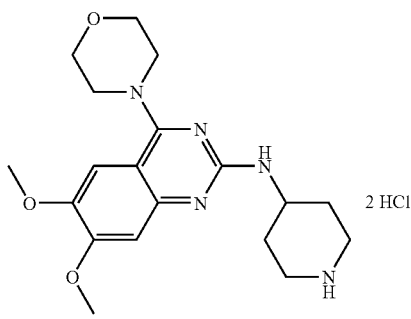

Step 1: 4-(6,7-Dimethoxy-4-morpholin-4-yl-quinazolin-2-ylamino)-piperidine-1-carboxylic acid tert-butyl ester A mixture of 2-chloro-6,7-dimethoxy-4-morpholin-4-yl-quinazoline (3.10 g, 10.01 mmol, 1.0 equiv; commercially available from Specs Research Laboratory, The Netherlands), 4-amino-piperidine-1-carboxylic acid tert-butyl ester (2.00 g, 10.01 mmol, 1.0 equiv; commercially available), rac-2,2'-bis(diphenylphosphino)-1,1'-binaphthalene (0.25 g, 0.40 mmol, 0.04 equiv), tris(dibenzylideneacetone)dipalladium(0) (0.21 g, 0.20 mmol, 0.02 equiv) and KOtert-Bu (1.35 g, 12.01 mmol, 1.2 equiv) in toluene (10 mL) was heated under Ar by microwave irradiation to 100° C. for 2 h. The crude reaction mixture was filtered through Hyflo Super Cel, a sat. solution of sodium chloride (100 mL) was added and the mixture extracted with ethyl acetate (3×50 mL). The combined organic phases were concentrated by evaporation under reduced pressure and the residue purified by silica column chromatography using a MPLC system (CombiFlash Companion, Isco Inc.) eluting with a gradient of heptane (+1% triethylamine)/ethyl acetate to provide 2.45 g (52%) of the title compound. MS (ISP): 474.4 [M+H]$^+$.

Step 2

A solution of 4-(6,7-dimethoxy-4-morpholin-4-yl-quinazolin-2-ylamino)-piperidine-1-carboxylic acid tert-butyl ester (2.45 g, 5.18 mmol) in ethanol (10 mL) and 4 M HCl in dioxane (40 mL) was stirred at rt for 2 h. The solvent was removed under reduced pressure and the crude product used in the consecutive step without further purification assuming quantitative deprotection and formation of the dihydrochloride salt. MS (ISP): 374.3 [M+H]$^+$.

Intermediate C24

(4-Phenyl-pteridin-2-yl)-piperidin-4-yl-amine dihydrochloride

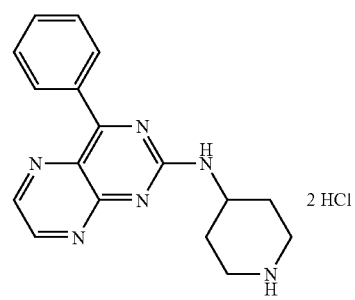

Step 1: 4-(4-Phenyl-pteridin-2-ylamino)-piperidine-1-carboxylic acid tert-butyl ester A mixture of 2-chloro-4-phenyl-pteridine (0.33 g, 1.36 mmol, 1.0 equiv; commercially available from Specs Research Laboratory, The Netherlands), 4-amino-piperidine-1-carboxylic acid tert-butyl ester (0.41 g, 2.04 mmol, 1.5 equiv; commercially available) and triethylamine (0.28 mL, 0.21 g, 2.04 mmol, 1.5 equiv) in anhydrous DMAc (2 mL) and acetonitrile (9 mL) was heated by microwave irradiation to 120° C. for 20 min. The organic phase was concentrated under reduced pressure and the crude material purified by silica column chromatography using a MPLC system (CombiFlash Companion, Isco Inc.) eluting with a gradient of heptane/ethyl acetate providing 0.5 g (91%) of the title compound. MS (ISP): 407.4 [M+H]$^+$.

Step 2

A solution of 4-(4-phenyl-pteridin-2-ylamino)-piperidine-1-carboxylic acid tert-butyl ester (0.5 g, 1.23 mmol) in 4 M HCl in dioxane (20 mL) was stirred at rt for 2 h. The solvent was removed under reduced pressure and the crude product used in the consecutive step without further purification assuming quantitative deprotection and formation of the dihydrochloride salt. MS (ISP): 307.5 [M+H]$^+$.

Intermediate C25

(4,6-Dimethoxy-[1,3,5]triazin-2-yl)-piperidin-4-yl-amine dihydrochloride

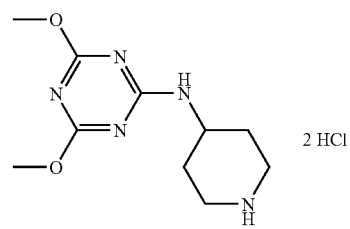

Step 1: 4-(4,6-Dimethoxy-[1,3,5]triazin-2-ylamino)-piperidine-1-carboxylic acid tert-butyl ester A mixture of 2-chloro-4,6-dimethoxy-[1,3,5]triazine (1.35 g, 7.68 mmol, 1.0 equiv; commercially available) and 4-amino-piperidine-1-carboxylic acid tert-butyl ester (2.00 g, 9.98 mmol, 1.3 equiv; commercially available) in acetonitrile (16 mL) was heated by microwave irradiation to 160° C. for 20 min. The organic phase was concentrated under reduced pressure and the residue extracted with ethyl acetate (3×50 mL) from a solution of 1 M NaOH (200 mL). The combined organic phases were dried over MgSO$_4$ and concentrated by evaporation under reduced pressure yielding 2.60 g (100%) of the title compound. MS (ISP): 340.4 [M+H]$^+$.

Step 2

A solution of 4-(4,6-dimethoxy-[1,3,5]triazin-2-ylamino)-piperidine-1-carboxylic acid tert-butyl ester (2.60 g, 7.66 mmol) in 4 M HCl in dioxane (100 mL) was stirred at 0° C. for 1 h. The solvent was removed under reduced pressure and the crude product used in the consecutive step without further purification assuming quantitative deprotection and formation of the dihydrochloride salt. MS (ISP): 240.4 [M+H]$^+$.

The aldehyde intermediates D1 to D34 were prepared following literature precedents or in analogy to literature precedents or as described below.

Synthesis of Aldehyde Intermediates D1 to D34 to be used in Table 3 and Table 4

Intermediate D1

1,4-Dimethoxy-naphthalene-2-carbaldehyde [CAS RN 75965-83-2]

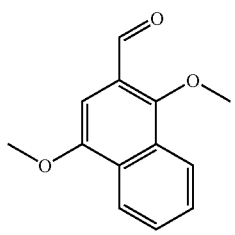

The title compound was prepared by treating (1,4-dimethoxy-naphthalen-2-yl)-methanol (6.5 g, 29.8 mmol, 1.0 equiv, prepared according to C. Flader, J. Liu and R. F. Borch *J. Med. Chem.* 2000, 43, 3157-3167) with activated MnO$_2$ (25.9 g, 297.8 mmol, 10.0 equiv) in dichloromethane for 4 h, after which time the reaction was filtered through Hyflo Super Cel and concentrated by evaporation of the solvent under reduced pressure affording 5.1 g (81%) of the title compound.

$^1$H NMR (300 MHz, CDCl$_3$): δ 4.02 (s, 3H), 4.10 (s, 3H), 7.14 (s, 1H), 7.61-7.65 (m, 2H), 8.18-8.30 (m, 2H), 10.58 (s, 1H).

Intermediate D2

3-Ethoxy-4-methyl-benzaldehyde [CAS RN 157143-20-9]

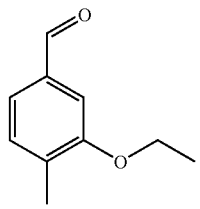

The title compound was prepared by reaction of commercially available 3-hydroxy-4-methyl-benzaldehyde with ethyl iodide in DMF using K$_2$CO$_3$ as base in analogy to the procedure described in M. J. Ashton, D. C. Cook, G. Fenton, J.-A. Karlsson, M. N. Palfreyman, D. Raeburn, A. J. Ratcliffe, J. E. Souness, S. Thurairatnam and N. Vicker *J. Med. Chem.* 1994, 37, 1696-1703.

Intermediate D3

4-Chloro-3-ethoxy-benzaldehyde [CAS RN 85259-46-7]

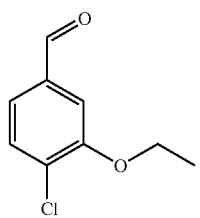

To a solution of 4-chloro-3-hydroxy-benzoic acid (3.0 g, 17.4 mmol, 1.0 equiv; commercially available) in DMF (15 mL) was added K$_2$CO$_3$ (4.81 g, 34.8 mmol, 2.0 equiv) and ethyl iodide (4.03 mL, 5.97 g, 38.2 mmol, 2.2 equiv). The reaction mixture was stirred for 6 h at rt, diluted with water (20 mL) and extracted with ethyl acetate (3×50 mL). The organic phases were dried over Na$_2$SO$_4$ and concentrated to afford 3.6 g (91%) of 4-chloro-3-ethoxy-benzoic acid ethyl ester. The crude ester was then dissolved in THF (20 mL) and cooled to −78° C. under Ar. A solution of diisobutylaluminium hydride (95 mL, 95.0 mmol, 6.0 equiv; 1 M solution in THF) was slowly added over a time period of 15 min, the cooling bath removed on completion of addition and the reaction allowed to reach 0° C. After 1 h the reaction was cooled to −78° C. and the excess hydride quenched by cautious addition of a solution of 1 M HCl (10 mL). The mixture was brought to rt, the organic phase separated and the aqueous layer extracted with ethyl acetate (3×100 mL). The combined organic phases were dried over Na$_2$SO$_4$ and concentrated by evaporation under reduced pressure providing 2.94 g (100%) of 4-chloro-3-ethoxy-benzyl alcohol. The crude alcohol (2.94 g, 15.75 mmol, 1.0 equiv) was dissolved in dichloromethane (15 mL) and activated MnO$_2$ (5.48 g, 63.0 mmol, 4.0 equiv)

was added. The reaction mixture was stirred for 16 h, after which time the reaction was filtered through Hyflo Super Cel and concentrated. The residue was purified by flash column chromatography on silica eluting with heptane/ethyl acetate (4:1) to yield 1.51 g (52%) of the title compound. ¹H NMR (300 MHz, CDCl₃): δ 1.51 (t, J=7.1 Hz, 3H), 4.19 (q, J=7.1 Hz, 2H), 7.37-7.42 (m, 2H), 7.55 (d, J=9.0 Hz, 1H), 9.94 (s, 1H).

Intermediate D4

3-Ethoxy-4-(3-methyl-but-2-enyloxy)-benzaldehyde

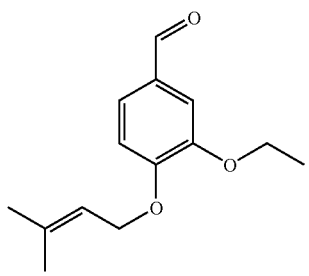

The title compound was prepared by reaction of 3-ethoxy-4-hydroxy-benzaldehyde with 1-bromo-3-methyl-2-butene in DMF using K₂CO₃ as base in analogy to the preparation of 3-ethoxy-4-methyl-benzaldehyde (intermediate D2).

Intermediate D5

Methanesulfonic acid 2-ethoxy-4-formyl-phenyl ester

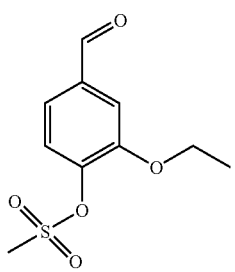

To a solution of 3-ethoxy-4-hydroxybenzaldehyde (3.0 g, 18.1 mmol, 1.0 equiv; commercially available) and N,N-dimethylaminopyridine (2.87 g, 23.5 mmol, 1.3 equiv) in dichloromethane (10 mL) under Ar at 0° C. was added methanesulfonyl chloride (1.68 mL, 2.48 g, 21.7 mmol, 1.2 equiv). After the reaction mixture was stirred for 1 h, water (100 mL) was added, the solution extracted with dichloromethane (3×50 mL) and the combined organic phases dried over MgSO₄. Removal of the solvent by evaporation under reduced pressure provided the title compound in quantitative yield (4.8 g). ¹H NMR (300 MHz, CDCl₃): □ 1.42 (t, J=7.0 Hz, 3H), 3.19 (s, 3H), 4.14 (q, J=7.0 Hz, 2H), 7.41 (s, 2H), 7.45 (s, 1H), 9.89 (s, 1H). ¹³C NMR (75 MHz, CDCl₃): δ 14.53, 38.94, 64.99, 112.20, 124.38, 125.17, 136.01, 142.92, 151.63, 190.65. MS (ISP): 245.2 [M+H]⁺.

Intermediate D6

3,4-Diisopropoxy-benzaldehyde [CAS RN 64000-54-0]

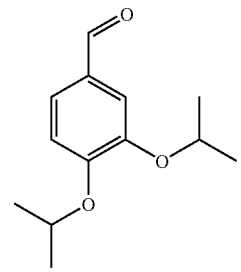

The title compound was prepared by reaction of 3,4-dihydroxybenzaldehyde with 2-bromopropane in DMF using K₂CO₃ as base in analogy to the preparation of 3-ethoxy-4-methyl-benzaldehyde (intermediate D2).

Intermediate D7

4-Methoxy-3-propoxy-benzaldehyde [CAS RN 5922-56-5]

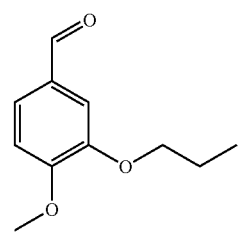

The title compound was prepared by reaction of isovanillin with propyl iodide in DMF using K₂CO₃ as base in analogy to the preparation of 3-ethoxy-4-methyl-benzaldehyde (intermediate D2).

Intermediate D8

3-(2-Fluoro-ethoxy)-4-methoxy-benzaldehyde

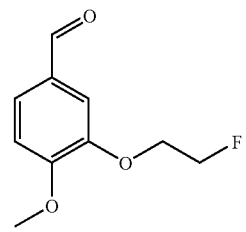

To a solution of 3-hydroxy-4-methoxy-benzaldehyde (10.0 g, 66.0 mmol, 1.0 equiv; commercially available) in anhydrous DMF (40 mL) was added K₂CO₃ (13.6 g, 99.0 mmol, 1.5 equiv) and 1-bromo-2-fluoro-ethane (9.2 mg, 72.0 mmol, 1.1 equiv) and the mixture stirred at rt for 48 h. The K$_2$CO$_3$ was removed by filtration and the organic phase concentrated under reduced pressure. To the residue was added a sat. solution of sodium chloride (100 mL) and the solution extracted with ethyl acetate (3×100 mL). The combined organic phases were dried over MgSO$_4$ and the product crystallized from a mixture of isopropanol/diethylether to yield 12.69 g (97%) of the title compound. $^1$H NMR (300 MHz, DMSO): δ 3.89 (s, 3H), 4.24-4.27 (m, 1H), 4.34-4.37 (m, 1H), 4.67-4.70 (m, 1H), 4.83-4.86 (m, 1H), 7.20 (d, J=8.4 Hz, 1H), 7.43 (d, J=1.9 Hz, 1H), 7.59 (dd, J=8.4 Hz, J=1.9 Hz, 1H), 9.84 (s, 1H). MS (ISP): 198.6 [M+H]$^+$.

Intermediate D9

3-Isobutoxy-4-methoxy-benzaldehyde [CAS RN 57724-26-2]

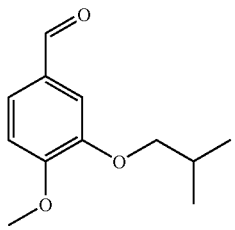

The title compound was prepared by reaction of isovanillin with 1-bromo-2-methyl propane as described in WO 04/000 806 A1 (Elbion A G).

Intermediate D10

3,5-Diisopropoxy-benzaldehyde [CAS RN 94169-64-9]

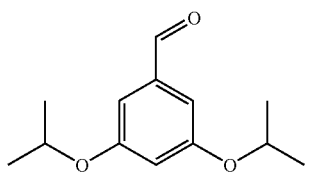

To a solution of 3,5-dihydroxy-benzaldehyde (5.0 g, 36.20 mmol, 1.0 equiv; commercially available) in anhydrous DMF (30 mL) was added K$_2$CO$_3$ (15.0 g, 108.60 mmol, 3.0 equiv) and 2-bromo-propane (13.36 g, 10.20 mL, 108.60 mmol, 3.0 equiv) and the mixture stirred at 100° C. for 18 h. The K$_2$CO$_3$ was removed by filtration and the organic phase concentrated under reduced pressure. To the residue was added a sat solution of sodium chloride (100 mL) and the solution extracted with ethyl acetate (3×100 mL). The combined organic phases were dried over MgSO$_4$ and the product purified by silica column chromatography using a MPLC system (CombiFlash Companion, Isco Inc.) eluting with a gradient of heptane/ ethyl acetate affording 6.64 g (83%) of the title compound and 0.59 g (9%) of 3-hydroxy-5-isopropoxy-benzaldehyde (intermediate D27, vide infra). $^1$H NMR (300 MHz, CDCl$_3$): δ 1.35 (d, J=6.1 Hz, 12H), 4.59 (hept, J=6.1 Hz, 2H), 6.66-6.68 (m, 1H), 6.96-6.97 (m, 2H), 9.88 (s, 1H). MS (ISP): 223.1 [M+H]$^+$.

Intermediate D11

3-Benzyloxy-5-ethoxy-benzaldehyde [CAS RN 227023-81-6]

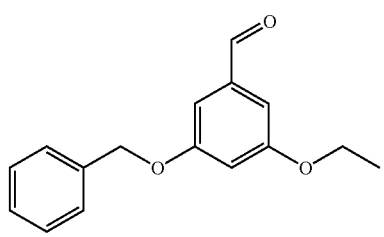

The title compound was prepared according to EP 0921 116 A1 (F. Hoffmann-La Roche A G).

Intermediate D12

3,5-Diethoxy-4-fluoro-benzaldehyde

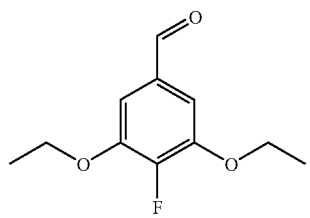

Step 1: tert-Butyl-(4-fluoro-benzyloxy)-dimethyl-silane

To a solution of (4-fluoro-phenyl)-methanol (12.16 g, 96.4 mmol, 1.0 equiv; commercially available) in anhydrous DMF (50 mL) at 0° C. under Ar was added imidazole (7.22 g, 106.1 mmol, 1.1 equiv) and tert-butyl-chloro-dimethyl-silane (15.99 g, 106.1 mmol, 1.1 equiv). After the addition was completed the cooling bath was removed and the reaction stirred for 18 h at rt. The reaction mixture was poured on ice, extracted with ethyl acetate (2×100 mL) and the combined organic phases washed with a sat. solution of sodium carbonate (2×100 mL) and sodium chloride (2×100 mL). The organic phase was dried over Na$_2$SO$_4$, concentrated by evaporation under reduced pressure yielding a brown oil that was purified by high vacuum distillation (bp 32-35° C. at 0.1 mbar) to give 23.0 g (99%) of the title compound. $^1$H NMR (400 MHz, CDCl$_3$): δ 0.00 (s, 6H), 0.84 (s, 9H), 4.60 (s, 2H), 6.89-6.94 (m, 2H), 7.16-7.20 (m, 2H). MS (EI): 183.1 [M-tert-Bu]$^+$.

Step 2: 5-(tert-Butyl-dimethyl-silanyloxymethyl)-2-fluoro-phenol

To a solution of tert-butyl-(4-fluoro-benzyloxy)-dimethyl-silane (5.00 g, 20.8 mmol, 1.0 equiv) in anhydrous THF (20 mL) was added at −78° C. under Ar a solution of sec-BuLi (17.6 mL, 22.8 mmol, 1.1 equiv, 1.3 M solution in hexane) within 30 min. Then a solution of trimethyl borate (2.37 mL, 2.20 g, 20.8 mmol, 1.0 equiv) in anhydrous THF (7.5 mL) was added slowly within 30 min and the cooling bath removed. A solution of conc. acetic acid (2.78 mL, 1.87 g, 31.2 mmol, 1.5 equiv) was slowly added followed by addition of a solution of 35% hydrogen peroxide in water (2.0 mL, 2.23 g, 22.9 mmol, 1.1 equiv) and the reaction mixture kept at 0° C. for 30 min. After stirring at rt for an additional 4 h, the reaction was extracted with diethyl ether (2×100 mL) and the combined organic phases washed with a solution of 10% NaOH (2×100 mL) and a sat. solution of sodium chloride (2×100 mL). The organic phase was dried over $Na_2SO_4$, concentrated by evaporation under reduced pressure and the crude material purified with column chromatography on silica eluting with hexane/ethyl acetate (19:1) providing 4.80 g (90%) of the title compound. $^1$H NMR (400 MHz, $CDCl_3$): δ 0.00 (s, 6H), 0.84 (s, 9H), 4.56 (s, 2H), 4.97 (br s, 1H), 6.68-6.72 (m, 1H), 6.87-6.94 (m, 2H). MS (EI): 256.2 [M]$^+$.

Step 3: 2-(tert-Butyl-dimethyl-silanyloxy)-4-(tert-butyl-dimethyl-silanyloxymethyl)-1-fluoro-benzene To a solution of 5-(tert-butyl-dimethyl-silanyloxymethyl)-2-fluoro-phenol (4.60 g, 17.9 mmol, 1.0 equiv) in anhydrous DMF (20 mL) at 0° C. under Ar was added imidazole (1.34 g, 19.7 mmol, 1.1 equiv) and tert-butyl-chloro-dimethyl-silane (2.97 g, 19.7 mmol, 1.1 equiv). After the addition was completed the cooling bath was removed and the reaction stirred for 18 h at rt. The reaction mixture was poured on ice, extracted with ethyl acetate (2×100 mL) and the combined organic phases washed with a sat. solution of sodium carbonate (2×100 mL) and sodium chloride (2×100 mL). The organic phase was dried over $Na_2SO_4$ and concentrated by evaporation under reduced pressure yielding 4.50 g (68%) of the title compound. $^1$H NMR (400 MHz, $CDCl_3$): δ 0.00 (s, 6H), 0.10 (s, 6H), 0.85 (s, 9H), 0.92 (s, 9H), 4.55 (s, 2H), 6.71-6.74 (m, 1H), 6.80-6.83 (m, 1H), 6.87-6.92 (m, 1H). MS (EI): 370.2 [M]$^+$.

Step 4: 3-(tert-Butyl-dimethyl-silanyloxy)-5-(tert-butyl-dimethyl-silanyloxymethyl)-2-fluoro-phenol To a solution of 2-(tert-butyl-dimethyl-silanyloxy)-4-(tert-butyl-dimethyl-silanyloxymethyl)-1-fluoro-benzene (23.70 g, 63.9 mmol, 1.0 equiv) in anhydrous THF (130 mL) was added at −78° C. under Ar a solution of sec-BuLi (54.5 mL, 71.6 mmol, 1.1 equiv, 1.3 M solution in hexane) within 30 min. Then a solution of trimethyl borate (7.13 mL, 6.64 g, 63.9 mmol, 1.0 equiv) in anhydrous THF (30 mL) was added slowly within 30 min and the cooling bath removed. A solution of conc. acetic acid (5.49 mL, 5.76 g, 95.9 mmol, 1.5 equiv) was slowly added followed by addition of a solution of 35% hydrogen peroxide in water (6.2 mL, 6.83 g, 70.3 mmol, 1.1 equiv) and the reaction mixture kept at 0° C. for 30 min. After stirring at rt for an additional 4 h, the reaction was extracted with diethyl ether (2×100 mL) and the combined organic phases washed with a solution of 10% NaOH (2×100 mL) and a sat. solution of sodium chloride (2×100 mL). The organic phase was dried over $Na_2SO_4$, concentrated by evaporation under reduced pressure and the crude material purified with column chromatography on silica eluting with hexane/ethyl acetate (19:1) providing 15.80 g (64%) of the title compound. $^1$H NMR (400 MHz, $CDCl_3$): δ 0.00 (s, 6H), 0.10 (s, 6H), 0.85 (s, 9H), 0.91 (s, 9H), 4.50 (s, 2H), 4.93 (br s, 1H), 6.37 (d, J=5.6 Hz, 1H), 6.47 (d, J=5.6 Hz, 1H). MS (EI): 329.2 [M-tert-Bu]$^+$.

Step 5: tert-Butyl-(3,5-diethoxy-4-fluoro-benzyloxy)-dimethyl-silane

To a solution of 3-(tert-butyl-dimethyl-silanyloxy)-5-(tert-butyl-dimethyl-silanyloxymethyl)-2-fluoro-phenol (5.80 g, 15.0 mmol, 1.0 equiv) in DMF (60 mL) was added $K_2CO_3$ (4.56 g, 33.0 mmol, 2.2 equiv) and ethyl bromide (2.46 mL, 3.60 g, 33.0 mmol, 2.2 equiv) and the reaction mixture stirred under Ar at 60° C. for 5 h. The $K_2CO_3$ was removed by filtration, the crude reaction mixture concentrated by evaporation under reduced pressure, the residue extracted with ethyl acetate (3×100 mL), the combined organic phases washed with water (2×100 ml) and dried over $Na_2SO_4$. The solvent was removed by evaporation under reduced pressure and the crude material purified with column chromatography on silica eluting with hexane/ethyl acetate (99:1) providing 3.10 g (63%) of the title compound. $^1$H NMR (400 MHz, $CDCl_3$): δ 0.00 (s, 6H), 0.85 (s, 9H), 1.33 (t, J=7.0 Hz, 6H), 4.00 (q, J=7.0 Hz, 4H), 4.55 (s, 2H), 6.47 (d, J=6.8 Hz, 2H). MS (ISP): 329.3 [M+H]$^+$.

Step 6: (3,5-Diethoxy-4-fluoro-phenyl)-methanol

To a solution of tert-butyl-(3,5-diethoxy-4-fluoro-benzyloxy)-dimethyl-silane (1.20 g, 3.65 mmol, 1.0 equiv) in methanol (8 mL) was added Dowex 50W-X8 (0.33 g, cation exchange resin) and the reaction mixture stirred under Ar at rt for 22 h. The resin was removed by filtration and the reaction mixture concentrated by evaporation under reduced pressure yielding the title compound in quantitative yield (0.78 g). $^1$H NMR (400 MHz, $CDCl_3$): δ 1.34 (t, J=7.0 Hz, 6H), 1.57 (t, J=5.4 Hz, 1H), 4.01 (q, J=7.0 Hz, 4H), 4.51 (d, J=5.4 Hz, 2H), 6.51 (d, J=6.8 Hz, 2H). MS (EI): 214.2 [M]$^+$.

Step 7

To a solution of (3,5-diethoxy-4-fluoro-phenyl)-methanol (2.30 g, 10.7 mmol, 1.0 equiv) in 1,2-dichloroethane (50 mL) was added activated $MnO_2$ (2.89 g, 33.3 mmol, 3.1 equiv). The reaction mixture was stirred for 21 h at 50° C. and then filtered through Hyflo Super Cel providing after evaporation of the solvent under reduced pressure 1.90 g (83%) of the title compound. $^1$H NMR (400 MHz, $CDCl_3$): δ 1.38 (t, J=7.0 Hz, 6H), 4.09 (q, J=7.0 Hz, 4H). 7.04 (d, J=7.2 Hz, 2H), 9.75 (s, 1H). MS (EI): 212.1 [M]$^+$.

Intermediate D13

2,6-Diethoxy-4-formyl-benzoic acid ethyl ester [CAS RN 55687-55-3]

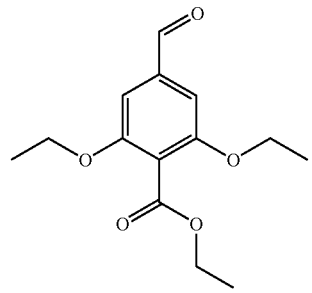

The title compound was prepared as described in DE 243 59 34 (F. Hoffmann-La Roche A G).

Intermediate D14

3-Ethoxy-4-iodo-5-methoxymethoxy-benzaldehyde [CAS RN 338451-02-8]

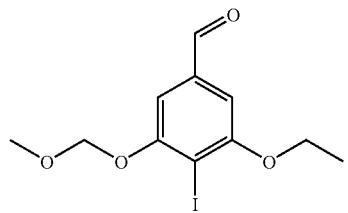

The title compound was prepared as described in WO 01/032 633 A1 (F. Hoffmann-La Roche A G).

Intermediate D15

3,5-Diethoxy-2-fluoro-benzaldehyde [CAS RN 277324-21-7]

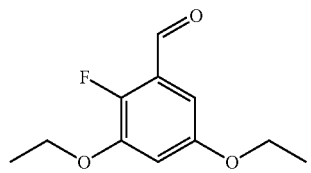

The title compound was prepared as described in WO 00/035 858 A1 (F. Hoffmann-La Roche A G).

Intermediate D16

3-Ethoxy-4-fluoro-benzaldehyde

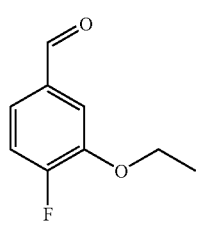

The title compound was prepared according to the procedure described for the synthesis of 4-chloro-3-ethoxy-benzaldehyde (intermediate D3) starting from 4-fluoro-3-hydroxy-benzoic acid in 73% overall yield after purification by flash column chromatography on silica eluting with hexane/ethyl acetate (10:1). $^1$H NMR (300 MHz, DMSO): δ 1.32 (t, J=7.0 Hz, 3H), 4.12 (q, J=7.0 Hz, 2H), 7.34-7.41 (m, 1H), 7.47-7.56 (m, 2H), 9.87 (s, 1H). MS (ISP): 186.1 [M+NH$_4$]$^+$.

Intermediate D17

3-Allyloxy-4-methoxy-benzaldehyde [CAS RN 225939-36-6]

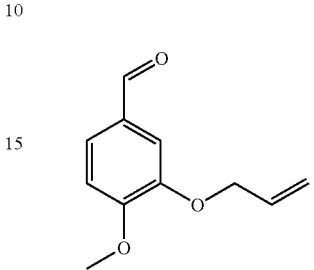

The title compound was prepared analogously to 3-ethoxy-4-methyl-benzaldehyde (intermediate D2) by reaction of 3-hydroxy-4-methoxy-benzaldehyde with allylbromide in DMF using K$_2$CO$_3$ as base (see also A. W. White, R. Almassy, A. H. Calvert, N. J. Curtin, R. J. Griffin, Z. Hostomsky, K. Maegley, D. R. Newell, S. Srinivasan and B. T. Golding *J. Med. Chem.* 2000, 43, 4084-4097).

Intermediate D18

8-Ethoxy-2,2-dimethyl-2H-chromene-6-carbaldehyde [CAS RN 210404-30-9]

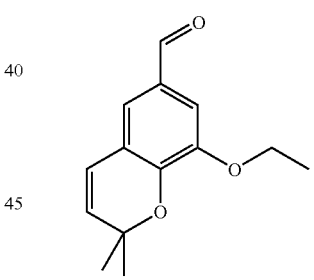

The title compound was prepared according to WO 01/083 476 A1 (Hoffmann-La Roche A G).

Intermediate D19

3,5-Diethoxy-benzaldehyde [CAS RN 120355-79-5]

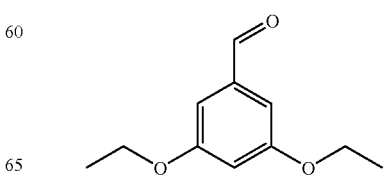

The title compound was prepared analogously to 3-ethoxy-4-methyl-benzaldehyde (intermediate D2) by reaction of 3,5-dihydroxybenzaldehyde with ethyl iodide in DMF using K₂CO₃ as base.

Intermediate D20

4-Chloro-3,5-diethoxy-benzaldehyde

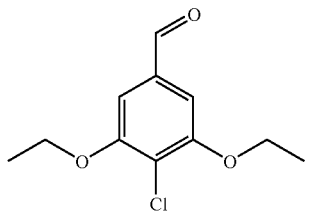

Step 1: 4-Chloro-3,5-diethoxy-benzoic acid ethyl ester

To a solution of 4-amino-3,5-diethoxy-benzoic acid ethyl ester (5.1 g, 20.13 mmol, 1.0 equiv; prepared as described in I. Kompis and A. Wick *Helv. Chim. Acta* 1977, 60, 3025-3034) in water (40 mL) and 37% HCl (40 mL) at 0° C. was added sodium nitrite (1.67 g, 24.16 mmol, 1.2 equiv). After 10 min copper(I) chloride (12.0 g, 120.81 mmol, 6.0 equiv) was added, the reaction mixture stirred for an additional 5 h at 0° C. and then the ice bath was removed. After stirring for 18 h, the crude reaction mixture was adjusted to pH=8 by addition of a solution of 1 M NaOH and the aqueous layer extracted with ethyl acetate (3×100 mL). The combined organic phases were dried over MgSO₄, concentrated by evaporation under reduced pressure and the crude material purified by silica column chromatography using a MPLC system (CombiFlash Companion, Isco Inc.) eluting with a gradient of heptane/ethyl acetate providing 5.0 g (91%) of the title compound. ¹H NMR (300 MHz, CDCl₃): δ 1.32 (t, J=7.0 Hz, 4H), 1.40 (t, J=7.0 Hz, 6H), 4.09 (q, J=7.0 Hz, 4H), 4.30 (q, J=7.0 Hz, 2H), 7.18 (s, 2H). ¹³C NMR (75 MHz, CDCl₃): δ 13.33, 13.66, 60.29, 64.16, 105.75, 115.88, 128.25, 154.49, 165.01. MS (ISP): 273.3 [M+H]⁺.

Step 2: (4-Chloro-3,5-diethoxy-phenyl)-methanol

To a solution of 4-chloro-3,5-diethoxy-benzoic acid ethyl ester (5.0 g, 18.33 mmol, 1.0 equiv) in dichloromethane (25 mL) was added slowly over a time period of 15 min under slight cooling to −30° C. a solution of diisobutylaluminium hydride (55.0 mL, 55.00 mmol, 3.0 equiv; 1 M solution in THF). After 30 min the excess hydride was quenched by cautious addition of methanol (10 mL) and water (2 mL). The mixture was stirred for 30 min, a solution of 1 M HCl was added and the aqueous layer extracted with ethyl acetate (3×100 mL). The combined organic phases were dried over MgSO₄, concentrated by evaporation under reduced pressure providing 4.0 g (95%) of the title compound. ¹H NMR (300 MHz, CDCl₃): δ 1.45 (t, J=7.0 Hz, 6H), 1.93 (br s, 1H), 4.09 (q, J=7.0 Hz, 4H), 4.62 (s, 2H), 6.57 (s, 2H). ¹³C NMR (75 MHz, CDCl₃): δ 14.74, 64.96, 65.18, 104.30, 110.65, 140.29, 155.66. MS (ISP): 231.4 [M+H]⁺.

Step 3

To a solution of (4-chloro-3,5-diethoxy-phenyl)-methanol (4.0 g, 17.34 mmol, 1.0 equiv) in THF (40 mL) was added activated MnO₂ (15.08 g, 173.4 mmol, 10.0 equiv) and the reaction mixture stirred for 18 h at rt. Filtration through Hyflo Super Cel and purification of the crude material by silica column chromatography using a MPLC system (CombiFlash Companion, Isco Inc.) eluting with a gradient of heptane/ethyl acetate provided 3.7 g (92%) of the title compound. ¹H NMR (300 MHz, CDCl₃): δ 1.50 (t, J=7.0 Hz, 6H), 4.19 (q, J=7.0 Hz, 4H), 7.07 (s, 2H), 9.89 (s, 1H). ¹³C NMR (75 MHz, CDCl₃): □ 14.61, 65.22, 106.26, 118.64, 135.08, 156.22, 191.01. MS (EI): 229.4 [M]⁺.

Intermediate D21

3,5-Diethoxy-4-pyrrol-1-yl-benzaldehyde

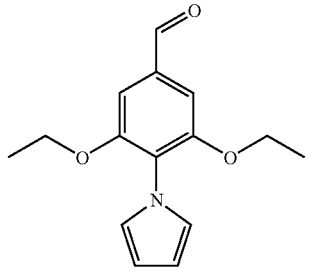

Step 1: 3,5-Diethoxy-4-pyrrol-1-yl-benzoic acid ethyl ester

To a solution of 4-amino-3,5-diethoxy-benzoic acid ethyl ester (3.0 g, 11.84 mmol, 1.0 equiv; prepared as described in I. Kompis and A. Wick *Helv. Chim. Acta* 1977, 60, 3025-3034) in heptane (10 mL) and conc. acetic acid (0.2 mL) was added 2,5-dimethoxy-tetrahydro-furan (1.88 g, 14.21 mmol, 1.2 equiv). After heating to reflux for 5 h, a Dean-Stark apparatus was attached and the reaction mixture heated for an additional time period of 5 h. Filtration of the crude reaction mixture and crystallization at 0° C. from heptane provided 2.94 g (82%) of the title compound. ¹H NMR (300 MHz, DMSO): δ 1.15 (t, J=7.0 Hz, 6H), 1.27 (t, J=7.1 Hz, 3H), 3.98 (q, J=7.0 Hz, 4H), 4.28 (q, J=7.1 Hz, 2H), 6.07-6.08 (m, 2H), 6.73-6.74 (m, 2H), 7.22 (s, 2H). ¹³C NMR (75 MHz, DMSO): δ 14.11, 14.35, 61.06, 64.57, 106.87, 107.64, 122.61, 123.33, 129.29, 153.75, 165.06. MS (ISP): 303.4 [M+H]⁺.

Step 2

To a solution of 3,5-diethoxy-4-pyrrol-1-yl-benzoic acid ethyl ester (1.51 g, 4.98 mmol, 1.0 equiv) in toluene (5 mL) was added slowly over a time period of 15 min under slight cooling to 20° C. a solution of diisobutylaluminium hydride (8.9 mL, 12.45 mmol, 2.5 equiv; 20% solution in toluene). After 1 h the excess hydride was quenched by cautious addition of water (10 mL) and a 28% solution of NaOH (2 mL). The mixture was stirred for 30 min and the organic phase filtered over Hyflo Super Cel. The aqueous layer was extracted with toluene (2×50 mL), the combined organic phases washed with a sat. solution of sodium chloride (2×50 mL) and concentrated by evaporation under reduced pressure to afford 1.30 g (100%) of (3,5-diethoxy-4-pyrrol-1-yl-phenyl)-methanol. The crude alcohol (1.30 g, 4.98 mmol, 1.0 equiv) was dissolved in toluene (20 mL) and activated $MnO_2$ (7.79 g, 89.5 mmol, 18.0 equiv) was added. The reaction mixture was heated to reflux for 7 h, after which time the reaction was filtered through Hyflo Super Cel and concentrated yielding 1.15 g (89% yield) of the title compound. $^1$H NMR (300 MHz, DMSO): δ 1.17 (t, J=7.0 Hz, 6H), 4.02 (q, J=7.0 Hz, 4H), 6.08-6.09 (m, 2H), 6.75-6.76 (m, 2H), 7.25 (s, 2H), 9.89 (s, 1H). MS (ISP): 260.1 [M+H]$^+$.

Intermediate D22

3-Ethoxy-4-(1-ethyl-propoxy)-benzaldehyde

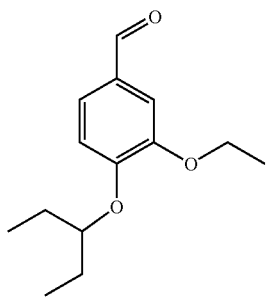

The title compound was prepared analogously to 3-ethoxy-4-methyl-benzaldehyde (intermediate D2) by reaction of 3-ethoxy-4-hydroxy-benzaldehyde with 3-bromo-pentane in DMF using $K_2CO_3$ as base. MS (ISP): 237.1 [M+H]$^+$.

Intermediate D23

4-Bromo-3,5-diethoxy-benzaldehyde [CAS RN 363166-11-4]

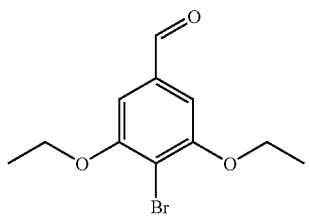

The title compound was prepared from 4-bromo-3,5-dihydroxy-benzoic acid as described in S. P. Dudek, H. D. Sikes and C. E. D. Chidsey *J. Am. Chem. Soc.* 2001, 123, 8033-8038.

Intermediate D24

4-Amino-3,5-diethoxy-benzaldehyde

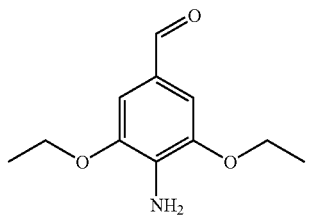

Step 1: (4-Amino-3,5-diethoxy-phenyl)-methanol

To a solution of 4-amino-3,5-diethoxy-benzoic acid ethyl ester (2.8 g, 11.05 mmol, 1.0 equiv; prepared as described in I. Kompis and A. Wick *Helv. Chim. Acta* 1977, 60, 3025-3034) in dichloromethane (50 mL) at 0° C. under Ar was slowly added diisobutylaluminium hydride (27.6 mL, 27.64 mmol, 2.5 equiv, 1 M solution in dichloromethane) over a time period of 15 min, the cooling bath removed on completion of addition. After 18 h the excess hydride was quenched by cautious addition of a sat. solution of potassium sodium tartrate (10 mL). The solidified mixture was extracted with dichloromethane (5×200 mL) and THF (2×150 mL), the combined organic phases washed with water (3×100 mL), dried over $MgSO_4$, concentrated by evaporation under reduced pressure and the crude material purified by column chromatography on silica eluting with a gradient of heptane/ethyl acetate (4:1→1:1) providing 1.10 g (47%) of the title compound. $^1$H NMR (300 MHz, CDCl$_3$): δ 1.42 (t, J=7.0 Hz, 3H), 3.82 (br s, 2H), 4.05 (q, J=7.0 Hz, 2H), 4.54 (s, 2H), 6.50 (s, 2H). $^{13}$C NMR (75 MHz, CDCl$_3$): δ 15.03, 64.21, 66.00, 104.51, 125.44, 129.89, 146.71. MS (ISP): 211.9 [M+H]$^+$.

Step 2

To a solution of (4-amino-3,5-diethoxy-phenyl)-methanol (0.79 g, 3.74 mmol, 1.0 equiv) in DMF (20 mL) was added activated $MnO_2$ (1.63 g, 18.70 mmol, 5.0 equiv). The reaction mixture was stirred for 24 h at rt, filtered through Hyflo Super Cel, the filtrate extracted with ethyl acetate (3×50 mL) and the combined organic phases dried over $MgSO_4$ providing 0.69 g (88%) of the title compound. $^1$H NMR (300 MHz, DMSO): δ

1.46 (t, J=7.0 Hz, 3H), 4.15 (q, J=7.0 Hz, 2H), 4.50 (br s, 2H), 7.04 (s, 2H), 9.70 (s, 1H). MS (ISP): 210.0 [M+H]⁺.

Intermediate D25

2-Chloro-3,5-diethoxy-benzaldehyde

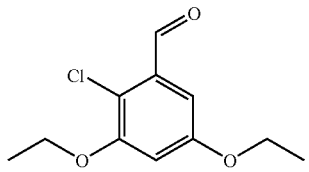

The title compound was prepared analogously to 3-ethoxy-4-methyl-benzaldehyde (intermediate D2) by reaction of 2-chloro-3,5-dihydroxy benzaldehyde with iodoethane in DMF using $K_2CO_3$ as base. MS (ISP): 229.3 [M+H]⁺.

Intermediate D26

3-Butoxy-4-methoxy-benzaldehyde

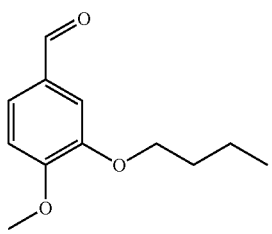

The title compound was prepared analogously to 3-ethoxy-4-methyl-benzaldehyde (intermediate D2) by reaction of 3-hydroxy-4-methoxy-benzaldehyde with 4-bromo-butane in DMF using $K_2CO_3$ as base. MS (ISP): 209.1 [M+H]⁺.

Intermediate D27

3-Hydroxy-5-isopropoxy-benzaldehyde

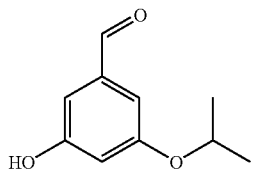

Isolated as a side-product in the synthesis of 3,5-diisopropoxy-benzaldehyde (intermediate D10, vide supra). ¹H NMR (300 MHz, CDCl₃): δ 1.34 (d, J=6.1 Hz, 6H), 4.58 (hept, J=6.1 Hz, 1H), 6.28 (br s, 1H), 6.68-6.69 (m, 1H), 6.95-6.98 (m, 2H), 9.85 (s, 1H). MS (ISN): 179.1 [M−H]⁻.

Intermediate D28

3-Ethoxy-4-methoxy-5-nitro benzaldehyde

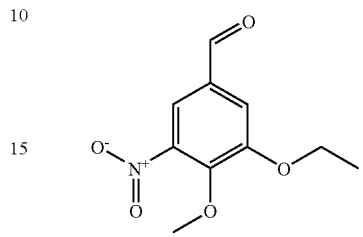

To a solution of 3-ethoxy-4-methoxybenzaldehyde (6.0 g, 33.3 mmol, 1.0 equiv; commercially available) in diethyl ether (50 mL) was added dropwise 65% nitric acid (4.12 mL, 5.81 g, 59.9 mmol, 1.8 equiv) over a period of 30 min at rt. After the addition was completed the reaction mixture was heated to reflux for 4 h. The reaction product precipitated out of solution, was filtered off, washed with cold diethyl ether (3×20 mL) and dried yielding 5.85 g (78%) of the title compound. ¹H NMR (300 MHz, CDCl₃): δ 1.53 (t, J=7.0 Hz, 3H), 4.04 (s, 3H), 4.26 (q, J=7.0 Hz, 2H), 7.37 (s, 1H), 7.61 (s, 1H), 10.40 (s, 1H). ¹³C NMR (75 MHz, CDCl₃): δ 14.34, 56.68, 65.35, 107.31, 110.48, 125.52, 143.56, 152.54, 152.70, 187.60. MS (ISP): 225.9 [M+H]⁺.

Intermediate D29

3-Ethylamino-4-methoxy-benzaldehyde

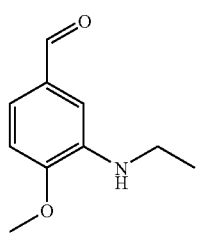

Through a solution of 2-(3-bromo-4-methoxy-phenyl)-[1,3]dioxolane (1.2 g, 4.63 mmol 1.0 equiv; prepared as described in WO 01/74775 A1, Sanofi-Synthelabo) in toluene (6 mL) was bubbled ethylamine for 10 min. To this solution was added KOtert-Bu (0.67 g, 6.95 mmol, 1.5 equiv), rac-2,2'-bis(diphenylphosphino)-1,1'-binaphthalene (0.029 g, 0.046 mmol, 0.01 equiv) and tris(dibenzylideneacetone)dipalladium(0) (0.021 g, 0.023 mmol, 0.005 equiv) and the solution heated to 110° C. under microwave irradiation for 20 min. A few drops of a solution of 37% HCl were added and the reaction mixture heated again under microwave irradiation to 100° C. for 5 min. Evaporation of the solvent and purification of the crude reaction product by column chromatography on silica eluting with hexane/ethyl acetate (7:3) provided 0.52 g (63%) of the title compound. ¹H NMR (300 MHz, CDCl₃): δ 1.24 (t, J=7.1 Hz, 3H), 3.16 (q, J=7.1 Hz, 2H), 3.86 (s, 3H), 4.17 (br s, 1H), 6.78 (d, J=8.1 Hz, 1H), 7.01 (d, J=1.9 Hz, 1H), 7.13 (dd, J=8.1 Hz, J=1.9 Hz, 1H). MS (ISP): 179.9 [M+H]$^+$.

Intermediate D30

4-Acetimido-3,5-diethoxy-benzaldehyde

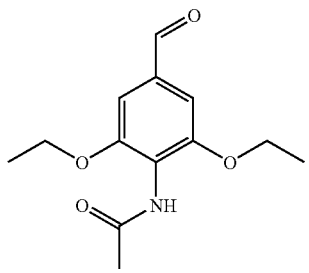

To a solution of 4-acetylamino-3,5-diethoxy-benzoic acid ethyl ester (1.0 g, 3.56 mmol, 1.0 equiv; [CAS RN 142955-43-9] prepared as described in EP 488 861 A1, Rhone Poulenc Chimie) in anhydrous THF (40 mL) was added lithium aluminium hydride (0.283 g, 7.47 mmol, 2.1 equiv) and the reaction mixture stirred at rt for 2 h. The crude reaction mixture was filtered over Hyflo Super Cel, the filtrate extracted with ethyl acetate (3×50 mL) and the combined organic phases dried over MgSO$_4$ providing 0.58 g (64%) of the benzyl alcohol. The crude reaction product (0.39 g, 1.54 mmol, 1.0 equiv) was dissolved in THF (20 mL) and activated MnO$_2$ (1.34 g, 15.40 mmol, 10.0 equiv) was added. After stirring at 60° C. for 2 h, the reaction mixture was filtered over Hyflo Super Cel and the solvent removed by evaporation under reduced pressure providing 0.35 g (90%) of the title compound. MS (ISP): 252.1 [M+H]$^+$.

Intermediate D31

3,5-Diethoxy-4-iodo-benzaldehyde [CAS RN 338454-05-0]

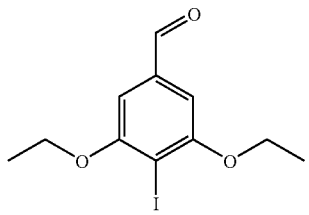

The title compound was prepared as described in WO 01/326 33 A1 (F. Hoffmann-La Roche A G).

Intermediate D32

5-Ethoxy-2-fluoro-4-(2-hydroxy-ethoxy)-benzaldehyde [CAS RN 376600-66-7]

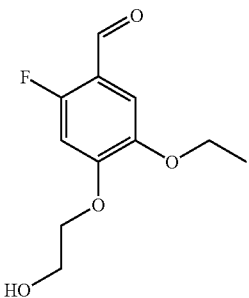

The title compound was prepared according to WO 01/090 051 (Hoffmann-La Roche A G).

Intermediate D33

5-Ethoxy-2-(2-methoxy-ethoxy)-benzaldehyde

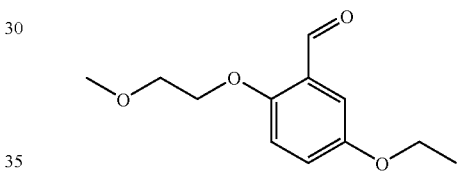

The title compound was prepared according to WO 00/035 858 A1 (Hoffmann-La Roche A G).

Intermediate D34

2,6-Diethoxy-4'-fluoro-biphenyl-4-carbaldehyde

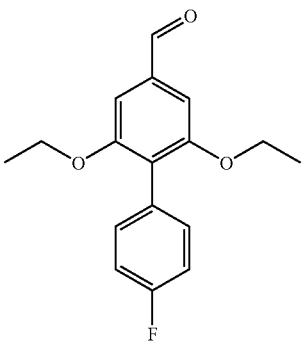

3,5-Diethoxy-4-iodo-benzaldehyde (14.05 g, 43.89 mmol, 1.0 equiv; intermediate D31) was dissolved under Ar in toluene (180 mL) and water (20 mL) and treated successively with 4-fluorophenyl boronic acid (12.28 g, 87.78 mmol, 2.0 equiv), K$_3$PO$_4$ (50.12 g, 236.12 mmol, 5.38 equiv), tricyclohexylphosphine (2.80 g, 9.66 mmol, 0.22 equiv), and palladium(II) acetate (1.08 g, 4.83 mmol, 0.11 equiv). The reaction mixture was heated to 100° C. for 18 h under scrupulous exclusion of oxygen, when GC indicated the absence of starting iodo-compound. The reaction mixture was poured on crashed ice/NH₄Cl, extracted with ethyl acetate (2×200 mL) and the combined organic phases washed with a sat. solution of NaCl (2×100 mL) and water (2×100 mL). The organic phase was dried over Na₂SO₄, concentrated by evaporation under reduced pressure and the crude material purified by silica column chromatography eluting with a mixture of hexane/ethyl acetate (9:1). Recrystallization from hexane/ethyl acetate provided 10.44 g (83%) of the title compound as white crystals. MS (EI): 288.2 [M]⁺.

Examples 28 to 287

According to the procedure described for the synthesis of example 27/step 3 further pyrimidine and quinazoline derivatives have been synthesized from (5-ethyl-pyrimidin-2-yl)-piperidin-4-yl-amine (intermediate C1), (4,6-dimethyl-pyrimidin-2-yl)-piperidin-4-yl-amine dihydrochloride (intermediate C2), piperidin-4-yl-pyrimidin-2-yl-amine dihydrobromide (intermediate C3), 2-(piperidin-4-ylamino)-pyrimidine-4-carboxylic acid methyl ester dihydrochloride (intermediate C4), piperidin-4-yl-(4-trifluoromethyl-pyrimidin-2-yl)-amine dihydrochloride (intermediate C5), 2-(piperidin-4-ylamino)-pyrimidin-4-ol dihydrochloride (intermediate C6), 2-(piperidin-4-ylamino)-pyrimidine-5-carboxylic acid dihydrochloride (intermediate C7), (4,6-dimethoxy-pyrimidin-2-yl)-piperidin-4-yl-amine dihydrochloride (intermediate C8), piperidin-4-yl-(5,5,7,7-tetramethyl-5,7-dihydro-furo[3,4-d]pyrimidin-2-yl)-amine dihydrochloride (intermediate C9), 4-amino-2-(piperidin-4-ylamino)-pyrimidine-5-carbonitrile dihydrochloride (intermediate C10), (5-phenyl-pyrimidin-2-yl)-piperidin-4-yl-amine dihydrochloride (intermediate C11), [5-(4-methoxy-phenyl)-pyrimidin-2-yl]-piperidin-4-yl-amine dihydrochloride (intermediate C12), piperidin-4-yl-(5-pyridin-3-yl-pyrimidin-2-yl)-amine dihydrochloride (intermediate C13), 4-[2-(piperidin-4-ylamino)-pyrimidin-5-yl]-benzamide dihydrochloride (intermediate C14), 2-(piperidin-4-ylamino)-4-trifluoromethyl-pyrimidine-5-carboxylic acid (4-chloro-phenyl)-amide dihydrochloride (intermediate C15), 2-(piperidin-4-ylamino)-4-trifluoromethyl-pyrimidine-5-carboxylic acid (4-trifluoromethoxy-phenyl)-amide dihydrochloride (intermediate C16), piperidin-4-yl-(4,6,7-trimethoxy-quinazolin-2-yl)-amine dihydrochloride (intermediate C17), N⁶-piperidin-4-yl-[1,3]dioxolo[4,5-g]quinazoline-6,8-diamine dihydrochloride (intermediate C18), [4-(2-fluoro-phenyl)-quinazolin-2-yl]-piperidin-4-yl-amine dihydrochloride (intermediate C19), [6-chloro-4-(2-fluoro-phenyl)-quinazolin-2-yl]-piperidin-4-yl-amine dihydrochloride (intermediate C20), (6,7-dimethoxy-4-piperidin-1-yl-quinazolin-2-yl)-piperidin-4-yl-amine dihydrochloride (intermediate C21), (6-chloro-4-morpholin-4-yl-quinazolin-2-yl)-piperidin-4-yl-amine dihydrochloride (intermediate C22), (6,7-dimethoxy-4-morpholin-4-yl-quinazolin-2-yl)-piperidin-4-yl-amine dihydrochloride (intermediate C23), (4-phenyl-pteridin-2-yl)-piperidin-4-yl-amine dihydrochloride (intermediate C24) and (4,6-dimethoxy-[1,3,5]triazin-2-yl)-piperidin-4-yl-amine dihydrochloride (intermediate C25) and the respective benzaldehyde intermediate as indicated in Table 3. The deprotected piperidines were either employed as the free amine, the corresponding hydrobromide or the corresponding hydrochloride salt. In case the hydrobromide or hydrochloride salt was used, N-ethyl diisopropylamine (58.3 mg, 0.45 mmol, 3.0 equiv) or triethylamine (45.5 mg, 0.45 mmol, 3.0 equiv) was added to the reaction mixture in addition. The results are compiled in Table 3 and comprise example 28 to example 287.

TABLE 3

| No. | MW | Compound Name | Starting Materials | ISP or ISN [M + H]⁺ or [M − H]⁻ found |
|---|---|---|---|---|
| 28 | 406.53 | [1-(1,4-dimethoxy-naphthalen-2-ylmethyl)-piperidin-4-yl]-(5-ethyl-pyrimidin-2-yl)-amine | (5-ethyl-pyrimidin-2-yl)-piperidin-4-yl-amine (intermediate C1) and 1,4-dimethoxy-naphthalene-2-carbaldehyde (intermediate D1) | [M + H]⁺ 407.3 |
| 29 | 354.50 | [1-(3-ethoxy-4-methyl-benzyl)-piperidin-4-yl]-(5-ethyl-pyrimidin-2-yl)-amine | (5-ethyl-pyrimidin-2-yl)-piperidin-4-yl-amine (intermediate C1) and 3-ethoxy-4-methyl-benzaldehyde (intermediate D2) | [M + H]⁺ 355.5 |
| 30 | 374.92 | [1-(4-Chloro-3-ethoxy-benzyl)-piperidin-4-yl]-(5-ethyl-pyrimidin-2-yl)-amine | (5-ethyl-pyrimidin-2-yl)-piperidin-4-yl-amine (intermediate C1) and 4-chloro-3-ethoxy-benzaldehyde (intermediate D3) | [M + H]⁺ 375.5 |
| 31 | 356.47 | 2-ethoxy-4-[4-(5-ethyl-pyrimidin-2-ylamino)-piperidin-1-ylmethyl]-phenol | (5-ethyl-pyrimidin-2-yl)-piperidin-4-yl-amine (intermediate C1) and 3-ethoxy-4-hydroxy-benzaldehyde (commercially available) | [M + H]⁺ 357.3 |
| 32 | 398.55 | [1-(3-ethoxy-4-isopropoxy-benzyl)-piperidin-4-yl]-(5-ethyl-pyrimidin-2-yl)-amine | (5-ethyl-pyrimidin-2-yl)-piperidin-4-yl-amine (intermediate C1) and 3-ethoxy-4-isopropoxy-benzaldehyde (commercially available) | [M + H]⁺ 399.3 |

TABLE 3-continued

| No. | MW | Compound Name | Starting Materials | ISP or ISN [M + H]+ or [M − H]− found |
|---|---|---|---|---|
| 33 | 424.59 | {1-[3-ethoxy-4-(3-methyl-but-2-enyloxy)-benzyl]-piperidin-4-yl}-(5-ethyl-pyrimidin-2-yl)-amine | (5-ethyl-pyrimidin-2-yl)-piperidin-4-yl-amine (intermediate C1) and 3-ethoxy-4-(3-methyl-but-2-enyloxy)-benzaldehyde (intermediate D4) | [M + H]+ 425.4 |
| 34 | 434.56 | methanesulfonic acid 2-ethoxy-4-[4-(5-ethyl-pyrimidin-2-ylamino)-piperidin-1-ylmethyl]-phenyl ester | (5-ethyl-pyrimidin-2-yl)-piperidin-4-yl-amine (intermediate C1) and methanesulfonic acid 2-ethoxy-4-formyl-phenyl ester (intermediate D5) | [M + H]+ 435.4 |
| 35 | 412.58 | [1-(3,4-diisopropoxy-benzyl)-piperidin-4-yl]-(5-ethyl-pyrimidin-2-yl)-amine | (5-ethyl-pyrimidin-2-yl)-piperidin-4-yl-amine (intermediate C1) and 3,4-diisopropoxy-benzaldehyde (intermediate D6) | [M + H]+ 413.4 |
| 36 | 384.52 | (5-ethyl-pyrimidin-2-yl)-[1-(4-methoxy-3-propoxy-benzyl)-piperidin-4-yl]-amine | (5-ethyl-pyrimidin-2-yl)-piperidin-4-yl-amine (intermediate C1) and 4-methoxy-3-propoxy-benzaldehyde (intermediate D7) | [M + H]+ 385.4 |
| 37 | 388.49 | (5-ethyl-pyrimidin-2-yl)-{1-[3-(2-fluoro-ethoxy)-4-methoxy-benzyl]-piperidin-4-yl}-amine | (5-ethyl-pyrimidin-2-yl)-piperidin-4-yl-amine (intermediate C1) and 3-(2-fluoro-ethoxy)-4-methoxy-benzaldehyde (intermediate D8) | [M + H]+ 389.3 |
| 38 | 398.55 | (5-ethyl-pyrimidin-2-yl)-[1-(3-isobutoxy-4-methoxy-benzyl)-piperidin-4-yl]-amine | (5-ethyl-pyrimidin-2-yl)-piperidin-4-yl-amine (intermediate C1) and 3-isobutoxy-4-methoxy-benzaldehyde (intermediate D9) | [M + H]+ 399.3 |
| 39 | 412.58 | [1-(3,5-diisopropoxy-benzyl)-piperidin-4-yl]-(5-ethyl-pyrimidin-2-yl)-amine | (5-ethyl-pyrimidin-2-yl)-piperidin-4-yl-amine (intermediate C1) and 3,5-diisopropoxy-benzaldehyde (intermediate D10) | [M + H]+ 413.4 |
| 40 | 446.59 | [1-(3-benzyloxy-5-ethoxy-benzyl)-piperidin-4-yl]-(5-ethyl-pyrimidin-2-yl)-amine | (5-ethyl-pyrimidin-2-yl)-piperidin-4-yl-amine (intermediate C1) and 3-benzyloxy-5-ethoxy-benzaldehyde (intermediate D11) | [M + H]+ 447.3 |
| 41 | 402.51 | [1-(3,5-Diethoxy-4-fluoro-benzyl)-piperidin-4-yl]-(5-ethyl-pyrimidin-2-yl)-amine | (5-ethyl-pyrimidin-2-yl)-piperidin-4-yl-amine (intermediate C1) and 3,5-diethoxy-4-fluoro-benzaldehyde (intermediate D12) | [M + H]+ 403.4 |
| 42 | 456.59 | 2,6-diethoxy-4-[4-(5-ethyl-pyrimidin-2-ylamino)-piperidin-1-ylmethyl]-benzoic acid ethyl ester | (5-ethyl-pyrimidin-2-yl)-piperidin-4-yl-amine (intermediate C1) and 2,6-diethoxy-4-formyl-benzoic acid ethyl ester (intermediate D13) | [M + H]+ 457.4 |
| 43 | 526.42 | [1-(3-ethoxy-4-iodo-5-methoxymethoxy-benzyl)-piperidin-4-yl]-(5-ethyl-pyrimidin-2-yl)-amine | (5-ethyl-pyrimidin-2-yl)-piperidin-4-yl-amine (intermediate C1) and 3-ethoxy-4-iodo-5-methoxymethoxy-benzaldehyde (intermediate D14) | [M + H]+ 527.1 |
| 44 | 402.51 | [1-(3,5-diethoxy-2-fluoro-benzyl)-piperidin-4-yl]-(5-ethyl-pyrimidin-2-yl)-amine | (5-ethyl-pyrimidin-2-yl)-piperidin-4-yl-amine (intermediate C1) and 3,5-diethoxy-2-fluoro-benzaldehyde (intermediate D15) | [M + H]+ 403.4 |
| 45 | 354.50 | (4,6-dimethyl-pyrimidin-2-yl)-[1-(3-ethoxy-4-methyl-benzyl)-piperidin- | (4,6-dimethyl-pyrimidin-2-yl)-piperidin-4-yl-amine dihydrochloride (intermediate | [M + H]+ 355.4 |

TABLE 3-continued

| No. | MW | Compound Name | Starting Materials | ISP or ISN [M + H]+ or [M − H]− found |
|---|---|---|---|---|
| | | 4-yl]-amine | C2) and 3-ethoxy-4-methyl-benzaldehyde (intermediate D2) | |
| 46 | 358.46 | (4,6-dimethyl-pyrimidin-2-yl)-[1-(3-ethoxy-4-fluoro-benzyl)-piperidin-4-yl]-amine | (4,6-dimethyl-pyrimidin-2-yl)-piperidin-4-yl-amine dihydrochloride (intermediate C2) and 3-ethoxy-4-fluoro-benzaldehyde (intermediate D16) | [M + H]+ 359.3 |
| 47 | 374.92 | [1-(4-chloro-3-ethoxy-benzyl)-piperidin-4-yl]-(4,6-dimethyl-pyrimidin-2-yl)-amine | (4,6-dimethyl-pyrimidin-2-yl)-piperidin-4-yl-amine dihydrochloride (intermediate C2) and 4-chloro-3-ethoxy-benzaldehyde (intermediate D3) | [M + H]+ 375.3 |
| 48 | 356.47 | 4-[4-(4,6-dimethyl-pyrimidin-2-ylamino)-piperidin-1-ylmethyl]-2-ethoxy-phenol | (4,6-dimethyl-pyrimidin-2-yl)-piperidin-4-yl-amine dihydrochloride (intermediate C2) and 3-ethoxy-4-hydroxy-benzaldehyde (commercially available) | [M + H]+ 357.3 |
| 49 | 370.50 | (4,6-dimethyl-pyrimidin-2-yl)-[1-(3-ethoxy-4-methoxy-benzyl)-piperidin-4-yl]-amine | (4,6-dimethyl-pyrimidin-2-yl)-piperidin-4-yl-amine dihydrochloride (intermediate C2) and 3-ethoxy-4-methoxy-benzaldehyde (commercially available) | [M + H]+ 371.2 |
| 50 | 398.55 | (4,6-dimethyl-pyrimidin-2-yl)-[1-(3-ethoxy-4-isopropoxy-benzyl)-piperidin-4-yl]-amine | (4,6-dimethyl-pyrimidin-2-yl)-piperidin-4-yl-amine dihydrochloride (intermediate C2) and 3-ethoxy-4-isopropoxy-benzaldehyde (commercially available) | [M + H]+ 399.4 |
| 51 | 384.52 | (4,6-dimethyl-pyrimidin-2-yl)-[1-(4-methoxy-3-propoxy-benzyl)-piperidin-4-yl]-amine | (4,6-dimethyl-pyrimidin-2-yl)-piperidin-4-yl-amine dihydrochloride (intermediate C2) and 4-methoxy-3-propoxy-benzaldehyde (intermediate D7) | [M + H]+ 385.4 |
| 52 | 388.49 | (4,6-dimethyl-pyrimidin-2-yl)-{1-[3-(2-fluoro-ethoxy)-4-methoxy-benzyl]-piperidin-4-yl}-amine | (4,6-dimethyl-pyrimidin-2-yl)-piperidin-4-yl-amine dihydrochloride (intermediate C2) and 3-(2-fluoro-ethoxy)-4-methoxy-benzaldehyde (intermediate D8) | [M + H]+ 389.3 |
| 53 | 382.51 | [1-(3-allyloxy-4-methoxy-benzyl)-piperidin-4-yl]-(4,6-dimethyl-pyrimidin-2-yl)-amine | (4,6-dimethyl-pyrimidin-2-yl)-piperidin-4-yl-amine dihydrochloride (intermediate C2) and 3-allyloxy-4-methoxy-benzaldehyde (intermediate D17) | [M + H]+ 383.3 |
| 54 | 398.55 | (4,6-dimethyl-pyrimidin-2-yl)-[1-(3-isobutoxy-4-methoxy-benzyl)-piperidin-4-yl]-amine | (4,6-dimethyl-pyrimidin-2-yl)-piperidin-4-yl-amine dihydrochloride (intermediate C2) and 3-isobutoxy-4-methoxy-benzaldehyde (intermediate D9) | [M + H]+ 399.4 |
| 55 | 422.57 | (4,6-dimethyl-pyrimidin-2-yl)-[1-(8-ethoxy-2,2-dimethyl-2H-chromen-6-ylmethyl)-piperidin-4-yl]-amine | (4,6-dimethyl-pyrimidin-2-yl)-piperidin-4-yl-amine dihydrochloride (intermediate C2) and 8-ethoxy-2,2-dimethyl-2H-chromene-6-carbaldehyde (intermediate D18) | [M + H]+ 423.3 |
| 56 | 384.52 | [1-(3,5-diethoxy-benzyl)-piperidin-4-yl]-(4,6-dimethyl-pyrimidin-2-yl)-amine | (4,6-dimethyl-pyrimidin-2-yl)-piperidin-4-yl-amine dihydrochloride (intermediate C2) and 3,5-diethoxy-benzaldehyde (intermediate D19) | [M + H]+ 385.4 |
| 57 | 412.58 | [1-(3,5-diisopropoxy-benzyl)-piperidin-4-yl]-(4,6-dimethyl-pyrimidin-2-yl)-amine | (4,6-dimethyl-pyrimidin-2-yl)-piperidin-4-yl-amine dihydrochloride (intermediate C2) and 3,5-diisopropoxy- | [M + H]+ 413.4 |

TABLE 3-continued

| No. | MW | Compound Name | Starting Materials | ISP or ISN [M + H]+ or [M − H]− found |
|---|---|---|---|---|
| 58 | 402.51 | [1-(3,5-diethoxy-4-fluoro-benzyl)-piperidin-4-yl]-(4,6-dimethyl-pyrimidin-2-yl)-amine | (4,6-dimethyl-pyrimidin-2-yl)-piperidin-4-yl-amine dihydrochloride (intermediate C2) and 3,5-diethoxy-4-fluoro-benzaldehyde (intermediate D12) | [M + H]+ 403.4 |
| 59 | 418.97 | [1-(4-chloro-3,5-diethoxy-benzyl)-piperidin-4-yl]-(4,6-dimethyl-pyrimidin-2-yl)-amine | (4,6-dimethyl-pyrimidin-2-yl)-piperidin-4-yl-amine dihydrochloride (intermediate C2) and 4-chloro-3,5-diethoxy-benzaldehyde (intermediate D20) | [M + H]+ 419.2 |
| 60 | 449.60 | [1-(3,5-diethoxy-4-pyrrol-1-yl-benzyl)-piperidin-4-yl]-(4,6-dimethyl-pyrimidin-2-yl)-amine | (4,6-dimethyl-pyrimidin-2-yl)-piperidin-4-yl-amine dihydrochloride (intermediate C2) and 3,5-diethoxy-4-pyrrol-1-yl-benzaldehyde (intermediate D21) | [M + H]+ 450.3 |
| 61 | 362.48 | (4,6-dimethyl-pyrimidin-2-yl)-[1-(2-phenyl-1H-imidazol-4-ylmethyl)-piperidin-4-yl]-amine | (4,6-dimethyl-pyrimidin-2-yl)-piperidin-4-yl-amine dihydrochloride (intermediate C2) and 2-phenyl-3H-imidazole-4-carbaldehyde (commercially available) | [M + H]+ 363.4 |
| 62 | 346.16 | [1-(4-chloro-3-ethoxy-benzyl)-piperidin-4-yl]-pyrimidin-2-yl-amine | piperidin-4-yl-pyrimidin-2-yl-amine dihydrobromide (intermediate C3) and 4-chloro-3-ethoxy-benzaldehyde (intermediate D3) | [M + H]+ 347.2 |
| 63 | 342.21 | [1-(3-ethoxy-4-methoxy-benzyl)-piperidin-4-yl]-pyrimidin-2-yl-amine | piperidin-4-yl-pyrimidin-2-yl-amine dihydrobromide (intermediate C3) and 3-ethoxy-4-methoxy-benzaldehyde (commercially available) | [M + H]+ 343.3 |
| 64 | 398.27 | {1-[3-ethoxy-4-(1-ethyl-propoxy)-benzyl]-piperidin-4-yl}-pyrimidin-2-yl-amine | piperidin-4-yl-pyrimidin-2-yl-amine dihydrobromide (intermediate C3) and 3-ethoxy-4-(1-ethyl-propoxy)-benzaldehyde (intermediate D22) | [M + H]+ 399.3 |
| 65 | 356.22 | [1-(3,5-diethoxy-benzyl)-piperidin-4-yl]-pyrimidin-2-yl-amine | piperidin-4-yl-pyrimidin-2-yl-amine dihydrobromide (intermediate C3) and 3,5-diethoxy-benzaldehyde (intermediate D19) | [M + H]+ 357.3 |
| 66 | 384.25 | [1-(3,5-diisopropoxy-benzyl)-piperidin-4-yl]-pyrimidin-2-yl-amine | piperidin-4-yl-pyrimidin-2-yl-amine dihydrobromide (intermediate C3) and 3,5-diisopropoxy-benzaldehyde (intermediate D10) | [M + H]+ 385.3 |
| 67 | 374.21 | [1-(3,5-diethoxy-4-fluoro-benzyl)-piperidin-4-yl]-pyrimidin-2-yl-amine | piperidin-4-yl-pyrimidin-2-yl-amine dihydrobromide (intermediate C3) and 3,5-diethoxy-4-fluoro-benzaldehyde (intermediate D12) | [M + H]+ 375.3 |
| 68 | 390.18 | [1-(4-chloro-3,5-diethoxy-benzyl)-piperidin-4-yl]-pyrimidin-2-yl-amine | piperidin-4-yl-pyrimidin-2-yl-amine dihydrobromide (intermediate C3) and 4-chloro-3,5-diethoxy-benzaldehyde (intermediate D20) | [M + H]+ 391.2 |
| 69 | 434.13 | [1-(4-bromo-3,5-diethoxy-benzyl)-piperidin-4-yl]-pyrimidin-2-yl-amine | piperidin-4-yl-pyrimidin-2-yl-amine dihydrobromide (intermediate C3) and 4-bromo-3,5-diethoxy-benzaldehyde (intermediate D23) | [M + H]+ 435.2 |
| 70 | 371.23 | [1-(4-amino-3,5-diethoxy-benzyl)- | piperidin-4-yl-pyrimidin-2-yl-amine dihydrobromide | [M + H]+ 372.3 |

TABLE 3-continued

| No. | MW | Compound Name | Starting Materials | ISP or ISN [M + H]+ or [M − H]− found |
|---|---|---|---|---|
| | | piperidin-4-yl]-pyrimidin-2-yl-amine | (intermediate C3) and 4-amino-3,5-diethoxy-benzaldehyde (intermediate D24) | |
| 71 | 421.25 | [1-(3,5-diethoxy-4-pyrrol-1-yl-benzyl)-piperidin-4-yl]-pyrimidin-2-yl-amine | piperidin-4-yl-pyrimidin-2-yl-amine dihydrobromide (intermediate C3) and 3,5-diethoxy-4-pyrrol-1-yl-benzaldehyde (intermediate D21) | [M + H]+ 422.3 |
| 72 | 390.18 | [1-(2-chloro-3,5-diethoxy-benzyl)-piperidin-4-yl]-pyrimidin-2-yl-amine | piperidin-4-yl-pyrimidin-2-yl-amine dihydrobromide (intermediate C3) and 2-chloro-3,5-diethoxy-benzaldehyde (intermediate D25) | [M + H]+ 391.2 |
| 73 | 384.48 | 2-[1-(3-ethoxy-4-methyl-benzyl)-piperidin-4-ylamino]-pyrimidine-4-carboxylic acid methyl ester | 2-(piperidin-4-ylamino)-pyrimidine-4-carboxylic acid methyl ester dihydrochloride (intermediate C4) and 3-ethoxy-4-methyl-benzaldehyde (intermediate D2) | [M + H]+ 385.4 |
| 74 | 404.90 | 2-[1-(4-chloro-3-ethoxy-benzyl)-piperidin-4-ylamino]-pyrimidine-4-carboxylic acid methyl ester | 2-(piperidin-4-ylamino)-pyrimidine-4-carboxylic acid methyl ester dihydrochloride (intermediate C4) and 4-chloro-3-ethoxy-benzaldehyde (intermediate D3) | [M + H]+ 405.4 |
| 75 | 428.53 | 2-[1-(3-isobutoxy-4-methoxy-benzyl)-piperidin-4-ylamino]-pyrimidine-4-carboxylic acid methyl ester | 2-(piperidin-4-ylamino)-pyrimidine-4-carboxylic acid methyl ester dihydrochloride (intermediate C4) and 3-isobutoxy-4-methoxy-benzaldehyde (intermediate D9) | [M + H]+ 429.4 |
| 76 | 414.51 | 2-[1-(3,5-diethoxy-benzyl)-piperidin-4-ylamino]-pyrimidine-4-carboxylic acid methyl ester | 2-(piperidin-4-ylamino)-pyrimidine-4-carboxylic acid methyl ester dihydrochloride (intermediate C4) and 3,5-diethoxy-benzaldehyde (intermediate D19) | [M + H]+ 415.4 |
| 77 | 442.56 | 2-[1-(3,5-diisopropoxy-benzyl)-piperidin-4-ylamino]-pyrimidine-4-carboxylic acid methyl ester | 2-(piperidin-4-ylamino)-pyrimidine-4-carboxylic acid methyl ester dihydrochloride (intermediate C4) and 3,5-diisopropoxy-benzaldehyde (intermediate D10) | [M + H]+ 443.4 |
| 78 | 432.50 | 2-[1-(3,5-diethoxy-4-fluoro-benzyl)-piperidin-4-ylamino]-pyrimidine-4-carboxylic acid methyl ester | 2-(piperidin-4-ylamino)-pyrimidine-4-carboxylic acid methyl ester dihydrochloride (intermediate C4) and 3,5-diethoxy-4-fluoro-benzaldehyde (intermediate D12) | [M + H]+ 433.3 |
| 79 | 448.95 | 2-[1-(4-chloro-3,5-diethoxy-benzyl)-piperidin-4-ylamino]-pyrimidine-4-carboxylic acid methyl ester | 2-(piperidin-4-ylamino)-pyrimidine-4-carboxylic acid methyl ester dihydrochloride (intermediate C4) and 4-chloro-3,5-diethoxy-benzaldehyde (intermediate D20) | [M + H]+ 449.2 |
| 80 | 479.58 | 2-[1-(3,5-diethoxy-4-pyrrol-1-yl-benzyl)-piperidin-4-ylamino]-pyrimidine-4-carboxylic acid methyl ester | 2-(piperidin-4-ylamino)-pyrimidine-4-carboxylic acid methyl ester dihydrochloride (intermediate C4) and 3,5-diethoxy-4-pyrrol-1-yl-benzaldehyde (intermediate D21) | [M + H]+ 480.3 |
| 81 | 439.48 | [1-(4-amino-3,5-diethoxy-benzyl)-piperidin-4-yl]-(4-trifluoromethyl- | piperidin-4-yl-(4-trifluoromethyl-pyrimidin-2-yl)-amine dihydrochloride (intermediate C5) and 4- | [M + H]+ 440.3 |

TABLE 3-continued

| No. | MW | Compound Name | Starting Materials | ISP or ISN [M + H]+ or [M − H]− found |
|---|---|---|---|---|
| | | pyrimidin-2-yl)-amine | amino-3,5-diethoxy-benzaldehyde (intermediate D24) | |
| 82 | 489.55 | [1-(3,5-diethoxy-4-pyrrol-1-yl-benzyl)-piperidin-4-yl]-(4-trifluoromethyl-pyrimidin-2-yl)-amine | piperidin-4-yl-(4-trifluoromethyl-pyrimidin-2-yl)-amine dihydrochloride (intermediate C5) and 3,5-diethoxy-4-pyrrol-1-yl-benzaldehyde (intermediate D21) | [M + H]+ 490.3 |
| 83 | 362.86 | 2-[1-(4-chloro-3-ethoxy-benzyl)-piperidin-4-ylamino]-pyrimidin-4-ol | 2-(piperidin-4-ylamino)-pyrimidin-4-ol dihydrochloride (intermediate C6) and 4-chloro-3-ethoxy-benzaldehyde (intermediate D3) | [M + H]+ 363.4 |
| 84 | 400.52 | 2-[1-(3,5-diisopropoxy-benzyl)-piperidin-4-ylamino]-pyrimidin-4-ol | 2-(piperidin-4-ylamino)-pyrimidin-4-ol dihydrochloride (intermediate C6) and 3,5-diisopropoxy-benzaldehyde (intermediate D10) | [M + H]+ 401.4 |
| 85 | 387.48 | 2-[1-(4-amino-3,5-diethoxy-benzyl)-piperidin-4-ylamino]-pyrimidin-4-ol | 2-(piperidin-4-ylamino)-pyrimidin-4-ol dihydrochloride (intermediate C6) and 4-amino-3,5-diethoxy-benzaldehyde (intermediate D24) | [M + H]+ 388.5 |
| 86 | 437.54 | 2-[1-(3,5-diethoxy-4-pyrrol-1-yl-benzyl)-piperidin-4-ylamino]-pyrimidin-4-ol | 2-(piperidin-4-ylamino)-pyrimidin-4-ol dihydrochloride (intermediate C6) and 3,5-diethoxy-4-pyrrol-1-yl-benzaldehyde (intermediate D21) | [M + H]+ 438.6 |
| 87 | 370.45 | 2-[1-(3-ethoxy-4-methyl-benzyl)-piperidin-4-ylamino]-pyrimidine-5-carboxylic acid | 2-(piperidin-4-ylamino)-pyrimidine-5-carboxylic acid dihydrochloride (intermediate C7) and 3-ethoxy-4-methyl-benzaldehyde (intermediate D2) | [M + H]+ 371.2 |
| 88 | 390.87 | 2-[1-(4-chloro-3-ethoxy-benzyl)-piperidin-4-ylamino]-pyrimidine-5-carboxylic acid | 2-(piperidin-4-ylamino)-pyrimidine-5-carboxylic acid dihydrochloride (intermediate C7) and 4-chloro-3-ethoxy-benzaldehyde (intermediate D3) | [M + H]+ 391.2 |
| 89 | 414.51 | 2-[1-(3-isobutoxy-4-methoxy-benzyl)-piperidin-4-ylamino]-pyrimidine-5-carboxylic acid | 2-(piperidin-4-ylamino)-pyrimidine-5-carboxylic acid dihydrochloride (intermediate C7) and 3-isobutoxy-4-methoxy-benzaldehyde (intermediate D9) | [M + H]+ 415.4 |
| 90 | 434.92 | 2-[1-(4-chloro-3,5-diethoxy-benzyl)-piperidin-4-ylamino]-pyrimidine-5-carboxylic acid | 2-(piperidin-4-ylamino)-pyrimidine-5-carboxylic acid dihydrochloride (intermediate C7) and 4-chloro-3,5-diethoxy-benzaldehyde (intermediate D20) | [M + H]+ 415.4 |
| 91 | 386.50 | (4,6-dimethoxy-pyrimidin-2-yl)-[1-(3-ethoxy-4-methyl-benzyl)-piperidin-4-yl]-amine | (4,6-dimethoxy-pyrimidin-2-yl)-piperidin-4-yl-amine dihydrochloride (intermediate C8) and 3-ethoxy-4-methyl-benzaldehyde (intermediate D2) | [M + H]+ 387.3 |
| 92 | 390.46 | (4,6-dimethoxy-pyrimidin-2-yl)-[1-(3-ethoxy-4-fluoro-benzyl)-piperidin-4-yl]-amine | (4,6-dimethoxy-pyrimidin-2-yl)-piperidin-4-yl-amine dihydrochloride (intermediate C8) and 3-ethoxy-4-fluoro-benzaldehyde (intermediate D16) | [M + H]+ 391.2 |
| 93 | 406.91 | [1-(4-chloro-3-ethoxy-benzyl)-piperidin-4-yl]-(4,6-dimethoxy-pyrimidin-2-yl)-amine | (4,6-dimethoxy-pyrimidin-2-yl)-piperidin-4-yl-amine dihydrochloride (intermediate C8) and 4-chloro-3-ethoxy- | [M + H]+ 407.3 |

TABLE 3-continued

| No. | MW | Compound Name | Starting Materials | ISP or ISN [M + H]+ or [M − H]− found |
|---|---|---|---|---|
| 94 | 388.47 | 4-[4-(4,6-dimethoxy-pyrimidin-2-ylamino)-piperidin-1-ylmethyl]-2-ethoxy-phenol | (4,6-dimethoxy-pyrimidin-2-yl)-piperidin-4-yl-amine dihydrochloride (intermediate C8) and 3-ethoxy-4-hydroxy-benzaldehyde (commercially available) | [M + H]+ 389.3 |
| 95 | 430.55 | (4,6-dimethoxy-pyrimidin-2-yl)-[1-(3-ethoxy-4-isopropoxy-benzyl)-piperidin-4-yl]-amine | (4,6-dimethoxy-pyrimidin-2-yl)-piperidin-4-yl-amine dihydrochloride (intermediate C8) and 3-ethoxy-4-isopropoxy-benzaldehyde (commercially available) | [M + H]+ 431.4 |
| 96 | 466.56 | methanesulfonic acid 4-[4-(4,6-dimethoxy-pyrimidin-2-ylamino)-piperidin-1-ylmethyl]-2-ethoxy-phenyl ester | (4,6-dimethoxy-pyrimidin-2-yl)-piperidin-4-yl-amine dihydrochloride (intermediate C8) and methanesulfonic acid 2-ethoxy-4-formyl-phenyl ester (intermediate D5) | [M + H]+ 467.3 |
| 97 | 420.48 | (4,6-dimethoxy-pyrimidin-2-yl)-{1-[3-(2-fluoro-ethoxy)-4-methoxy-benzyl]-piperidin-4-yl}-amine | (4,6-dimethoxy-pyrimidin-2-yl)-piperidin-4-yl-amine dihydrochloride (intermediate C8) and 3-(2-fluoro-ethoxy)-4-methoxy-benzaldehyde (intermediate D8) | [M + H]+ 421.3 |
| 98 | 414.51 | [1-(3-allyloxy-4-methoxy-benzyl)-piperidin-4-yl]-(4,6-dimethoxy-pyrimidin-2-yl)-amine | (4,6-dimethoxy-pyrimidin-2-yl)-piperidin-4-yl-amine dihydrochloride (intermediate C8) and 3-allyloxy-4-methoxy-benzaldehyde (intermediate D17) | [M + H]+ 415.4 |
| 99 | 430.55 | [1-(3-butoxy-4-methoxy-benzyl)-piperidin-4-yl]-(4,6-dimethoxy-pyrimidin-2-yl)-amine | (4,6-dimethoxy-pyrimidin-2-yl)-piperidin-4-yl-amine dihydrochloride (intermediate C8) and 3-butoxy-4-methoxy-benzaldehyde (intermediate D26) | [M + H]+ 431.4 |
| 100 | 454.57 | (4,6-dimethoxy-pyrimidin-2-yl)-[1-(8-ethoxy-2,2-dimethyl-2H-chromen-6-ylmethyl)-piperidin-4-yl]-amine | (4,6-dimethoxy-pyrimidin-2-yl)-piperidin-4-yl-amine dihydrochloride (intermediate C8) and 8-ethoxy-2,2-dimethyl-2H-chromene-6-carbaldehyde (intermediate D17) | [M + H]+ 455.3 |
| 101 | 416.52 | [1-(3,5-diethoxy-benzyl)-piperidin-4-yl]-(4,6-dimethoxy-pyrimidin-2-yl)-amine | (4,6-dimethoxy-pyrimidin-2-yl)-piperidin-4-yl-amine dihydrochloride (intermediate C8) and 3,5-diethoxy-benzaldehyde (intermediate D19) | [M + H]+ 417.4 |
| 102 | 402.49 | 3-[4-(4,6-dimethoxy-pyrimidin-2-ylamino)-piperidin-1-ylmethyl]-5-isopropoxy-phenol | (4,6-dimethoxy-pyrimidin-2-yl)-piperidin-4-yl-amine dihydrochloride (intermediate C8) and 3-hydroxy-5-isopropoxy-benzaldehyde (intermediate D27) | [M + H]+ 403.4 |
| 103 | 444.58 | [1-(3,5-diisopropoxy-benzyl)-piperidin-4-yl]-(4,6-dimethoxy-pyrimidin-2-yl)-amine | (4,6-dimethoxy-pyrimidin-2-yl)-piperidin-4-yl-amine dihydrochloride (intermediate C8) and 3,5-diisopropoxy-benzaldehyde (intermediate D10) | [M + H]+ 445.4 |
| 104 | 434.51 | [1-(3,5-diethoxy-4-fluoro-benzyl)-piperidin-4-yl]-(4,6-dimethoxy-pyrimidin-2-yl)-amine | (4,6-dimethoxy-pyrimidin-2-yl)-piperidin-4-yl-amine dihydrochloride (intermediate C8) and 3,5-diethoxy-4-fluoro-benzaldehyde (intermediate D12) | [M + H]+ 435.4 |

TABLE 3-continued

| No. | MW | Compound Name | Starting Materials | ISP or ISN [M + H]+ or [M − H]− found |
|---|---|---|---|---|
| 105 | 495.42 | [1-(4-bromo-3,5-diethoxy-benzyl)-piperidin-4-yl]-(4,6-dimethoxy-pyrimidin-2-yl)-amine | (4,6-dimethoxy-pyrimidin-2-yl)-piperidin-4-yl-amine dihydrochloride (intermediate C8) and 4-bromo-3,5-diethoxy-benzaldehyde (intermediate D23) | [M + H]+ 496.8 |
| 106 | 558.42 | (4,6-dimethoxy-pyrimidin-2-yl)-[1-(3-ethoxy-4-iodo-5-methoxymethoxy-benzyl)-piperidin-4-yl]-amine | (4,6-dimethoxy-pyrimidin-2-yl)-piperidin-4-yl-amine dihydrochloride (intermediate C8) and 3-ethoxy-4-iodo-5-methoxymethoxy-benzaldehyde (intermediate D14) | [M + H]+ 559.2 |
| 107 | 481.60 | [1-(3,5-diethoxy-4-pyrrol-1-yl-benzyl)-piperidin-4-yl]-(4,6-dimethoxy-pyrimidin-2-yl)-amine | (4,6-dimethoxy-pyrimidin-2-yl)-piperidin-4-yl-amine dihydrochloride (intermediate C8) and 3,5-diethoxy-4-pyrrol-1-yl-benzaldehyde (intermediate D21) | [M + H]+ 482.4 |
| 108 | 447.49 | (4,6-dimethoxy-pyrimidin-2-yl)-[1-(3-ethoxy-4-methoxy-5-nitro-benzyl)-piperidin-4-yl]-amine | (4,6-dimethoxy-pyrimidin-2-yl)-piperidin-4-yl-amine dihydrochloride (intermediate C8) and 3-ethoxy-4-methoxy-5-nitro-benzaldehyde (intermediate D28) | [M + H]+ 448.2 |
| 109 | 401.51 | (4,6-dimethoxy-pyrimidin-2-yl)-[1-(3-ethylamino-4-methoxy-benzyl)-piperidin-4-yl]-amine | (4,6-dimethoxy-pyrimidin-2-yl)-piperidin-4-yl-amine dihydrochloride (intermediate C8) and 3-ethylamino-4-methoxy-benzaldehyde (intermediate D29) | [M + H]+ 402.4 |
| 110 | 428.55 | [1-(3-ethoxy-4-fluoro-benzyl)-piperidin-4-yl]-(5,5,7,7-tetramethyl-5,7-dihydro-furo[3,4-d]pyrimidin-2-yl)-amine | piperidin-4-yl-(5,5,7,7-tetramethyl-5,7-dihydro-furo[3,4-d]pyrimidin-2-yl)-amine dihydrochloride (intermediate C9) and 3-ethoxy-4-fluoro-benzaldehyde (intermediate D16) | [M + H]+ 429.5 |
| 111 | 445.01 | [1-(4-chloro-3-ethoxy-benzyl)-piperidin-4-yl]-(5,5,7,7-tetramethyl-5,7-dihydro-furo[3,4-d]pyrimidin-2-yl)-amine | piperidin-4-yl-(5,5,7,7-tetramethyl-5,7-dihydro-furo[3,4-d]pyrimidin-2-yl)-amine dihydrochloride (intermediate C9) and 4-chloro-3-ethoxy-benz-aldehyde (intermediate D3) | [M + H]+ 445.3 |
| 112 | 426.56 | 2-ethoxy-4-[4-(5,5,7,7-tetramethyl-5,7-dihydro-furo[3,4-d]pyrimidin-2-ylamino)-piperidin-1-ylmethyl]-phenol | piperidin-4-yl-(5,5,7,7-tetramethyl-5,7-dihydro-furo[3,4-d]pyrimidin-2-yl)-amine dihydrochloride (intermediate C9) and 3-ethoxy-4-hydroxy-benzaldehyde (commercially available) | [M + H]+ 427.3 |
| 113 | 458.58 | {1-[3-(2-fluoro-ethoxy)-4-methoxy-benzyl]-piperidin-4-yl}-5,5,7,7-tetramethyl-5,7-dihydro-furo[3,4-d]pyrimidin-2-yl)-amine | piperidin-4-yl-(5,5,7,7-tetramethyl-5,7-dihydro-furo[3,4-d]pyrimidin-2-yl)-amine dihydrochloride (intermediate C9) and 3-(2-fluoro-ethoxy)-4-methoxy-benzaldehyde (intermediate D8) | [M + H]+ 459.4 |
| 114 | 452.60 | [1-(3-allyloxy-4-methoxy-benzyl)-piperidin-4-yl]-(5,5,7,7-tetramethyl-5,7-dihydro-furo[3,4-d]pyrimidin-2-yl)-amine | piperidin-4-yl-(5,5,7,7-tetramethyl-5,7-dihydro-furo[3,4-d]pyrimidin-2-yl)-amine dihydrochloride (intermediate C9) and 3-allyloxy-4-methoxy-benzaldehyde (intermediate D17) | [M + H]+ 453.2 |
| 115 | 492.66 | [1-(8-ethoxy-2,2-dimethyl-2H-chromen-6-ylmethyl)-piperidin-4-yl]-(5,5,7,7-tetramethyl-5,7- | piperidin-4-yl-(5,5,7,7-tetramethyl-5,7-dihydro-furo[3,4-d]pyrimidin-2-yl)-amine dihydrochloride | [M + H]+ 493.4 |

TABLE 3-continued

| No. | MW | Compound Name | Starting Materials | ISP or ISN [M + H]+ or [M − H]− found |
|---|---|---|---|---|
|  |  | dihydro-furo[3,4-d]pyrimidin-2-yl)-amine | (intermediate C9) and 8-ethoxy-2,2-dimethyl-2H-chromene-6-carbaldehyde (intermediate D18) |  |
| 116 | 454.61 | [1-(3,5-diethoxy-benzyl)-piperidin-4-yl]-(5,5,7,7-tetramethyl-5,7-dihydro-furo[3,4-d]pyrimidin-2-yl)-amine | piperidin-4-yl-(5,5,7,7-tetramethyl-5,7-dihydro-furo[3,4-d]pyrimidin-2-yl)-amine dihydrochloride (intermediate C9) and 3,5-diethoxy-benzaldehyde (intermediate D19) | [M + H]+ 455.3 |
| 117 | 440.59 | 3-isopropoxy-5-[4-(5,5,7,7-tetramethyl-5,7-dihydro-furo[3,4-d]pyrimidin-2-ylamino)-piperidin-1-ylmethyl]-phenol | piperidin-4-yl-(5,5,7,7-tetramethyl-5,7-dihydro-furo[3,4-d]pyrimidin-2-yl)-amine dihydrochloride (intermediate C9) and 3-hydroxy-5-isopropoxy-benzaldehyde (intermediate D27) | [M + H]+ 441.5 |
| 118 | 472.60 | [1-(3,5-diethoxy-4-fluoro-benzyl)-piperidin-4-yl]-(5,5,7,7-tetramethyl-5,7-dihydro-furo[3,4-d]pyrimidin-2-yl)-amine | piperidin-4-yl-(5,5,7,7-tetramethyl-5,7-dihydro-furo[3,4-d]pyrimidin-2-yl)-amine dihydrochloride (intermediate C9) and 3,5-diethoxy-4-fluoro-benzaldehyde (intermediate D12) | [M + H]+ 473.3 |
| 119 | 519.69 | [1-(3,5-diethoxy-4-pyrrol-1-yl-benzyl)-piperidin-4-yl]-(5,5,7,7-tetramethyl-5,7-dihydro-furo[3,4-d]pyrimidin-2-yl)-amine | piperidin-4-yl-(5,5,7,7-tetramethyl-5,7-dihydro-furo[3,4-d]pyrimidin-2-yl)-amine dihydrochloride (intermediate C9) and 3,5-diethoxy-4-pyrrol-1-yl-benzaldehyde (intermediate D21) | [M + H]+ 520.4 |
| 120 | 366.47 | 4-amino-2-[1-(3-ethoxy-4-methyl-benzyl)-piperidin-4-ylamino]-pyrimidine-5-carbonitrile | 4-amino-2-(piperidin-4-ylamino)-pyrimidine-5-carbonitrile dihydrochloride (intermediate C10) and 3-ethoxy-4-methyl-benzaldehyde (intermediate D2) | [M + H]+ 367.2 |
| 121 | 370.43 | 4-amino-2-[1-(3-ethoxy-4-fluoro-benzyl)-piperidin-4-ylamino]-pyrimidine-5-carbonitrile | 4-amino-2-(piperidin-4-ylamino)-pyrimidine-5-carbonitrile dihydrochloride (intermediate C10) and 3-ethoxy-4-fluoro-benzaldehyde (intermediate D16) | [M + H]+ 371.2 |
| 122 | 386.89 | 4-amino-2-[1-(3-ethoxy-4-methoxy-benzyl)-piperidin-4-ylamino]-pyrimidine-5-carbonitrile | 4-amino-2-(piperidin-4-ylamino)-pyrimidine-5-carbonitrile dihydrochloride (intermediate C10) and 4-chloro-3-ethoxy-benzaldehyde (intermediate D3) | [M + H]+ 387.3 |
| 123 | 382.47 | 4-amino-2-[1-(3-ethoxy-4-methoxy-benzyl)-piperidin-4-ylamino]-pyrimidine-5-carbonitrile | 4-amino-2-(piperidin-4-ylamino)-pyrimidine-5-carbonitrile dihydrochloride (intermediate C10) and 3-ethoxy-4-methoxy-benzaldehyde (commercially available) | [M + H]+ 383.3 |
| 124 | 410.52 | 4-amino-2-[1-(3-isobutoxy-4-methoxy-benzyl)-piperidin-4-ylamino]-pyrimidine-5-carbonitrile | 4-amino-2-(piperidin-4-ylamino)-pyrimidine-5-carbonitrile dihydrochloride (intermediate C10) and 3-isobutoxy-4-methoxy-benzaldehyde (intermediate D9) | [M + H]+ 411.4 |
| 125 | 410.52 | 4-amino-2-[1-(3-ethoxy-4-isopropoxy-benzyl)-piperidin-4-ylamino]-pyrimidine-5-carbonitrile | 4-amino-2-(piperidin-4-ylamino)-pyrimidine-5-carbonitrile dihydrochloride (intermediate C10) and 3- | [M + H]+ 411.4 |

TABLE 3-continued

| No. | MW | Compound Name | Starting Materials | ISP or ISN [M + H]+ or [M − H]− found |
|---|---|---|---|---|
| | | | ethoxy-4-isopropoxy-benzaldehyde (commercially available) | |
| 126 | 438.58 | 4-amino-2-{1-[3-ethoxy-4-(1-ethyl-propoxy)-benzyl]-piperidin-4-ylamino}-pyrimidine-5-carbonitrile | 4-amino-2-(piperidin-4-ylamino)-pyrimidine-5-carbonitrile dihydrochloride (intermediate C10) and 3-ethoxy-4-(1-ethyl-propoxy)-benzaldehyde (intermediate D22) | [M + H]+ 439.3 |
| 127 | 400.46 | 4-amino-2-{1-[3-(2-fluoro-ethoxy)-4-methoxy-benzyl]-piperidin-4-ylamino}-pyrimidine-5-carbonitrile | 4-amino-2-(piperidin-4-ylamino)-pyrimidine-5-carbonitrile dihydrochloride (intermediate C10) and 3-(2-fluoro-ethoxy)-4-methoxy-benzaldehyde (intermediate D8) | [M + H]+ 401.3 |
| 128 | 394.48 | 2-[1-(3-allyloxy-4-methoxy-benzyl)-piperidin-4-ylamino]-4-amino-pyrimidine-5-carbonitrile | 4-amino-2-(piperidin-4-ylamino)-pyrimidine-5-carbonitrile dihydrochloride (intermediate C10) and 3-allyloxy-4-methoxy-benzaldehyde (intermediate D17) | [M + H]+ 395.3 |
| 129 | 410.52 | 4-amino-2-[1-(3-butoxy-4-methoxy-benzyl)-piperidin-4-ylamino]-pyrimidine-5-carbonitrile | 4-amino-2-(piperidin-4-ylamino)-pyrimidine-5-carbonitrile dihydrochloride (intermediate C10) and 3-butoxy-4-methoxy-benzaldehyde (intermediate D26) | [M + H]+ 411.4 |
| 130 | 434.54 | 4-amino-2-[1-(8-ethoxy-2,2-dimethyl-2H-chromen-6-ylmethyl)-piperidin-4-ylamino]-pyrimidine-5-carbonitrile | 4-amino-2-(piperidin-4-ylamino)-pyrimidine-5-carbonitrile dihydrochloride (intermediate C10) and 8-ethoxy-2,2-dimethyl-2H-chromene-6-carbaldehyde (intermediate D18) | [M + H]+ 435.4 |
| 131 | 396.49 | 4-amino-2-[1-(3,5-diethoxy-benzyl)-piperidin-4-ylamino]-pyrimidine-5-carbonitrile | 4-amino-2-(piperidin-4-ylamino)-pyrimidine-5-carbonitrile dihydrochloride (intermediate C10) and 3,5-diethoxy-benzaldehyde (intermediate D19) | [M + H]+ 397.3 |
| 132 | 382.47 | 4-amino-2-[1-(3-hydroxy-5-isopropoxy-benzyl)-piperidin-4-ylamino]-pyrimidine-5-carbonitrile | 4-amino-2-(piperidin-4-ylamino)-pyrimidine-5-carbonitrile dihydrochloride (intermediate C10) and 3-hydroxy-5-isopropoxy-benzaldehyde (intermediate D27) | [M + H]+ 383.3 |
| 133 | 424.55 | 4-amino-2-[1-(3,5-diisopropoxy-benzyl)-piperidin-4-ylamino]-pyrimidine-5-carbonitrile | 4-amino-2-(piperidin-4-ylamino)-pyrimidine-5-carbonitrile dihydrochloride (intermediate C10) and 3,5-diisopropoxy-benzaldehyde (intermediate D10) | [M + H]+ 425.3 |
| 134 | 414.49 | 4-amino-2-[1-(3,5-diethoxy-4-fluoro-benzyl)-piperidin-4-ylamino]-pyrimidine-5-carbonitrile | 4-amino-2-(piperidin-4-ylamino)-pyrimidine-5-carbonitrile dihydrochloride (intermediate C10) and 3,5-diethoxy-4-fluoro-benzaldehyde (intermediate D12) | [M + H]+ 415.4 |
| 135 | 430.94 | 4-amino-2-[1-(4-chloro-3,5-diethoxy-benzyl)-piperidin-4-ylamino]-pyrimidine-5-carbonitrile | 4-amino-2-(piperidin-4-ylamino)-pyrimidine-5-carbonitrile dihydrochloride (intermediate C10) and 4-chloro-3,5-diethoxy-benzaldehyde (intermediate D20) | [M + H]+ 431.3 |
| 136 | 475.40 | 4-amino-2-[1-(4-bromo-3,5-diethoxy-benzyl)-piperidin-4-ylamino]- | 4-amino-2-(piperidin-4-ylamino)-pyrimidine-5-carbonitrile dihydrochloride | [M + H]+ 476.6 |

TABLE 3-continued

| No. | MW | Compound Name | Starting Materials | ISP or ISN [M + H]+ or [M − H]− found |
|---|---|---|---|---|
| | | pyrimidine-5-carbonitrile | (intermediate C10) and 4-bromo-3,5-diethoxy-benzaldehyde (intermediate D23) | |
| 137 | 538.39 | 4-amino-2-[1-(3-ethoxy-4-iodo-5-methoxymethoxy-benzyl)-piperidin-4-ylamino]-pyrimidine-5-carbonitrile | 4-amino-2-(piperidin-4-ylamino)-pyrimidine-5-carbonitrile dihydrochloride (intermediate C10) and 3-ethoxy-4-iodo-5-methoxymethoxy-benzaldehyde (intermediate D14) | [M + H]+ 539.3 |
| 138 | 461.57 | 4-amino-2-[1-(3,5-diethoxy-4-pyrrol-1-yl-benzyl)-piperidin-4-ylamino]-pyrimidine-5-carbonitrile | 4-amino-2-(piperidin-4-ylamino)-pyrimidine-5-carbonitrile dihydrochloride (intermediate C10) and 3,5-diethoxy-4-pyrrol-1-yl-benzaldehyde (intermediate D21) | [M + H]+ 462.6 |
| 139 | 430.94 | 4-amino-2-[1-(2-chloro-3,5-diethoxy-benzyl)-piperidin-4-ylamino]-pyrimidine-5-carbonitrile | 4-amino-2-(piperidin-4-ylamino)-pyrimidine-5-carbonitrile dihydrochloride (intermediate C10) and 2-chloro-3,5-diethoxy-benzaldehyde (intermediate D25) | [M + H]+ 431.3 |
| 140 | 402.24 | [1-(3-ethoxy-4-methyl-benzyl)-piperidin-4-yl]-(5-phenyl-pyrimidin-2-yl)-amine | (5-phenyl-pyrimidin-2-yl)-piperidin-4-yl-amine dihydrochloride (intermediate C11) and 3-ethoxy-4-methyl-benzaldehyde (intermediate D2) | [M + H]+ 403.3 |
| 141 | 406.22 | [1-(3-ethoxy-4-fluoro-benzyl)-piperidin-4-yl]-(5-phenyl-pyrimidin-2-yl)-amine | (5-phenyl-pyrimidin-2-yl)-piperidin-4-yl-amine dihydrochloride (intermediate C11) and 3-ethoxy-4-fluoro-benzaldehyde (intermediate D16) | [M + H]+ 407.3 |
| 142 | 422.19 | [1-(4-chloro-3-ethoxy-benzyl)-piperidin-4-yl]-(5-phenyl-pyrimidin-2-yl)-amine | (5-phenyl-pyrimidin-2-yl)-piperidin-4-yl-amine dihydrochloride (intermediate C11) and 4-chloro-3-ethoxy-benzaldehyde (intermediate D3) | [M + H]+ 423.3 |
| 143 | 404.22 | 2-ethoxy-4-[4-(5-phenyl-pyrimidin-2-ylamino)-piperidin-1-ylmethyl]-phenol | (5-phenyl-pyrimidin-2-yl)-piperidin-4-yl-amine dihydrochloride (intermediate C11) and 3-ethoxy-4-hydroxy-benzaldehyde (commercially available) | [M + H]+ 405.3 |
| 144 | 418.24 | [1-(3-ethoxy-4-methoxy-benzyl)-piperidin-4-yl]-(5-phenyl-pyrimidin-2-yl)-amine | (5-phenyl-pyrimidin-2-yl)-piperidin-4-yl-amine dihydrochloride (intermediate C11) and 3-ethoxy-4-methoxy-benzaldehyde (commercially available) | [M + H]+ 419.3 |
| 145 | 446.27 | [1-(3-ethoxy-4-isopropoxy-benzyl)-piperidin-4-yl]-(5-phenyl-pyrimidin-2-yl)-amine | (5-phenyl-pyrimidin-2-yl)-piperidin-4-yl-amine dihydrochloride (intermediate C11) and 3-ethoxy-4-isopropoxy-benzaldehyde (commercially available) | [M + H]+ 447.3 |
| 146 | 474.3 | {1-[3-ethoxy-4-(1-ethyl-propoxy)-benzyl]-piperidin-4-yl}-(5-phenyl-pyrimidin-2-yl)-amine | (5-phenyl-pyrimidin-2-yl)-piperidin-4-yl-amine dihydrochloride (intermediate C11) and 3-ethoxy-4-(1-ethyl-propoxy)-benzaldehyde (intermediate D22) | [M + H]+ 475.3 |
| 147 | 436.23 | {1-[3-(2-fluoro-ethoxy)-4-methoxy-benzyl]-piperidin-4-yl}-(5-phenyl-pyrimidin-2-yl)- | (5-phenyl-pyrimidin-2-yl)-piperidin-4-yl-amine dihydrochloride (intermediate C11) and 3-(2-fluoro- | [M + H]+ 437.3 |

TABLE 3-continued

| No. | MW | Compound Name | Starting Materials | ISP or ISN [M + H]+ or [M − H]− found |
|---|---|---|---|---|
| | | amine | ethoxy)-4-methoxy-benzaldehyde (intermediate D8) | |
| 148 | 430.24 | [1-(3-allyloxy-4-methoxy-benzyl)-piperidin-4-yl]-(5-phenyl-pyrimidin-2-yl)-amine | (5-phenyl-pyrimidin-2-yl)-piperidin-4-yl-amine dihydrochloride (intermediate C11) and 3-allyloxy-4-methoxy-benzaldehyde (intermediate D17) | [M + H]+ 431.3 |
| 149 | 470.27 | [1-(8-ethoxy-2,2-dimethyl-2H-chromen-6-ylmethyl)-piperidin-4-yl]-(5-phenyl-pyrimidin-2-yl)-amine | (5-phenyl-pyrimidin-2-yl)-piperidin-4-yl-amine dihydrochloride (intermediate C11) and 8-ethoxy-2,2-dimethyl-2H-chromene-6-carbaldehyde (intermediate D18) | [M + H]+ 471.3 |
| 150 | 432.25 | [1-(3,5-diethoxy-benzyl)-piperidin-4-yl]-(5-phenyl-pyrimidin-2-yl)-amine | (5-phenyl-pyrimidin-2-yl)-piperidin-4-yl-amine dihydrochloride (intermediate C11) and 3,5-diethoxy-benzaldehyde (intermediate D19) | [M + H]+ 433.3 |
| 151 | 418.24 | 3-isopropoxy-5-[4-(5-phenyl-pyrimidin-2-ylamino)-piperidin-1-ylmethyl]-phenol | (5-phenyl-pyrimidin-2-yl)-piperidin-4-yl-amine dihydrochloride (intermediate C11) and 3-hydroxy-5-isopropoxy-benzaldehyde (intermediate D27) | [M + H]+ 419.3 |
| 152 | 460.28 | [1-(3,5-diisopropoxy-benzyl)-piperidin-4-yl]-(5-phenyl-pyrimidin-2-yl)-amine | (5-phenyl-pyrimidin-2-yl)-piperidin-4-yl-amine dihydrochloride (intermediate C11) and 3,5-diisopropoxy-benzaldehyde (intermediate D10) | [M + H]+ 461.3 |
| 153 | 450.24 | [1-(3,5-diethoxy-4-fluoro-benzyl)-piperidin-4-yl]-(5-phenyl-pyrimidin-2-yl)-amine | (5-phenyl-pyrimidin-2-yl)-piperidin-4-yl-amine dihydrochloride (intermediate C11) and 3,5-diethoxy-4-fluoro-benzaldehyde (intermediate D12) | [M + H]+ 451.3 |
| 154 | 466.21 | [1-(4-chloro-3,5-diethoxy-benzyl)-piperidin-4-yl]-(5-phenyl-pyrimidin-2-yl)-amine | (5-phenyl-pyrimidin-2-yl)-piperidin-4-yl-amine dihydrochloride (intermediate C11) and 4-chloro-3,5-diethoxy-benzaldehyde (intermediate D20) | [M + H]+ 467.3 |
| 155 | 510.16 | [1-(4-bromo-3,5-diethoxy-benzyl)-piperidin-4-yl]-(5-phenyl-pyrimidin-2-yl)-amine | (5-phenyl-pyrimidin-2-yl)-piperidin-4-yl-amine dihydrochloride (intermediate C11) and 4-bromo-3,5-diethoxy-benzaldehyde (intermediate D23) | [M + H]+ 511.2 |
| 156 | 447.26 | [1-(4-amino-3,5-diethoxy-benzyl)-piperidin-4-yl]-(5-phenyl-pyrimidin-2-yl)-amine | (5-phenyl-pyrimidin-2-yl)-piperidin-4-yl-amine dihydrochloride (intermediate C11) and 4-amino-3,5-diethoxy-benzaldehyde (intermediate D24) | [M + H]+ 448.3 |
| 157 | 497.28 | [1-(3,5-diethoxy-4-pyrrol-1-yl-benzyl)-piperidin-4-yl]-(5-phenyl-pyrimidin-2-yl)-amine | (5-phenyl-pyrimidin-2-yl)-piperidin-4-yl-amine dihydrochloride (intermediate C11) and 3,5-diethoxy-4-pyrrol-1-yl-benzaldehyde (intermediate D21) | [M + H]+ 498.3 |
| 158 | 410.22 | [1-(2-phenyl-1H-imidazol-4-ylmethyl)-piperidin-4-yl]-(5-phenyl-pyrimidin-2-yl)-amine | (5-phenyl-pyrimidin-2-yl)-piperidin-4-yl-amine dihydrochloride (intermediate C11) and 2-phenyl-3H-imidazole-4-carbaldehyde (commercially available) | [M + H]+ 411.3 |
| 159 | 432.57 | [1-(3-ethoxy-4-methyl-benzyl)-piperidin-4-yl]-[5-(4-methoxy-phenyl)-pyrimidin-2-yl]-amine | [5-(4-methoxy-phenyl)-pyrimidin-2-yl]-piperidin-4-yl-amine dihydrochloride (intermediate C12) and 3- | [M + H]+ 433.3 |

TABLE 3-continued

| No. | MW | Compound Name | Starting Materials | ISP or ISN [M + H]+ or [M − H]− found |
|---|---|---|---|---|
| | | | ethoxy-4-methyl-benzaldehyde (intermediate D2) | |
| 160 | 436.53 | [1-(3-ethoxy-4-fluoro-benzyl)-piperidin-4-yl]-[5-(4-methoxy-phenyl)-pyrimidin-2-yl]-amine | [5-(4-methoxy-phenyl)-pyrimidin-2-yl]-piperidin-4-yl-amine dihydrochloride (intermediate C12) and 3-ethoxy-4-fluoro-benzaldehyde (intermediate D16) | [M + H]+ 437.3 |
| 161 | 452.99 | [1-(4-chloro-3-ethoxy-benzyl)-piperidin-4-yl]-[5-(4-methoxy-phenyl)-pyrimidin-2-yl]-amine | [5-(4-methoxy-phenyl)-pyrimidin-2-yl]-piperidin-4-yl-amine dihydrochloride (intermediate C12) and 4-chloro-3-ethoxy-benzaldehyde (intermediate D3) | [M + H]+ 453.6 |
| 162 | 434.54 | 2-ethoxy-4-{4-[5-(4-methoxy-phenyl)-pyrimidin-2-ylamino]-piperidin-1-ylmethyl}-phenol | [5-(4-methoxy-phenyl)-pyrimidin-2-yl]-piperidin-4-yl-amine dihydrochloride (intermediate C12) and 3-ethoxy-4-hydroxy-benzaldehyde (commercially available) | [M + H]+ 435.4 |
| 163 | 448.57 | [1-(3-ethoxy-4-methoxy-benzyl)-piperidin-4-yl]-[5-(4-methoxy-phenyl)-pyrimidin-2-yl]-amine | [5-(4-methoxy-phenyl)-pyrimidin-2-yl]-piperidin-4-yl-amine dihydrochloride (intermediate C12) and 3-ethoxy-4-methoxy-benzaldehyde (commercially available) | [M + H]+ 449.2 |
| 164 | 462.59 | [1-(3,5-diethoxy-benzyl)-piperidin-4-yl]-[5-(4-methoxy-phenyl)-pyrimidin-2-yl]-amine | [5-(4-methoxy-phenyl)-pyrimidin-2-yl]-piperidin-4-yl-amine dihydrochloride (intermediate C12) and 3,5-diethoxy-benzaldehyde (intermediate D19) | [M + H]+ 463.3 |
| 165 | 490.65 | [1-(3,5-diisopropoxy-benzyl)-piperidin-4-yl]-[5-(4-methoxy-phenyl)-pyrimidin-2-yl]-amine | [5-(4-methoxy-phenyl)-pyrimidin-2-yl]-piperidin-4-yl-amine dihydrochloride (intermediate C12) and 3,5-diisopropoxy-benzaldehyde (intermediate D10) | [M + H]+ 491.4 |
| 166 | 480.58 | [1-(3,5-diethoxy-4-fluoro-benzyl)-piperidin-4-yl]-[5-(4-methoxy-phenyl)-pyrimidin-2-yl]-amine | [5-(4-methoxy-phenyl)-pyrimidin-2-yl]-piperidin-4-yl-amine dihydrochloride (intermediate C12) and 3,5-diethoxy-4-fluoro-benzaldehyde (intermediate D12) | [M + H]+ 481.3 |
| 167 | 497.04 | [1-(4-chloro-3,5-diethoxy-benzyl)-piperidin-4-yl]-[5-(4-methoxy-phenyl)-pyrimidin-2-yl]-amine | [5-(4-methoxy-phenyl)-pyrimidin-2-yl]-piperidin-4-yl-amine dihydrochloride (intermediate C12) and 4-chloro-3,5-diethoxy-benzaldehyde (intermediate D20) | [M + H]+ 497.3 |
| 168 | 403.53 | [1-(3-ethoxy-4-methyl-benzyl)-piperidin-4-yl]-(5-pyridin-3-yl-pyrimidin-2-yl)-amine | piperidin-4-yl-(5-pyridin-3-yl-pyrimidin-2-yl)-amine dihydrochloride (intermediate C13) and 3-ethoxy-4-methyl-benzaldehyde (intermediate D2) | [M + H]+ 403.7 |
| 169 | 407.49 | [1-(3-ethoxy-4-fluoro-benzyl)-piperidin-4-yl]-(5-pyridin-3-yl-pyrimidin-2-yl)-amine | piperidin-4-yl-(5-pyridin-3-yl-pyrimidin-2-yl)-amine dihydrochloride (intermediate C13) and 3-ethoxy-4-fluoro-benzaldehyde (intermediate D16) | [M + H]+ 407.7 |
| 170 | 423.95 | [1-(4-chloro-3-ethoxy-benzyl)-piperidin-4-yl]-(5-pyridin-3-yl-pyrimidin-2-yl)-amine | piperidin-4-yl-(5-pyridin-3-yl-pyrimidin-2-yl)-amine dihydrochloride (intermediate C13) and 4-chloro-3-ethoxy- | [M + H]+ 423.7 |

TABLE 3-continued

| No. | MW | Compound Name | Starting Materials | ISP or ISN [M + H]+ or [M − H]− found |
|---|---|---|---|---|
| | | | benzaldehyde (intermediate D3) | |
| 171 | 405.50 | 2-ethoxy-4-[4-(5-pyridin-3-yl-pyrimidin-2-ylamino)-piperidin-1-ylmethyl]-phenol | piperidin-4-yl-(5-pyridin-3-yl-pyrimidin-2-yl)-amine dihydrochloride (intermediate C13) and 3-ethoxy-4-hydroxy-benzaldehyde (commercially available) | [M + H]+ 405.7 |
| 172 | 419.53 | [1-(3-ethoxy-4-methoxy-benzyl)-piperidin-4-yl]-(5-pyridin-3-yl-pyrimidin-2-yl)-amine | piperidin-4-yl-(5-pyridin-3-yl-pyrimidin-2-yl)-amine dihydrochloride (intermediate C13) and 3-ethoxy-4-methoxy-benzaldehyde (commercially available) | [M + H]+ 419.7 |
| 173 | 433.56 | [1-(3,5-diethoxy-benzyl)-piperidin-4-yl]-(5-pyridin-3-yl-pyrimidin-2-yl)-amine | piperidin-4-yl-(5-pyridin-3-yl-pyrimidin-2-yl)-amine dihydrochloride (intermediate C13) and 3,5-diethoxy-benzaldehyde (intermediate D19) | [M + H]+ 433.8 |
| 174 | 461.61 | [1-(3,5-diisopropoxy-benzyl)-piperidin-4-yl]-(5-pyridin-3-yl-pyrimidin-2-yl)-amine | piperidin-4-yl-(5-pyridin-3-yl-pyrimidin-2-yl)-amine dihydrochloride (intermediate C13) and 3,5-diisopropoxy-benzaldehyde (intermediate D10) | [M + H]+ 461.8 |
| 175 | 451.55 | [1-(3,5-diethoxy-4-fluoro-benzyl)-piperidin-4-yl]-(5-pyridin-3-yl-pyrimidin-2-yl)-amine | piperidin-4-yl-(5-pyridin-3-yl-pyrimidin-2-yl)-amine dihydrochloride (intermediate C13) and 3,5-diethoxy-4-fluoro-benzaldehyde (intermediate D12) | [M + H]+ 451.8 |
| 176 | 468.00 | [1-(4-chloro-3,5-diethoxy-benzyl)-piperidin-4-yl]-(5-pyridin-3-yl-pyrimidin-2-yl)-amine | piperidin-4-yl-(5-pyridin-3-yl-pyrimidin-2-yl)-amine dihydrochloride (intermediate C13) and 4-chloro-3,5-diethoxy-benzaldehyde (intermediate D20) | [M + H]+ 467.7 |
| 177 | 448.57 | [1-(4-amino-3,5-diethoxy-benzyl)-piperidin-4-yl]-(5-pyridin-3-yl-pyrimidin-2-yl)-amine | piperidin-4-yl-(5-pyridin-3-yl-pyrimidin-2-yl)-amine dihydrochloride (intermediate C13) and 4-amino-3,5-diethoxy-benzaldehyde (intermediate D24) | [M + H]+ 448.7 |
| 178 | 498.63 | [1-(3,5-diethoxy-4-pyrrol-1-yl-benzyl)-piperidin-4-yl]-(5-pyridin-3-yl-pyrimidin-2-yl)-amine | piperidin-4-yl-(5-pyridin-3-yl-pyrimidin-2-yl)-amine dihydrochloride (intermediate C13) and 3,5-diethoxy-4-pyrrol-1-yl-benzaldehyde (intermediate D21) | [M + H]+ 498.9 |
| 179 | 445.57 | 4-{2-[1-(3-ethoxy-4-methyl-benzyl)-piperidin-4-ylamino]-pyrimidin-5-yl}-benzamide | 4-[2-(piperidin-4-ylamino)-pyrimidin-5-yl]-benzamide dihydrochloride (intermediate C14) and 3-ethoxy-4-methyl-benzaldehyde (intermediate D2) | [M + H]+ 445.8 |
| 180 | 449.53 | 4-{2-[1-(3-ethoxy-4-fluoro-benzyl)-piperidin-4-ylamino]-pyrimidin-5-yl}-benzamide | 4-[2-(piperidin-4-ylamino)-pyrimidin-5-yl]-benzamide dihydrochloride (intermediate C14) and 3-ethoxy-4-fluoro-benzaldehyde (intermediate D16) | [M + H]+ 449.8 |
| 181 | 465.98 | 4-{2-[1-(4-chloro-3-ethoxy-benzyl)-piperidin-4-ylamino]-pyrimidin-5-yl}-benzamide | 4-[2-(piperidin-4-ylamino)-pyrimidin-5-yl]-benzamide dihydrochloride (intermediate C14) and 4-chloro-3-ethoxy-benzaldehyde (intermediate D3) | [M + H]+ 465.7 |
| 182 | 447.54 | 4-{2-[1-(3-ethoxy-4-hydroxy-benzyl)-piperidin-4-ylamino]-pyrimidin-5-yl}-benzamide | 4-[2-(piperidin-4-ylamino)-pyrimidin-5-yl]-benzamide dihydrochloride (intermediate C14) and 3-ethoxy-4-hydroxy-benzaldehyde (commercially available) | [M + H]+ 447.7 |

TABLE 3-continued

| No. | MW | Compound Name | Starting Materials | ISP or ISN [M + H]+ or [M − H]− found |
|---|---|---|---|---|
| 183 | 461.57 | 4-{2-[1-(3-ethoxy-4-methoxy-benzyl)-piperidin-4-ylamino]-pyrimidin-5-yl}-benzamide | 4-[2-(piperidin-4-ylamino)-pyrimidin-5-yl]-benzamide dihydrochloride (intermediate C14) and 3-ethoxy-4-methoxy-benzaldehyde (commercially available) | [M + H]+ 461.8 |
| 184 | 547.2 | 2-[1-(3-ethoxy-4-methyl-benzyl)-piperidin-4-ylamino]-4-trifluoromethyl-pyrimidine-5-carboxylic acid (4-chloro-phenyl)-amide | 2-(piperidin-4-ylamino)-4-trifluoromethyl-pyrimidine-5-carboxylic acid (4-chloro-phenyl)-amide dihydrochloride (intermediate C15) and 3-ethoxy-4-methyl-benz-aldehyde (intermediate D2) | [M + H]+ 548.3 |
| 185 | 551.17 | 2-[1-(3-ethoxy-4-fluoro-benzyl)-piperidin-4-ylamino]-4-trifluoromethyl-pyrimidine-5-carboxylic acid (4-chloro-phenyl)-amide | 2-(piperidin-4-ylamino)-4-trifluoromethyl-pyrimidine-5-carboxylic acid (4-chloro-phenyl)-amide dihydrochloride (intermediate C15) and 3-ethoxy-4-fluoro-benzaldehyde (intermediate D16) | [M + H]+ 552.2 |
| 186 | 567.14 | 2-[1-(4-chloro-3-ethoxy-benzyl)-piperidin-4-ylamino]-4-trifluoromethyl-pyrimidine-5-carboxylic acid (4-chloro-phenyl)-amide | 2-(piperidin-4-ylamino)-4-trifluoromethyl-pyrimidine-5-carboxylic acid (4-chloro-phenyl)-amide dihydrochloride (intermediate C15) and 4-chloro-3-ethoxy-benzaldehyde (intermediate D3) | [M + H]+ 568.2 |
| 187 | 549.18 | 2-[1-(3-ethoxy-4-hydroxy-benzyl)-piperidin-4-ylamino]-4-trifluoromethyl-pyrimidine-5-carboxylic acid (4-chloro-phenyl)-amide | 2-(piperidin-4-ylamino)-4-trifluoromethyl-pyrimidine-5-carboxylic acid (4-chloro-phenyl)-amide dihydrochloride (intermediate C15) and 3-ethoxy-4-hydroxy-benzaldehyde (commercially available) | [M + H]+ 548.2 |
| 188 | 563.19 | 2-[1-(3-ethoxy-4-methoxy-benzyl)-piperidin-4-ylamino]-4-trifluoromethyl-pyrimidine-5-carboxylic acid (4-chloro-phenyl)-amide | 2-(piperidin-4-ylamino)-4-trifluoromethyl-pyrimidine-5-carboxylic acid (4-chloro-phenyl)-amide dihydrochloride (intermediate C15) and 3-ethoxy-4-methoxy-benzaldehyde (commercially available) | [M + H]+ 564.3 |
| 189 | 581.18 | 2-{1-[3-(2-fluoro-ethoxy)-4-methoxy-benzyl]-piperidin-4-ylamino}-4-trifluoromethyl-pyrimidine-5-carboxylic acid (4-chloro-phenyl)-amide | 2-(piperidin-4-ylamino)-4-trifluoromethyl-pyrimidine-5-carboxylic acid (4-chloro-phenyl)-amide dihydrochloride (intermediate C15) and 3-(2-fluoro-ethoxy)-4-methoxy-benzaldehyde (intermediate D8) | [M + H]+ 582.2 |
| 190 | 577.21 | 2-[1-(3,5-diethoxy-benzyl)-piperidin-4-ylamino]-4-trifluoromethyl-pyrimidine-5-carboxylic acid (4-chloro-phenyl)-amide | 2-(piperidin-4-ylamino)-4-trifluoromethyl-pyrimidine-5-carboxylic acid (4-chloro-phenyl)-amide dihydrochloride (intermediate C15) and 3,5-diethoxy-benzaldehyde (intermediate D19) | [M + H]+ 578.3 |
| 191 | 605.24 | 2-[1-(3,5-diisopropoxy-benzyl)-piperidin-4-ylamino]-4-trifluoromethyl-pyrimidine-5-carboxylic acid (4-chloro-phenyl)-amide | 2-(piperidin-4-ylamino)-4-trifluoromethyl-pyrimidine-5-carboxylic acid (4-chloro-phenyl)-amide dihydrochloride (intermediate C15) and 3,5-diisopropoxy-benzaldehyde (intermediate D10) | [M − H]− 604.3 |
| 192 | 595.2 | 2-[1-(3,5-diethoxy-4-fluoro-benzyl)-piperidin-4-ylamino]-4- | 2-(piperidin-4-ylamino)-4-trifluoromethyl-pyrimidine-5-carboxylic acid (4-chloro- | [M + H]+ 596.3 |

TABLE 3-continued

| No. | MW | Compound Name | Starting Materials | ISP or ISN [M + H]+ or [M − H]− found |
|---|---|---|---|---|
| | | trifluoromethyl-pyrimidine-5-carboxylic acid (4-chloro-phenyl)-amide | phenyl)-amide dihydrochloride (intermediate C15) and 3,5-diethoxy-4-fluoro-benzaldehyde (intermediate D12) | |
| 193 | 611.17 | 2-[1-(4-chloro-3,5-diethoxy-benzyl)-piperidin-4-ylamino]-4-trifluoromethyl-pyrimidine-5-carboxylic acid (4-chloro-phenyl)-amide | 2-(piperidin-4-ylamino)-4-trifluoromethyl-pyrimidine-5-carboxylic acid (4-chloro-phenyl)-amide dihydrochloride (intermediate C15) and 4-chloro-3,5-diethoxy-benzaldehyde (intermediate D20) | [M − H]− 610.2 |
| 194 | 592.22 | 2-[1-(4-amino-3,5-diethoxy-benzyl)-piperidin-4-ylamino]-4-trifluoromethyl-pyrimidine-5-carboxylic acid (4-chloro-phenyl)-amide | 2-(piperidin-4-ylamino)-4-trifluoromethyl-pyrimidine-5-carboxylic acid (4-chloro-phenyl)-amide dihydrochloride (intermediate C15) and 4-amino-3,5-diethoxy-benzaldehyde (intermediate D24) | [M − H]− 591.3 |
| 195 | 642.23 | 2-[1-(3,5-diethoxy-4-pyrrol-1-yl-benzyl)-piperidin-4-ylamino]-4-trifluoromethyl-pyrimidine-5-carboxylic acid (4-chloro-phenyl)-amide | 2-(piperidin-4-ylamino)-4-trifluoromethyl-pyrimidine-5-carboxylic acid (4-chloro-phenyl)-amide dihydrochloride (intermediate C15) and 3,5-diethoxy-4-pyrrol-1-yl-benzaldehyde (intermediate D21) | [M + H]+ 643.3 |
| 196 | 597.22 | 2-[1-(3-ethoxy-4-methyl-benzyl)-piperidin-4-ylamino]-4-trifluoromethyl-pyrimidine-5-carboxylic acid (4-trifluoromethoxy-phenyl)-amide | 2-(piperidin-4-ylamino)-4-trifluoromethyl-pyrimidine-5-carboxylic acid (4-trifluoromethoxy-phenyl)-amide dihydrochloride (intermediate C16) and 3-ethoxy-4-methyl-benzaldehyde (intermediate D2) | [M + H]+ 598.3 |
| 197 | 599.2 | 2-[1-(3-ethoxy-4-hydroxy-benzyl)-piperidin-4-ylamino]-4-trifluoromethyl-pyrimidine-5-carboxylic acid (4-trifluoromethoxy-phenyl)-amide | 2-(piperidin-4-ylamino)-4-trifluoromethyl-pyrimidine-5-carboxylic acid (4-trifluoromethoxy-phenyl)-amide dihydrochloride intermediate C16) and 3-ethoxy-4-hydroxy-benzaldehyde (commercially available) | [M + H]+ 600.2 |
| 198 | 613.21 | 2-[1-(3-ethoxy-4-methoxy-benzyl)-piperidin-4-ylamino]-4-trifluoromethyl-pyrimidine-5-carboxylic acid (4-trifluoromethoxy-phenyl)-amide | 2-(piperidin-4-ylamino)-4-trifluoromethyl-pyrimidine-5-carboxylic acid (4-trifluoro-methoxy-phenyl)-amide dihydrochloride (intermediate C16) and 3-ethoxy-4-methoxy-benzaldehyde (commercially available) | [M + H]+ 614.3 |
| 199 | 631.2 | 2-{1-[3-(2-fluoro-ethoxy)-4-methoxy-benzyl]-piperidin-4-ylamino}-4-trifluoromethyl-pyrimidine-5-carboxylic acid (4-trifluoromethoxy-phenyl)-amide | 2-(piperidin-4-ylamino)-4-trifluoromethyl-pyrimidine-5-carboxylic acid (4-trifluoro-methoxy-phenyl)-amide dihydrochloride (intermediate C16) and 3-(2-fluoro-ethoxy)-4-methoxy-benzaldehyde (intermediate D8) | [M + H]+ 632.3 |
| 200 | 655.26 | 2-[1-(3,5-diisopropoxy-benzyl)-piperidin-4-ylamino]-4-trifluoromethyl-pyrimidine-5-carboxylic acid (4-trifluoromethoxy-phenyl)-amide | 2-(piperidin-4-ylamino)-4-trifluoromethyl-pyrimidine-5-carboxylic acid (4-trifluoromethoxy-phenyl)-amide dihydrochloride (intermediate C16) and 3,5-diisopropoxy-benzaldehyde (intermediate D10) | [M + H]+ 656.4 |
| 201 | 661.19 | 2-[1-(4-chloro-3,5-diethoxy-benzyl)- | 2-(piperidin-4-ylamino)-4-trifluoromethyl-pyrimidine-5- | [M + H]+ 662.3 |

TABLE 3-continued

| No. | MW | Compound Name | Starting Materials | ISP or ISN [M + H]+ or [M − H]− found |
|---|---|---|---|---|
| | | piperidin-4-ylamino]-4-trifluoromethyl-pyrimidine-5-carboxylic acid (4-trifluoromethoxy-phenyl)-amide | carboxylic acid (4-trifluoromethoxy-phenyl)-amide dihydrochloride (intermediate C16) and 4-chloro-3,5-diethoxy-benzaldehyde (intermediate D20) | |
| 202 | 642.24 | 2-[1-(4-amino-3,5-diethoxy-benzyl)-piperidin-4-ylamino]-4-trifluoromethyl-pyrimidine-5-carboxylic acid (4-trifluoromethoxy-phenyl)-amide | 2-(piperidin-4-ylamino)-4-trifluoromethyl-pyrimidine-5-carboxylic acid (4-trifluoromethoxy-phenyl)-amide dihydrochloride (intermediate C16) and 4-amino-3,5-diethoxy-benzaldehyde (intermediate D24) | [M + H]+ 643.3 |
| 203 | 692.25 | 2-[1-(3,5-diethoxy-4-pyrrol-1-yl-benzyl)-piperidin-4-ylamino]-4-trifluoromethyl-pyrimidine-5-carboxylic acid (4-trifluoromethoxy-phenyl)-amide | 2-(piperidin-4-ylamino)-4-trifluoromethyl-pyrimidine-5-carboxylic acid (4-trifluoromethoxy-phenyl)-amide dihydrochloride (intermediate C16) and 3,5-diethoxy-4-pyrrol-1-yl-benzaldehyde (intermediate D21) | [M − H]− 691.3 |
| 204 | 470.54 | [1-(3-ethoxy-4-fluoro-benzyl)-piperidin-4-yl]-(4,6,7-trimethoxy-quinazolin-2-yl)-amine | piperidin-4-yl-(4,6,7-trimethoxy-quinazolin-2-yl)-amine dihydrochloride (intermediate C17) and 3-ethoxy-4-fluoro-benzaldehyde (intermediate D16) | [M + H]+ 471.3 |
| 205 | 487.00 | [1-(4-chloro-3-ethoxy-benzyl)-piperidin-4-yl]-(4,6,7-trimethoxy-quinazolin-2-yl)-amine | piperidin-4-yl-(4,6,7-trimethoxy-quinazolin-2-yl)-amine dihydrochloride (intermediate C17) and 4-chloro-3-ethoxy-benzaldehyde (intermediate D3) | [M + H]+ 487.4 |
| 206 | 514.6 | [1-(3,5-diethoxy-4-fluoro-benzyl)-piperidin-4-yl]-(4,6,7-trimethoxy-quinazolin-2-yl)-amine | piperidin-4-yl-(4,6,7-trimethoxy-quinazolin-2-yl)-amine dihydrochloride (intermediate C17) and 3,5-diethoxy-4-fluoro-benzaldehyde (intermediate D12) | [M + H]+ 515.4 |
| 207 | 483.54 | N6-[1-(3,5-diethoxy-4-fluoro-benzyl)-piperidin-4-yl]-[1,3]dioxolo[4,5-g]quinazoline-6,8-diamine | N6-piperidin-4-yl-[1,3]dioxolo[4,5-g]quinazoline-6,8-diamine dihydrochloride (intermediate C18) and 3,5-diethoxy-4-fluoro-benzaldehyde (intermediate D12) | [M + H]+ 484.4 |
| 208 | 470.60 | [1-(3-ethoxy-4-methyl-benzyl)-piperidin-4-yl]-[4-(2-fluoro-phenyl)-quinazolin-2-yl]-amine | [4-(2-fluoro-phenyl)-quinazolin-2-yl]-piperidin-4-yl-amine dihydrochloride (intermediate C19) and 3-ethoxy-4-methyl-benzaldehyde (intermediate D2) | [M + H]+ 471.4 |
| 209 | 491.01 | [1-(4-chloro-3-ethoxy-benzyl)-piperidin-4-yl]-[4-(2-fluoro-phenyl)-quinazolin-2-yl]-amine | [4-(2-fluoro-phenyl)-quinazolin-2-yl]-piperidin-4-yl-amine dihydrochloride (intermediate C19) and 4-chloro-3-ethoxy-benzaldehyde (intermediate D3) | [M + H]+ 491.3 |
| 210 | 472.57 | 2-ethoxy-4-{4-[4-(2-fluoro-phenyl)-quinazolin-2-ylamino]-piperidin-1-ylmethyl}-phenol | [4-(2-fluoro-phenyl)-quinazolin-2-yl]-piperidin-4-yl-amine dihydrochloride (intermediate C19) and 3-ethoxy-4-hydroxy-benzaldehyde (commercially available) | [M + H]+ 473.2 |
| 211 | 504.23 | {1-[3-(2-fluoro-ethoxy)-4-methoxy-benzyl]-piperidin-4-yl}-[4-(2- | [4-(2-fluoro-phenyl)-quinazolin-2-yl]-piperidin-4-yl-amine dihydrochloride | [M + H]+ 505.2 |

TABLE 3-continued

| No. | MW | Compound Name | Starting Materials | ISP or ISN [M + H]+ or [M − H]− found |
|---|---|---|---|---|
| | | fluoro-phenyl)-quinazolin-2-yl]-amine | (intermediate C19) and 3-(2-fluoro-ethoxy)-4-methoxy-benzaldehyde (intermediate D8) | |
| 212 | 514.65 | [4-(2-fluoro-phenyl)-quinazolin-2-yl]-[1-(3-isobutoxy-4-methoxy-benzyl)-piperidin-4-yl]-amine | [4-(2-fluoro-phenyl)-quinazolin-2-yl]-piperidin-4-yl-amine dihydrochloride (intermediate C19) and 3-isobutoxy-4-methoxy-benzaldehyde (intermediate D9) | [M + H]+ 515.4 |
| 213 | 515.27 | [1-(4-amino-3,5-diethoxy-benzyl)-piperidin-4-yl]-[4-(2-fluoro-phenyl)-quinazolin-2-yl]-amine | [4-(2-fluoro-phenyl)-quinazolin-2-yl]-piperidin-4-yl-amine dihydrochloride (intermediate C19) and 4-amino-3,5-diethoxy-benzaldehyde (intermediate D24) | [M + H]+ 516.4 |
| 214 | 557.67 | N-(2,6-diethoxy-4-{4-[4-(2-fluoro-phenyl)-quinazolin-2-ylamino]-piperidin-1-ylmethyl}-phenyl)-acetamide | [4-(2-fluoro-phenyl)-quinazolin-2-yl]-piperidin-4-yl-amine dihydrochloride (intermediate C19) and N-(2,6-diethoxy-4-formyl-phenyl)-acetamide (intermediate D30) | [M + H]+ 558.4 |
| 215 | 525.46 | [1-(4-chloro-3-ethoxy-benzyl)-piperidin-4-yl]-[6-chloro-4-(2-fluoro-phenyl)-quinazolin-2-yl]-amine | [6-chloro-4-(2-fluoro-phenyl)-quinazolin-2-yl]-piperidin-4-yl-amine dihydrochloride (intermediate C20) and 4-chloro-3-ethoxy-benzaldehyde (intermediate D3) | [M + H]+ 525.2 |
| 216 | 521.04 | [6-chloro-4-(2-fluoro-phenyl)-quinazolin-2-yl]-[1-(3-ethoxy-4-methoxy-benzyl)-piperidin-4-yl]-amine | [6-chloro-4-(2-fluoro-phenyl)-quinazolin-2-yl]-piperidin-4-yl-amine dihydrochloride (intermediate C20) and 3-ethoxy-4-methoxy-benzaldehyde (commercially available) | [M + H]+ 521.3 |
| 217 | 660.96 | [6-chloro-4-(2-fluoro-phenyl)-quinazolin-2-yl]-[1-(3,5-diethoxy-4-iodo-benzyl)-piperidin-4-yl]-amine | [6-chloro-4-(2-fluoro-phenyl)-quinazolin-2-yl]-piperidin-4-yl-amine dihydrochloride (intermediate C20) and 3,5-diethoxy-4-iodo-benzaldehyde (intermediate D31) | [M + H]+ 661.2 |
| 218 | 550.08 | [1-(4-amino-3,5-diethoxy-benzyl)-piperidin-4-yl]-[6-chloro-4-(2-fluoro-phenyl)-quinazolin-2-yl]-amine | [6-chloro-4-(2-fluoro-phenyl)-quinazolin-2-yl]-piperidin-4-yl-amine dihydrochloride (intermediate C20) and 4-amino-3,5-diethoxy-benzaldehyde (intermediate D24) | [M + H]+ 550.4 |
| 219 | 600.14 | [6-chloro-4-(2-fluoro-phenyl)-quinazolin-2-yl]-[1-(3,5-diethoxy-4-pyrrol-1-yl-benzyl)-piperidin-4-yl]-amine | [6-chloro-4-(2-fluoro-phenyl)-quinazolin-2-yl]-piperidin-4-yl-amine dihydrochloride (intermediate C20) and 3,5-diethoxy-4-pyrrol-1-yl-benzaldehyde (intermediate D21) | [M + H]+ 600.4 |
| 220 | 519.69 | (6,7-dimethoxy-4-piperidin-1-yl-quinazolin-2-yl)-[1-(3-ethoxy-4-methyl-benzyl)-piperidin-4-yl]-amine | (6,7-dimethoxy-4-piperidin-1-yl-quinazolin-2-yl)-piperidin-4-yl-amine dihydrochloride (intermediate C21) and 3-ethoxy-4-methyl-benzaldehyde (intermediate D2) | [M + H]+ 520.4 |
| 221 | 523.65 | (6,7-dimethoxy-4-piperidin-1-yl-quinazolin-2-yl)-[1-(3-ethoxy-4-fluoro-benzyl)-piperidin-4-yl]-amine | (6,7-dimethoxy-4-piperidin-1-yl-quinazolin-2-yl)-piperidin-4-yl-amine dihydrochloride (intermediate C21) and 3-ethoxy-4-fluoro-benzaldehyde (intermediate D16) | [M + H]+ 524.4 |

TABLE 3-continued

| No. | MW | Compound Name | Starting Materials | ISP or ISN [M + H]+ or [M − H]− found |
|---|---|---|---|---|
| 222 | 540.11 | [1-(4-chloro-3-ethoxy-benzyl)-piperidin-4-yl]-(6,7-dimethoxy-4-piperidin-1-yl-quinazolin-2-yl)-amine | (6,7-dimethoxy-4-piperidin-1-yl-quinazolin-2-yl)-piperidin-4-yl-amine dihydrochloride (intermediate C21) and 4-chloro-3-ethoxy-benzaldehyde (intermediate D3) | [M + H]+ 540.3 |
| 223 | 535.69 | (6,7-dimethoxy-4-piperidin-1-yl-quinazolin-2-yl)-[1-(3-ethoxy-4-methoxy-benzyl)-piperidin-4-yl]-amine | (6,7-dimethoxy-4-piperidin-1-yl-quinazolin-2-yl)-piperidin-4-yl-amine dihydrochloride (intermediate C21) and 3-ethoxy-4-methoxy-benzaldehyde (commercially available) | [M + H]+ 536.4 |
| 224 | 549.72 | [1-(3,4-diethoxy-benzyl)-piperidin-4-yl]-(6,7-dimethoxy-4-piperidin-1-yl-quinazolin-2-yl)-amine | (6,7-dimethoxy-4-piperidin-1-yl-quinazolin-2-yl)-piperidin-4-yl-amine dihydrochloride (intermediate C21) and 3,4-diethoxy-benzaldehyde (commercially available) | [M + H]+ 550.4 |
| 225 | 563.74 | (6,7-dimethoxy-4-piperidin-1-yl-quinazolin-2-yl)-[1-(3-ethoxy-4-isopropoxy-benzyl)-piperidin-4-yl]-amine | (6,7-dimethoxy-4-piperidin-1-yl-quinazolin-2-yl)-piperidin-4-yl-amine dihydrochloride (intermediate C21) and 3-ethoxy-4-isopropoxy-benzaldehyde (commercially available) | [M + H]+ 564.4 |
| 226 | 565.71 | 2-{4-[4-(6,7-dimethoxy-4-piperidin-1-yl quinazolin-2-ylamino)-piperidin-1-ylmethyl]-2-ethoxy-phenoxy}-ethanol | (6,7-dimethoxy-4-piperidin-1-yl-quinazolin-2-yl)-piperidin-4-yl-amine dihydrochloride (intermediate C21) and 3-ethoxy-4-(2-hydroxy-ethoxy)-benzaldehyde (commercially available) | [M + H]+ 566.4 |
| 227 | 549.72 | (6,7-dimethoxy-4-piperidin-1-yl-quinazolin-2-yl)-[1-(4-methoxy-3-propoxy-benzyl)-piperidin-4-yl]-amine | (6,7-dimethoxy-4-piperidin-1-yl-quinazolin-2-yl)-piperidin-4-yl-amine dihydrochloride (intermediate C21) and 4-methoxy-3-propoxy-benzaldehyde (intermediate D7) | [M + H]+ 550.5 |
| 228 | 553.68 | (6,7-dimethoxy-4-piperidin-1-yl-quinazolin-2-yl)-{1-[3-(2-fluoro-ethoxy)-4-methoxy-benzyl]-piperidin-4-yl}-amine | (6,7-dimethoxy-4-piperidin-1-yl-quinazolin-2-yl)-piperidin-4-yl-amine dihydrochloride (intermediate C21) and 3-(2-fluoro-ethoxy)-4-methoxy-benzaldehyde (intermediate D8) | [M + H]+ 554.3 |
| 229 | 547.70 | [1-(3-allyloxy-4-methoxy-benzyl)-piperidin-4-yl]-(6,7-dimethoxy-4-piperidin-1-yl-quinazolin-2-yl)-amine | (6,7-dimethoxy-4-piperidin-1-yl-quinazolin-2-yl)-piperidin-4-yl-amine dihydrochloride (intermediate C21) and 3-allyloxy-4-methoxy-benzaldehyde (intermediate D17) | [M + H]+ 548.5 |
| 230 | 563.74 | [1-(3-butoxy-4-methoxy-benzyl)-piperidin-4-yl]-(6,7-dimethoxy-4-piperidin-1-yl-quinazolin-2-yl)-amine | (6,7-dimethoxy-4-piperidin-1-yl-quinazolin-2-yl)-piperidin-4-yl-amine dihydrochloride (intermediate C21) and 3-butoxy-4-methoxy-benzaldehyde (intermediate D26) | [M + H]+ 564.4 |
| 231 | 563.74 | (6,7-dimethoxy-4-piperidin-1-yl-quinazolin-2-yl)-[1-(3-isobutoxy-4-methoxy-benzyl)-piperidin-4-yl]-amine | (6,7-dimethoxy-4-piperidin-1-yl-quinazolin-2-yl)-piperidin-4-yl-amine dihydrochloride (intermediate C21) and 3-isobutoxy-4-methoxy-benzaldehyde (intermediate D9) | [M + H]+ 564.4 |
| 232 | 597.76 | [1-(3-benzyloxy-4-methoxy-benzyl)- | (6,7-dimethoxy-4-piperidin-1-yl-quinazolin-2-yl)- | [M + H]+ 598.4 |

TABLE 3-continued

| No. | MW | Compound Name | Starting Materials | ISP or ISN [M + H]+ or [M − H]− found |
|---|---|---|---|---|
| | | piperidin-4-yl]-(6,7-dimethoxy-4-piperidin-1-yl-quinazolin-2-yl)-amine | piperidin-4-yl-amine dihydrochloride (intermediate C21) and 3-benzyloxy-4-methoxy-benzaldehyde (commercially available) | |
| 233 | 583.70 | 2-{4-[4-(6,7-dimethoxy-4-piperidin-1-yl-quinazolin-2-ylamino)-piperidin-1-ylmethyl]-2-ethoxy-5-fluoro-phenoxy}-ethanol | (6,7-dimethoxy-4-piperidin-1-yl-quinazolin-2-yl)-piperidin-4-yl-amine dihydrochloride (intermediate C21) and 5-ethoxy-2-fluoro-4-(2-hydroxy-ethoxy)-benzaldehyde (intermediate D32) | [M + H]+ 584.3 |
| 234 | 587.76 | (6,7-dimethoxy-4-piperidin-1-yl-quinazolin-2-yl)-[1-(8-ethoxy-2,2-dimethyl-2H-chromen-6-ylmethyl)-piperidin-4-yl]-amine | (6,7-dimethoxy-4-piperidin-1-yl-quinazolin-2-yl)-piperidin-4-yl-amine dihydrochloride (intermediate C21) and 8-ethoxy-2,2-dimethyl-2H-chromene-6-carbaldehyde (intermediate D18) | [M + H]+ 588.4 |
| 235 | 549.72 | [1-(3,5-diethoxy-benzyl)-piperidin-4-yl]-(6,7-dimethoxy-4-piperidin-1-yl-quinazolin-2-yl)-amine | (6,7-dimethoxy-4-piperidin-1-yl-quinazolin-2-yl)-piperidin-4-yl-amine dihydrochloride (intermediate C21) and 3,5-diethoxy-benzaldehyde (intermediate D19) | [M + H]+ 550.4 |
| 236 | 577.77 | [1-(3,5-diisopropoxy-benzyl)-piperidin-4-yl]-(6,7-dimethoxy-4-piperidin-1-yl-quinazolin-2-yl)-amine | (6,7-dimethoxy-4-piperidin-1-yl-quinazolin-2-yl)-piperidin-4-yl-amine dihydrochloride (intermediate C21) and 3,5-diisopropoxy-benzaldehyde (intermediate D10) | [M + H]+ 578.4 |
| 237 | 567.71 | [1-(3,5-diethoxy-4-fluoro-benzyl)-piperidin-4-yl]-(6,7-dimethoxy-4-piperidin-1-yl-quinazolin-2-yl)-amine | (6,7-dimethoxy-4-piperidin-1-yl-quinazolin-2-yl)-piperidin-4-yl-amine dihydrochloride (intermediate C21) and 3,5-diethoxy-4-fluoro-benzaldehyde (intermediate D12) | [M + H]+ 568.4 |
| 238 | 584.16 | [1-(4-chloro-3,5-diethoxy-benzyl)-piperidin-4-yl]-(6,7-dimethoxy-4-piperidin-1-yl-quinazolin-2-yl)-amine | (6,7-dimethoxy-4-piperidin-1-yl-quinazolin-2-yl)-piperidin-4-yl-amine dihydrochloride (intermediate C21) and 4-chloro-3,5-diethoxy-benz-aldehyde (intermediate D20) | [M + H]+ 584.3 |
| 239 | 628.62 | [1-(4-bromo-3,5-diethoxy-benzyl)-piperidin-4-yl]-(6,7-dimethoxy-4-piperidin-1-yl-quinazolin-2-yl)-amine | (6,7-dimethoxy-4-piperidin-1-yl-quinazolin-2-yl)-piperidin-4-yl-amine dihydrochloride (intermediate C21) and 4-bromo-3,5-diethoxy-benzaldehyde (intermediate D23) | [M + H]+ 628.3 |
| 240 | 614.79 | [1-(3,5-diethoxy-4-pyrrol-1-yl-benzyl)-piperidin-4-yl]-(6,7-dimethoxy-4-piperidin-1-yl-quinazolin-2-yl)-amine | (6,7-dimethoxy-4-piperidin-1-yl-quinazolin-2-yl)-piperidin-4-yl-amine dihydrochloride (intermediate C21) and 3,5-diethoxy-4-pyrrol-1-yl-benzaldehyde (intermediate D21) | [M + H]+ 615.4 |
| 241 | 496.05 | (6-chloro-4-morpholin-4-yl-quinazolin-2-yl)-[1-(3-ethoxy-4-methyl-benzyl)-piperidin-4-yl]-amine | (6-chloro-4-morpholin-4-yl-quinazolin-2-yl)-piperidin-4-yl-amine dihydrochloride (intermediate C22) and 3-ethoxy-4-methyl-benzaldehyde (intermediate D2) | [M + H]+ 496.4 |
| 242 | 500.02 | (6-chloro-4-morpholin-4-yl-quinazolin-2-yl)-[1-(3-ethoxy-4-fluoro-benzyl)-piperidin-4-yl]-amine | (6-chloro-4-morpholin-4-yl-quinazolin-2-yl)-piperidin-4-yl-amine dihydrochloride (intermediate C22) and 3- | [M + H]+ 500.2 |

TABLE 3-continued

| No. | MW | Compound Name | Starting Materials | ISP or ISN [M + H]+ or [M − H]− found |
|---|---|---|---|---|
| 243 | 544.07 | (6-chloro-4-morpholin-4-yl-quinazolin-2-yl)-[1-(3,5-diethoxy-4-fluoro-benzyl)-piperidin-4-yl]-amine | ethoxy-4-fluoro-benzaldehyde (intermediate D16) (6-chloro-4-morpholin-4-yl-quinazolin-2-yl)-piperidin-4-yl-amine dihydrochloride (intermediate C22) and 3,5-diethoxy-4-fluoro-benzaldehyde (intermediate D12) | [M + H]+ 544.3 |
| 244 | 541.10 | [1-(4-amino-3,5-diethoxy-benzyl)-piperidin-4-yl]-(6-chloro-4-morpholin-4-yl-quinazolin-2-yl)-amine | (6-chloro-4-morpholin-4-yl-quinazolin-2-yl)-piperidin-4-yl-amine dihydrochloride (intermediate C22) and 4-amino-3,5-diethoxy-benzaldehyde (intermediate D24) | [M + H]+ 541.3 |
| 245 | 591.16 | (6-chloro-4-morpholin-4-yl-quinazolin-2-yl)-[1-(3,5-diethoxy-4-pyrrol-1-yl-benzyl)-piperidin-4-yl]-amine | (6-chloro-4-morpholin-4-yl-quinazolin-2-yl)-piperidin-4-yl-amine dihydrochloride (intermediate C22) and 3,5-diethoxy-4-pyrrol-1-yl-benzaldehyde (intermediate D21) | [M + H]+ 591.5 |
| 246 | 521.66 | (6,7-dimethoxy-4-morpholin-4-yl-quinazolin-2-yl)-[1-(3-ethoxy-4-methyl-benzyl)-piperidin-4-yl]-amine | (6,7-dimethoxy-4-morpholin-4-yl-quinazolin-2-yl)-piperidin-4-yl-amine dihydrochloride (intermediate C23) and 3-ethoxy-4-methyl-benzaldehyde (intermediate D2) | [M + H]+ 522.3 |
| 247 | 525.62 | (6,7-dimethoxy-4-morpholin-4-yl-quinazolin-2-yl)-[1-(3-ethoxy-4-fluoro-benzyl)-piperidin-4-yl]-amine | (6,7-dimethoxy-4-morpholin-4-yl-quinazolin-2-yl)-piperidin-4-yl-amine dihydrochloride (intermediate C23) and 3-ethoxy-4-fluoro-benzaldehyde (intermediate D16) | [M + H]+ 526.3 |
| 248 | 542.08 | [1-(4-chloro-3-ethoxy-benzyl)-piperidin-4-yl]-(6,7-dimethoxy-4-morpholin-4-yl-quinazolin-2-yl)-amine | (6,7-dimethoxy-4-morpholin-4-yl-quinazolin-2-yl)-piperidin-4-yl-amine dihydrochloride (intermediate C23) and 4-chloro-3-ethoxy-benzaldehyde (intermediate D3) | [M + H]+ 542.2 |
| 249 | 523.63 | 4-[4-(6,7-dimethoxy-4-morpholin-4-yl-quinazolin-2-ylamino)-piperidin-1-ylmethyl]-2-ethoxy-phenol | (6,7-dimethoxy-4-morpholin-4-yl-quinazolin-2-yl)-piperidin-4-yl-amine dihydrochloride (intermediate C23) and 3-ethoxy-4-hydroxy-benzaldehyde (commercially available) | [M + H]+ 524.3 |
| 250 | 537.66 | (6,7-dimethoxy-4-morpholin-4-yl-quinazolin-2-yl)-[1-(3-ethoxy-4-methoxy-benzyl)-piperidin-4-yl]-amine | (6,7-dimethoxy-4-morpholin-4-yl-quinazolin-2-yl)-piperidin-4-yl-amine dihydrochloride (intermediate C23) and 3-ethoxy-4-methoxy-benzaldehyde (commercially available) | [M + H]+ 538.3 |
| 251 | 565.71 | (6,7-dimethoxy-4-morpholin-4-yl-quinazolin-2-yl)-[1-(3-ethoxy-4-isopropoxy-benzyl)-piperidin-4-yl]-amine | (6,7-dimethoxy-4-morpholin-4-yl-quinazolin-2-yl)-piperidin-4-yl-amine dihydrochloride (intermediate C23) and 3-ethoxy-4-isopropoxy-benzaldehyde (commercially available) | [M + H]+ 566.3 |
| 252 | 551.69 | (6,7-dimethoxy-4-morpholin-4-yl-quinazolin-2-yl)-[1-(4-methoxy-3-propoxy-benzyl)-piperidin-4-yl]-amine | (6,7-dimethoxy-4-morpholin-4-yl-quinazolin-2-yl)-piperidin-4-yl-amine dihydrochloride (intermediate C23) and 4-methoxy-3-propoxy-benzaldehyde (intermediate D7) | [M + H]+ 552.3 |

TABLE 3-continued

| No. | MW | Compound Name | Starting Materials | ISP or ISN [M + H]+ or [M − H]− found |
|---|---|---|---|---|
| 253 | 555.65 | (6,7-dimethoxy-4-morpholin-4-yl-quinazolin-2-yl)-{1-[3-(2-fluoro-ethoxy)-4-methoxy-benzyl]-pipendin-4-yl}-amine | (6,7-dimethoxy-4-morpholin-4-yl-quinazolin-2-yl)-piperidin-4-yl-amine dihydrochloride (intermediate C23) and 3-(2-fluoro-ethoxy)-4-methoxy-benzaldehyde (intermediate D8) | [M + H]+ 556.3 |
| 254 | 549.67 | [1-(3-allyloxy-4-methoxy-benzyl)-piperidin-4-yl]-(6,7-dimethoxy-4-morpholin-4-yl-quinazolin-2-yl)-amine | (6,7-dimethoxy-4-morpholin-4-yl-quinazolin-2-yl)-piperidin-4-yl-amine dihydrochloride (intermediate C23) and 3-allyloxy-4-methoxy-benzaldehyde (intermediate D17) | [M + H]+ 550.3 |
| 255 | 565.71 | [1-(3-butoxy-4-methoxy-benzyl)-piperidin-4-yl]-(6,7-dimethoxy-4-morpholin-4-yl-quinazolin-2-yl)-amine | (6,7-dimethoxy-4-morpholin-4-yl-quinazolin-2-yl)-piperidin-4-yl-amine dihydrochloride (intermediate C23) and 3-butoxy-4-methoxy-benzaldehyde (intermediate D26) | [M + H]+ 566.3 |
| 256 | 565.71 | (6,7-dimethoxy-4-morpholin-4-yl-quinazolin-2-yl)-[1-(3-isobutoxy-4-methoxy-benzyl)-piperidin-4-yl]-amine | (6,7-dimethoxy-4-morpholin-4-yl-quinazolin-2-yl)-piperidin-4-yl-amine dihydrochloride (intermediate C23) and 3-isobutoxy-4-methoxy-benzaldehyde (intermediate D9) | [M + H]+ 566.3 |
| 257 | 589.74 | (6,7-dimethoxy-4-morpholin-4-yl-quinazolin-2-yl)-[1-(8-ethoxy-2,2-dimethyl-2H-chromen-6-ylmethyl)-piperidin-4-yl]-amine | (6,7-dimethoxy-4-morpholin-4-yl-quinazolin-2-yl)-piperidin-4-yl-amine dihydrochloride (intermediate C23) and 8-ethoxy-2,2-dimethyl-2H-chromene-6-carbaldehyde (intermediate D18) | [M + H]+ 590.3 |
| 258 | 551.69 | [1-(3,5-diethoxy-benzyl)-piperidin-4-yl]-(6,7-dimethoxy-4-morpholin-4-yl-quinazolin-2-yl)-amine | (6,7-dimethoxy-4-morpholin-4-yl-quinazolin-2-yl)-piperidin-4-yl-amine dihydrochloride (intermediate C23) and 3,5-diethoxy-benzaldehyde (intermediate D19) | [M + H]+ 552.3 |
| 259 | 537.66 | 3-[4-(6,7-dimethoxy-4-morpholin-4-yl-quinazolin-2-ylamino)-piperidin-1-ylmethyl]-5-isopropoxy-phenol | (6,7-dimethoxy-4-morpholin-4-yl-quinazolin-2-yl)-piperidin-4-yl-amine dihydrochloride (intermediate C23) and 3-hydroxy-5-isopropoxy-benzaldehyde (intermediate D27) | [M + H]+ 538.3 |
| 260 | 579.74 | [1-(3,5-diisopropoxy-benzyl)-piperidin-4-yl]-(6,7-dimethoxy-4-morpholin-4-yl-quinazolin-2-yl)-amine | (6,7-dimethoxy-4-morpholin-4-yl-quinazolin-2-yl)-piperidin-4-yl-amine dihydrochloride (intermediate C23) and 3,5-diisopropoxy-benzaldehyde (intermediate D10) | [M + H]+ 580.3 |
| 261 | 569.68 | [1-(3,5-diethoxy-4-fluoro-benzyl)-piperidin-4-yl]-(6,7-dimethoxy-4-morpholin-4-yl-quinazolin-2-yl)-amine | (6,7-dimethoxy-4-morpholin-4-yl-quinazolin-2-yl)-piperidin-4-yl-amine dihydrochloride (intermediate C23) and 3,5-diethoxy-4-fluoro-benz-aldehyde (intermediate D12) | [M + H]+ 570.3 |
| 262 | 586.13 | [1-(4-chloro-3,5-diethoxy-benzyl)-piperidin-4-yl]-(6,7-dimethoxy-4-morpholin-4-yl-quinazolin-2-yl)-amine | (6,7-dimethoxy-4-morpholin-4-yl-quinazolin-2-yl)-piperidin-4-yl-amine dihydrochloride (intermediate C23) and 4-chloro-3,5-diethoxy-benzaldehyde (intermediate D20) | [M + H]+ 586.3 |
| 263 | 630.59 | [1-(4-bromo-3,5-diethoxy-benzyl)- | (6,7-dimethoxy-4-morpholin-4-yl-quinazolin-2-yl)- | [M + H]+ 632.2 |

TABLE 3-continued

| No. | MW | Compound Name | Starting Materials | ISP or ISN [M + H]+ or [M − H]− found |
|---|---|---|---|---|
| | | piperidin-4-yl]-(6,7-dimethoxy-4-morpholin-4-yl-quinazolin-2-yl)-amine | piperidin-4-yl-amine dihydrochloride (intermediate C23) and 4-bromo-3,5-diethoxy-benzaldehyde (intermediate D23) | |
| 264 | 566.70 | [1-(4-amino-3,5-diethoxy-benzyl)-piperidin-4-yl]-(6,7-dimethoxy-4-morpholin-4-yl-quinazolin-2-yl)-amine | (6,7-dimethoxy-4-morpholin-4-yl-quinazolin-2-yl)-piperidin-4-yl-amine dihydrochloride (intermediate C23) and 4-amino-3,5-diethoxy-benzaldehyde (intermediate D24) | [M + H]+ 567.3 |
| 265 | 616.76 | [1-(3,5-diethoxy-4-pyrrol-1-yl-benzyl)-piperidin-4-yl]-(6,7-dimethoxy-4-morpholin-4-yl-quinazolin-2-yl)-amine | (6,7-dimethoxy-4-morpholin-4-yl-quinazolin-2-yl)-piperidin-4-yl-amine dihydrochloride (intermediate C23) and 3,5-diethoxy-4-pyrrol-1-yl-benzaldehyde (intermediate D21) | [M + H]+ 617.3 |
| 266 | 529.64 | (6,7-dimethoxy-4-morpholin-4-yl-quinazolin-2-yl)-[1-(2-phenyl-1H-imidazol-4-ylmethyl)-piperidin-4-yl]-amine | (6,7-dimethoxy-4-morpholin-4-yl-quinazolin-2-yl)-piperidin-4-yl-amine dihydrochloride (intermediate C23) and 2-phenyl-3H-imidazole-4-carbaldehyde (commercially available) | [M + H]+ 530.3 |
| 267 | 470.24 | [1-(3-ethoxy-4-methoxy-benzyl)-piperidin-4-yl]-(4-phenyl-pteridin-2-yl)-amine | (4-phenyl-pteridin-2-yl)-piperidin-4-yl-amine dihydrochloride (intermediate C24) and 3-ethoxy-4-methoxy-benzaldehyde (commercially available) | [M + H]+ 470.5 |
| 268 | 484.26 | [1-(3,5-diethoxy-benzyl)-piperidin-4-yl]-(4-phenyl-pteridin-2-yl)-amine | (4-phenyl-pteridin-2-yl)-piperidin-4-yl-amine dihydrochloride (intermediate C24) and 3,5-diethoxy-benzaldehyde (intermediate D19) | [M + H]+ 484.4 |
| 269 | 512.29 | [1-(3,5-diisopropoxy-benzyl)-piperidin-4-yl]-(4-phenyl-pteridin-2-yl)-amine | (4-phenyl-pteridin-2-yl)-piperidin-4-yl-amine dihydrochloride (intermediate C24) and 3,5-diisopropoxy-benzaldehyde (intermediate D10) | [M + H]+ 512.5 |
| 270 | 387.48 | (4,6-dimethoxy-[1,3,5]triazin-2-yl)-[1-(3-ethoxy-4-methyl-benzyl)-piperidin-4-yl]-amine | (4,6-dimethoxy-[1,3,5]triazin-2-yl)-piperidin-4-yl-amine dihydrochloride (intermediate C25) and 3-ethoxy-4-methyl-benzaldehyde (intermediate D2) | [M + H]+ 388.3 |
| 271 | 391.45 | (4,6-dimethoxy-[1,3,5]triazin-2-yl)-[1-(3-ethoxy-4-fluoro-benzyl)-piperidin-4-yl]-amine | (4,6-dimethoxy-[1,3,5]triazin-2-yl)-piperidin-4-yl-amine dihydrochloride (intermediate C25) and 3-ethoxy-4-fluoro-benzaldehyde (intermediate D16) | [M + H]+ 392.4 |
| 272 | 407.90 | [1-(4-chloro-3-ethoxy-benzyl)-piperidin-4-yl]-(4,6-dimethoxy-[1,3,5]triazin-2-yl)-amine | (4,6-dimethoxy-[1,3,5]triazin-2-yl)-piperidin-4-yl-amine dihydrochloride (intermediate C25) and 4-chloro-3-ethoxy-benz-aldehyde (intermediate D3) | [M + H]+ 408.3 |
| 273 | 417.51 | [1-(3,4-diethoxy-benzyl)-piperidin-4-yl]-(4,6-dimethoxy-[1,3,5]triazin-2-yl)-amine | (4,6-dimethoxy-[1,3,5]triazin-2-yl)-piperidin-4-yl-amine dihydrochloride (intermediate C25) and 3,4-diethoxy-benzaldehyde (commercially available) | [M + H]+ 418.2 |
| 274 | 417.51 | (4,6-dimethoxy-[1,3,5]triazin-2-yl)-[1-(4-methoxy-3-propoxy-benzyl)-piperidin-4-yl]- | (4,6-dimethoxy-[1,3,5]triazin-2-yl)-piperidin-4-yl-amine dihydrochloride (intermediate C25) and 4- | [M + H]+ 418.2 |

TABLE 3-continued

| No. | MW | Compound Name | Starting Materials | ISP or ISN [M + H]+ or [M − H]− found |
|---|---|---|---|---|
| | | amine | methoxy-3-propoxy-benzaldehyde (intermediate D7) | |
| 275 | 421.47 | (4,6-dimethoxy-[1,3,5]triazin-2-yl)-{1-[3-(2-fluoro-ethoxy)-4-methoxy-benzyl]-piperidin-4-yl}-amine | (4,6-dimethoxy-[1,3,5]triazin-2-yl)-piperidin-4-yl-amine dihydrochloride (intermediate C25) and 3-(2-fluoro-ethoxy)-4-methoxy-benzaldehyde (intermediate D8) | [M + H]+ 422.2 |
| 276 | 415.49 | [1-(3-allyloxy-4-methoxy-benzyl)-piperidin-4-yl]-(4,6-dimethoxy-[1,3,5]triazin-2-yl)-amine | (4,6-dimethoxy-[1,3,5]triazin-2-yl)-piperidin-4-yl-amine dihydrochloride (intermediate C25) and 3-allyloxy-4-methoxy-benzaldehyde (intermediate D17) | [M + H]+ 416.4 |
| 277 | 431.54 | [1-(3-butoxy-4-methoxy-benzyl)-piperidin-4-yl]-(4,6-dimethoxy-[1,3,5]triazin-2-yl)-amine | (4,6-dimethoxy-[1,3,5]triazin-2-yl)-piperidin-4-yl-amine dihydrochloride (intermediate C25) and 3-butoxy-4-methoxy-benzaldehyde (intermediate D26) | [M + H]+ 432.4 |
| 278 | 431.54 | (4,6-dimethoxy-[1,3,5]triazin-2-yl)-[1-(3-isobutoxy-4-methoxy-benzyl)-piperidin-4-yl]-amine | (4,6-dimethoxy-[1,3,5]triazin-2-yl)-piperidin-4-yl-amine dihydrochloride (intermediate C25) and 3-isobutoxy-4-methoxy-benzaldehyde (intermediate D9) | [M + H]+ 432.3 |
| 279 | 465.55 | [1-(3-benzyloxy-4-methoxy-benzyl)-piperidine-4-yl]-(4,6-dimethoxy-[1,3,5]triazin-2-yl)-amine | (4,6-dimethoxy-[1,3,5]triazin-2-yl)-piperidin-4-yl-amine dihydrochloride (intermediate C25) and 3-benzyloxy-4-methoxy-benzaldehyde (commercially available) | [M + H]+ 466.3 |
| 280 | 447.54 | (4,6-dimethoxy-[1,3,5]triazin-2-yl)-{1-[5-ethoxy-2-(2-methoxy-ethoxy)-benzyl]-piperidin-4-yl}-amine | (4,6-dimethoxy-[1,3,5]triazin-2-yl)-piperidin-4-yl-amine dihydrochloride (intermediate C25) and 5-ethoxy-2-(2-methoxy-ethoxy)-benzaldehyde (intermediate D33) | [M + H]+ 448.2 |
| 281 | 417.51 | [1-(3,5-diethoxy-benzyl)-piperidin-4-yl]-(4,6-dimethoxy-[1,3,5]triazin-2-yl)-amine | (4,6-dimethoxy-[1,3,5]triazin-2-yl)-piperidin-4-yl-amine dihydrochloride (intermediate C25) and 3,5-diethoxy-benzaldehyde (intermediate D19) | [M + H]+ 418.2 |
| 282 | 435.50 | [1-(3,5-diethoxy-4-fluoro-benzyl)-piperidin-4-yl]-(4,6-dimethoxy-[1,3,5]triazin-2-yl)-amine | (4,6-dimethoxy-[1,3,5]triazin-2-yl)-piperidin-4-yl-amine dihydrochloride (intermediate C25) and 3,5-diethoxy-4-fluoro-benzaldehyde (intermediate D12) | [M + H]+ 436.3 |
| 283 | 496.41 | [1-(4-bromo-3,5-diethoxy-benzyl)-piperidin-4-yl]-(4,6-dimethoxy-[1,3,5]triazin-2-yl)-amine | (4,6-dimethoxy-[1,3,5]triazin-2-yl)-piperidin-4-yl-amine dihydrochloride (intermediate C25) and 4-bromo-3,5-diethoxy-benzaldehyde (intermediate D23) | [M + H]+ 498.3 |
| 284 | 482.58 | [1-(3,5-diethoxy-4-pyrrol-1-yl-benzyl)-piperidin-4-yl]-(4,6-dimethoxy-[1,3,5]triazin-2-yl)-amine | (4,6-dimethoxy-[1,3,5]triazin-2-yl)-piperidin-4-yl-amine dihydrochloride (intermediate C25) and 3,5-diethoxy-4-pyrrol-1-yl-benzaldehyde (intermediate D21) | [M + H]+ 483.3 |
| 285 | 643.80 | [1-(2,6-diethoxy-4'-fluoro-biphenyl-4- | (6,7-dimethoxy-4-piperidin-1-yl-quinazolin-2-yl)- | [M + H]+ 644.5 |

TABLE 3-continued

| No. | MW | Compound Name | Starting Materials | ISP or ISN [M + H]+ or [M − H]− found |
|---|---|---|---|---|
| | | ylmethyl)-piperidin-4-yl]-(6,7-dimethoxy-4-piperidin-1-yl-quinazolin-2-yl)-amine | piperidin-4-yl-amine dihydrochloride (intermediate C21) and 2,6-diethoxy-4'-fluoro-biphenyl-4-carbaldehyde (intermediate D34) | |
| 286 | 521.66 | 4-[4-(6,7-dimethoxy-4-piperidin-1-yl-quinazolin-2-ylamino)-piperidin-1-ylmethyl]-2-ethoxy-phenol | (6,7-dimethoxy-4-piperidin-1-yl-quinazolin-2-yl)-piperidin-4-yl-amine dihydrochloride (intermediate C21) and 3-ethoxy-4-hydroxy-benzaldehyde (commercially available) | [M + H]+ 522.5 |
| 287 | 511.60 | [1-(2,6-diethoxy-4'-fluoro-biphenyl-4-ylmethyl)-piperidin-4-yl]-(4,6-dimethoxy-[1,3,5]triazin-2-yl)-amine | (4,6-dimethoxy-[1,3,5]triazin-2-yl)-piperidin-4-yl-amine dihydrochloride (intermediate C25) and 2,6-diethoxy-4'-fluoro-biphenyl-4-carbaldehyde (intermediate D34) | [M + H]+ 512.4 |

The triazine and pyrimidine piperidine intermediates C26 to C35 were prepared following literature precedents or as described below.

Synthesis of Triazine and Pyrimidine Piperidine Intermediates C26 to C35 to be Used in Table 4

Intermediate C26

2-[4-Methoxy-6-(piperidin-4-ylamino)-[1,3,5]triazin-2-ylamino]-ethanol

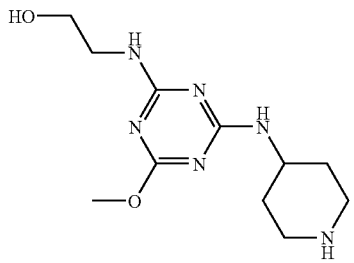

Step 1: 4-(4-Chloro-6-methoxy-[1,3,5]triazin-2-ylamino)-piperidine-1-carboxylic acid tert-butyl ester To a stirred solution of 2,4-dichloro-6-methoxy-1,3,5-triazine (10.0 g, 55.6 mmol, 1.0 equiv) and 4-amino-piperidine-1-carboxylic acid tert-butyl ester (11.4 g, 55.6 mmol, 1.0 equiv) in acetonitrile (300 mL) was added drop by drop N-ethyl diisopropylamine (48.5 mL, 36.6 g, 278 mmol, 5.0 equiv) keeping the temperature below 25° C. After stirring the reaction mixture at rt for 16 h, the heterogeneous mixture was poured onto ice water and extracted three times with ethyl acetate. The combined organic layers were washed with brine and water, dried over MgSO4, filtered and concentrated by evaporation under reduced pressure. The crude product was purified by column chromatography on silica eluting with a gradient of dichloromethane/methanol to give 11.4 g (60%) of the title compound as a off-white foam. MS (ISP): 344.3 [M+H]+.

Step 2: 4-[4-(2-Hydroxy-ethylamino)-6-methoxy-[1,3,5]triazin-2-ylamino]-piperidine-1-carboxylic acid tert-butyl ester To a stirred solution of 4-(4-chloro-6-methoxy-[1,3,5]triazin-2-ylamino)-piperidine-1-carboxylic acid tert-butyl ester (1.03 g, 3.0 mmol, 1.0 equiv) in acetonitrile (45 mL) was added N-ethyl diisopropylamine (1.56 mL, 1.18 g, 9.0 mmol, 3.0 equiv) at rt, followed by 2-amino-ethanol (0.36 mL, 0.37 g, 6.0 mmol, 2.0 equiv). The reaction mixture was heated to 50° C. for 3.5 h, then poured into crashed ice and extracted twice with ethyl acetate. The combined organic layers were washed with brine and water, then dried over MgSO4, filtered and concentrated by evaporation under reduced pressure. The crude product was purified by column chromatography on silica eluting with a gradient of dichloromethane/methanol to give 1.00 g (90%) of the title compound as colorless foam. MS (ISP): 369.1 [M+H]+.

Step 3

To a stirred solution of 4-[4-(2-hydroxy-ethylamino)-6-methoxy-[1,3,5]triazin-2-ylamino]-piperidine-1-carboxylic acid tert-butyl ester (1.00 g, 2.7 mmol, 1.0 equiv) in ethanol (30 mL) was added 4 M HCl in dioxane (3.40 mL, 13.6 mmol, 5.0 equiv) drop by drop. The reaction mixture was subsequently stirred at rt for 72 h and at 80° C. for 2 h. It was then cooled down to rt, poured into ice water and the pH was adjusted to 9-10 by addition of a sat. solution of potassium carbonate. The solution was extracted six times with a mixture of dichloromethane/isopropanol (4:1). The combined organic layers were concentrated by evaporation under reduced pressure to yield 0.60 g (83%) of the title compound as light yellow oil. MS (ISP): 269.2 [M+H]+.

Intermediate C27

6-Methoxy-N-(2-methoxy-ethyl)-N'-piperidin-4-yl-[1,3,5]triazine-2,4-diamine

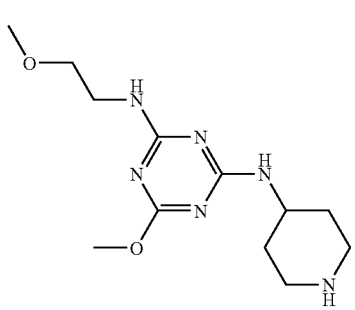

The compound was prepared in analogy to the synthesis of 4-[4-(2-hydroxy-ethylamino)-6-methoxy-[1,3,5]triazin-2-ylamino]-piperidine-1-carboxylic acid tert-butyl ester (intermediate C26/step 2) from 4-(4-chloro-6-methoxy-[1,3,5]triazin-2-ylamino)-piperidine-1-carboxylic acid tert-butyl ester (intermediate C26/step 1) and 2-methoxy-ethylamine, followed by BOC cleavage in analogy to the procedure described for 2-[4-methoxy-6-(piperidin-4-ylamino)-[1,3,5]triazin-2-ylamino]-ethanol (intermediate C26/step 3). MS (ISP): 283.0 [M+H]$^+$.

Intermediate C28

6-Methoxy-N-methyl-N'-piperidin-4-yl-[1,3,5]triazine-2,4-diamine

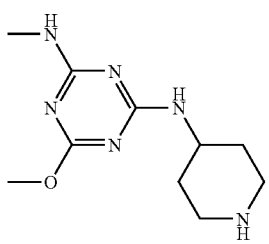

The compound was prepared in analogy to the synthesis of 4-[4-(2-hydroxy-ethylamino)-6-methoxy-[1,3,5]triazin-2-ylamino]-piperidine-1-carboxylic acid tert-butyl ester (intermediate C26/step 2) from 4-(4-chloro-6-methoxy-[1,3,5]triazin-2-ylamino)-piperidine-1-carboxylic acid tert-butyl ester (intermediate C26/step 1) and methylamine (12 M solution in water) and N-ethyl diisopropylamine in acetonitrile at rt, followed by BOC cleavage in analogy to the procedure described for 2-[4-methoxy-6-(piperidin-4-ylamino)-[1,3,5]triazin-2-ylamino]-ethanol (intermediate C26/step 3). MS (ISP): 239.1 [M+H]$^+$.

Intermediate C29

[4-Methoxy-6-(piperidin-4-ylamino)-[1,3,5]triazin-2-ylamino]-acetic acid tert-butyl ester

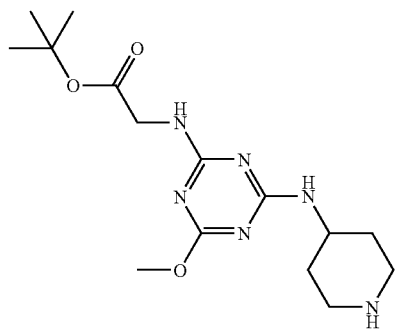

The compound was prepared in analogy to the synthesis of 4-[4-(2-hydroxy-ethylamino)-6-methoxy-[1,3,5]triazin-2-ylamino]-piperidine-1-carboxylic acid tert-butyl ester (intermediate C26/step 2) from 4-(4-chloro-6-methoxy-[1,3,5]triazin-2-ylamino)-piperidine-1-carboxylic acid tert-butyl ester (intermediate C26/step 1) and tert-butyl glycinate and N-ethyl diisopropylamine in acetonitrile at 50° C., followed by BOC cleavage with 4 M HCl in dioxane and methanol at rt in analogy to the procedure described for 2-[4-methoxy-6-(piperidin-4-ylamino)-[1,3,5]triazin-2-ylamino]-ethanol (intermediate C26/step 3). MS (ISP): 339.2 [M+H]$^+$.

Intermediate C30

(4-Methoxy-6-thiomorpholin-4-yl-[1,3,5]triazin-2-yl)-piperidin-4-yl-amine

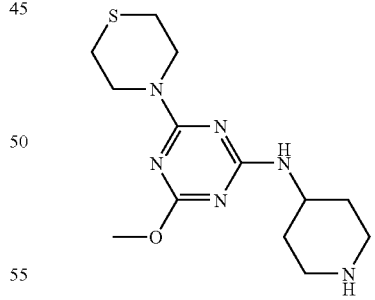

The compound was prepared in analogy to the synthesis of 4-[4-(2-hydroxy-ethylamino)-6-methoxy-[1,3,5]triazin-2-ylamino]-piperidine-1-carboxylic acid tert-butyl ester (intermediate C26/step 2) from 4-(4-chloro-6-methoxy-[1,3,5]triazin-2-ylamino)-piperidine-1-carboxylic acid tert-butyl ester (intermediate C26/step 1) and thiomorpholine and N-ethyl diisopropylamine in acetonitrile at 50° C., followed by BOC cleavage with 4 M HCl in dioxane and methanol at rt in analogy to the procedure described for 2-[4-methoxy-6-(piperidin-4-ylamino)-[1,3,5]triazin-2-ylamino]-ethanol (intermediate C26/step 3). MS (ISP): 311.0 [M+H]+.

Intermediate C31

Methanesulfonic acid 2-(piperidin-4-ylamino)-pyrimidin-5-yl ester

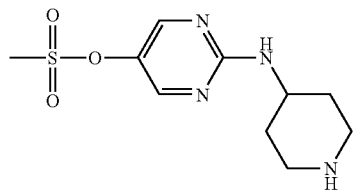

Step 1: 4-(5-Bromo-pyrimidin-2-ylamino)-piperidine-1-carboxylic acid tert-butyl ester To a stirred solution of 5-bromo-2-chloropyrimidine (10.0 g, 51.7 mmol, 1.0 equiv) and 4-amino-piperidine-1-carboxylic acid tert-butyl ester (10.6 g, 51.7 mmol, 1.0 equiv) in acetonitrile (250 mL) was added at rt drop by drop N-ethyl diisopropylamine (45.2 mL 34.4 g, 266 mmol, 5.1 equiv). Then, the reaction mixture was heated to reflux for 16 h, poured into crashed ice and extracted twice with ethyl acetate. The combined organic layers were washed with brine and water, dried over MgSO4, filtered and concentrated by evaporation under reduced pressure. The crude product was purified by column chromatography on silica eluting with a gradient of dichloromethane/methanol to give 14.4 g (78%) of the title compound as a colorless solid. MS (ISP): 357.0 [M+H]+.

Step 2: 4-(5-Hydroxy-pyrimidin-2-ylamino)-piperidine-1-carboxylic acid tert-butyl ester To a stirred solution of 4-(5-bromo-pyrimidin-2-ylamino)-piperidine-1-carboxylic acid tert-butyl ester (12.4 g, 34.8 mmol, 1.0 equiv) in dioxane (100 mL) was added bis(pinacolato)diboron (13.25 g, 52.2 mmol, 1.5 equiv) and potassium acetate (10.4 g, 105 mmol, 3.0 equiv). After 15 min, bis(triphenylphosphine) palladium(II) chloride (1.47 g, 2.1 mmol, 0.06 equiv) was added and the reaction mixture was warmed up to 90° C. After 3 h, the reaction mixture was cooled down to 0° C. and glacial acetic acid (3.02 mL, 3.17 g, 52.2 mmol, 1.5 equiv) was added, followed by a solution of 30% hydrogen peroxide in water (6.58 mL, 7.44 g, 76.5 mmol, 1.5 equiv) and then warmed up to rt. After 16 h, the reaction mixture was poured into ice water and extracted twice with dichloromethane. The combined organic layers were washed with brine and water, dried over MgSO4, filtered and concentrated by evaporation under reduced pressure. The crude product was purified by column chromatography on silica eluting with a gradient of dichloromethane/methanol to give 6.81 g (66%) of the title compound as yellow foam. MS (ISP): 295.3 [M+H]+.

Step 3: 4-(5-Methanesulfonyloxy-pyrimidin-2-ylamino)-piperidine-1-carboxylic acid tert-butyl ester To a stirred solution of 4-(5-hydroxy-pyrimidin-2-ylamino)-piperidine-1-carboxylic acid tert-butyl ester (0.74 g, 2.5 mmol, 1.0 equiv) in dichloromethane (20 mL) were added N-ethyl diisopropylamine (1.09 mL, 0.82 g, 6.3 mmol, 2.5 equiv), followed by methanesulfonyl chloride (0.24 mL, 0.35 g, 3.0 mmol, 1.2 equiv). After stirring for 4 h, the reaction mixture was poured into ice water and extracted twice with dichloromethane. The combined organic layers were washed with water, then dried over MgSO4, filtered and concentrated by evaporation under reduced pressure. The crude product was purified by column chromatography on silica eluting with a gradient of dichloromethane/methanol to give 0.87 g (93%) of the title compound as colorless foam. MS (ISP): 373.1 [M+H]+.

Step 4: Methanesulfonic acid 2-(piperidin-4-ylamino)-pyrimidin-5-yl ester

To a solution of 4-(5-methanesulfonyloxy-pyrimidin-2-ylamino)-piperidine-1-carboxylic acid tert-butyl ester (0.85 g, 2.3 mmol, 1.0 equiv) in ethanol (15 mL) was added 4 M HCl in dioxane (2.85 mL, 11.4 mmol, 5.0 equiv) and the mixture was warmed up to 50° C. After 16 h, the reaction mixture was cooled down to rt, then poured into ice water and the pH was adjusted to 9-10 by addition of a sat. solution of potassium carbonate. Then, this solution was extracted three times with dichloromethane/isopropanol (4:1). The combined organic layers were concentrated by evaporation under reduced pressure to yield 0.62 g (99%) of the title compound as a colorless solid. MS (ISP): 273.0 [M+H]+.

Intermediate C32

[2-(Piperidin-4-ylamino)-pyrimidin-5-yloxy]-acetonitrile

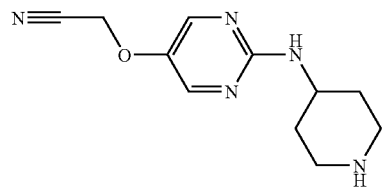

Step 1: 4-(5-Cyanomethoxy-pyrimidin-2-ylamino)-piperidine-1-carboxylic acid tert-butyl ester To a stirred solution of 4-(5-hydroxy-pyrimidin-2-ylamino)-piperidine-1-carboxylic acid tert-butyl ester (0.74 g, 2.5 mmol, 1.0 equiv; intermediate C31/step 2) in DMF (10 mL) was added potassium carbonate (1.05 g, 7.5 mmol, 3.0 equiv), followed by bromoacetonitrile (0.21 mL, 0.37 g, 3.0 mmol, 1.2 equiv). After 90 min, the reaction mixture was poured into ice water and extracted twice with diethylether. The combined organic layers were washed with water, dried over MgSO4, filtered and concentrated by evaporation under reduced pressure. The crude product was purified by column chromatography on silica eluting with a gradient of dichloromethane/methanol to give 0.70 g (84%) of the title compound as a light yellow solid. MS (ISP): 334.3 [M+H]+.

Step 2

To a stirred solution of 4-(5-cyanomethoxy-pyrimidin-2-ylamino)-piperidine-1-carboxylic acid tert-butyl ester (0.67 g, 2.0 mmol, 1.0 equiv) in dichloromethane (15 mL) was added drop by drop 90% trifluoroacetic acid (1.82 mL, 2.55 g, 20 mmol, 10 equiv) and the reaction was stirred at rt for 16 h. The reaction mixture was evaporated and the residue partitioned between water and dichloromethane. The pH of the water phase was adjusted to 9-10 by addition of a sat. solution of potassium carbonate and the mixture extracted three times with dichloromethane. The combined organic layers were washed with water, dried over MgSO$_4$, filtered and concentrated by evaporation under reduced pressure. The crude product was purified by column chromatography on silica eluting with a gradient of dichloromethane/methanol (+25% ammonia in water) to give 0.32 g (69%) of the title compound as colorless oil. MS (ISP): 234.0 [M+H]$^+$.

Intermediate C33 rac-3-[2-(Piperidin-4-ylamino)-pyrimidin-5-yloxy]-propane-1,2-diol

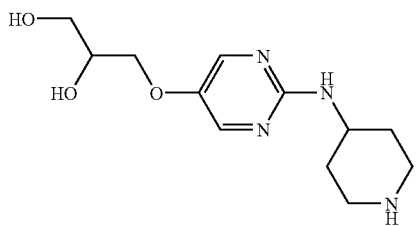

The title compound was prepared in analogy to the synthesis of 4-(5-cyanomethoxy-pyrimidin-2-ylamino)-piperidine-1-carboxylic acid tert-butyl ester (intermediate C32/step 1) from 4-(5-hydroxy-pyrimidin-2-ylamino)-piperidine-1-carboxylic acid tert-butyl ester (intermediate C31/step 2) by reaction with rac-toluene-4-sulfonic acid 2,2-dimethyl-[1,3]dioxolan-4-ylmethyl ester (commercially available) and potassium carbonate in DMF at rt for 48 h, followed by BOC and isopropylidene cleavage with 4 M HCl in dioxane and ethanol at 60° C. in analogy to the procedure described for 2-[4-methoxy-6-(piperidin-4-ylamino)-[1,3,5]triazin-2-ylamino]-ethanol (intermediate C26/step 3) and subsequent ion exchange chromatography on Q-Sepharose Fast Flow. MS (ISP): 269.1 [M+H]$^+$.

Intermediate C34

3-[2-(Piperidin-4-ylamino)-pyrimidin-5-yloxy]-propan-1-ol

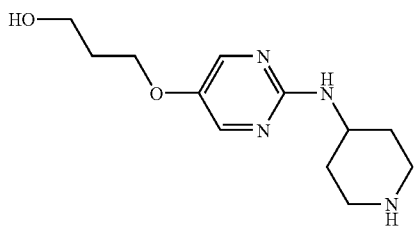

The compound was prepared in analogy to the synthesis of 4-(5-cyanomethoxy-pyrimidin-2-ylamino)-piperidine-1-carboxylic acid tert-butyl ester (intermediate C32/step 1) from 4-(5-hydroxy-pyrimidin-2-ylamino)-piperidine-1-carboxylic acid tert-butyl ester (intermediate C31/step 2) by reaction with rac-2-(3-bromopropoxy)tetrahydro-2H-pyran (commercially available) and potassium carbonate in DMF at 100° C., followed by BOC and THP cleavage with 90% trifluoroacetic acid in dichloromethane at rt for 16 h in analogy to the procedure described for [2-(piperidin-4-ylamino)-pyrimidin-5-yloxy]-acetonitrile (intermediate C32/step 2). MS (ISP): 253.0 [M+H]$^+$.

Intermediate C35

2-[2-(Piperidin-4-ylamino)-pyrimidin-5-yloxy]-acetamide

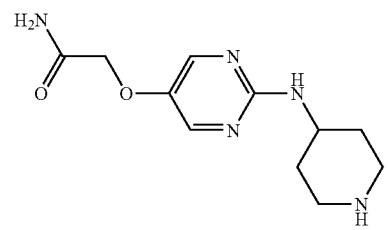

The compound was prepared in analogy to the synthesis of 4-(5-cyanomethoxy-pyrimidin-2-ylamino)-piperidine-1-carboxylic acid tert-butyl ester (intermediate C32/step 1) from 4-(5-hydroxy-pyrimidin-2-ylamino)-piperidine-1-carboxylic acid tert-butyl ester (intermediate C31/step 2) by reaction with 2-bromo-acetamide and potassium carbonate in DMF at rt, followed by BOC cleavage with 4 M HCl in dioxane and DMF at 85° C. in analogy to the procedure described for 2-[4-methoxy-6-(piperidin-4-ylamino)-[1,3,5]triazin-2-ylamino]-ethanol (intermediate C26/step 3). MS (ISP): 252.0 [M+H]$^+$.

Example 288

2-{4-[1-(3,5-Diethoxy-4-fluoro-benzyl)-piperidin-4-ylamino]-6-methoxy-[1,3,5]triazin-2-ylamino}-ethanol To a solution of 2-[4-methoxy-6-(piperidin-4-ylamino)-[1,3,5]triazin-2-ylamino]-ethanol (0.19 g, 0.71 mmol, 1.0 equiv; intermediate C26) and 3,5-diethoxy-4-fluoro-benzaldehyde (0.17 g, 0.78 mmol, 1.1 equiv; intermediate D12) in ethanol (10 mL) under an atmosphere of Ar was added N-ethyl diisopropylamine (0.28 mL, 0.21 g, 1.63 mmol, 2.29 equiv) and glacial acetic acid (0.10 mL, 0.10 g, 1.67 mmol, 2.35 equiv) and the mixture heated to 50° C. for 2 h. After cooling down to 30° C., sodium cyanoborohydride (0.12 g, 1.91 mmol, 2.7 equiv) was added and the reaction mixture heated again to 50° C. for 1.5 h. It was then poured into crashed ice, the pH of the water phase adjusted to ~10 by addition of a sat. solution of sodium carbonate and the mixture extracted three times with dichloromethane. The combined organic phases were washed with water, dried over MgSO$_4$, filtered and concentrated by evaporation under reduced pressure. The crude product was purified by column chromatography on silica eluting with a gradient of dichloromethane/methanol to give 0.15 g (45%) of the title compound as light yellow oil. MS (ISP): 465.2 [M+H]$^+$.

Examples 289 to 314

According to the procedure described for the synthesis of example 288 further triazine and pyrimidine derivatives have been synthesized from 2-[4-methoxy-6-(piperidin-4-ylamino)-[1,3,5]triazin-2-ylamino]-ethanol (intermediate C26), 6-methoxy-N-(2-methoxy-ethyl)-N'-piperidin-4-yl-[1,3,5]triazine-2,4-diamine (intermediate C27), 6-methoxy-N-methyl-N'-piperidin-4-yl-[1,3,5]triazine-2,4-diamine (intermediate C28), [4-methoxy-6-(piperidin-4-ylamino)-[1,3,5]triazin-2-ylamino]-acetic acid tert-butyl ester (intermediate C29), (4-methoxy-6-thiomorpholin-4-yl-[1,3,5]triazin-2-yl)-piperidin-4-yl-amine (intermediate C30), methanesulfonic acid 2-(piperidin-4-ylamino)-pyrimidin-5-yl ester (intermediate C31), [2-(piperidin-4-ylamino)-pyrimidin-5-yloxy]-acetonitrile (intermediate C32), rac-3-[2-(piperidin-4-ylamino)-pyrimidin-5-yloxy]-propane-1,2-diol (intermediate C33), 3-[2-(piperidin-4-ylamino)-pyrimidin-5-yloxy]-propan-1-ol (intermediate C34) and 2-[2-(piperidin-4-ylamino)-pyrimidin-5-yloxy]-acetamide (intermediate C35) and the respective benzaldehyde intermediate as indicated in Table 4. The results are compiled in Table 4 and comprise example 289 to example 314.

TABLE 4

| No. | MW | Compound Name | Starting Materials | ISP [M + H]$^+$ found |
|---|---|---|---|---|
| 289 | 480.99 | 2-{4-[1-(4-chloro-3,5-diethoxy-benzyl)-piperidin-4-ylamino]-6-methoxy-[1,3,5]triazin-2-ylamino}-ethanol | 2-[4-methoxy-6-(piperidin-4-ylamino)-[1,3,5]triazin-2-ylamino]-ethanol (intermediate C26) and 4-chloro-3,5-diethoxy-benzaldehyde (intermediate D20) | [M + H]$^+$ 481.2 |
| 290 | 540.64 | 2-{4-[1-(2,6-diethoxy-4'-fluoro-biphenyl-4-ylmethyl)-piperidin-4-ylamino]-6-methoxy-[1,3,5]triazin-2-ylamino}-ethanol | 2-[4-methoxy-6-(piperidin-4-ylamino)-[1,3,5]triazin-2-ylamino]-ethanol (intermediate C26) and 2,6-diethoxy-4'-fluoro-biphenyl-4-carbaldehyde (intermediate D34) | [M + H]$^+$ 541.4 |
| 291 | 478.57 | N-[1-(3,5-diethoxy-4-fluoro-benzyl)-piperidin-4-yl]-6-methoxy-N'-(2-methoxy-ethyl)-[1,3,5]triazine-2,4-diamine | 6-methoxy-N-(2-methoxy-ethyl)-N'-piperidin-4-yl-[1,3,5]triazine-2,4-diamine (intermediate C27) and 3,5-diethoxy-4-fluoro-benzaldehyde (intermediate D12) | [M + H]$^+$ 479.1 |
| 292 | 495.02 | N-[1-(4-chloro-3,5-diethoxy-benzyl)-piperidin-4-yl]-6-methoxy-N'-(2-methoxy-ethyl)-[1,3,5]triazine-2,4-diamine | 6-methoxy-N-(2-methoxy-ethyl)-N'-piperidin-4-yl-[1,3,5]triazine-2,4-diamine (intermediate C27) and 4-chloro-3,5-diethoxy-benzaldehyde (intermediate D20) | [M + H]$^+$ 495.3 |
| 293 | 554.66 | N-[1-(2,6-diethoxy-4'-fluoro-biphenyl-4-ylmethyl)-piperidin-4-yl]-6-methoxy-N'-(2-methoxy-ethyl)-[1,3,5]triazine-2,4-diamine | 6-methoxy-N-(2-methoxy-ethyl)-N'-piperidin-4-yl-[1,3,5]triazine-2,4-diamine (intermediate C27) and 2,6-diethoxy-4'-fluoro-biphenyl-4-carbaldehyde (intermediate D34) | [M + H]$^+$ 555.3 |
| 294 | 434.51 | N-[1-(3,5-diethoxy-4-fluoro-benzyl)-piperidin-4-yl]-6-methoxy-N'-methyl-[1,3,5]triazine-2,4-diamine | 6-methoxy-N-methyl-N'-piperidin-4-yl-[1,3,5]triazine-2,4-diamine (intermediate C28) and 3,5-diethoxy-4-fluoro-benzaldehyde (intermediate D12) | [M + H]$^+$ 435.2 |
| 295 | 450.97 | N-[1-(4-chloro-3,5-diethoxy-benzyl)-piperidin-4-yl]-6-methoxy-N'-methyl-[1,3,5]triazine-2,4-diamine | 6-methoxy-N-methyl-N'-piperidin-4-yl-[1,3,5]triazine-2,4-diamine (intermediate C28) and 4-chloro-3,5-diethoxy-benzaldehyde (intermediate D20) | [M + H]$^+$ 451.1 |
| 296 | 510.61 | N-[1-(2,6-diethoxy-4'-fluoro-biphenyl-4-ylmethyl)-piperidin-4-yl]-6-methoxy-N'-methyl-[1,3,5]triazine-2,4-diamine | 6-methoxy-N-methyl-N'-piperidin-4-yl-[1,3,5]triazine-2,4-diamine (intermediate C28) and 2,6-diethoxy-4'-fluoro-biphenyl-4-carbaldehyde (intermediate D34) | [M + H]$^+$ 511.4 |
| 297 | 534.63 | {4-[1-(3,5-diethoxy-4-fluoro-benzyl)-piperidin-4-ylamino]-6-methoxy- | [4-methoxy-6-(piperidin-4-ylamino)-[1,3,5]triazin-2-ylamino]-acetic acid tert- | [M + H]$^+$ 535.2 |

TABLE 4-continued

| No. | MW | Compound Name | Starting Materials | ISP [M + H]+ found |
|---|---|---|---|---|
| | | [1,3,5]triazin-2-ylamino}-acetic acid tert-butyl ester | butyl ester (intermediate C29) and 3,5-diethoxy-4-fluoro-benzaldehyde (intermediate D12) | |
| 298 | 551.08 | {4-[1-(4-chloro-3,5-diethoxy-benzyl)-piperidin-4-ylamino]-6-methoxy-[1,3,5]triazin-2-ylamino}-acetic acid tert-butyl ester | [4-methoxy-6-(piperidin-4-ylamino)-[1,3,5]triazin-2-ylamino]-acetic acid tert-butyl ester (intermediate C29) and 4-chloro-3,5-diethoxy-benzaldehyde (intermediate D20) | [M + H]+ 551.3 |
| 299 | 610.73 | {4-[1-(2,6-diethoxy-4'-fluoro-biphenyl-4-ylmethyl)-piperidin-4-ylamino]-6-methoxy-[1,3,5]triazin-2-ylamino}-acetic acid tert-butyl ester | [4-methoxy-6-(piperidin-4-ylamino)-[1,3,5]triazin-2-ylamino]-acetic acid tert-butyl ester (intermediate C29) and 2,6-diethoxy-4'-fluoro-biphenyl-4-carbaldehyde (intermediate D34) | [M + H]+ 611.3 |
| 300 | 506.64 | [1-(3,5-diethoxy-4-fluoro-benzyl)-piperidin-4-yl]-(4-methoxy-6-thiomorpholin-4-yl-[1,3,5]triazin-2-yl)-amine | (4-methoxy-6-thiomorpholin-4-yl-[1,3,5]triazin-2-yl)-piperidin-4-yl-amine (intermediate C30) and 3,5-diethoxy-4-fluoro-benzaldehyde (intermediate D12) | [M + H]+ 507.3 |
| 301 | 523.10 | [1-(4-chloro-3,5-diethoxy-benzyl)-piperidin-4-yl]-(4-methoxy-6-thiomorpholin-4-yl-[1,3,5]triazin-2-yl)-amine | (4-methoxy-6-thiomorpholin-4-yl-[1,3,5]triazin-2-yl)-piperidin-4-yl-amine (intermediate C30) and 4-chloro-3,5-diethoxy-benzaldehyde (intermediate D20) | [M + H]+ 523.3 |
| 302 | 582.74 | [1-(2,6-diethoxy-4'-fluoro-biphenyl-4-ylmethyl)-piperidin-4-yl]-(4-methoxy-6-thiomorpholin-4-yl-[1,3,5]triazin-2-yl)-amine | (4-methoxy-6-thiomorpholin-4-yl-[1,3,5]triazin-2-yl)-piperidin-4-yl-amine (intermediate C30) and 2,6-diethoxy-4'-fluoro-biphenyl-4-carbaldehyde (intermediate D34) | [M + H]+ 583.3 |
| 303 | 468.55 | methanesulfonic acid 2-[1-(3,5-diethoxy-4-fluoro-benzyl)-piperidin-4-ylamino]-pyrimidin-5-yl ester | methanesulfonic acid 2-(piperidin-4-ylamino)-pyrimidin-5-yl ester (intermediate C31) and 3,5-diethoxy-4-fluoro-benzaldehyde (intermediate D12) | [M + H]+ 469.3 |
| 304 | 485.00 | methanesulfonic acid 2-[1-(4-chloro-3,5-diethoxy-benzyl)-piperidin-4-ylamino]-pyrimidin-5-yl ester | methanesulfonic acid 2-(piperidin-4-ylamino)-pyrimidin-5-yl ester (intermediate C31) and 4-chloro-3,5-diethoxy-benzaldehyde (intermediate D20) | [M + H]+ 485.2 |
| 305 | 544.65 | methanesulfonic acid 2-[1-(2,6-diethoxy-4'-fluoro-biphenyl-4-ylmethyl)-piperidin-4-ylamino]-pyrimidin-5-yl ester | methanesulfonic acid 2-(piperidin-4-ylamino)-pyrimidin-5-yl ester (intermediate C31) and 2,6-diethoxy-4'-fluoro-biphenyl-4-carbaldehyde (intermediate D34) | [M + H]+ 545.2 |
| 306 | 429.49 | {2-[1-(3,5-diethoxy-4-fluoro-benzyl)-piperidin-4-ylamino]-pyrimidin-5-yloxy}-acetonitrile | [2-(piperidin-4-ylamino)-pyrimidin-5-yloxy]-acetonitrile (intermediate C32) and 3,5-diethoxy-4-fluoro-benzaldehyde (intermediate D12) | [M + H]+ 430.4 |
| 307 | 445.95 | {2-[1-(4-chloro-3,5-diethoxy-benzyl)-piperidin-4-ylamino]-pyrimidin-5-yloxy}-acetonitrile | [2-(piperidin-4-ylamino)-pyrimidin-5-yloxy]-acetonitrile (intermediate C32) and 4-chloro-3,5-diethoxy-benzaldehyde (intermediate D20) | [M + H]+ 446.3 |
| 308 | 505.59 | {2-[1-(2,6-diethoxy-4'-fluoro-biphenyl-4-ylmethyl)-piperidin-4- | [2-(piperidin-4-ylamino)-pyrimidin-5-yloxy]-acetonitrile (intermediate | [M + H]+ 506.2 |

TABLE 4-continued

| No. | MW | Compound Name | Starting Materials | ISP [M + H]+ found |
|---|---|---|---|---|
|  |  | ylamino]-pyrimidin-5-yloxy}-acetonitrile | C32) and 2,6-diethoxy-4'-fluoro-biphenyl-4-carbaldehyde (intermediate D34) |  |
| 309 | 480.99 | rac-3-{2-[1-(4-chloro-3,5-diethoxy-benzyl)-piperidin-4-ylamino]-pyrimidin-5-yloxy}-propane-1,2-diol | rac-3-[2-(piperidin-4-ylamino)-pyrimidin-5-yloxy]-propane-1,2-diol (intermediate C33) and 4-chloro-3,5-diethoxy-benzaldehyde (intermediate D20) | [M + H]+ 481.2 |
| 310 | 540.63 | rac-3-{2-[1-(2,6-diethoxy-4'-fluoro-biphenyl-4-ylmethyl)-piperidin-4-ylamino]-pyrimidin-5-yloxy}-propane-1,2-diol | rac-3-[2-(piperidin-4-ylamino)-pyrimidin-5-yloxy]-propane-1,2-diol (intermediate C33) and 2,6-diethoxy-4'-fluoro-biphenyl-4-carbaldehyde (intermediate D34) | [M + H]+ 541.2 |
| 311 | 464.99 | 3-{2-[1-(4-chloro-3,5-diethoxy-benzyl)-piperidin-4-ylamino]-pyrimidin-5-yloxy}-propan-1-ol | 3-[2-(piperidin-4-ylamino)-pyrimidin-5-yloxy]-propan-1-ol (intermediate C34) and 4-chloro-3,5-diethoxy-benzaldehyde (intermediate D20) | [M + H]+ 465.2 |
| 312 | 524.63 | 3-{2-[1-(2,6-diethoxy-4'-fluoro-biphenyl-4-ylmethyl)-piperidin-4-ylamino]-pyrimidin-5-yloxy}-propan-1-ol | 3-[2-(piperidin-4-ylamino)-pyrimidin-5-yloxy]-propan-1-ol (intermediate C34) and 2,6-diethoxy-4'-fluoro-biphenyl-4-carbaldehyde (intermediate D34) | [M + H]+ 525.1 |
| 313 | 463.96 | 2-{2-[1-(4-chloro-3,5-diethoxy-benzyl)-piperidin-4-ylamino]-pyrimidin-5-yloxy}-acetamide | 2-[2-(piperidin-4-ylamino)-pyrimidin-5-yloxy]-acetamide (intermediate C35) and 4-chloro-3,5-diethoxy-benzaldehyde (intermediate D20) | [M + H]+ 464.2 |
| 314 | 523.61 | 2-{2-[1-(2,6-diethoxy-4'-fluoro-biphenyl-4-ylmethyl)-piperidin-4-ylamino]-pyrimidin-5-yloxy}-acetamide | 2-[2-(piperidin-4-ylamino)-pyrimidin-5-yloxy]-acetamide (intermediate C35) and 2,6-diethoxy-4'-fluoro-biphenyl-4-carbaldehyde (intermediate D34) | [M + H]+ 524.3 |

Example 315

{4-[1-(3,5-Diethoxy-4-fluoro-benzyl)-piperidin-4-ylamino]-6-methoxy-[1,3,5]triazin-2-ylamino}-acetic acid To a stirred solution of {4-[1-(3,5-diethoxy-4-fluoro-benzyl)-piperidin-4-ylamino]-6-methoxy-[1,3,5]triazin-2-ylamino}-acetic acid tert-butyl ester (0.09 g, 0.2 mmol, 1.0 equiv; example 297) in THF/methanol (1:1) (4 mL) was added drop by drop a 1 M solution of LiOH in water (0.42 mL, 0.42 mmol, 2.1 equiv). After 16 h, the reaction mixture was poured into ice water, the pH adjusted to 3-4 with diluted HCl and the mixture extracted three times with dichloromethane/isopropanol (4:1). The combined organic layers were concentrated by evaporation under reduced pressure to yield 0.031 g (32%) of the title compound as a colorless solid. MS (ISN): 477.2 [M−H]−.

Examples 316 and 317

According to the procedure described for the synthesis of example 315 further triazine derivatives have been synthesized from {4-[1-(4-chloro-3,5-diethoxy-benzyl)-piperidin-4-ylamino]-6-methoxy-[1,3,5]triazin-2-ylamino}-acetic acid tert-butyl ester (example 298) and from {4-[1-(2,6-diethoxy-4'-fluoro-biphenyl-4-ylmethyl)-piperidin-4-ylamino]-6-methoxy-[1,3,5]triazin-2-ylamino}-acetic acid tert-butyl ester (example 299) as indicated in Table 5. The results are compiled in Table 5 and comprise example 316 and example 317.

TABLE 5

| No. | MW | Compound Name | Starting Materials | ISP or ISN [M + H]+ or [M − H]− found |
|---|---|---|---|---|
| 316 | 494.98 | {4-[1-(4-chloro-3,5-diethoxy-benzyl)-piperidin-4-ylamino]-6-methoxy-[1,3,5]triazin-2-ylamino}-acetic acid | {4-[1-(4-chloro-3,5-diethoxy-benzyl)-piperidin-4-ylamino]-6-methoxy-[1,3,5]triazin-2-ylamino}-acetic acid tert-butyl ester (example 298) | [M + H]+ 495.2 |
| 317 | 554.62 | {4-[1-(2,6-diethoxy-4'-fluoro-biphenyl-4-ylmethyl)-piperidin-4-ylamino]-6-methoxy-[1,3,5]triazin-2-ylamino}-acetic acid | {4-[1-(2,6-diethoxy-4'-fluoro-biphenyl-4-ylmethyl)-piperidin-4-ylamino]-6-methoxy-[1,3,5]triazin-2-ylamino}-acetic acid tert-butyl ester (example 299) | [M − H]− 553.2 |

Example A

Film coated tablets containing the following ingredients can be manufactured in a conventional manner:

| Ingredients | Per tablet | |
|---|---|---|
| Kernel: | | |
| Compound of formula I | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titanium dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magnesium stearate and compressed to yield kernels of 120 or 350 mg respectively. The kernels are lacquered with an aqueous solution/suspension of the above mentioned film coat.

Example B

Capsules containing the following ingredients can be manufactured in a conventional manner:

| Ingredients | Per capsule |
|---|---|
| Compound of formula I | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
|---|---|
| Compound of formula I | 3.0 mg |
| Gelatine | 150.0 mg |
| Phenol | 4.7 mg |
| Sodium carbonate | to obtain a final pH of 7 |
| Water for injection solutions | ad 1.0 ml |

Example D

Soft gelatin capsules containing the following ingredients can be manufactured in a conventional manner:

| Capsule contents | |
|---|---|
| Compound of formula I | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titanium dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

| | |
|---|---|
| Compound of formula I | 50.0 mg |
| Lactose, fine powder | 1015.0 mg |
| Microcrystalline cellulose (AVICEL PH 102) | 1400.0 mg |
| Sodium carboxymethyl cellulose | 14.0 mg |
| Polyvinylpyrrolidone K 30 | 10.0 mg |
| Magnesium stearate | 10.0 mg |
| Flavoring additives | 1.0 mg |

The active ingredient is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

It is to be understood that the invention is not limited to the particular embodiments of the invention described above, as variations of the particular embodiments may be made and still fall within the scope of the appended claims.

What is claimed is:

1. A compound of formula I:

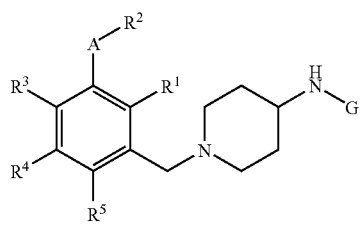

I wherein

A is —O— or —NH—;

$R^1$ is selected from the group consisting of hydrogen, $C_{1-7}$-alkoxy and halogen;

$R^2$ is selected from the group consisting of $C_{2-7}$-alkyl, $C_{2-7}$-alkenyl, halogen-$C_{1-7}$-alkyl, $C_{1-7}$-alkoxy-$C_{1-7}$-alkyl, and benzyl, or, in case $R^3$ and $R^4$ form a ring, $R^2$ can also be methyl;

$R^3$ is selected from the group consisting of phenyl substituted by halogen, $R^4$ is selected from the group consisting of hydrogen, hydroxy, $C_{1-7}$-alkoxy, amino, nitro, hydroxy-$C_{1-7}$-alkoxy, $C_{1-7}$-alkoxy-$C_{1-7}$-alkoxy, and —O-benzyl;

or $R^3$ and $R^4$ are bonded to each other to form a ring together with the carbon atoms they are attached to and $R^3$ and $R^4$ together are —CH=CH—CH=CH— or —O—C(CH$_3$)$_2$—CH=CH—;

$R^5$ is selected from the group consisting of hydrogen, halogen, $C_{1-7}$-alkoxy and $C_{1-7}$-alkoxy-$C_{1-7}$-alkoxy;

G is

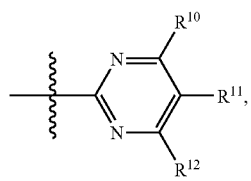

G1 wherein $R^{10}$ is selected from the group consisting of hydrogen, $C_{1-7}$-alkyl, halogen, halogen-$C_{1-7}$-alkyl, unsubstituted phenyl, phenyl substituted by one to three groups selected from the group consisting of $C_{1-7}$-alkyl, $C_{1-7}$-alkoxy, halogen, halogen-$C_{1-7}$-alkyl and —COOH, —OR$^{26}$, wherein R$^{26}$ is selected from the group consisting of hydrogen, $C_{1-7}$-alkyl, unsubstituted phenyl and phenyl substituted by one to three groups selected from the group consisting of $C_{1-7}$-alkyl, $C_{1-7}$-alkoxy and halogen, —C(O)OR$^{27}$, wherein R$^{27}$ is $C_{1-7}$-alkyl, thiazolyl, thienyl, and azetidinyl, or, in case $R^{11}$ is cyano, $R^{10}$ can also be amino;

$R^{11}$ is selected from the group consisting of hydrogen, $C_{1-7}$-alkyl, halogen, halogen-$C_{1-7}$-alkyl, cyano, nitro, —COOH, —CONHR$^{28}$, wherein R$^{28}$ is selected from the group consisting of hydrogen, $C_{1-7}$-alkyl, unsubstituted phenyl and phenyl substituted by one to three groups selected from the group consisting of $C_{1-7}$-alkyl, $C_{1-7}$-alkoxy, halogen and halogen-$C_{1-7}$-alkoxy, —OR$^{30}$, wherein R$^{30}$ is selected from the group consisting of hydroxy-$C_{1-7}$-alkyl, cyano-$C_{1-7}$-alkyl, $C_{1-7}$-alkylsulfonyl and —CH$_2$—CONH$_2$, unsubstituted phenyl, phenyl substituted by one to three groups selected from the group consisting of $C_{1-7}$-alkyl, $C_{1-7}$-alkoxy, halogen, halogen-$C_{1-7}$-alkyl, —COOH and —CONH$_2$, and pyridyl;

$R^{12}$ is selected from the group consisting of hydrogen, $C_{1-7}$-alkyl, $C_{1-7}$-alkoxy, halogen, halogen-$C_{1-7}$-alkyl, —COOR$^{28}$, wherein R$^{28}$ is hydrogen or $C_{1-7}$-alkyl, and hydroxy-$C_{1-7}$-alkylamino;

or a pharmaceutically acceptable salt thereof.

2. The compound according to claim 1, wherein A is O.

3. The compound according to claim 1, wherein $R^1$ is hydrogen or halogen.

4. The compound according to claim 1, wherein $R^2$ is selected from the group consisting of $C_{2-7}$-alkyl, $C_{2-7}$-alkenyl, halogen-$C_{1-7}$-alkyl, $C_{1-7}$-alkoxy-$C_{1-7}$-alkyl and benzyl.

5. The compound according to claim 1, wherein $R^2$ is selected from the group consisting of ethyl, propyl, isopropyl, allyl, 2-fluoroethyl, methoxymethyl, butyl, isobutyl and benzyl.

6. The compound according to claim 1, wherein $R^4$ is selected from the group consisting of hydrogen, hydroxy, $C_{1-7}$-alkoxy, nitro, $C_{1-7}$-alkoxy-$C_{1-7}$-alkoxy, and —O-benzyl.

7. The compound according to claim 1, wherein $R^5$ is hydrogen.

8. The compound according to claim 1, wherein G is

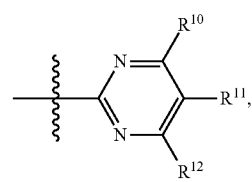

G1 and wherein $R^{10}$ is selected from the group consisting of hydrogen, $C_{1-7}$-alkyl, halogen, halogen-$C_{1-7}$-alkyl, unsubstituted phenyl, phenyl substituted by one to three groups selected from the group consisting of $C_{1-7}$-alkyl, $C_{1-7}$-alkoxy, halogen, halogen-$C_{1-7}$-alkyl and —COOH, —OR$^{26}$, wherein R$^{26}$ is selected from the group consisting of hydrogen, $C_{1-7}$-alkyl, unsubstituted phenyl and phenyl substituted by one to three groups selected from the group consisting of $C_{1-7}$-alkyl, $C_{1-7}$-alkoxy and halogen, —C(O)OR²⁷, wherein R²⁷ is C₁₋₇-alkyl, thiazolyl, thienyl, and azetidinyl, or, in case R¹¹ is cyano, R¹⁰ can also be amino;

- R¹¹ is selected from the group consisting of hydrogen, C₁₋₇-alkyl, halogen, halogen-C₁₋₇-alkyl, cyano, nitro, —COOH, —CONHR²⁸, wherein R²⁸ is selected from the group consisting of hydrogen, C₁₋₇-alkyl, unsubstituted phenyl and phenyl substituted by one to three groups selected from the group consisting of C₁₋₇-alkyl, C₁₋₇-alkoxy, halogen and halogen-C₁₋₇-alkoxy, —OR³⁰, wherein R³⁰ is selected from the group consisting of hydroxy-C₁₋₇-alkyl, cyano-C₁₋₇-alkyl, C₁₋₇-alkylsulfonyl and —CH₂—CONH₂, unsubstituted phenyl, phenyl substituted by one to three groups selected from the group consisting of C₁₋₇-alkyl, C₁₋₇-alkoxy, halogen, halogen-C₁₋₇-alkyl, —COOH and —CONH₂, and pyridyl;
- R¹² is selected from the group consisting of hydrogen, C₁₋₇-alkyl, C₁₋₇-alkoxy, halogen, halogen-C₁₋₇-alkyl, —COOR²⁸, wherein R²⁸ is hydrogen or C₁₋₇-alkyl, and hydroxy-C₁₋₇-alkylamino.

9. The compound according to claim 1, wherein

R¹⁰ is hydrogen or C₁₋₇-alkyl;

R¹¹ is selected from the group consisting of hydrogen, C₁₋₇-alkyl, —COOH, —CONH₂, unsubstituted phenyl, phenyl substituted by one to three groups selected from the group consisting of C₁₋₇-alkyl, C₁₋₇-alkoxy, halogen, halogen-C₁₋₇-alkyl, —COOH and —CONH₂, and pyridyl; and R¹² is hydrogen or C₁₋₇-alkyl.

10. The compound according to claim 1, selected from the group consisting of

[1-(4-chloro-3-ethoxy-benzyl)-piperidin-4-yl]-(5-ethyl-pyrimidin-2-yl)-amine,
[1-(4-chloro-3,5-diethoxy-benzyl)-piperidin-4-yl]-(4,6-dimethyl-pyrimidin-2-yl)-amine,
[1-(4-chloro-3,5-diethoxy-benzyl)-piperidin-4-yl]-pyrimidin-2-yl-amine,
2-[1-(4-chloro-3-ethoxy-benzyl)-piperidin-4-ylamino]-pyrimidine-5-carboxylic acid,
2-[1-(4-chloro-3,5-diethoxy-benzyl)-piperidin-4-ylamino]-pyrimidine-5-carboxylic acid,
[1-(4-chloro-3-ethoxy-benzyl)-piperidin-4-yl]-(5-phenyl-pyrimidin-2-yl)-amine,
[1-(4-chloro-3,5-diethoxy-benzyl)-piperidin-4-yl]-(5-phenyl-pyrimidin-2-yl)-amine,
[1-(4-chloro-3-ethoxy-benzyl)-piperidin-4-yl]-[5-(4-methoxy-phenyl)-pyrimidin-2-yl]-amine,
[1-(4-chloro-3,5-diethoxy-benzyl)-piperidin-4-yl]-[5-(4-methoxy-phenyl)-pyrimidin-2-yl]-amine,
[1-(4-chloro-3-ethoxy-benzyl)-piperidin-4-yl]-(5-pyridin-3-yl-pyrimidin-2-yl)-amine,
[1-(3,5-diethoxy-4-fluoro-benzyl)-piperidin-4-yl]-(5-pyridin-3-yl-pyrimidin-2-yl)-amine,
[1-(4-chloro-3,5-diethoxy-benzyl)-piperidin-4-yl]-(5-pyridin-3-yl-pyrimidin-2-yl)-amine,
4-{2-[1-(4-chloro-3-ethoxy-benzyl)-piperidin-4-ylamino]-pyrimidin-5-yl}-benzamide, or a pharmaceutically acceptable salt thereof.

11. A pharmaceutical composition, comprising a therapeutically effective amount of a compound according to claim 1 as well as a pharmaceutically acceptable carrier and/or adjuvant.

* * * * *